US008734795B2

(12) United States Patent
Wang et al.

(10) Patent No.: US 8,734,795 B2
(45) Date of Patent: May 27, 2014

(54) LIGHT TARGETING MOLECULES AND USES THEREOF

(75) Inventors: Xinzhong Wang, Wayland, MA (US); Veronique Bailly, Somerville, MA (US); Alexey Lugovskoy, Woburn, MA (US); Graham K. Farrington, Acton, MA (US); Christilyn Graff, Cambridge, MA (US); Scott Glaser, San Diego, CA (US)

(73) Assignee: Biogen Idec MA Inc., Cambridge, MA (US)

( * ) Notice: Subject to any disclaimer, the term of this patent is extended or adjusted under 35 U.S.C. 154(b) by 389 days.

(21) Appl. No.: 12/610,204

(22) Filed: Oct. 30, 2009

(65) Prior Publication Data

US 2010/0119511 A1 May 13, 2010

Related U.S. Application Data

(60) Provisional application No. 61/110,359, filed on Oct. 31, 2008.

(51) Int. Cl.
| A61K 39/395 | (2006.01) |
| C07K 16/00 | (2006.01) |
| C12N 15/13 | (2006.01) |
| C12N 15/63 | (2006.01) |
| C12N 5/00 | (2006.01) |
| C12P 21/00 | (2006.01) |
| G01N 33/53 | (2006.01) |

(52) U.S. Cl.
USPC .......... 424/134.1; 424/174.1; 535/387.3; 535/389.7; 536/23.53

(58) Field of Classification Search
USPC .......... 424/134.1, 174.1; 535/387.3, 389.7; 536/23.56
See application file for complete search history.

(56) References Cited

U.S. PATENT DOCUMENTS

| 4,753,894 A | 6/1988 | Frankel et al. |
| 4,797,368 A | 1/1989 | Carter et al. |
| 4,980,286 A | 12/1990 | Morgan et al. |
| 5,091,513 A | 2/1992 | Huston et al. |
| 5,132,405 A | 7/1992 | Huston et al. |
| 5,169,774 A | 12/1992 | Frankel et al. |
| 5,258,498 A | 11/1993 | Huston et al. |
| 5,399,346 A | 3/1995 | Anderson et al. |
| 5,436,146 A | 7/1995 | Shenk et al. |
| 5,476,786 A | 12/1995 | Huston |
| 5,482,858 A | 1/1996 | Huston et al. |
| 5,534,254 A | 7/1996 | Huston et al. |
| 5,571,894 A | 11/1996 | Wels et al. |
| 5,629,197 A | 5/1997 | Ring et al. |
| 5,677,171 A | 10/1997 | Hudziak et al. |
| 5,705,157 A | 1/1998 | Greene |
| 5,720,937 A | 2/1998 | Hudziak et al. |
| 5,720,954 A | 2/1998 | Hudziak et al. |
| 5,725,856 A | 3/1998 | Hudziak et al. |
| 5,753,204 A | 5/1998 | Huston et al. |
| 5,770,195 A | 6/1998 | Hudziak et al. |
| 5,772,997 A | 6/1998 | Hudziak et al. |
| 5,783,186 A | 7/1998 | Arakawa et al. |
| 5,783,404 A | 7/1998 | Koski |
| 5,821,337 A | 10/1998 | Carter et al. |
| 5,824,311 A | 10/1998 | Greene et al. |
| 5,837,846 A | 11/1998 | Huston et al. |
| 5,855,866 A | 1/1999 | Thorpe et al. |
| 5,877,305 A | 3/1999 | Huston et al. |
| 5,939,531 A | 8/1999 | Wels et al. |
| 5,994,071 A | 11/1999 | Ross et al. |
| 5,994,523 A | 11/1999 | Kawakami et al. |
| 6,048,551 A | 4/2000 | Hilfinger et al. |
| 6,054,297 A | 4/2000 | Carter et al. |
| 6,054,561 A | 4/2000 | Ring |
| 6,123,939 A | 9/2000 | Shawver et al. |
| 6,140,467 A | 10/2000 | Ware |
| 6,165,464 A | 12/2000 | Hudziak et al. |
| 6,207,147 B1 | 3/2001 | Hiserodt et al. |
| 6,207,804 B1 | 3/2001 | Huston et al. |
| 6,235,878 B1 | 5/2001 | Nishi et al. |
| 6,346,388 B1 | 2/2002 | Brigham-Burke et al. |
| 6,368,596 B1 | 4/2002 | Ghetie et al. |
| 6,387,371 B1 | 5/2002 | Hudziak et al. |
| 6,399,063 B1 | 6/2002 | Hudziak et al. |
| 6,407,213 B1 | 6/2002 | Carter et al. |
| 6,417,168 B1 | 7/2002 | Greene et al. |
| 6,441,143 B1 | 8/2002 | Koski |
| 6,458,356 B1 | 10/2002 | Arakawa et al. |
| 6,475,986 B1 | 11/2002 | Aggarwal |
| 6,479,254 B2 | 11/2002 | Ebner et al. |

(Continued)

FOREIGN PATENT DOCUMENTS

| EP | 0153114 | 8/1985 |
| EP | 0623679 | 5/1988 |
| EP | 0318554 | 6/1989 |
| EP | 0396387 | 11/1990 |
| EP | 0502812 | 9/1992 |
| EP | 0590058 | 4/1994 |
| EP | 0625200 | 11/1994 |
| EP | 0711565 | 5/1996 |
| EP | 1106183 | 10/1996 |
| EP | 0865448 | 12/1996 |

(Continued)

OTHER PUBLICATIONS

Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*

(Continued)

Primary Examiner — Lynn Bristol
(74) Attorney, Agent, or Firm — Lando & Anastasi LLP

(57) ABSTRACT

LIGHT-targeting molecules (e.g., LIGHT fusion molecules), anti-HER2 antibody molecules, compositions, e.g., pharmaceutical compositions thereof, are disclosed. Methods of using these molecules to treat, prevent and/or diagnose hyperproliferative, e.g., neoplastic, diseases or conditions, including, but not limited to, cancer and metastasis are also provided.

22 Claims, 27 Drawing Sheets

(56) References Cited

U.S. PATENT DOCUMENTS

| | | |
|---|---|---|
| 6,495,520 B2 | 12/2002 | Ebner et al. |
| 6,512,097 B1 | 1/2003 | Marks et al. |
| 6,590,090 B1 | 7/2003 | Nishi et al. |
| 6,627,196 B1 | 9/2003 | Baughman et al. |
| 6,635,743 B1 | 10/2003 | Ebner et al. |
| 6,639,055 B1 | 10/2003 | Carter et al. |
| 6,719,971 B1 | 4/2004 | Carter et al. |
| 6,733,752 B1 | 5/2004 | Greene et al. |
| 6,800,738 B1 | 10/2004 | Carter et al. |
| 6,884,418 B1 | 4/2005 | Shawver et al. |
| 6,949,245 B1 | 9/2005 | Sliwkowski |
| 6,998,108 B1 | 2/2006 | Ware |
| 7,041,292 B1 | 5/2006 | Sliwkowski |
| 7,064,111 B1 | 6/2006 | Todo et al. |
| 7,097,840 B2 | 8/2006 | Erickson et al. |
| 7,099,861 B2 | 8/2006 | Youn |
| 7,118,742 B2 | 10/2006 | Ware |
| 7,138,497 B2 | 11/2006 | Houston et al. |
| 7,226,592 B2 | 6/2007 | Kreysch |
| 7,241,576 B2 | 7/2007 | Aggarwal |
| 7,244,826 B1 | 7/2007 | Marks et al. |
| 7,309,486 B1 | 12/2007 | Zamoyski |
| 7,332,580 B2 | 2/2008 | Adams et al. |
| 7,332,585 B2 | 2/2008 | Adams et al. |
| 7,371,376 B1 | 5/2008 | Fendly |
| 7,371,379 B2 | 5/2008 | Baughman et al. |
| 7,435,797 B2 | 10/2008 | Lowman et al. |
| 7,449,181 B2 | 11/2008 | Noguchi et al. |
| 7,449,184 B2 | 11/2008 | Allison et al. |
| 7,501,122 B2 | 3/2009 | Adams et al. |
| 7,507,704 B1 | 3/2009 | Zamoyski |
| 7,569,663 B2 | 8/2009 | Tykocinski et al. |
| 7,845,302 B2 | 12/2010 | Loui et al. |
| 2002/0165193 A1 | 11/2002 | Greene et al. |
| 2003/0053984 A1 | 3/2003 | Tschopp et al. |
| 2003/0060605 A1 | 3/2003 | Ware |
| 2003/0086924 A1 | 5/2003 | Sliwkowski |
| 2003/0103971 A1 | 6/2003 | Hariharan et al. |
| 2003/0119149 A1 | 6/2003 | Reddy |
| 2003/0147884 A1 | 8/2003 | Paton et al. |
| 2003/0166546 A1 | 9/2003 | Aggarwal |
| 2003/0170234 A1 | 9/2003 | Hellmann |
| 2003/0171551 A1 | 9/2003 | Rosenblatt et al. |
| 2003/0215442 A1 | 11/2003 | Fraser et al. |
| 2003/0216596 A1 | 11/2003 | Sugio et al. |
| 2003/0224397 A1 | 12/2003 | Lowman et al. |
| 2004/0037823 A9 | 2/2004 | Paton et al. |
| 2004/0038349 A1 | 2/2004 | Hilbert et al. |
| 2004/0053248 A1 | 3/2004 | Tang et al. |
| 2004/0058367 A1 | 3/2004 | Matsui et al. |
| 2004/0116330 A1 | 6/2004 | Naito et al. |
| 2004/0138160 A1 | 7/2004 | Naito et al. |
| 2004/0141950 A1 | 7/2004 | Noelle et al. |
| 2004/0171823 A1 | 9/2004 | Nadler et al. |
| 2004/0202664 A1 | 10/2004 | Greene et al. |
| 2004/0259156 A1 | 12/2004 | Zhu |
| 2005/0002928 A1 | 1/2005 | Hellmann |
| 2005/0025754 A1 | 2/2005 | Fu |
| 2005/0025789 A1 | 2/2005 | Nieland et al. |
| 2005/0079184 A1 | 4/2005 | Hsing-Chang et al. |
| 2005/0085433 A1 | 4/2005 | Breidenstein et al. |
| 2005/0163747 A1 | 7/2005 | Hilbert et al. |
| 2005/0163774 A1 | 7/2005 | Rosenblum et al. |
| 2005/0202462 A1 | 9/2005 | Matsui et al. |
| 2005/0208043 A1 | 9/2005 | Adams et al. |
| 2005/0238640 A1 | 10/2005 | Sliwkowski |
| 2005/0272118 A1 | 12/2005 | Clark et al. |
| 2005/0287605 A1 | 12/2005 | Matsui et al. |
| 2006/0013819 A1 | 1/2006 | Kelsey |
| 2006/0018899 A1 | 1/2006 | Kao et al. |
| 2006/0025576 A1 | 2/2006 | Miller et al. |
| 2006/0034842 A1 | 2/2006 | Adams et al. |
| 2006/0035839 A1 | 2/2006 | Guichard et al. |
| 2006/0073140 A1 | 4/2006 | Greene et al. |
| 2006/0073143 A1 | 4/2006 | Adams et al. |
| 2006/0193854 A1 | 8/2006 | Adams et al. |
| 2006/0198843 A1 | 9/2006 | Adams et al. |
| 2006/0210561 A1 | 9/2006 | Baughman et al. |
| 2006/0216285 A1 | 9/2006 | Adams et al. |
| 2006/0263368 A1 | 11/2006 | Rosenblum et al. |
| 2006/0275305 A1 | 12/2006 | Bryant |
| 2007/0003514 A1 | 1/2007 | Penichet et al. |
| 2007/0010658 A1 | 1/2007 | Holtet et al. |
| 2007/0020261 A1 | 1/2007 | Sliwkowski et al. |
| 2007/0025911 A1 | 2/2007 | Sun et al. |
| 2007/0037255 A1 | 2/2007 | Lowman et al. |
| 2007/0071675 A1 | 3/2007 | Wu et al. |
| 2007/0071759 A1 | 3/2007 | Shin et al. |
| 2007/0184055 A1 | 8/2007 | Sliwkowski |
| 2007/0237764 A1 | 10/2007 | Birtalan et al. |
| 2007/0269429 A1 | 11/2007 | Kelsey et al. |
| 2007/0269435 A1 | 11/2007 | Gillies et al. |
| 2007/0286843 A1 | 12/2007 | Pfizenmaier et al. |
| 2007/0292419 A1 | 12/2007 | Hellmann |
| 2007/0292435 A1 | 12/2007 | Ware |
| 2008/0014197 A1 | 1/2008 | Wang et al. |
| 2008/0038271 A1 | 2/2008 | Amler et al. |
| 2008/0050373 A1 | 2/2008 | Cohen |
| 2008/0112957 A1 | 5/2008 | Fendly et al. |
| 2008/0159981 A1 | 7/2008 | Caligiuri et al. |
| 2008/0187533 A1 | 8/2008 | Hellmann |
| 2008/0261243 A1 | 10/2008 | Lorence et al. |
| 2008/0299115 A1 | 12/2008 | Lowman et al. |
| 2008/0317753 A1 | 12/2008 | Amler et al. |
| 2009/0010935 A1 | 1/2009 | Greene et al. |
| 2009/0081223 A1 | 3/2009 | Allison et al. |
| 2009/0092640 A1 | 4/2009 | Fu |
| 2009/0093429 A1 | 4/2009 | Fu et al. |
| 2009/0104191 A1 | 4/2009 | Greene et al. |
| 2011/0020340 A1* | 1/2011 | Fu .............................. 424/134.1 |
| 2013/0101549 A1 | 4/2013 | Wang et al. |

FOREIGN PATENT DOCUMENTS

| | | |
|---|---|---|
| EP | 0922099 | 7/1997 |
| EP | 1058562 | 3/1999 |
| EP | 931147 A1 | 7/1999 |
| EP | 1274840 | 4/2001 |
| EP | 1189634 | 3/2002 |
| EP | 1210372 | 6/2002 |
| EP | 1248645 | 10/2002 |
| EP | 1308168 | 5/2003 |
| EP | 1514934 | 3/2005 |
| EP | 1641491 | 4/2006 |
| EP | 1695986 | 8/2006 |
| EP | 1997894 | 12/2008 |
| WO | 85/03523 | 8/1985 |
| WO | 88/09344 | 12/1988 |
| WO | 89/06692 | 7/1989 |
| WO | 92/08801 | 5/1992 |
| WO | 92/08801 A1 | 5/1992 |
| WO | 92/22653 | 12/1992 |
| WO | 93/12220 | 6/1993 |
| WO | 93/16185 | 8/1993 |
| WO | 93/17715 | 9/1993 |
| WO | 93/21319 | 10/1993 |
| WO | 94/04679 | 3/1994 |
| WO | 94/22478 | 10/1994 |
| WO | 96/01653 | 1/1996 |
| WO | 96/32480 | 10/1996 |
| WO | 97/20858 | 12/1996 |
| WO | 97/00271 | 1/1997 |
| WO | 98/03648 | 7/1997 |
| WO | 97/34911 | 9/1997 |
| WO | 98/17797 | 4/1998 |
| WO | 98/33914 | 8/1998 |
| WO | 99/02563 | 1/1999 |
| WO | 99/02567 | 1/1999 |
| WO | 99/11662 | 3/1999 |
| WO | 99/31140 | 6/1999 |
| WO | 99/35262 | 7/1999 |
| WO | 99/42584 | 8/1999 |
| WO | 99/44645 | 9/1999 |
| WO | 99/55367 | 11/1999 |

(56) References Cited

FOREIGN PATENT DOCUMENTS

| | | |
|---|---|---|
| WO | 99/55720 | 11/1999 |
| WO | 99/56129 | 11/1999 |
| WO | 00/20641 | 4/2000 |
| WO | 00/45836 | 8/2000 |
| WO | 00/53223 | 9/2000 |
| WO | 00/69460 | 11/2000 |
| WO | 01/00238 | 1/2001 |
| WO | 01/00244 | 1/2001 |
| WO | 01/00245 | 1/2001 |
| WO | 01/09187 | 2/2001 |
| WO | 01/15730 | 3/2001 |
| WO | 01/25450 | 4/2001 |
| WO | 01/49318 | 7/2001 |
| WO | 01/77342 | 10/2001 |
| WO | 01/79496 | 10/2001 |
| WO | 01/89566 | 11/2001 |
| WO | 02/32463 | 4/2002 |
| WO | 02/34780 | 5/2002 |
| WO | 02/34780 A2 | 5/2002 |
| WO | 02/41914 | 5/2002 |
| WO | 02/45653 | 6/2002 |
| WO | 02/066049 | 8/2002 |
| WO | 02/066050 | 8/2002 |
| WO | 02/081649 | 10/2002 |
| WO | 02/087618 | 11/2002 |
| WO | 02/087619 | 11/2002 |
| WO | 03/006509 | 1/2003 |
| WO | 03/012072 | 2/2003 |
| WO | 03/028638 | 4/2003 |
| WO | 03/039591 | 5/2003 |
| WO | 03/039592 | 5/2003 |
| WO | 03/040307 | 5/2003 |
| WO | 03/068801 | 8/2003 |
| WO | 03/080106 | 10/2003 |
| WO | 03/087131 | 10/2003 |
| WO | 03/089575 | 10/2003 |
| WO | 2004/024076 | 3/2004 |
| WO | 2004/032960 | 4/2004 |
| WO | 2004/032961 | 4/2004 |
| WO | 2004/039394 A1 | 5/2004 |
| WO | 2004/039841 | 5/2004 |
| WO | 2004/039956 | 5/2004 |
| WO | 2004/041170 | 5/2004 |
| WO | 2004/065577 | 8/2004 |
| WO | 2004/094612 | 11/2004 |
| WO | 2005/002628 | 1/2005 |
| WO | 2005/003177 | 1/2005 |
| WO | 2005/010377 | 2/2005 |
| WO | 2005/014618 | 2/2005 |
| WO | 2005/016962 | 2/2005 |
| WO | 2005/053728 | 6/2005 |
| WO | 2005/099756 | 10/2005 |
| WO | 2005/117983 | 12/2005 |
| WO | 2006/007398 | 1/2006 |
| WO | 2006/007400 | 1/2006 |
| WO | 2006/008074 | 1/2006 |
| WO | 2006/019693 | 2/2006 |
| WO | 2006/033700 | 3/2006 |
| WO | 2006/054961 | 5/2006 |
| WO | 2006/063042 | 6/2006 |
| WO | 2006/078307 | 7/2006 |
| WO | 2006/087637 | 8/2006 |
| WO | 2006/096861 | 9/2006 |
| WO | 2006/116107 | 11/2006 |
| WO | 2006/116107 A2 | 11/2006 |
| WO | 2007/002905 | 1/2007 |
| WO | 2007/013950 | 2/2007 |
| WO | 2007/016185 | 2/2007 |
| WO | 2007/016542 A2 | 2/2007 |
| WO | 2007/064919 A2 | 6/2007 |
| WO | 2007/077028 A2 | 7/2007 |
| WO | 2007/094842 | 8/2007 |
| WO | 2007/145862 A2 | 12/2007 |
| WO | 2008/019290 | 2/2008 |
| WO | 2008/051612 | 5/2008 |
| WO | 2008/051612 A2 | 5/2008 |
| WO | 2008/077028 A2 | 6/2008 |
| WO | 2008/098183 | 8/2008 |
| WO | 2008/109440 | 9/2008 |
| WO | 2008/144029 | 11/2008 |
| WO | 2008/146101 | 12/2008 |
| WO | 2011/139629 A2 | 11/2011 |

OTHER PUBLICATIONS

Coleman (Research in Immunol. 145:33-36 (1994)).*
Boon et al., "Human tumor antigens recognized by T lymphocytes," J. Exp. Med, 183: 725-729 (1996).
Browning et al., "Characterization of lymphotoxin-alpha beta complexes on the surface of mouse lymphocytes," J Immunol., 159(7):3288-3298 (1997).
Castellano et al., "Mechanisms regulating expression of the tumor necrosis factor-related light gene. Role of calcium-signaling pathway in the transcriptional control," J. Biol Chem., 277(45):42841-42851 (2002).
Cannon et al., "Induction of transgene expression in Tg.AC(v-UA-ras) transgenic mice concomitant with DNA hypomethylation," Mol. Carcinog., 21:244-250 (1998).
Chen et al., "Costimulation of T cells for tumor immunity," Immunol. Today, 14: 483-486 (1993).
Crowe et al., "A lymphotoxin-beta-specific receptor," Science, 264(5159):707-710 (1994).
Cyster, "Chemokines and cell migration in secondary lymphoid organs," Science, 286; 2098~2102 (1999).
Ware, "Network communications: lymphotoxins, LIGHT, and TNF," Annu. Rev. Immunol., 23:787-819 (2005).
Wick et al., "Antigenic cancer cells grow progressively in immune hosts: without evidence for T cell exhaustion or systemic anergy," J. Exp. Med., 186: 229-238 (1997).
Dougall et al., "RANK is essential for osteoclast and lymph node development," Genes. Dev., 13:2412-2424 (1999).
Ettinger, "The role of tumor necrosis factor and lymphotoxin in lymphoid organ development," Curr. Top. Microbiol. Immunol., 251:203-210 (2000).
Fan et al., "NK-cell activation by LIGHT triggers tumor-specific CD8+ T-cell immunity to reject established tumors," Blood, 107: 1342-1351 (2006).
Fidler, "The pathogenesis of cancer metastasis: the 'seed and soil' hypothesis revisited," Nat. Rev. Cancer, 3: 453-458 (2003).
Fu et al., "Development and maturation of secondary lymphoid tissues," Annu. Rev. Immunol., 17:399-433 (1999).
Ghobrial et al., "Targeting Apoptosis Pathways in Cancer Therapy," CA Cancer J. Clin., 55 (3): 178-194 (2005).
Houghton, "LIGHTing the way for tumor immunity," Nat. Immunol., 5(2):123-124 (2004).
International Search Report issued in PCT/US2004/018631 (2004).
International Search Report issued in PCT/US2008/53448 (2008).
Kang.et al., "Signaling via LTbetaR on the lamina propria stromal cells of the gut is required for IgA production," Nat. Immunol., 3: 576-582 (2002).
Kim et al., "Regulation of peripheral lymph node genesis by the tumor necrosis factor family member TRANCE," J. Exp. Med.,. 192:1467-1478 (2000).
Kong et al., "Activated T cells regulate bone loss and joint destruction in adjuvant arthritis through osteoprotegerin ligand" Nature, 402: 304-309 (1999).
Koscielny et al., "Breast Cancer: Relationship between the size of the primary tumour and the probability of metastatic dissemination," Br. J. Cancer, 49: 709-715 (1984).
Koscielny et al., "A simulation model of the natural history of human breast cancer," Br. J. Cancer, 52: 515-524 (1985).
Leder, et al., "v-HA-ras transgene abrogates the initiation step in mouse skin tumorgenesis: effects of phorbol esters and terinoic acid," Proc. Natl. Acad. Sci. USA, 87: 9178-9182 (1990).
Mauri et al., "LIGHT, a new member of the TNF superfamily, and lymphotoxin alpha are ligands for herpesvirus entry mediator.," Immunity, 8:21-30 (1998).

(56) References Cited

OTHER PUBLICATIONS

Melero et al., "Monoclonal antibodies against the 4-1BB T-cell activation molecule eradicate established tumors," Nat. Med. 3:682-685 (1997).

Mezhir et al., "Ionizing radiation: a genetic switch for cancer therapy," Cancer Gene Therapy, 13: 1-6 (2006).

Montgomery et al., "Herpes simplex virus-1 entry into cells mediated by a novel member of the TNF/NGF receptor family," Cell, 87(3):427-36 (1996).

Nahta et al., "Mechanisms of disease: understanding resistance to HER2-targeted therapy in human breast cancer," Nat. Clin. Pract. Oncol., 3(5):269-280 (2006).

Ochsenbein et al., "Roles of tumor localization, second signals and cross priming in cytotoxic T-cell induction," Nature. 411: 1058-1064 (2001).

Ostrand-Rosenberg, "Cell-based vaccine for the stimulation of immunity to metastatic cancers," Immunol. Rev., 170:101-114 (1991).

Peace et al., "Lysis of ras oncogene-transformed cells by specific cytotoxic T lymphocytes elicited by primary in vitro immunization with mutated ras peptide," J. Exp. Med., 179:473-479 (1994).

Rooney et al., "The lymphotoxin-beta receptor is necessary and sufficient for LIGHT-mediated apoptosis of tumor cells," J. Biol. Chem., 275: 14307-14315 (2000).

Rosenberg et al., "Progress in human tumor immunology and immunotherapy," Nature, 411: 380-384 (2001).

Rosenberg et al., "Cancer immunotherapy: moving beyond current vaccines," Nat. Med., 10(9): 909-915 (2004).

Rosenberg et al., "Shedding Light on Immunotherapy for Cancer," N. Engl. J. Med., 350(14): 1461-1463 (2004).

Ruddle, "Lymphoid neo-organeogenesis: tymphotoxin's role in inflammation and development," Immuno. Res., 19: 119-125 (1999).

Sarma et al., "Cytotoxic T lymphocytes to an unmutated tumor rejection antigen P1A: normal development but restrained effector function in vivo," J. Exp. Med., 189: 811-820 (1999).

Scheu et al., "Targeted disruption of LIGHT causes defects in costimulatory T cell activation and reveals cooperation with lymphotoxin beta in mesenteric lymph node genesis," J. Exp. Med., 195(12):1613-1624 (2002).

Schreiber, "Tumor Immunology," In: Fundametal Immunology (ed, Paul, W.E.), Lippincott Rave Press, New York 1247-1280 (1999).

Schneider et al., "Lymphotoxin and LIGHT signaling pathways and target genes," Immunol. Rev., 202: 49-66 (2004).

Sha et al., "Selective expression of an antigen receptor on CD8-bearing T lymphocytes in transgenic mice," Nature, 335;271-274 (1988).

Tamada et al., "Modulation of T-cell-mediated immunity in tumor and graft-versus-host disease models through the LIGHT co-stimulatory pathway," Nat. Med., 6(3):283-289 (2000).

Tamada et al., "Renewed interest in cancer immunotherapy with the tumor necrosis factor superfamily molecules," Cancer Immunol. Immunother, 55: 355-362 (2006).

Wang et al., "The complementation of lymphotoxin deficiency with LIGHT, a newly discovered TNF family member, for the restoration of secondary lymphoid structure and function," Eur. J. Immunol., 32(7):1969-1979 (2002).

Wang et al., "The Role of LIGHT in T Cell-Mediated Immunity," Immunol. Res., 30(2): 201-214 (2004).

Wang et al., "The critical role of LIGHT in promoting intestinal inflammation and Crohn's disease," J. Immunol., 174 (12):8173-8182 (2005).

Wang et al., "The regulation of T cell homeostasis and autoimmunity by T cell derived LIGHT," J. Clinic. Invest., 108: 1771-1780 (2001).

Wu et al., "The requirement of membrane lymphotoxin for the presence of dendritic cells in lymphoid tissues," J. Exp Med. 190: 629-638 (1999).

Ye et al., "Modulation of LIGHT-HVEM costimulation prolongs cardiac allograft survival," J. Exp. Med., 195: 795-800 (2002).

Ye et al., "Gene therapy for cancer using single-chain Fv fragments specific for 4-1BB," Nat. Med., 8: 343-348 (2002).

Yu et al., "A newly identified member of tumor necrosis factor receptor superfamily (TR6) suppresses LIGHT-mediated apoptosis," J. Biol. Chem., 274(20):13733-13736 (1999).

Yu et al., "Priming of naïve T cells inside tumor leads to eradication of established tumors," Nat. Immunol., 5 (2):141-149 (2004).

Yu et al., "Targeting the primary tumor to generate CTL for the effective eradication of spontaneous metastases," J. Immunol., 179(3):1960-1968 (2007).

Zhai et al., "LIGHT, a novel ligand for lymphotox in beta receptor and TR2/HVEM induces apoptosis and suppresses in vivo tumor formation via gene transfer," J. Clin. Invest., 102(6):1142-1151 (1998).

Zinkernagel, "Immunity against solid tumors?" Int. J. Cancer, 93:1-5 (2001).

International Search Report in related International Application PCT/US09/062870, dated Feb. 18, 2010.

Granger et al., "Genomic characterization of LIGHT reveals linkage to an immune response locus on chromosome 19p13.3 and distinct isoforms generated by alternate splicing or proteolysis", The Journal of Immunology, pp. 5122-5128, 2001.

Hu et al., "Cripto monoclonal antibodies" Drug News Perspect, 18(5), Jun. 2005.

International Search Report and Written Opinion in corresponding International Application PCT/US09/062870, dated May 27, 2010.

Muller et al., "A novel antibody-4-1 BBL fusion protein for targeted costimulation in cancer immunotherapy", Immunother, vol. 13, No. 8, Oct. 2008.

Sachdev et al., "A chimeric humanized single-chain antibody against the type I insulin-like growth factor (IGF) receptor renders breast cancer cells refractory to the mitogenic effects of IGF-II", Cancer Research, 63, pp. 627-635, Feb. 1, 2003.

Schietinger et al., "A mutant chaperone converts a wild-type protein into a tumor-specific antigen", Science, vol. 314, pp. 304-308, Oct. 13, 2006.

Ware, "Targeting lymphocyte activation through the lymphotoxin and light pathways", Immunological Reviews, vol. 223, pp. 186-201, 2008.

Winkles et al., "Role of TWEAK and Fn14 in tumor biology", Frontiers in Bioscience, vol. 12, pp. 2761-2771, Jan. 1, 2007.

Xing et al., Cripto: a novel target for antibody-based cancer immunotherapy, vol. 64, pp. 4018-4023, Jun. 1, 2004.

Zhang et al., "The therapeutic potential of agents targeting the type I insulin-like growth factor receptor", Ashley Publications Ltd., London, GB Lnkd-doi: 10.1517/13543784.13.12.1569, vol. 13, No. 12, pp. 1354-3784, Dec. 1, 2004.

International Search Report for PCT/US2011/033752 dated Mar. 2, 2012.

Written Opinion for PCT/US2011/033752 dated Oct. 26, 2012.

International Preliminary Report on Patentability for PCT/US2011/033752 dated Oct. 30, 2012.

\* cited by examiner

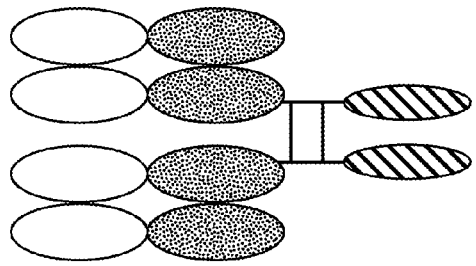
Dimeric form of Fab-LIGHT fusion protein was generated by including the full CH1 hinge region of IgG1. Dimer is stabilized by the formation of double disulfide bonds.
*Trimer:* DKKVEPKSCDK GGGGSGGGGSGGGGS NPA...LIGHT
*Dimer:* DKKVEPKSCDK THTCPPCP GGGGSGGGGSGGGGS NPA....LIGHT
Fig. 24

LIGHT TARGETING MOLECULES AND USES THEREOF

CROSS-REFERENCE TO RELATED APPLICATIONS

This application claims priority to U.S. Patent Application Ser. No. 61/110,359, filed on Oct. 31, 2008, under 35 U.S.C. §119, the contents of which are hereby incorporated by reference in their entirety. This application also incorporates by reference the International Application filed with the U.S. Receiving Office on Oct. 30, 2009, entitled "LIGHT Targeting Molecules and Uses Thereof" and bearing PCT/US09/62870.

SEQUENCE LISTING

This application contains a Sequence Listing which has been submitted via EFS-Web and is hereby incorporated by reference in its entirety. Said ASCII copy, created on Oct. 30, 2009, is named 983815_1_B2047_706010_seqTxt.txt, and is 130,331 bytes in size.

BACKGROUND

LIGHT, also known as TNFSF14 or CD258, is a member of the TNF superfamily (TNFSF) of ligands. Its name is derived from lymphotoxin-like, exhibits inducible expression and competes with HSV glycoprotein D for herpes virus entry mediator (HVEM), a receptor expressed by T lymphocytes. LIGHT is expressed on the surface of T cells upon activation in a tightly regulated manner (Castellano et al. (2002) *J. Biol. Chem.* 277 42841-51). LIGHT mediates its biological effects by binding one of three TNF superfamily receptors, including the lymphotoxin β receptor (LTβR) (Crowe et al. (1994) *Science* 264 707-10, Browning et al. (1997) *J Immunol* 159: 3288-98), the herpes virus entry mediator (HVEM) (Montgomery et al. (1996) *Cell* 87(3): 427-36), and decoy receptor 3 (DcR3) (Yu et al. (1999) *J. Biol. Chem.* 274 13733-6). Upon interaction with its receptors, LIGHT exhibits a number of immunostimulatory activities, including regulation of chemokine expression and cell adhesion molecules (Wang, J. et al. (2002) *Eur. J. Immunol.* 32:1969-1979). For example, LIGHT and LTα$_1$β$_2$ cooperate in lymphoid organogenesis and the development of lymphoid structures (Scheu, S. et al. (2002) *J. Exp. Med.* 195: 1613-1624; Wang, J. et al. (2002) supra). Signaling of LTβR via a LIGHT transgene has been shown to be sufficient to induce up-regulation of expression of chemokines and adhesion molecules (Wang, J. et al. (2004) *J. Clin. Invest.* 113: 826-835). LIGHT has also been shown to mediate CD28-independent co-stimulatory activity for T cell priming and expansion, which can lead to enhanced T cell immunity against tumors and/or increased autoimmunity (Tamada, K. et al. (2000) *Nat. Med.* 6:283-289; Ware, C. F. (2005) *Annu. Rev. Immunol.* 23:787-819; Wang, J. et al. (2005) *J. Immunol.* 174:8173-8182).

Given the broad range of immunostimulatory activities associated with LIGHT, the need still exists for identifying novel targeting agents for harnessing these LIGHT-associated activities for the treatment of various hyperproliferative diseases, for example, neoplastic diseases including cancer and metastasis.

SUMMARY

The present invention is based, at least in part, on the generation of LIGHT-targeting molecules (e.g., LIGHT proteins or nucleic acids encoding LIGHT proteins) that are selectively delivered to a hyperproliferative, e.g., cancerous, cell or tissue, thereby eliciting one or more anti-tumor responses, including, but not limited to, tumor cell killing and/or anti-tumor immunity. In one exemplary embodiment, the LIGHT-targeting molecule includes at least one fusion protein of a mammalian (e.g., human) LIGHT protein, or a functional variant or a fragment thereof, and an antibody molecule that binds to HER2 (referred to herein as "LIGHT-anti-HER2 fusion"). In other embodiments, novel antibody molecules against HER2 are disclosed. Thus, the present invention provides, at least in part, LIGHT-targeting molecules (e.g., LIGHT fusion molecules), anti-HER2 antibody molecules, compositions, e.g., pharmaceutical compositions thereof, as well as methods of using these molecules to treat, prevent and/or diagnose hyperproliferative, e.g., neoplastic, diseases or conditions, including, but not limited to, cancer and metastasis.

Accordingly, in one aspect, the invention features a LIGHT targeting molecule that includes at least one LIGHT moiety (e.g., a LIGHT protein, or a functional variant or a fragment thereof (e.g., the extracellular domain of LIGHT or a portion thereof), and at least one target targeting moiety (e.g., a binding agent, such as an antibody molecule) that interacts, e.g., binds to, a target protein on a hyperproliferative cell (e.g., a cell surface protein expressed on a cancer or tumor cell or tissue), thereby targeting, delivering, or otherwise bringing, the LIGHT moiety to the hyperproliferative cell or tissue. In embodiments, the LIGHT molecule is linked (e.g., by chemical coupling, genetic or polypeptide fusion, non-covalent association or otherwise) to the targeting moiety. For example, the LIGHT molecule can be fused, with or without a linking group (e.g., a peptidic linking group), to the targeting moiety as a genetic or a polypeptide fusion. In other embodiments, the LIGHT molecule is covalently attached to the antibody molecule via a reactive group with or without a linking group (e.g., a non-proteinaceous biocompatible polymer). The LIGHT targeting molecule can be a monomer, dimer, trimer, tetramer, pentamer, sixmer or more of at least one LIGHT moiety and at least one targeting moiety. In embodiments, the LIGHT targeting molecules comprises, or consists essentially of, one, two, three, four, five, six, seven or eight contiguous or non-contiguous polypeptide chains. In other embodiments, the LIGHT targeting molecule comprises, or consists essentially of, one, two, three, four, five or six monomeric or dimeric subunits, each subunit comprising at least one LIGHT moiety and at least one targeting moiety. For example, the LIGHT targeting molecule may include at least one, two, three, four, five or six LIGHT fusion molecules, each fusion molecule comprising at least one LIGHT moiety and at least one targeting moiety. In some embodiments, the LIGHT fusion molecule can be a single chain polypeptide (e.g., a LIGHT moiety fused to a single chain or a single domain antibody), or at least two, three, four, five, six or more non-contiguous polypeptides forming, e.g., a dimer, trimer, tetramer, pentamer, sixmer or higher complex of non-contiguous polypeptides (e.g., a LIGHT moiety fused to one chain of an antibody molecule, e.g., a two-chain antibody or antigen-binding fragment thereof (e.g., a Fab fragment as depicted in FIG. 1 and FIG. 24). In other embodiment, the LIGHT targeting molecule comprises, or consists essentially of, two or three, LIGHT fusion molecules, each one comprising, or consisting essentially of, one LIGHT moiety (e.g., a LIGHT moiety as described herein) and one targeting moiety (e.g., a targeting moiety as described herein, e.g., a Fab antibody fragment). In another embodiment, the LIGHT targeting molecule has a trimeric or a dimeric configuration as shown in FIG. 1 or FIG. 24, respectively.

In embodiments, the LIGHT moiety of the LIGHT targeting molecule comprises, or consists essentially of, at least one LIGHT protein, or a functional variant or a fragment thereof. The LIGHT protein can be a soluble form of mammalian (e.g., human) LIGHT, e.g., a soluble form of an extracellular domain of mammalian (e.g., human) LIGHT (e.g., a full extracellular domain of LIGHT or a portion thereof). In one embodiment, the LIGHT protein, variant or fragment thereof, has one or more LIGHT-associated activities, including, but not limited to: (i) binding to one or more LIGHT-receptors (e.g., lymphotoxin β receptor (LTβR), the herpes virus entry mediator (HVEM), and/or decoy receptor 3 (DcR3)); (ii) inducing expression of one or more of chemokines or cytokines (e.g., CXCL10 (IP-10), CCL21, CXCL9, IL-5, IL-8 and/or TNF), chemokine or cytokine receptors (e.g., IL-10RA), adhesion molecules, and/or co-stimulatory molecules; (iii) activating T cells, e.g., lymphocytes (e.g., cytotoxic T lymphocytes), CD4- or CD8-expressing T cells, and/or regulatory T cells; (iv) recruiting T cells into a hyperproliferative, e.g., tumor, cell or tissue; (v) activating and/or enhancing tumor-reactive T cell proliferation; (vi) creating a lymphoid-like microenvironment, e.g., at a hyperproliferative, e.g., a tumor cell or tissue; (vii) inducing apoptosis of a hyperproliferative (e.g., tumor) cell or tissue; and/or (viii) stimulating an immune response in a subject, e.g., stimulating a subject's immune system against a hyperproliferative, e.g., a tumor or a cancerous, cell or tissue.

Exemplary LIGHT proteins of the LIGHT moiety include, or consist essentially of, the amino acid sequence from: (i) about amino acids 93 to 240 of SEQ ID NO:1 (corresponding to a portion of the extracellular domain of human LIGHT isoform 1); about amino acids 253 to 400 of SEQ ID NO:2 (corresponding to the portion of the LIGHT extracellular domain fused to the heavy chain fragment of a Fab antibody molecule of the anti-HER2 antibody molecule 71F10 via a delta 4 linker, referred to herein as "pBIIB71F10-130"); about amino acids 258 to 405 of SEQ ID NO:3 (corresponding to the portion of the LIGHT extracellular domain fused to the heavy chain fragment of a Fab antibody molecule of the anti-HER2 antibody molecule 71F10 via a $G_4S$ delta 4 linker, referred to herein as "pBIIB71F10-131"); about amino acids 245 to 392 of SEQ ID NO:4 (corresponding to the portion of the LIGHT extracellular domain fused to the heavy chain fragment of a Fab antibody molecule of the anti-HER2 antibody molecule 71F10 via a $(G_4S)_4$ linker, referred to herein as "pBIIB71F10-132"), or an amino acid sequence substantially identical thereto (e.g., a sequence at least about 85%, 90%, 95% or higher identical thereto); or (ii) an amino acid sequence encoded by a nucleotide sequence chosen from one or more of: about nucleotides 277 to 720 of SEQ ID NO:5 (nucleotide sequence corresponding to a portion of the extracellular domain of human LIGHT isoform 1); about nucleotides 757 to 1200 of SEQ ID NO:6 (nucleotide sequence corresponding to the portion of the LIGHT extracellular domain fused to the heavy chain fragment of the 71F10 Fab antibody molecule via the delta 4 linker (pBIIB71F10-130); about nucleotides 772 to 1215 of SEQ ID NO:7 (nucleotide sequence corresponding to the portion of the LIGHT extracellular domain fused to the heavy chain fragment of the 71F10 Fab antibody molecule via the $G_4S$ delta 4 linker (pBIIB71F10-131); or about nucleotides 733 to 1176 of SEQ ID NO:8 (nucleotide sequence corresponding to the portion of the LIGHT extracellular domain fused to fused to the heavy chain fragment of the 71F10 Fab antibody molecule via the $(G_4S)_4$ linker (pBIIB71F10-132), or a nucleotide sequence substantially identical thereto (e.g., a sequence at least about 85%, 90%, 95% or higher identical thereto).

The LIGHT moiety may, optionally, include, or consist essentially of, one or more amino acid residues (e.g., at least 10 to 35, 15 to 30, or about 20 to 26 amino acid residues) from the extracellular domain of LIGHT or a mutated form thereof, e.g., from about amino acids 61 to 92 of SEQ ID NO:1, corresponding to human LIGHT isoform 1; about amino acids 225 to 252 of SEQ ID NO:2, corresponding to 71F10 Fab-hLIGHT fusion via the delta 4 linker (pBIIB71F10-130); about amino acids 230 to 257 of SEQ ID NO:3, corresponding to 71F10 Fab-hLIGHT fusion via the $G_4S$ delta 4 linker (pBIIB71F10-131); or an amino acid sequence substantially identical thereto; or an amino acid sequence encoded by the nucleotide sequence from about nucleotides 181 to 276 of SEQ ID NO:5, corresponding to the nucleotide sequence encoding human LIGHT isoform 1; about nucleotides 673 to 756 of SEQ ID NO:6, corresponding to the nucleotide sequence encoding 71F10 Fab-hLIGHT fusion via the delta 4 linker (pBIIB71F10-130); about nucleotides 688 to 771 of SEQ ID NO:7, corresponding to the nucleotide sequence encoding 71F10 Fab-hLIGHT fusion via the $G_4S$ delta 4 linker (pBIIB 71F10-131), or a nucleotide sequence substantially identical thereto (e.g., a sequence at least about 85%, 90%, 95% or higher identical thereto).

Variants of the LIGHT protein, or soluble fragments thereof (e.g., LIGHT extracellular domain or a portion thereof), altered to increase one or more properties of LIGHT, e.g., protein stability, immune enhancing function, can be used. For example, the LIGHT protein can be modified to have one or more protelolytic sites substantially inactivated (e.g., by deletion, mutation and/or otherwise inactivating, e.g., by amino acid insertion, of a proteolytic site). In one embodiment, amino acids EQLI (SEQ ID NO:9) comprising a proteolytic site at position 82 to 83 of the human LIGHT sequence (human LIGHT isoform 1, SEQ ID NO:1), or amino acids EKLI (SEQ ID NO:10) from positions 79-82 of the mouse LIGHT sequence are removed. In other embodiments, the LIGHT protein is from non-human origin, e.g., murine LIGHT, can be used. The amino acid and corresponding nucleotide sequences for full length mouse LIGHT are shown in SEQ ID NOs:113 and 114, respectively.

In other embodiments, the targeting moiety delivers, directs or brings, the LIGHT moiety to a desired site, e.g., a hyperproliferative, e.g., cancerous, cell or tissue, such that the LIGHT moiety induces one or more LIGHT-associated activities (e.g., one or more of the LIGHT-associated activities as described herein) against the desired site (e.g., the hyperproliferative, e.g., cancerous, cell or tissue). In certain embodiments, the targeting moiety may have an anti-tumor or cancer cell effect substantially independent from the LIGHT moiety (e.g., by inhibiting one or more activities of a cell surface protein or receptor involved in tumor growth, proliferation and/or survival, including but not limited to, receptor phosphorylation, receptor oligomerization, and/or preventing or retarding tumor cell growth or metastasis).

Without being bound by theory, Applicants believe that the targeted delivery to a tumor of LIGHT via the LIGHT targeting molecules of the invention can inhibit, block or otherwise reduce hyperproliferative and/or tumor growth through at least one or more of the following activities: (i) activation of lymphotoxin β receptor (LTβR) (e.g., triggering one or more of tumor cell cytotoxicity through LTβR signaling and/or recruitment of cytotoxic T lymphocytes into tumors); (ii) activation of HVEM; (iii) inducing expression of one or more of chemokines or cytokines (e.g., CXCL10 (IP-10), CCL21, CXCL9, IL-5, IL-8 and/or TNF), chemokine or cytokine receptors (e.g., IL-10RA), adhesion molecules, and/or co-stimulatory molecules; (iv) activating T cells, e.g., lymphocytes (e.g., cytotoxic T lymphocytes), CD4- or CD8-expressing T cells, and/or regulatory T cells; and/or (v) directing anti-tumor activity, for example, via the targeting moiety (e.g., a Fab antibody molecule) or the LIGHT moiety, thereby inducing targeted tumor cell death by mounting an effective T cell response against hyperproliferative cells or tumors, including primary tumors and metastasis. In some embodiments, the LIGHT targeting moiety causes a reduction, inhibition, or otherwise blockade of growth factor signaling (e.g., reduction of one or more signaling pathways, such a phosphorylation, receptor dimerization). A schematic of one proposed mechanism of action for the LIGHT targeting molecule is shown herein as FIG. 3.

Exemplary hyperproliferative, e.g., cancerous, cells or tissues, that can be targeted with the targeting moiety, include, but are not limited to, cancers or solid tumors of the breast, lung, stomach, ovaries, prostate, pancreas, colon, colorectum, renal, bladder, liver, head, neck, brain, as well as soft-tissue malignancies, including lymphoid malignacies, leukemia and myeloma. The targeting moiety can bind to one or more target molecules, e.g., soluble or cell surface proteins expressed on one or more of the hyperproliferative cells or tissues described herein. For example, the targeting moiety can bind to one or more of a growth factor receptor (e.g., HER2/neu, HER3, HER4, epidermal growth factor receptor (EGFR), insulin growth factor receptor (IGFR), Met, Ron, Cripto); a cancer-related integrin or integrin receptor (e.g., αvβ6, α6β4, laminin receptor (LAMR); and/or CD23, CD20, CD16, EpCAM, Tweak receptor (FN14) carcinoembryonic antigen (CEA), prostate specific membrane antigen (PSMA), TAG-72, and/or VEGF, among others. Additional examples of target molecules recognized by the targeting moieties are described herein.

In certain embodiments, the targeting moiety is an antibody molecule or a receptor ligand (e.g., a growth factor or a hormone). In embodiments where the targeting moiety is an antibody molecule, the antibody molecule can be a monoclonal or single specificity antibody, or an antigen-binding fragment thereof (e.g., a Fab, a F(ab')$_2$, an Fv, a single chain Fv fragment, a single domain antibody or a variant thereof (e.g., a heavy or light chain variable domain monomer or dimer, e.g., $V_H$, $V_{HH}$)); a single chain Fc fragment, a diabody (dAb), a camelid antibody; one, two, or all three complementarity determining regions (CDRs) grafted onto a repertoire of VH or VL domains, or other scaffolds (such as, e.g., a fibronectin domain or scaffold, T cell receptor, an Affibody molecule (e.g., an Affibody protein Z scaffold or other molecules as described, e.g., in Lee et al. (2008) *Clin Cancer Res* 14(12):3840-3849; Ahlgren et al. (2009) *J. Nucl. Med.* 50:781-789), Lipocalin, ankyrin repeats, LDL receptor domain, RNA aptamer, PDZ domain and microbody) (or a combination of one or more of the aforesaid antibody molecules). The antibody molecule can interact with, e.g., bind to, the desired cell surface protein (e.g., a cell surface protein as described herein). For example, the antibody molecule may include a combination of a single chain (e.g., a single chain Fc) and a Fab or a scFv. In other embodiments, the antibody molecule can be a multispecific (e.g., bivalent or bispecific) antibody or fragment thereof. In some embodiments, the antibody molecule binds to a single epitope on the cell surface protein. In other embodiments, the antibody molecule is a multi-specific antibody and binds to two or more epitopes on one or more cell surface proteins (e.g., one or more cell surface proteins as described herein). Typically, the antibody molecule is a human, a humanized, a chimeric, a camelid, a shark, or an in vitro generated antibody (or a functional fragment thereof, e.g., an antigen binding fragment as described herein). In certain embodiments, the antibody molecule binds to the cell surface protein with an affinity characterized by a dissociation constant (Kd) at least of $1 \times 10^{-7}$ M, $1 \times 10^{-8}$ M, $1 \times 10^{-9}$ M, $1 \times 10^{-10}$ M, $1 \times 10^{-11}$ M, $1 \times 10^{-12}$ M, $1 \times 10^{-13}$ M.

The antibody molecule can be full-length (e.g., can include at least one, and typically two, complete heavy chains, and at least one, and typically two, complete light chains) or can include an antigen-binding fragment (e.g., a Fab, F(ab')$_2$, Fv, a single chain Fv fragment, or other antigen binding fragment as described herein). In yet other embodiments, the antibody molecule has a heavy chain constant region (or a portion thereof, e.g., a CH1 region) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4 of, e.g., a human, antibody. In another embodiment, the antibody molecule has a light chain constant region chosen from, e.g., the (e.g., human) light chain constant regions of kappa or lambda, or a portion thereof. The constant region can be altered, e.g., mutated, to modify the properties of the antibody (e.g., to increase or decrease one or more of: Fc receptor binding, antibody glycosylation, the number of cysteine residues (—S—S— bonds), effector cell function, and/or complement function).

Exemplary LIGHT targeting molecules are shown as FIGS. 1-3 (schematic forms), 6, and 24 (dimeric form) or as SEQ ID NOs:2-4, 6-8, 101-104, 109-110, 162-163, 167-168, 173-174 and 178-179 (including nucleotide and amino acid sequences). Examples of these molecules include, but are not limited to, a fusion or a conjugate of a LIGHT moiety and a Fab fragment in monomeric, dimeric or trimeric form. In one embodiment, the N-terminal end of the LIGHT moiety (e.g., a human LIGHT fragment as described herein (e.g., about amino acids 93 to 240 of SEQ ID NO:1 (corresponding to a portion of the extracellular domain of human LIGHT isoform 1)) is covalently linked, e.g., as a polypeptide fusion, via a linking group to the C-terminal region of the Fab heavy chain constant region (e.g., a portion of, or the full, CH1 hinge region of IgG1) fused to the Fab heavy chain variable domain, while the heavy and light chains of the Fab associate with each other (FIG. 1 or FIG. 24). In one embodiment, the portion of the Fab CH1 region used in the fusion contributes to the assembly of three LIGHT-Fab fusions as a trimer depicted in FIG. 1, and exemplified by LIGHT fusions pBIIB71F10-130, pBIIB71F10-131, pBIIB71F10-132, pBIIBCD23-204 and pBIIBC06-117 (see Examples 6, 7 and 27 herein). In other embodiments, the full CH1 region of the IgG1 (e.g., about amino acids 225 to 232 of SEQ ID NO:172) is used in the fusion, which contributes to the assembly of two LIGHT-Fab fusions as a a dimer stabilized by the formation of one or more disulfide bonds as depicted in FIG. 24 (Example 28).

In certain embodiments, the LIGHT targeting molecules can include at least two non-contiguous polypeptide having the following configuration: a first polypeptide having a light chain variable domain ($V_L$) fused to a light chain constant region ($C_L$), for example, $V_L$-$C_L$; and a second polypeptide having a heavy chain variable domain ($V_H$) fused to a portion or full heavy chain constant region ($C_H$, particularly, $C_{H1}$), which is fused, with or without a linking group (L), to the N-terminal end of the LIGHT moiety (e.g., a human LIGHT fragment as described herein) for example, $V_H$-$C_H$-(optionally)-L-LIGHT moiety. The LIGHT-Fab fusions can associate as dimers or as trimeric complexes (e.g., a trimeric complex of about 220 kD) or as dimeric complexes (e.g., a dimeric complex of about 150 kD). In other embodiments, a LIGHT-full antibody fusion or conjugate can be used, e.g., a fusion or conjugate wherein an N- or C-terminal region of the LIGHT moiety is covalently linked, e.g., as a polypeptide fusion, to the C-terminal end of each of the heavy chains of the full antibody (e.g., forming a LIGHT dimeric complex of about 200 kDa) (FIG. 2). In yet other embodiments, a single chain Fc fused to a C-terminal end of the VH region of a Fab is covalently linked, e.g., as a polypeptide fusion, to the LIGHT moiety in monomeric, dimeric or trimeric form (FIG. 2). In yet other embodiments, the LIGHT moiety s covalently linked, e.g., as a polypeptide fusion, to a single chain Fv in monomeric, dimeric or trimeric form (FIG. 2). In another embodiment, one or more Affibody domains are covalently linked to the LIGHT moiety (FIG. 2). In yet another embodiment, a LIGHT moiety fused to an immunoglobulin Fc region is covalently linked, e.g., as a polypeptide fusion, to a Fab in a monomeric, a dimeric or a trimeric form (FIG. 2 or FIG. 24).

In certain embodiments, the LIGHT moiety and the targeting moiety are functionally linked (e.g., by chemical coupling, genetic or polypeptide fusion, non-covalent association or otherwise). For example, the LIGHT molecule can be fused, with or without a linking group (e.g., a peptide linking group), to the targeting moiety as a genetic or a polypeptide fusion. In other embodiments, the LIGHT molecule is covalently attached to antibody molecule via a reactive group, optionally, via a biocompatible, non-proteinaceous polymer. The linking group can be any linking group apparent to those of skill in the art. For instance, the linking group can be a biocompatible polymer with a length of 1 to 100 atoms. In one embodiment, the linking group includes or consists of polyglycine, polyserine, polylysine, polyglutamate, polyisoleucine, or polyarginine residues, or a combination thereof. For example, the polyglycine or polyserine linkers can include at least five, ten, fifteen or twenty glycine and serine residues in the following configuration, $(Gly)_4$-Ser (SEQ ID NO: 145), in one, two, three, four, five or more repeats, e.g., three or four repeats of $(Gly)_4$-Ser (SEQ ID NO: 134). In other embodiments, linking group may include one or more amino acid residues (e.g., at least 10 to 35, 15 to 30, or about 20 to 26 amino acid residues) from the extracellular domain of LIGHT or a mutated form thereof, e.g., from about amino acids 61 to 92 of SEQ ID NO:1 of human LIGHT isoform 1, about amino acids 225 to 252 of SEQ ID NO:2 of 71F10 Fab-hLIGHT fusion heavy chain with the delta 4 linker (pBIIB71F10-130), about amino acids 230 to 257 of SEQ ID NO:3 of 71F10 Fab-hLIGHT fusion heavy chain with the $G_4S$ delta 4 linker (pBIIB71F10-131), or an amino acid sequence substantially identical thereto; or an amino acid sequence encoded by the nucleotide sequence from about nucleotides 181 to 276 of SEQ ID NO:5 of human LIGHT isoform 1, about nucleotides 673 to 756 of SEQ ID NO:6 of 71F10 Fab-hLIGHT fusion heavy chain with the delta 4 linker (pBIIB71F10-130), about nucleotides 688 to 771 of SEQ ID NO:7 of 71F10 Fab-hLIGHT fusion heavy chain with the $G_4S$ delta 4 linker (pBIIB71F10-131), or a nucleotide sequence substantially identical thereto (e.g., a sequence at least about 85%, 90%, 95% or higher identical thereto). Alternatively, the linking group may include a combination of one or more $(Gly)_4$-Ser (SEQ ID NO: 146) repeats and one or more amino acid residues (e.g., at least 10 to 35, 15 to 30, or about 20 to 26 amino acid residues) from the extracellular domain of LIGHT or a mutated form thereof, e.g., from about amino acids 61 to 92 of SEQ ID NO:1 of human LIGHT isoform 1, about amino acids 225 to 252 of SEQ ID NO:2 of 71F10 Fab-hLIGHT fusion heavy chain with the delta 4 linker (pBIIB71F10-130), about amino acids 230 to 257 of SEQ ID NO:3 of 71F10 Fab-hLIGHT fusion heavy chain with the $G_4S$ delta 4 linker (pBIIB71F10-131), or an amino acid sequence substantially identical thereto; or an amino acid sequence encoded by the nucleotide sequence from about nucleotides 181 to 276 of SEQ ID NO:5 of human LIGHT isoform 1, about nucleotides 673 to 756 of SEQ ID NO:6 of 71F10 Fab-hLIGHT fusion heavy chain with the delta 4 linker (pBIIB71F10-130), about nucleotides 688 to 771 of SEQ ID NO:7 of 71F10 Fab-hLIGHT fusion heavy chain with the $G_4S$ delta 4 linker (pBIIB71F10-131), or a nucleotide sequence substantially identical thereto (e.g., a sequence at least about 85%, 90%, 95% or higher identical thereto). Exemplary linkers that can be used in the LIGHT fusions are shown as SEQ ID NO:132 (delta 4), SEQ ID NO:133 ($G_4S$ delta 4) and SEQ ID NO:134 ($G_4S$), or amino acid sequences substantially identical thereto.

In other embodiments, the LIGHT moiety and the targeting moiety are chemically coupled, e.g., by the covalent attachment of one reactive group, e.g., a succinimidyl or maleimide containing group, to a defined amino acid of the LIGHT or the targeting moiety. In those embodiments where the LIGHT moiety and the targeting moiety are chemically coupled, the reactive group may optionally be coupled to a biocompatible polymer, e.g., a polymer having monomers chosen from one or more of AEA ((2-amino) ethoxy acetic acid), AEEA ([2-(2-amino)ethoxy)]ethoxy acetic acid) and OA (8-amino octanoic acid, also called 8-amino caprylic acid, of formula $NH_2—(CH_2)_7—COOH$), or a combination thereof. The linking group can include any combinations of the aforesaid biocompatible polymers.

In one exemplary embodiment, the LIGHT targeting molecule comprises, or consists essentially of, at least one fusion molecule of a mammalian (e.g., human) LIGHT protein, or a functional variant or a fragment thereof, and an antibody molecule that binds to HER2 (referred to herein as "LIGHT-anti-HER2 fusion"). In certain embodiments, the LIGHT-anti-HER2 fusion comprises at least three fusion molecules in a trimer of about 200 to 250 kDa, typically about 220 KDa as shown in FIGS. 1 and 3 (e.g., having the amino acid sequence of SEQ ID NOs:2-4, or an amino acid sequence substantially identical thereto); or at least two fusion molecules in a dimer of about 100 to 200 kDa, typically about 150 kDa as shown in FIGS. 2 and 24 (having the amino acid sequence of SEQ ID NO:178, or an amino acid sequence substantially identical thereto). The light chain associated to the LIGHT-anti-HER2 heavy chains described herein can have the amino acid sequence shown in SEQ ID NO:109, or an amino acid sequence substantially identical thereto (or encoded by a nucleotide sequence shown in SEQ ID NO:110 or a nucleotide sequence substantially identical thereto).

Without being bound by theory, the LIGHT-anti-HER2 fusions are believed to trigger dual anti-cancer effects by inducing tumor cell killing mediated by the anti-HER2 antibody molecule, as well as stimulating localized LIGHT-mediated anti-tumor immunity. In certain embodiments, the LIGHT-anti-HER2 fusions can have one or more of the following activities: (i) bind to HER2 with an affinity characterized by a dissociation constant (Kd) of at least $1\times10^{-7}$ M, $1\times10^{-8}$ M, $1\times10^{-9}$ M, $1\times10^{-10}$ M, $1\times10^{-11}$M, $1\times10^{-12}$ M, $1\times10^{-13}$ M; (ii) bind substantially selectively to HER2, e.g., without significant cross reactivity with other HER-family members (iii) bind to a linear or a conformation epitope on HER2 chosen from epitope of domain 1 (D1) (corresponding to about amino acids 1 to 196 of human HER2 shown in FIG. 4), epitope of domain 2 (D2) (corresponding to about amino acids 197 to 318 of human HER2 shown in FIG. 4), epitope of domain 3 (D3) (corresponding to about amino acids 319 to 508 of human HER2 shown in FIG. 4), or epitope of domain 4 (D4) (corresponding to about amino acids 508 to 630 of human HER2 shown in FIG. 4), or a combination thereof, e.g., epitope D1-2 (corresponding to about amino acids 1 to 318 of human HER2 shown in FIG. 4) or epitope D1-3 (corresponding to about amino acids 1 to 508 of human HER2 shown in FIG. 4); (iv) inhibit, block or reduce HER2 signaling (e.g., inhibit, block or reduce phosphorylation of one or more of HER2, AKT and/or MAP kinase; or inhibit, block or reduce homodimerization of HER2 or heterodimerization of HER2 and HER3, and/or HER2 with EGFR; (v) inhibit activity and/or induce cell killing of a HER2 expressing cell in vitro (e.g., MCF7 and SKBR-3 cell) and in vivo; (vi) trigger an anti-tumor immune response in vivo, e.g., in an animal model (such as a mouse tumor model carrying breast tumor cells, or a HER2-dependent colorectal and gastric xenograft tumor model), or in a human subject; and/or (vii) inducing a prolonged reduction of tumor growth or metastasis, e.g., after prolonged monotherapy or combination therapy, or after tumor relapse is detected following another chemotherapeutic therapy (e.g., standard chemotherapy or anti-HER2 antibody therapy).

In one embodiment, the LIGHT-anti-HER2 fusion comprises, or consists essentially of, at least one mammalian (e.g., human) LIGHT protein, or a variant or a fragment thereof (e.g., a LIGHT protein as described herein) and an anti-HER2 specific antibody molecule or a fragment thereof (e.g., an antibody molecule as described herein).

As described herein, the invention additionally features an antibody molecule (e.g., isolated or purified protein or polypeptide) that selectively binds to HER2 (e.g., an anti-HER2 antibody as described herein). The anti-HER2 antibodies described herein can be present in a LIGHT-targeting molecule of the invention, or can be present as single or combined entities distinct from the targeting molecules described herein.

In certain embodiments, the anti-HER2 antibody molecules present in the LIGHT-targeting molecules or as single or combined entities include one or more of the following features:

In embodiments, the anti-HER2 antibody molecule is an antibody molecule or a Fab fragment from an antibody selected from the group consisting of BIIB71F10 (comprising, or consisting of, the amino acid sequence of SEQ ID NOs:11 and 13, VH and VL, respectively, or the VH and VL amino acid of the ATCC Patent Deposit Designation PTA-10355 corresponding to the CHO cell deposit of 71F10 Fab LIGHT, or encoded by the nucleotide sequence of SEQ ID NOs: 12 and 14, VH and VL, respectively, or the nucleotide sequence of the ATCC Patent Deposit Designation PTA-10355 encoding the VH and VL amino acid of the 71F10 Fab LIGHT); BIIB69A09 (comprising, or consisting of, the amino acid sequence of SEQ ID NOs:15 and 17, VH and VL, respectively, or encoded by the nucleotide sequence of SEQ ID NOs:16 and 18, VH and VL, respectively); BIIB67F10 (comprising, or consisting of, the amino acid sequence of SEQ ID NOs:19 and 21, VH and VL, respectively, or encoded by the nucleotide sequence of SEQ ID NOs:20 and 22, VH and VL, respectively); BIIB67F11 (comprising, or consisting of, the amino acid sequence of SEQ ID NOs:23 and 25, VH and VL, respectively, or the VH and VL amino acid of the ATCC Patent Deposit Designation PTA-10357 corresponding to the CHO cell deposit of 67F11 Fab LIGHT, or encoded by the nucleotide sequence of SEQ ID NOs: 24 and 26, VH and VL, respectively, or the nucleotide sequence of the ATCC Patent Deposit Designation PTA-10357 encoding the VH and VL amino acid of the 67F11 Fab LIGHT); BIIB66A12 (comprising, or consisting of, the amino acid sequence of SEQ ID NOs:27 and 29, VH and VL, respectively; or encoded by the nucleotide sequence of SEQ ID NOs: 28 and 30, VH and VL, respectively); BIIB66C01 (comprising, or consisting of, the amino acid sequence of SEQ ID NOs:31 and 33, VH and VL, respectively or encoded by the nucleotide sequence of SEQ ID NOs: 32 and 34, VH and VL, respectively); BIIB65C10 (comprising, or consisting of, the amino acid sequence of SEQ ID NOs:35 and 37, VH and VL, respectively, or the VH and VL amino acid of the ATCC Patent Deposit Designation PTA-10358 corresponding to the CHO deposit of 65C10 Fab LIGHT, or encoded by the nucleotide sequence of SEQ ID NOs:36 and 38, VH and VL, respectively, or the nucleotide sequence of the ATCC Patent Deposit Designation PTA-10358 encoding the VH and VL amino acid of the 65C10 Fab LIGHT); BIIB65H09 (comprising, or consisting of, the amino acid sequence of SEQ ID NOs:39 and 41, VH and VL, respectively), or the VH and VL amino acid of the ATCC Patent Deposit Designation PTA-10356 corresponding to the CHO cell deposit of 65H09Fab LIGHT, or encoded by the nucleotide sequence of SEQ ID NOs: 40 and 42, VH and VL, respectively, or the nucleotide sequence of the ATCC Patent Deposit Designation PTA-10356 encoding the VH and VL amino acid of the 65H09Fab LIGHT); and BIIB65B03 (comprising, or consisting of, the amino acid sequence of SEQ ID NOs:43 and 45, VH and VL, respectively, or encoded by the nucleotide sequence of SEQ ID NOs: 44 and 46, VH and VL, respectively) (also referred to herein as "71F10," "69A09," "67F10," "67F11," "66A12," "66C01," "65C10," "65H09" and "65B03"); or amino or nucleotide sequence substantially identical thereto (e.g., a sequence at least about 85%, 90%, 95% or higher identical thereto). Amino acid and corresponding nucleotide sequences of VH and VL domains of each of these Fabs are shown as SEQ ID NOs:11-46. For simplicity purposes, the nucleotide and amino acid sequences disclosed herein are collectively referred to herein by their corresponding SEQ ID NOs, e.g., SEQ ID NOs:39-42, when referring to the amino acid sequence of SEQ ID NOs:39 and 41, VH and VL, respectively, and/or the corresponding ATCC deposit; or encoded by the nucleotide sequence of SEQ ID NOs: 40 and 42, VH and VL, respectively, and/or the corresponding ATCC deposit.

In other embodiments, the anti-HER2 antibody molecule has a functional activity comparable to an antibody molecule or a Fab fragment from an antibody selected from the group consisting of BIIB71F10 (comprising, or consisting essentially of, the amino or nucleotide sequence as described herein as SEQ ID NOs:11-14), BIIB69A09 (comprising, or consisting essentially of, the amino or nucleotide sequence as described herein as SEQ ID NOs:15-18); BIIB67F10 (comprising, or consisting essentially of, the amino or nucleotide sequence as described herein as SEQ ID NOs:19-22); BIIB67F11 (comprising, or consisting essentially of, the amino or nucleotide sequence as described herein as SEQ ID NOs:23-26); BIIB66A12 (comprising, or consisting essentially of, the amino or nucleotide sequence as described herein as SEQ ID NOs:27-30); BIIB66C01 (comprising, or consisting essentially of, the amino or nucleotide sequence as described herein as SEQ ID NOs:31-34); BIIB65C10 (comprising, or consisting essentially of, the amino or nucleotide sequence as described herein as SEQ ID NOs:35-38); BIIB65H09 (comprising, or consisting essentially of, the amino or nucleotide sequence as described herein as SEQ ID NOs:39-42) and BIIB65B03 (comprising, or consisting essentially of, the amino or nucleotide sequence as described herein as SEQ ID NOs:43-46), or an amino or nucleotide sequence substantially identical thereto (e.g., a sequence at least about 85%, 90%, 95% or higher identical thereto).

In other embodiments, the anti-HER2 antibody molecule can cross-react with HER2 from one or more species chosen from human, mouse, rat, and/or cyno origin. The anti-HER2 antibody molecule can bind to HER2 with an EC50 in the range of about 1 to 120 nM, about 1 to 100 nM, about 1 to 80 nM, about 1 to 70 nM, about 1 to 60 nM, about 1 to 40 nM, about 1 to 30 nM, about 1 to 20 nM, about 1 to 15 nM, about 1 to 12 nM, about 1 to 5 nM, about 1 to 2 nM, or about 1 to 1 nM. In other embodiments, the anti-HER2 antibody molecule inhibits or reduces one or more HER2-associated biological activities with an $IC_{50}$ of about 50 nM to 5 pM, typically about 100 to 250 pM or less, e.g., better inhibition. For example, the anti-HER2 antibody molecule can have one or more of the following activities: (i) inhibit, block or reduce HER2 signaling with an $IC_{50}$ of about 50 nM to 5 pM, typically about 100 to 250 pM or less, e.g., better inhibition (e.g., inhibit, block or reduce phosphorylation of one or more of HER2, AKT or MAP kinase; or inhibit, block or reduce homodimerization of HER2 or heterodimerization of HER2 and HER3, or HER2 with EGFR); (ii) internalize with a slow kinetics estimated to be less than or equal to the rate of internalization for control anti-HER2 antibody, which is $8e^{-6}s^{-1}$ in SKBR-3 cells and $2.1e^{-5}s^{-1}$ in BT-474 cells; and/or (iii) inhibit activity and/or induce cell killing of a HER2 expressing cell in vitro (e.g., MCF7 and SKBR-3 cell) and in vivo. In one embodiment, the anti-HER2 antibody molecule associates with HER2 with kinetics in the range of $10^4$ to $10^7$ $M^{-1}s^{-1}$, typically $10^5$ to $10^6 M^{-1}s^{-1}$. In another embodiment, the anti-HER2 antibody molecule binds to human HER2 with a kD of 0.1-100 nM. In yet another embodiment, the anti-HER2 antibody molecule has dissociation kinetics in the range of $10^{-2}$ to $10^{-6}$ $s^{-1}$, typically $10^{-2}$ to $10^{-5}$ $s^{-1}$. In one embodiment, the anti-HER2 antibody molecule binds to HER2, e.g., human HER2, with an affinity and/or kinetics similar (e.g., within a factor 20, 10, or 5) to a monoclonal antibody selected from the group consisting of BIIB71F10 (comprising, or consisting essentially of, the amino or nucleotide sequence as described herein as SEQ ID NOs:11-14, or ATCC Patent Deposit PTA-10355); BIIB69A09 (comprising, or consisting essentially of, the amino or nucleotide sequence as described herein as SEQ ID NOs:15-18); BIIB67F10 (comprising, or consisting essentially of, the amino or nucleotide sequence as described herein as SEQ ID NOs:19-22); BIIB67F11 (comprising, or consisting essentially of, the amino or nucleotide sequence as described herein as SEQ ID NOs:23-26, or ATCC Patent Deposit PTA-10357); BIIB66A12 (comprising, or consisting essentially of, the amino or nucleotide sequence as described herein as SEQ ID NOs:27-30); BIIB66C01 (comprising, or consisting essentially of, the amino or nucleotide sequence as described herein as SEQ ID NOs:31-34); BIIB65C10 (comprising, or consisting essentially of, the amino or nucleotide sequence as described herein as SEQ ID NOs:35-38, or ATCC Patent Deposit PTA-10358); BIIB65H09 (comprising, or consisting essentially of, the amino or nucleotide sequence as described herein as SEQ ID NOs:39-42, or ATCC Patent Deposit PTA-10356) and BIIB65B03 (comprising, or consisting essentially of, the amino or nucleotide sequence as described herein as SEQ ID NOs:43-46). The affinity and binding kinetics of the anti-HER2 antibody molecule can be tested using, e.g., biosensor technology (BIACORE™).

In still another embodiment, the anti-HER2 antibody molecule specifically binds to an epitope, e.g., a linear or a conformational epitope, of HER2, e.g., mammalian, e.g., human HER2. In embodiments, the anti-HER2 antibody molecule competes for binding (e.g., binds to the same or similar, e.g., partially overlapping epitope) as an antibody selected from the group consisting of BIIB71F10 (comprising, or consisting essentially of, the amino or nucleotide sequence as described herein as SEQ ID NOs:11-14, or ATCC Patent Deposit PTA-10355); BIIB69A09 (comprising, or consisting essentially of, the amino or nucleotide sequence as described herein as SEQ ID NOs:15-18); BIIB67F10 (comprising, or consisting essentially of, the amino or nucleotide sequence as described herein as SEQ ID NOs:19-22); BIIB67F11 (comprising, or consisting essentially of, the amino or nucleotide sequence as described herein as SEQ ID NOs:23-26, or ATCC Patent Deposit PTA-10357); BIIB66A12 (comprising, or consisting essentially of, the amino or nucleotide sequence as described herein as SEQ ID NOs:27-30); BIIB66C01 (comprising, or consisting essentially of, the amino or nucleotide sequence as described herein as SEQ ID NOs:31-34); BIIB65C10 (comprising, or consisting essentially of, the amino or nucleotide sequence as described herein as SEQ ID NOs:35-38, or ATCC Patent Deposit PTA-10358); BIIB65H09 (comprising, or consisting essentially of, the amino or nucleotide sequence as described herein as SEQ ID NOs:39-42, or ATCC Patent Deposit PTA-10356) and BIIB65B03 (comprising, or consisting essentially of, the amino or nucleotide sequence as described herein as SEQ ID NOs:43-46). In embodiments, the anti-HER2 antibody molecule binds to a linear or a conformation epitope on HER2 chosen from epitope D1 (corresponding to about amino acids 1 to 196 of human HER2 shown in FIG. 4), epitope D2 (corresponding to about amino acids 197 to 318 of human HER2 shown in FIG. 4), epitope D3 (corresponding to about amino acids 319 to 508 of human HER2 shown in FIG. 4), or epitope D4 (corresponding to about amino acids 508 to 630 of human HER2 shown in FIG. 4), or a combination thereof, e.g., epitope D1-2 (corresponding to about amino acids 1 to 318 of human HER2 shown in FIG. 4) or epitope D1-3 (corresponding to about amino acids 1 to 508 of human HER2 shown in FIG. 4).

In one embodiment, the anti-HER2 antibody molecule includes one, two, three, four, five or all six CDR's from an antibody selected from the group consisting of BIIB71F10 (SEQ ID NOs:11 (VH), 13 (VL), or ATCC Patent Deposit PTA-10355), BIIB69A09 (SEQ ID NOs:15, 17), BIIB67F10 (SEQ ID NOs:19, 21), BIIB67F11 (SEQ ID NOs:23, 25, or ATCC Patent Deposit PTA-10357), BIIB66A12 (SEQ ID NOs:27, 29), BIIB66C01 (SEQ ID NOs:31, 33), BIIB65C10 (SEQ ID NOs:35, 37, or ATCC Patent Deposit PTA-10358), BIIB65H09 (SEQ ID NOs:39, 41, or ATCC Patent Deposit PTA-10356) and BIIB65B03 (SEQ ID NOs:43, 45), or closely related CDRs, e.g., CDRs which are identical or which have at least one amino acid alteration, but not more than two, three or four alterations (e.g., substitutions (e.g., conservative substitutions), deletions, or insertions). Optionally, the antibody molecule may include any CDR described herein.

In embodiments, the heavy chain immunoglobulin variable domain of the anti-HER2 antibody molecule comprises a heavy chain CDR1, CDR2, and/or CDR3, or having a CDR that differs by fewer than 3, 2, or 1 amino acid substitutions (e.g., conservative substitutions) from a heavy chain CDR1, CDR2, and/or CDR3 of monoclonal antibody selected from the group consisting of BIIB71F10 (SEQ ID NO:47 (CDR1), SEQ ID NO:48 (CDR2), and/or SEQ ID NO:49 (CDR3), or a CDR from ATCC Patent Deposit PTA-10355); BIIB69A09 (SEQ ID NO:50 (CDR1), SEQ ID NO:51 (CDR2), and/or SEQ ID NO:52 (CDR3)); BIIB67F10 (SEQ ID NO:53 (CDR1), SEQ ID NO:54 (CDR2), and/or SEQ ID NO:55 (CDR3)); BIIB67F11 (SEQ ID NO:56 (CDR1), SEQ ID NO:57 (CDR2), and/or SEQ ID NO:58 (CDR3), or a CDR from ATCC Patent Deposit PTA-10357); BIIB66A12 (SEQ ID NO:59 (CDR1), SEQ ID NO:60 (CDR2) and/or SEQ ID NO:61 (CDR3)); BIIB66C01 (SEQ ID NO:62 (CDR1), SEQ ID NO:63 (CDR2), and/or SEQ ID NO:64 (CDR3)); BIIB65C10 (SEQ ID NO:65 (CDR1), SEQ ID NO:66 (CDR2), and/or SEQ ID NO:67 (CDR3), or a CDR from ATCC Patent Deposit PTA-10358); BIIB65H09 (SEQ ID NO:68 (CDR1), SEQ ID NO:69 (CDR2), and/or SEQ ID NO:70 (CDR3), or a CDR from ATCC Patent Deposit PTA-10356); and BIIB65B03 (SEQ ID NO:71 (CDR1), SEQ ID NO:72 (CDR2), and/or SEQ ID NO:73 (CDR3)).

In other embodiments, the light chain immunoglobulin variable domain of the anti-HER2 antibody molecule comprises a light chain CDR1, CDR2, and/or CDR3, or having a CDR that differs by fewer than 3, 2, or 1 amino acid substitutions (e.g., conservative substitutions) from a light chain CDR1, CDR2, and/or CDR3 of monoclonal antibody selected from the group consisting of BIIB71F10 (SEQ ID NO:74 (CDR1), SEQ ID NO:75 (CDR2), and/or SEQ ID NO:76 (CDR3), or a CDR from ATCC Patent Deposit PTA-10355); BIIB69A09 (SEQ ID NO:77 (CDR1), SEQ ID NO:78 (CDR2), and/or SEQ ID NO:79 (CDR3)); BIIB67F10 (SEQ ID NO:80 (CDR1), SEQ ID NO:81 (CDR2), and/or SEQ ID NO:82 (CDR3)); BIIB67F11 (SEQ ID NO:83 (CDR1), SEQ ID NO:84 (CDR2), and/or SEQ ID NO:85 (CDR3), or a CDR from ATCC Patent Deposit PTA-10357); BIIB66A12 (SEQ ID NO:86 (CDR1), SEQ ID NO:87 (CDR2), and/or SEQ ID NO:88 (CDR3)); BIIB66C01 (SEQ ID NO:89 (CDR1), SEQ ID NO:90 (CDR2), and/or SEQ ID NO:91 (CDR3)); BIIB65C10 (SEQ ID NO:92 (CDR1), SEQ ID NO:93 (CDR2), and/or SEQ ID NO:94 (CDR3), or a CDR from ATCC Patent Deposit PTA-10358); BIIB65H09 (SEQ ID NO:95 (CDR1), SEQ ID NO:96 (CDR2), and/or SEQ ID NO:97 (CDR3), or a CDR from ATCC Patent Deposit PTA-10356) and BIIB65B03 (SEQ ID NO:98 (CDR1), SEQ ID NO:99 (CDR2), and/or SEQ ID NO:100 (CDR3)).

In certain embodiments, the amino acid sequence of the heavy chan variable domain of BIIB71F10 includes the amino acid sequence shown as SEQ ID NO:11, or is encoded by a nucleotide sequence shown as SEQ ID NO:12 or SEQ ID NO:156. The amino acid sequence of the light chan variable domain of BIIB71F10 includes the amino acid sequence shown as SEQ ID NO:13, or is encoded by a nucleotide sequence shown as SEQ ID NO:14. In other embodiments, the heavy chain and light chain variable domains of BIIB71F10 include the amino acid sequence, or is encoded by the nucleotide sequence, of ATCC Patent Deposit PTA-10355. In certain embodiments, the heavy chain variable domain of the anti-HER2 antibody molecule includes one or more of: SYGMV (SEQ ID NO:47), in CDR1, SISSSGGLTWYADSVKG (SEQ ID NO:48), in CDR2, and/or PPGIAVARDY (SEQ ID NO:49), in CDR3. In other embodiments, the light chain variable domain of the anti-HER2 antibody molecule includes one or more of: RASQGISNYLA (SEQ ID NO:74), in CDR1, AASTLQS (SEQ ID NO:75), in CDR2, and/or QKYNSALLT (SEQ ID NO:76), in CDR3, or has at least one, two or three CDRs from the heavy chain and/or light chain variable domain of ATCC Patent Deposit PTA-10355.

In certain embodiments, the amino acid sequence of the heavy chan variable domain of BIIB65H09 includes the amino acid sequence shown as SEQ ID NO:39, or is encoded by a nucleotide sequence shown as SEQ ID NO:40. The amino acid sequence of the light chan variable domain of BIIB65H09 includes the amino acid sequence shown as SEQ ID NO:41, or is encoded by a nucleotide sequence shown as SEQ ID NO:42. In other embodiments, the heavy chain and light chain variable domains of BIIB65H09 include the amino acid sequence, or is encoded by the nucleotide sequence, of ATCC Patent Deposit PTA-10356. In certain embodiments, the heavy chain variable domain of the anti-HER2 antibody molecule includes one or more of: WYSMW (SEQ ID NO:68), in CDR1, SIVSSGGQTRYADSVKG (SEQ ID NO:69), in CDR2, and/or VKGYYYYIDV (SEQ ID NO:70), in CDR3. In other embodiments, the light chain variable domain of the anti-HER2 antibody molecule includes one or more of: RASQSVDSSYLS (SEQ ID NO:95), in CDR1, GASTRAT (SEQ ID NO:96), in CDR2, and/or QQH-GYSSRT (SEQ ID NO:97), in CDR3, or has at least one, two or three CDRs from the heavy chain and/or light chain variable domain of ATCC Patent Deposit PTA-10356.

In certain embodiments, the amino acid sequence of the heavy chan variable domain of BIIB67F11 includes the amino acid sequence shown as SEQ ID NO:23, or is encoded by a nucleotide sequence shown as SEQ ID NO:24. The amino acid sequence of the light chan variable domain of BIIB67F11 includes the amino acid sequence shown as SEQ ID NO:25, or is encoded by a nucleotide sequence shown as SEQ ID NO:26. In other embodiments, the heavy chain and light chain variable domains of BIIB67F11 include the amino acid sequence, or is encoded by the nucleotide sequence, of ATCC Patent Deposit PTA-10357. In certain embodiments, the heavy chain variable domain of the anti-HER2 antibody molecule includes one or more of: NYYMM (SEQ ID NO:56), in CDR1, VIGSSGGMTNYADSVKG (SEQ ID NO:57), in CDR2, and/or GYPTGYYDSSGWVYSYY-GIDV (SEQ ID NO:58), in CDR3. In other embodiments, the light chain variable domain of the anti-HER2 antibody molecule includes one or more of: QASQDTDNRLH (SEQ ID NO:83), in CDR1, DAVNLKR (SEQ ID NO:84), in CDR2, and/or QHSDGLSLA (SEQ ID NO:85), in CDR3, or has at least one, two or three CDRs from the heavy chain and/or light chain variable domain of ATCC Patent Deposit PTA-10357.

In certain embodiments, the amino acid sequence of the heavy chan variable domain of BIIB65C10 includes the amino acid sequence shown as SEQ ID NO:35, or is encoded by a nucleotide sequence shown as SEQ ID NO:36. The amino acid sequence of the light chan variable domain of BIIB65C10 includes the amino acid sequence shown as SEQ ID NO:37, or is encoded by a nucleotide sequence shown as SEQ ID NO:38. In other embodiments, the heavy chain and light chain variable domains of BIIB65C10 include the amino acid sequence, or is encoded by the nucleotide sequence, of ATCC Patent Deposit PTA-10358. In certain embodiments, the heavy chain variable domain of the anti-HER2 antibody molecule includes one or more of: YYPMM (SEQ ID NO:65), in CDR1, SIWPSGGFTKYADSVKG (SEQ ID NO:66), in CDR2, and/or VSSSSWYGYLY (SEQ ID NO:67), in CDR3. In other embodiments, the light chain variable domain of the anti-HER2 antibody molecule includes one or more of: SGSSSNIGRNTVN (SEQ ID NO:92), in CDR1, SNNQRPS (SEQ ID NO:93), in CDR2, and/or AAWDDSLNAWV (SEQ ID NO:94), in CDR3, or has at least one, two or three CDRs from the heavy chain and/or light chain variable domain of ATCC Patent Deposit PTA-10358.

In certain embodiments, the amino acid sequence of the heavy chan variable domain of BIIB-65B03 includes the amino acid sequence shown as SEQ ID NO:43, or is encoded by a nucleotide sequence shown as SEQ ID NO:44. The amino acid sequence of the light chan variable domain of BIIB65B03 includes the amino acid sequence shown as SEQ ID NO:45, or is encoded by a nucleotide sequence shown as SEQ ID NO:46. In certain embodiments, the heavy chain variable domain of the anti-HER2 antibody molecule includes one or more of: WYRMN (SEQ ID NO:71), in CDR1, SIYSSGGPTNYADSVKG (SEQ ID NO:72), in CDR2, and/or EKPDYYDSSGYLDY (SEQ ID NO:73), in CDR3. In other embodiments, the light chain variable domain of the anti-HER2 antibody molecule includes one or more of: RASQSVSSSYLA (SEQ ID NO:98), in CDR1, GASSRAT (SEQ ID NO:99), in CDR2, and/or HQYGRPPV (SEQ ID NO:100), in CDR3.

In certain embodiments, the amino acid sequence of the heavy chan variable domain of BIIB66A12 includes the amino acid sequence shown as SEQ ID NO:27, or is encoded by a nucleotide sequence shown as SEQ ID NO:28. The amino acid sequence of the light chan variable domain of BIIB66A12 includes the amino acid sequence shown as SEQ ID NO:29, or is encoded by a nucleotide sequence shown as SEQ ID NO:30. In certain embodiments, the heavy chain variable domain of the anti-HER2 antibody molecule includes one or more of: MYSMQ (SEQ ID NO:59), in CDR1, VIGSSGGQTGYADSVK G (SEQ ID NO:60), in CDR2, and/or VRDYYGSGSYYLDP (SEQ ID NO:61), in CDR3. In other embodiments, the light chain variable domain of the anti-HER2 antibody molecule includes one or more of: RASQSISSYLN (SEQ ID NO:86), in CDR1, AASSLQS (SEQ ID NO:87), in CDR2, and/or QQSYSTSWT (SEQ ID NO:88), in CDR3.

In certain embodiments, the amino acid sequence of the heavy chan variable domain of BIIB66C01 includes the amino acid sequence shown as SEQ ID NO:31, or is encoded by a nucleotide sequence shown as SEQ ID NO:32. The amino acid sequence of the light chan variable domain of BIIB66C01 includes the amino acid sequence shown as SEQ ID NO:33, or is encoded by a nucleotide sequence shown as SEQ ID NO:34. In certain embodiments, the heavy chain variable domain of the anti-HER2 antibody molecule includes one or more of: WYSMS (SEQ ID NO:62), in CDR1, SISSSGGPTHYADSVKG (SEQ ID NO:63), in CDR2, and/or DSSYSGTS (SEQ ID NO:64), in CDR3. In other embodiments, the light chain variable domain of the anti-HER2 antibody molecule includes one or more of: SGSSSNIGSEYVY (SEQ ID NO:89), in CDR1, RNDQRPS (SEQ ID NO:90), in CDR2, and/or TTWDDSLSGPV (SEQ ID NO:91), in CDR3.

In certain embodiments, the amino acid sequence of the heavy chan variable domain of BIIB67F10 includes the amino acid sequence shown as SEQ ID NO:19, or is encoded by a nucleotide sequence shown as SEQ ID NO:20. The amino acid sequence of the light chain variable domain of BIIB67F10 includes the amino acid sequence shown as SEQ ID NO:21, or is encoded by a nucleotide sequence shown as SEQ ID NO:22. In certain embodiments, the heavy chain variable domain of the anti-HER2 antibody molecule includes one or more of: PYMMV (SEQ ID NO:53), in CDR1, WISPSGGYTFYADSVKG (SEQ ID NO:54), in CDR2, and/or GTYPLTY (SEQ ID NO:55), in CDR3. In other embodiments, the light chain variable domain of the anti-HER2 antibody molecule includes one or more of: SGD-KLGDKYVS (SEQ ID NO:80), in CDR1, QDSKWPS (SEQ ID NO:81), in CDR2, and/or QVWDISHVV (SEQ ID NO:82), in CDR3.

In certain embodiments, the amino acid sequence of the heavy chan variable domain of BIIB69A09 includes the amino acid sequence shown as SEQ ID NO:15, or is encoded by a nucleotide sequence shown as SEQ ID NO:16. The amino acid sequence of the light chan variable domain of BIIB69A09 includes the amino acid sequence shown as SEQ ID NO:17, or is encoded by a nucleotide sequence shown as SEQ ID NO:18. In certain embodiments, the heavy chain variable domain of the anti-HER2 antibody molecule includes one or more of: RYNMW (SEQ ID NO:50), in CDR1, VIRSSGGYTGYADSVKG (SEQ ID NO:51), in CDR2, and/or WNSGYSYWDYYYGMDV (SEQ ID NO:52), in CDR3. In other embodiments, the light chain variable domain of the anti-HER2 antibody molecule includes one or more of: RASQSISSYLN (SEQ ID NO:77), in CDR1, AASSLQS (SEQ ID NO:78), in CDR2, and/or QQFNTYPIT (SEQ ID NO:79), in CDR3.

In other embodiments, the antibody molecule of the fusion includes one or more CDRs including an amino acid sequence selected from the group consisting of the amino acid sequence of SEQ ID NOs:50-73 and 77-100.

In yet another embodiment, the anti-HER2 antibody molecule includes at least one, two, or three Chothia hypervariable loops from a heavy chain variable region of an antibody chosen from, e.g., BIIB71F10 (SEQ ID NOs:11-12, or a Chothia hypervariable loop from ATCC Patent Deposit PTA-10355), BIIB69A09 (SEQ ID NOs:15-16), BIIB67F10 (SEQ ID NOs:19-20), BIIB67F11 (SEQ ID NOs:23-24, or a Chothia hypervariable loop from ATCC Patent Deposit PTA-10357), BIIB66A12 (SEQ ID NOs:27-28), BIIB66C01 (SEQ ID NOs:31-32), BIIB65C10 (SEQ ID NOs:35-36, or a Chothia hypervariable loop from ATCC Patent Deposit PTA-10358), BIIB65H09 (SEQ ID NOs:39-40, or a Chothia hypervariable loop from ATCC Patent Deposit PTA-10356) or BIIB65B03 (SEQ ID NOs:43-44). In yet another embodiment, the antibody molecule includes at least one, two, or three hypervariable loops from a light chain variable region of an antibody chosen from, e.g., BIIB71F10 (SEQ ID NOs:13-14, or a Chothia hypervariable loop from ATCC Patent Deposit PTA-10355), BIIB69A09 (SEQ ID NOs:17-18), BIIB67F10 (SEQ ID NOs:21-22), BIIB67F11 (SEQ ID NOs:25-26, or a Chothia hypervariable loop from ATCC Patent Deposit PTA-10357), BIIB66A12 (SEQ ID NOs:29-30), BIIB66C01 (SEQ ID NOs:33-34), BIIB65C10 (SEQ ID NOs:37-38, or a Chothia hypervariable loop from ATCC Patent Deposit PTA-10358), BIIB65H09 (SEQ ID NOs:41-42, or a Chothia hypervariable loop from ATCC Patent Deposit PTA-10356) or BIIB65B03 (SEQ ID NOs:45-46). In yet another embodiment, the antibody or fragment thereof includes at least one, two, three, four, five, or six hypervariable loops from the heavy and light chain variable regions of an antibody chosen from, e.g., BIIB71F10 (SEQ ID NOs:11-14, or a hypervariable loop from ATCC Patent Deposit PTA-10355), BIIB69A09 (SEQ ID NOs:15-18); BIIB67F10 (SEQ ID NOs:19-22), BIIB67F11 (SEQ ID NOs:23-26, or a hypervariable loop from ATCC Patent Deposit PTA-10357), BIIB66A12 (SEQ ID NOs:27-30), BIIB66C01 (SEQ ID NOs:31-34), BIIB65C10 (SEQ ID NOs:35-38, or a hypervariable loop from ATCC Patent Deposit PTA-10358), BIIB65H09 (SEQ ID NOs:39-42, or a hypervariable loop from ATCC Patent Deposit PTA-10356) or BIIB65B03 (SEQ ID NOs:43-46), or closely related hypervariable loops, e.g., hypervariable loops which are identical or which have at least one amino acid alteration, but not more than two, three or four alterations, from the sequences disclosed herein. Optionally, the protein may include any hypervariable loop described herein.

In still another example, the anti-HER2 antibody molecule includes at least one, two, or three hypervariable loops that have the same canonical structures as the corresponding hypervariable loop of BIIB71F10 (SEQ ID NOs:11-14, or a hypervariable loop from ATCC Patent Deposit PTA-10355), BIIB69A09 (SEQ ID NOs:15-18), BIIB67F10 (SEQ ID NOs:19-22), BIIB67F11 (SEQ ID NOs:23-26, or a hypervariable loop from ATCC Patent Deposit PTA-10357), BIIB66A12 (SEQ ID NOs:27-30), BIIB66C01 (SEQ ID NOs:31-34), BIIB65C10 (SEQ ID NOs:35-38, or a hypervariable loop from ATCC Patent Deposit PTA-10358), BIIB65H09 (SEQ ID NOs:39-42, or a hypervariable loop from ATCC Patent Deposit PTA-10356) or BIIB65B03 (SEQ ID NOs:43-46), e.g., the same or similar canonical structures as at least loop 1 and/or loop 2 of the heavy and/or light chain variable domains of BIIB71F10 (SEQ ID NOs:11-14, or a hypervariable loop from ATCC Patent Deposit PTA-10355), BIIB69A09 (SEQ ID NOs:15-18), BIIB67F10 (SEQ ID NOs:19-22), BIIB67F11 (SEQ ID NOs:23-26, or a hypervariable loop from ATCC Patent Deposit PTA-10357), BIIB66A12 (SEQ ID NOs:27-30), BIIB66C01 (SEQ ID NOs:31-34), BIIB65C10 (SEQ ID NOs:35-38, or a hypervariable loop from ATCC Patent Deposit PTA-10358), BIIB65H09 (SEQ ID NOs:39-42, or a hypervariable loop from ATCC Patent Deposit PTA-10356) or BIIB65B03 (SEQ ID NOs:43-46). See, e.g., Chothia et al. (1992) *J. Mol. Biol.* 227:799-817; Tomlinson et al. (1992) *J. Mol. Biol.* 227:776-798 for descriptions of hypervariable loop canonical structures. These structures can be determined by inspection of the tables described in these references.

In one embodiment, the heavy chain framework of the anti-HER2 antibody molecule (e.g., FR1, FR2, FR3, individually, or a sequence encompassing FR1, FR2, and FR3, but excluding CDRs) includes an amino acid sequence, which is at least 80%, 85%, 90%, 95%, 97%, 98%, 99% or higher identical to the heavy chain framework of BIIB71F10 (SEQ ID NO:11 or ATCC Patent Deposit PTA-10355), BIIB69A09 (SEQ ID NO:15); BIIB67F10 (SEQ ID NO:19); BIIB67F11 (SEQ ID NO:23 or ATCC Patent Deposit PTA-10357), BIIB66A12 (SEQ ID NO:27), BIIB66C01 (SEQ ID NO:31), BIIB65C10 (SEQ ID NO:35 or ATCC Patent Deposit PTA-10358), BIIB65H09 (SEQ ID NO:39 or ATCC Patent Deposit PTA-10356) or BIIB65B03 (SEQ ID NO:43). In embodiments, the heavy chain framework of the anti-HER2 antibody molecule has an amino acid sequence substantially homologous to human V segment sequence HV3-23 (SEQ ID NO:107) (see, e.g., Chothia et al. (1992) *J. Mol. Biol.* 227: 799-817; Tomlinson et al. (1992) *J. Mol. Biol.* 227:776-798).

In another embodiment, the light chain framework of the anti-HER2 antibody molecule (e.g., FR1, FR2, FR3, individually, or a sequence encompassing FR1, FR2, and FR3, but excluding CDRs) includes, or consists essentially of, an amino acid sequence, which is at least 80%, 85%, 90%, 95%, 97%, 98%, 99% or higher identical to the light chain framework of BIIB71F10 (SEQ ID NO:13 or ATCC Patent Deposit PTA-10355), BIIB69A09 (SEQ ID NO:17); BIIB67F10 (SEQ ID NO:21); BIIB67F11 (SEQ ID NO:25 or ATCC Patent Deposit PTA-10357), BIIB66A12 (SEQ ID NO:29), BIIB66C01 (SEQ ID NO:33), BIIB65C10 (SEQ ID NO:37 or ATCC Patent Deposit PTA-10358), BIIB65H09 (SEQ ID NO:41 or ATCC Patent Deposit PTA-10356) or BIIB65B03 (SEQ ID NO:45). In embodiments, the heavy chain framework of the anti-HER2 antibody molecule has an amino acid sequence substantially homologous to human a VLκ I subgroup germline sequence, e.g., a VLκ consensus sequence.

In certain embodiments, the heavy chain immunoglobulin variable domain of the anti-HER2 antibody molecule includes, or consists essentially of, an amino acid sequence encoded by a nucleotide sequence that hybridizes under high stringency conditions to the complement of the nucleotide sequence encoding a heavy chain variable domain of BIIB71F10 (SEQ ID NO:12; SEQ ID NO:156, or ATCC Patent Deposit PTA-10355), BIIB69A09 (SEQ ID NO:16), BIIB67F10 (SEQ ID NO:20), BIIB67F11 (SEQ ID NO:24, or ATCC Patent Deposit PTA-10357), BIIB66A12 (SEQ ID NO:28), BIIB66C01 (SEQ ID NO:32), BIIB65C10 (SEQ ID NO:36, or ATCC Patent Deposit PTA-10358), BIIB65H09 (SEQ ID NO:40, or ATCC Patent Deposit PTA-10356) or BIIB65B03 (SEQ ID NO:44); or includes an amino acid sequence that is at least 80%, 85%, 90%, 95%, 97%, 98%, 99% or higher identical to the amino acid sequence of the heavy chain variable domain of BIIB71F10 (SEQ ID NO:11 or ATCC Patent Deposit PTA-10355), BIIB69A09 (SEQ ID NO:15), BIIB67F10 (SEQ ID NO:19), BIIB67F11 (SEQ ID NO:23 or ATCC Patent Deposit PTA-10357), BIIB66A12 (SEQ ID NO:27), BIIB66C01 (SEQ ID NO:31), BIIB65C10 (SEQ ID NO:35 or ATCC Patent Deposit PTA-10358), BIIB65H09 (SEQ ID NO:39 or ATCC Patent Deposit PTA-10356) or BIIB65B03 (SEQ ID NO:43).

In other embodiments, the light chain immunoglobulin variable domain of the anti-HER2 antibody molecule includes, or consists essentially of, an amino acid sequence encoded by a nucleotide sequence that hybridizes under high stringency conditions to the complement of the nucleotide sequence encoding a light chain variable domain of BIIB71F10 (SEQ ID NO:14 or ATCC Patent Deposit PTA-10355), BIIB69A09 (SEQ ID NO:18), BIIB67F10 (SEQ ID NO:22), BIIB67F11 (SEQ ID NO:26 or ATCC Patent Deposit PTA-10357), BIIB66A12 (SEQ ID NO:30), BIIB66C01 (SEQ ID NO:34), BIIB65C10 (SEQ ID NO:38 or ATCC Patent Deposit PTA-10358), BIIB65H09 (SEQ ID NO:42 or ATCC Patent Deposit PTA-10356) or BIIB65B03 (SEQ ID NO:46); or includes an amino acid sequence that is at least 80%, 85%, 90%, 95%, 97%, 98%, 99% or higher identical to a light chain variable domain of BIIB71F10 (SEQ ID NO:13 or ATCC Patent Deposit PTA-10355), BIIB69A09 (SEQ ID NO:17), BIIB67F10 (SEQ ID NO:21), BIIB67F11 (SEQ ID NO:25 or ATCC Patent Deposit PTA-10357), BIIB66A12 (SEQ ID NO:29), BIIB66C01 (SEQ ID NO:33), BIIB65C10 (SEQ ID NO:37 or ATCC Patent Deposit PTA-10358), BIIB65H09 (SEQ ID NO:41 or ATCC Patent Deposit PTA-10356) or BIIB65B03 (SEQ ID NO:45).

In certain embodiments, the LIGHT/HER2 fusions include, or consist essentially of, the amino acid sequence shown in any of 71F10 Fab-hLIGHT fusion heavy chain with the delta 4 linker (pBIIB71F10-130) (SEQ ID NO:2), 71F10 Fab-hLIGHT fusion heavy chain with the $G_4S$ delta 4 linker (pBIIB71F10-131) (SEQ ID NO:3), 71F10 Fab-hLIGHT fusion heavy chain with the $(G_4S)_4$ linker (pBIIB71F10-132) (SEQ ID NO:4), or an amino sequence substantially identical thereto (e.g., a sequence at least about 85%, 90%, 95% or higher identical thereto); an amino acid sequence encoded by the nucleotide sequence shown in any of 71F10 Fab-hLIGHT fusion heavy chain with the delta 4 linker (pBIIB71F10-130) (SEQ ID NO:6), 71F10 Fab-hLIGHT fusion heavy chain with the $G_4S$ delta 4 linker (pBIIB71F10-131) (SEQ ID NO:7), 71F10 Fab-hLIGHT fusion heavy chain with the $(G_4S)_4$ linker (pBIIB71F10-132) (SEQ ID NO:8), or a nucleotide sequence substantially identical thereto (e.g., a sequence at least about 85%, 90%, 95% or higher identical thereto). In certain embodiments, the LIGHT/HER2 fusions may also include, or consist essentially of, a second chain (fused or in association with the aforesaid chains) comprising or consisting essentially of the amino acid sequence shown in SEQ ID NO:109, or an amino sequence substantially identical thereto (e.g., a sequence at least about 85%, 90%, 95% or higher identical thereto); an amino acid sequence encoded by the nucleotide sequence shown in any of SEQ ID NO:110, or a nucleotide sequence substantially identical thereto (e.g., a sequence at least about 85%, 90%, 95% or higher identical thereto). In other embodiments, the LIGHT/HER2 fusions may also include, or consist essentially of, a second chain (fused or in association with the aforesaid chains) comprising or consisting essentially of the amino acid sequence of ATCC Patent Deposit PTA-10355, PTA-10356, PTA-10357 or PTA-10358, or an amino sequence substantially identical thereto (e.g., a sequence at least about 85%, 90%, 95% or higher identical thereto); an amino acid sequence encoded by the nucleotide sequence of ATCC Patent Deposit PTA-10355, PTA-10356, PTA-10357 or PTA-10358, or a nucleotide sequence substantially identical thereto (e.g., a sequence at least about 85%, 90%, 95% or higher identical thereto).

In another exemplary embodiment, the LIGHT targeting molecule comprises at least one fusion molecule of a mammalian (e.g., human) LIGHT protein, or a functional variant or a fragment thereof, and an antibody molecule that binds to CD23 (referred to herein as "LIGHT-anti-CD23 Fab fusion"). In one embodiment, the LIGHT-anti-CD23 fusion comprises, or consists essentially of the amino acid sequence shown in any of anti-CD23 Fab-hLIGHT fusion heavy chain with the $(G_4S)_3$ or $(G_4S)_4$ linker (pBIIB CD23-204) (SEQ ID NO:101 or 174, respectively), or an amino sequence substantially identical thereto (e.g., a sequence at least about 85%, 90%, 95% or higher identical thereto); an amino acid sequence encoded by the nucleotide sequence shown in any of anti-CD23 Fab-hLIGHT fusion heavy chain with the $(G_4S)_3$ or $(G_4S)_4$ linker (pBIIB CD23-204) (SEQ ID NO:102 or 173, respectively), or a nucleotide sequence substantially identical thereto (e.g., a sequence at least about 85%, 90%, 95% or higher identical thereto). In certain embodiments, the LIGHT/CD23 fusions may also include, or consist essentially of, a second chain (fused or in association with the aforesaid chains) comprising or consisting essentially of the amino acid sequence shown in SEQ ID NO:103, or an amino sequence substantially identical thereto (e.g., a sequence at least about 85%, 90%, 95% or higher identical thereto); an amino acid sequence encoded by the nucleotide sequence shown in any of anti-CD23 Fab-hLIGHT fusion light chain (SEQ ID NO:104), or a nucleotide sequence substantially identical thereto (e.g., a sequence at least about 85%, 90%, 95% or higher identical thereto).

In yet another exemplary embodiment, the LIGHT targeting molecule comprises at least one fusion molecule of a mammalian (e.g., human) LIGHT protein, or a functional variant or a fragment thereof, and an antibody molecule that binds to insulin growth factor receptor (referred to herein as "LIGHT-anti-IGFR Fab fusion"). In one embodiment, the LIGHT-anti-IGFR Fab fusion comprises, or consists essentially of the amino acid sequence shown in any of anti-IGFR Fab-hLIGHT fusion heavy chain with the $(G_4S)_4$ linker (BIIB C06-117) (SEQ ID NO:163), or an amino sequence substantially identical thereto (e.g., a sequence at least about 85%, 90%, 95% or higher identical thereto); an amino acid sequence encoded by the nucleotide sequence shown in any of anti-IGFR Fab-hLIGHT fusion heavy chain with the $(G_4S)_4$ linker (BIIB C06-117) (SEQ ID NO:162), or a nucleotide sequence substantially identical thereto (e.g., a sequence at least about 85%, 90%, 95% or higher identical thereto). In certain embodiments, the LIGHT/IGFR fusions may also include, or consist essentially of, a second chain (fused or in association with the aforesaid chains) comprising or consisting essentially of the amino acid sequence shown in SEQ ID NO:168, or an amino sequence substantially identical thereto (e.g., a sequence at least about 85%, 90%, 95% or higher identical thereto); an amino acid sequence encoded by the nucleotide sequence shown in any of anti-IGFR Fab-hLIGHT fusion light chain (SEQ ID NO:167), or a nucleotide sequence substantially identical thereto (e.g., a sequence at least about 85%, 90%, 95% or higher identical thereto).

In another aspect, the invention features an antibody molecule (e.g., isolated or purified protein or polypeptide) that selectively binds to HER2 (e.g., an anti-HER2 antibody as described herein). The antibody molecule can be a monoclonal or single specificity antibody, or an antigen-binding fragment thereof (e.g., an Fab; a F(ab')$_2$; an Fv; a single chain Fv fragment; a single domain antibody or a variant thereof (e.g., a heavy or light chain variable domain monomer or dimer, e.g., $V_H$, $V_{HH}$)); a single chain Fc fragment; a diabody (dAb); a camelid antibody; or one, two, or all three complementarity determining regions (CDRs) grafted onto a repertoire of VH or VL domains, or other scaffolds (such as, e.g., a fibronectin domain, T cell receptor, Affibody molecule as described herein (e.g., an Affibody protein Z scaffold), fibronectin scaffold, Lipocalin, ankyrin repeats, LDL receptor domain, RNA aptamer, PDZ domain and microbody) (or a combination of one or more of the aforesaid antibody molecules). The antibody molecule can interact with, e.g., bind to, HER2, e.g., mammalian (e.g., human) HER2. For example, the antibody molecule may include a combination of a single chain (e.g., a single chain Fc) and a Fab or a scFv. In other embodiments, the antibody molecule can be a multispecific (e.g., bivalent or bispecific) antibody or fragment thereof. In some embodiments, the antibody molecule binds to a single epitope on HER2. In other embodiments, the antibody molecule is a multi-specific antibody and binds to two or more epitopes on one or more cell surface proteins (e.g., HER2 and one or more cell surface proteins as described herein). Typically, the antibody molecule is a human, humanized, chimeric, camelid, or in vitro generated antibody (or functional fragment thereof, e.g., an antibody fragment as described herein). In embodiments, the anti-HER2 antibody is generated by in vitro selection in phage. In certain embodiments, the antibody molecule binds to the cell surface protein with an affinity characterized by a dissociation constant (Kd) at least of $1\times10^{-7}$ M, $1\times10^{-8}$ M, $1\times10^{-9}$ M, $1\times10^{-10}$ M, $1\times10^{-11}$ M, $1\times10^{-12}$ M, $1\times10^{-13}$ M.

The antibody molecule can be full-length (e.g., can include at least one, and typically two, complete heavy chains, and at least one, and typically two, complete light chains) or can include an antigen-binding fragment (e.g., a Fab, F(ab')$_2$, Fv or a single chain Fv fragment). In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues (—S—S— bonds), effector cell function, and/or complement function).

In certain embodiments, the anti-HER2 antibody molecules can have one or more of the activities described herein for an anti-HER2 antibody molecule.

In one embodiment, the anti-HER2 antibody molecule is an antibody molecule or a Fab fragment from, or has a functional activity comparable to, an antibody or Fab fragment selected from the group consisting of BIIB71F10, BIIB69A09, BIIB67F10, BIIB67F11, BIIB66A12, BIIB66C01, BIIB65C10, BIIB65H09 and BIIB65B03, as described herein.

In other embodiments, the anti-HER2 antibody molecule can cross-react with HER2 from one or more species chosen from human, mouse, rat, or cyno origin, and/or have one or more binding properties, e.g., affinity and/or kinetics, as described herein.

In still another embodiment, the anti-HER2 antibody molecule specifically binds to an epitope, e.g., a linear or a conformational epitope, of HER2, e.g., mammalian, e.g., human HER2, e.g., a HER2 epitope as described herein.

In one embodiment, the anti-HER2 antibody molecule includes one, two, three, four, five or all six CDR's from an antibody selected from the group consisting of BIIB71F10, BIIB69A09, BIIB67F10, BIIB67F11, BIIB66A12, BIIB66C01, BIIB65C10, BIIB65H09 and BIIB65B03, as described herein, or closely related CDRs, e.g., CDRs which are identical or which have at least one amino acid alteration, but not more than two, three or four alterations (e.g., substitutions (e.g., conservative substitutions), deletions, or insertions). Optionally, the antibody molecule may include any CDR described herein.

The amino acid sequence of the heavy chan variable domain of BIIB71F10 has the amino acid sequence shown as SEQ ID NO:11, or is encoded by a nucleotide sequence shown as SEQ ID NO:12 or SEQ ID NO:156. The amino acid sequence of the light chan variable domain of BIIB71F10 has the amino acid sequence shown as SEQ ID NO:13, or is encoded by a nucleotide sequence shown as SEQ ID NO:14. The heavy chain and light chain variable domains of BIIB71F10 include the amino acid sequence, or is encoded by the nucleotide sequence, of ATCC Patent Deposit PTA-10355.

The amino acid sequence of the heavy chan variable domain of BIIB65H09 includes the amino acid sequence shown as SEQ ID NO:39, or is encoded by a nucleotide sequence shown as SEQ ID NO:40. The amino acid sequence of the light chan variable domain of BIIB65H09 includes the amino acid sequence shown as SEQ ID NO:41, or is encoded by a nucleotide sequence shown as SEQ ID NO:42. The heavy chain and light chain variable domains of BIIB65H09 include the amino acid sequence, or is encoded by the nucleotide sequence, of ATCC Patent Deposit PTA-10356.

The amino acid sequence of the heavy chan variable domain of BIIB67F11 includes the amino acid sequence shown as SEQ ID NO:23, or is encoded by a nucleotide sequence shown as SEQ ID NO:24. The amino acid sequence of the light chan variable domain of BIIB67F11 includes the amino acid sequence shown as SEQ ID NO:25, or is encoded by a nucleotide sequence shown as SEQ ID NO:26. The heavy chain and light chain variable domains of BIIB67F11 include the amino acid sequence, or is encoded by the nucleotide sequence, of ATCC Patent Deposit PTA-10357.

The amino acid sequence of the heavy chan variable domain of BIIB65C10 includes the amino acid sequence shown as SEQ ID NO:35, or is encoded by a nucleotide sequence shown as SEQ ID NO:36. The amino acid sequence of the light chan variable domain of BIIB65C10 includes the amino acid sequence shown as SEQ ID NO:37, or is encoded by a nucleotide sequence shown as SEQ ID NO:38. The heavy chain and light chain variable domains of BIIB65C10 include the amino acid sequence, or is encoded by the nucleotide sequence, of ATCC Patent Deposit PTA-10358.

The amino acid sequence of the heavy chan variable domain of BIIB65B03 includes the amino acid sequence shown as SEQ ID NO:43, or is encoded by a nucleotide sequence shown as SEQ ID NO:44. The amino acid sequence of the light chan variable domain of BIIB65B03 includes the amino acid sequence shown as SEQ ID NO:45, or is encoded by a nucleotide sequence shown as SEQ ID NO:46.

The amino acid sequence of the heavy chan variable domain of BIIB66A12 includes the amino acid sequence shown as SEQ ID NO:27, or is encoded by a nucleotide sequence shown as SEQ ID NO:28. The amino acid sequence of the light chan variable domain of BIIB66A12 includes the amino acid sequence shown as SEQ ID NO:29, or is encoded by a nucleotide sequence shown as SEQ ID NO:30.

The amino acid sequence of the heavy chan variable domain of BIIB66C01 includes the amino acid sequence shown as SEQ ID NO:31, or is encoded by a nucleotide sequence shown as SEQ ID NO:32. The amino acid sequence of the light chan variable domain of BIIB66C01 includes the amino acid sequence shown as SEQ ID NO:33, or is encoded by a nucleotide sequence shown as SEQ ID NO:34.

The amino acid sequence of the heavy chan variable domain of BIIB67F10 includes the amino acid sequence shown as SEQ ID NO:19, or is encoded by a nucleotide sequence shown as SEQ ID NO:20. The amino acid sequence of the light chan variable domain of BIIB67F10 includes the amino acid sequence shown as SEQ ID NO:21, or is encoded by a nucleotide sequence shown as SEQ ID NO:22.

The amino acid sequence of the heavy chan variable domain of BIIB69A09 includes the amino acid sequence shown as SEQ ID NO:15, or is encoded by a nucleotide sequence shown as SEQ ID NO:16. The amino acid sequence of the light chan variable domain of BIIB69A09 includes the amino acid sequence shown as SEQ ID NO:17, or is encoded by a nucleotide sequence shown as SEQ ID NO:18.

In yet another embodiment, the anti-HER2 antibody molecule includes at least one, two, or three Chothia hypervariable loops from a heavy chain variable region of an antibody chosen from, e.g., BIIB71F10, BIIB69A09, BIIB67F10, BIIB67F11, BIIB66A12, BIIB66C01, BIIB65C10, BIIB65H09 or BIIB65B03, PTA-10355, PTA-10356, PTA-10357, or PTA-10358, as described herein. In yet another embodiment, the antibody or fragment thereof includes at least one, two, or three hypervariable loops from a light chain variable region of an antibody chosen from, e.g., BIIB71F10, BIIB69A09, BIIB67F10, BIIB67F11, BIIB66A12, BIIB66C01, BIIB65C10, BIIB65H09 or BIIB65B03, or PTA-10355, PTA-10356, PTA-10357, or PTA-10358, as described herein. In yet another embodiment, the antibody or fragment thereof includes at least one, two, three, four, five, or six hypervariable loops from the heavy and light chain variable regions of an antibody chosen from, e.g., BIIB71F10, BIIB69A09, BIIB67F10, BIIB67F11, BIIB66A12, BIIB66C01, BIIB65C10, BIIB65H09 and BIIB65B03, or PTA-10355, PTA-10356, PTA-10357, or PTA-10358, as described herein.

In still another example, the anti-HER2 antibody molecule includes at least one, two, or three hypervariable loops that have the same canonical structures as the corresponding hypervariable loop of BIIB71F10, BIIB69A09, BIIB67F10, BIIB67F11, BIIB66A12, BIIB66C01, BIIB65C10, BIIB65H09 and BIIB65B03, or PTA-10355, PTA-10356, PTA-10357, or PTA-10358, as described herein, e.g., the same or similar canonical structures as at least loop 1 and/or loop 2 of the heavy and/or light chain variable domains of BIIB71F10, BIIB69A09, BIIB67F10, BIIB67F11, BIIB66A12, BIIB66C01, BIIB65C10, BIIB65H09 and BIIB65B03, or PTA-10355, PTA-10356, PTA-10357, or PTA-10358, as described herein.

In one embodiment, the heavy chain framework of the anti-HER2 antibody molecule (e.g., FR1, FR2, FR3, individually, or a sequence encompassing FR1, FR2, and FR3, but excluding CDRs) includes an amino acid sequence, which is at least 85%, 90%, 95%, 97%, 98%, 99% or higher identical to the heavy chain framework of BIIB71F10 (SEQ ID NO:11), BIIB69A09 (SEQ ID NO:15); BIIB67F10 (SEQ ID NO:19); BIIB67F11 (SEQ ID NO:23), BIIB66A12 (SEQ ID NO:27), BIIB66C01 (SEQ ID NO:31), BIIB65C10 (SEQ ID NO:35), BIIB65H09 (SEQ ID NO:39) or BIIB65B03 (SEQ ID NO:43), or PTA-10355, PTA-10356, PTA-10357, or PTA-10358, or a heavy chain as described herein. In embodiments, the heavy chain framework of the anti-HER2 antibody molecule has an amino acid sequence substantially homologous to human V segment sequence HV3-23 (SEQ ID NO:107).

In another embodiment, the light chain framework of the anti-HER2 antibody molecule (e.g., FR1, FR2, FR3, individually, or a sequence encompassing FR1, FR2, and FR3, but excluding CDRs) includes an amino acid sequence, which is at least 85%, 90%, 95%, 97%, 98%, 99% or higher identical to the light chain framework of BIIB71F10 (SEQ ID NO:13), BIIB69A09 (SEQ ID NO:17); BIIB67F10 (SEQ ID NO:21); BIIB67F11 (SEQ ID NO:25), BIIB66A12 (SEQ ID NO:29), BIIB66C01 (SEQ ID NO:33), BIIB65C10 (SEQ ID NO:37), BIIB65H09 (SEQ ID NO:41) or BIIB65B03 (SEQ ID NO:45), PTA-10355, PTA-10356, PTA-10357, or PTA-10358, or a light chain framework as described herein. In embodiments, the heavy chain framework of the anti-HER2 antibody molecule has an amino acid sequence substantially homologous to human a VLκ I subgroup germline sequence, e.g., a VLκ consensus sequence.

In certain embodiments, the heavy chain immunoglobulin variable domain of the anti-HER2 antibody molecule includes, or consists essentially of, an amino acid sequence encoded by a nucleotide sequence that hybridizes under high stringency conditions to the complement of the nucleotide sequence encoding a heavy chain variable domain of BIIB71F10 (SEQ ID NO:12; SEQ ID NO:156), BIIB69A09 (SEQ ID NO:16); BIIB67F10 (SEQ ID NO:20); BIIB67F11 (SEQ ID NO:24), BIIB66A12 (SEQ ID NO:28), BIIB66C01 (SEQ ID NO:32), BIIB65C10 (SEQ ID NO:36), BIIB65H09 (SEQ ID NO:40) or BIIB65B03 (SEQ ID NO:44), or PTA-10355, PTA-10356, PTA-10357, or PTA-10358; or includes an amino acid sequence that is at least 85%, 90%, 95%, 97%, 98%, 99% or higher identical to the amino acid sequence of the heavy chain variable domain of BIIB71F10 (SEQ ID NO:11), BIIB69A09 (SEQ ID NO:15); BIIB67F10 (SEQ ID NO:19); BIIB67F11 (SEQ ID NO:23), BIIB66A12 (SEQ ID NO:27), BIIB66C01 (SEQ ID NO:31), BIIB65C10 (SEQ ID NO:35), BIIB65H09 (SEQ ID NO:39) or BIIB65B03 (SEQ ID NO:43), or PTA-10355, PTA-10356, PTA-10357, or PTA-10358.

In other embodiments, the light chain immunoglobulin variable domain of the anti-HER2 antibody molecule includes, or consists essentially of, an amino acid sequence encoded by a nucleotide sequence that hybridizes under high stringency conditions to the complement of the nucleotide sequence encoding a light chain variable domain of BIIB71F10 (SEQ ID NO:14), BIIB69A09 (SEQ ID NO:18); BIIB67F10 (SEQ ID NO:22); BIIB67F11 (SEQ ID NO:26), BIIB66A12 (SEQ ID NO:30), BIIB66C01 (SEQ ID NO:34), BIIB65C10 (SEQ ID NO:38), BIIB65H09 (SEQ ID NO:42) or BIIB65B03 (SEQ ID NO:46), or PTA-10355, PTA-10356, PTA-10357, or PTA-10358; or includes an amino acid sequence that is at least 80%, 85%, 90%, 95%, 97%, 98%, 99% or higher identical to a light chain variable domain of BIIB71F10 (SEQ ID NO:13), BIIB69A09 (SEQ ID NO:17); BIIB67F10 (SEQ ID NO:21); BIIB67F11 (SEQ ID NO:25), BIIB66A12 (SEQ ID NO:29), BIIB66C01 (SEQ ID NO:33), BIIB65C10 (SEQ ID NO:37), BIIB65H09 (SEQ ID NO:41) or BIIB65B03 (SEQ ID NO:45), or PTA-10355, PTA-10356, PTA-10357, or PTA-10358.

In some embodiments, the LIGHT targeting molecules and/or antibody molecules described herein are conjugated to an agent selected from the group consisting of cytotoxic agent, a therapeutic agent, cytostatic agent, a biological toxin, a prodrug, a peptide, a protein, an enzyme, a virus, a lipid, a biological response modifier, pharmaceutical agent, a lymphokine, a heterologous antibody or fragment thereof, a detectable label, polyethylene glycol (PEG), and a combination of two or more of any said agents. In further embodiments, the cytotoxic agent is selected from the group consisting of a radionuclide, a biotoxin, an enzymatically active toxin, a cytostatic or cytotoxic therapeutic agent, a prodrugs, an immunologically active ligand, a biological response modifier, or a combination of two or more of any said cytotoxic agents. In further embodiments, the detectable label is selected from the group consisting of an enzyme, a fluorescent label, a chemiluminescent label, a bioluminescent label, a radioactive label, or a combination of two or more of any said detectable labels.

In another aspect, the invention features nucleic acid molecules (e.g., isolated or purified nucleic acids) comprising, or consisting essentially of, a nucleotide sequence encoding the LIGHT targeting molecules and/or the anti-HER2 antibody molecules described herein. In certain embodiments, nucleic acids comprise, or consist essentially of, a nucleotide sequence encoding a LIGHT-moiety (e.g., a nucleotide sequence encoding a LIGHT protein, or a functional fragment or variant thereof) and a nucleotide sequence encoding a targeting moiety functionally linked (e.g., by genetic fusion, non-covalent association or otherwise).

Exemplary nucleic acid molecules of the invention comprise, or consist essentially of, nucleotide sequences encoding LIGHT proteins of the LIGHT moiety include, or consist essentially of, the amino acid sequence from: about amino acids 93 to 240 of human LIGHT isoform 1 (corresponding to a portion of the human LIGHT extracellular domain shown as SEQ ID NO:1), about amino acids 253 to 400 of 71F10 Fab-hLIGHT fusion heavy chain with the delta 4 linker (pBIIB71F10-130) (corresponding to the portion of the LIGHT extracellular domain fused to anti-HER2 antibody molecule shown as SEQ ID NO:2), about amino acids 258 to 405 of 71F10 Fab-hLIGHT fusion heavy chain with the $G_4S$ delta 4 linker (pBIIB71F10-131) (corresponding to the portion of the LIGHT extracellular domain fused to anti-HER2 antibody molecule shown as SEQ ID NO:3), about amino acids 245 to 392 of 71F10 Fab-hLIGHT fusion heavy chain with the $(G_4S)4$ linker (pBIIB71F10-132) (corresponding to the portion of the LIGHT extracellular domain fused to anti-HER2 antibody molecule shown as SEQ ID NO:4), or an amino sequence substantially identical thereto (e.g., a sequence at least about 85%, 90%, 95% or higher identical thereto); In other embodiments, the nucleic acids comprise, or consist essentially of, the nucleotide sequence from: about nucleotides 277 to 720 of, human LIGHT isoform 1 (nucleotide sequence corresponding to a portion of the human LIGHT extracellular domain shown as SEQ ID NO:5), about nucleotides 757 to 1200 of 71F10 Fab-hLIGHT fusion heavy chain with the delta 4 linker (pBIIB71F10-130) (nucleotide sequence corresponding to the portion of the LIGHT extracellular domain fused to anti-HER2 antibody molecule shown as SEQ ID NO:6), about nucleotides 772 to 1215 of 71F10 Fab-hLIGHT fusion heavy chain with the $G_4S$ delta 4 linker (pBIIB71F10-131) (nucleotide sequence corresponding to the portion of the LIGHT extracellular domain fused to anti-HER2 antibody molecule shown as SEQ ID NO:7), about nucleotides 733 to 1176 of 71F10 Fab-hLIGHT fusion heavy chain with the $(G_4S)_4$ linker (pBIIB71F10-132) (nucleotide sequence corresponding to the portion of the LIGHT extracellular domain fused to anti-HER2 antibody molecule shown as SEQ ID NO:8), or a nucleotide sequence substantially identical thereto (e.g., a sequence at least about 85%, 90%, 95% or higher identical thereto). The LIGHT moiety may, optionally, include, or consist essentially of, one or more amino acid residues (e.g., at least 10 to 35, 15 to 30, or about 20 to 26 amino acid residues) from the extracellular domain of LIGHT or a mutated form thereof, e.g., from about amino acids 61 to 92 of human LIGHT isoform 1 (SEQ ID NO:1), about amino acids 225 to 252 of 71F10 Fab-hLIGHT fusion heavy chain with the delta 4 linker (pBIIB71F10-130) (SEQ ID NO:2), about amino acids 230 to 257 of 71F10 Fab-hLIGHT fusion heavy chain with the $G_4S$ delta 4 linker (pBIIB71F10-131) (SEQ ID NO:3), or an amino acid sequence substantially identical thereto; or an amino acid sequence encoded by the nucleotide sequence from about nucleotides 181 to 276 of human LIGHT isoform 1 (SEQ ID NO:5), about nucleotides 673 to 756 of 71F10 Fab-hLIGHT fusion heavy chain with the delta 4 linker (pBIIB71F10-130) (SEQ ID NO:6), about nucleotides 688 to 771 of 71F10 Fab-hLIGHT fusion heavy chain with the $G_4S$ delta 4 linker (pBIIB71F10-131) (SEQ ID NO:7), or a nucleotide sequence substantially identical thereto (e.g., a sequence at least about 85%, 90%, 95% or higher identical thereto). Variants of the LIGHT protein, or soluble fragments thereof, altered to increase one or more properties of LIGHT, e.g., protein stability, immune enhancing function, may used. For example, the LIGHT protein can be modified to have one or more protelolytic sites inactivated (e.g., by deletion, mutation or insertion, of a proteolytic site). In one embodiment, amino acids EQLI (SEQ ID NO:9) comprising a proteolytic site at position 82 to 83 of the human LIGHT sequence (human LIGHT isoform 1, SEQ ID NO:1), or amino acids EKLI (SEQ ID NO:10) from positions 79-82 of the mouse LIGHT sequence are removed. In other embodiments, the LIGHT protein is from non-human origin, e.g., murine LIGHT, can be used. The amino acid and corresponding nucleotide sequences for full length mouse LIGHT are shown in SEQ ID NOs:113 and 114, respectively.

The nucleotide sequence encoding the LIGHT molecule can be genetically fused, with or without a nucleotide sequence encoding a linking group, to a nucleotide sequence encoding the targeting moiety as a genetic fusion. In other embodiments, the nucleotide sequences encoding the LIGHT molecule and the targeting moiety can be individually expressed, and covalently attached to each other via a reactive group, optionally, via a biocompatible polymer (e.g., as described herein). Nucleic acids encoding the linking groups can include at least five, ten, fifteen or twenty glycine and serine residues in the following configuration, $(Gly)_4$-Ser (SEQ ID NO:145), in one, two, three, four, five or more repeats, e.g., four repeats of $(Gly)_4$-Ser (SEQ ID NO: 134). In other embodiments, linking group may include one or more amino acid residues (e.g., at least 10 to 35, 15 to 30, or about 20 to 26 amino acid residues) from the extracellular domain of LIGHT or a mutated form thereof, e.g., from about amino acids 61 to 92 of human LIGHT isoform 1 (SEQ ID NO:1), about amino acids 225 to 252 of 71F10 Fab-hLIGHT fusion heavy chain with the delta 4 linker (pBIIB71F10-130) (SEQ ID NO:2), about amino acids 230 to 257 of 71F10 Fab-hLIGHT fusion heavy chain with the $G_4S$ delta 4 linker (pBIIB71F10-131) (SEQ ID NO:3), or an amino acid sequence substantially identical thereto; or an amino acid sequence encoded by the nucleotide sequence from about nucleotides 181 to 276 of human LIGHT isoform 1 (SEQ ID NO:5), about nucleotides 673 to 756 of 71F10 Fab-hLIGHT fusion heavy chain with the delta 4 linker (pBIIB71F10-130) (SEQ ID NO:6), about nucleotides 688 to 771 of 71F10 Fab-hLIGHT fusion heavy chain with the $G_4S$ delta 4 linker (pBIIB71F10-131) (SEQ ID NO:7), or a nucleotide sequence substantially identical thereto (e.g., a sequence at least about 85%, 90%, 95% or higher identical thereto). Alternatively, the linking group encoded by the nucleic acids may include a combination of one or more $(Gly)_4$-Ser (SEQ ID NO: 146) repeats and one or more amino acid residues (e.g., at least 10 to 35, 15 to 30, or about 20 to 26 amino acid residues) from the extracellular domain of LIGHT or a mutated form thereof, e.g., from about amino acids 61 to 92 of human LIGHT isoform 1 (SEQ ID NO:1), about amino acids 225 to 252 of 71F10 Fab-hLIGHT fusion heavy chain with the delta 4 linker (pBIIB71F10-130) (SEQ ID NO:2), about amino acids 230 to 257 of 71F10 Fab-hLIGHT fusion heavy chain with the G4S delta 4 linker (pBIIB71F10-131) (SEQ ID NO:3), or an amino acid sequence substantially identical thereto; or an amino acid sequence encoded by the nucleotide sequence from about nucleotides 181 to 276 of human LIGHT isoform 1 (SEQ ID NO:5), about nucleotides 673 to 756 of 71F10 Fab-hLIGHT fusion heavy chain with the delta 4 linker (pBIIB71F10-130) (SEQ ID NO:6), about nucleotides 688 to 771 of 71F10 Fab-hLIGHT fusion heavy chain with the G4S delta 4 linker (pBIIB71F10-131) (SEQ ID NO:7), or a nucleotide sequence substantially identical thereto (e.g., a sequence at least about 85%, 90%, 95% or higher identical thereto).

In one exemplary embodiment, the nucleic acid molecules encode a LIGHT targeting molecule that comprises, or consists essentially of, at least one fusion molecule of a mammalian (e.g., human) LIGHT protein, or a functional variant or a fragment thereof, and an antibody molecule that binds to HER2 (referred to herein as "LIGHT-anti-HER2 fusion"). In one embodiment, the nucleic acids encoding LIGHT-anti-HER2 fusion comprises, or consists essentially of, at least one mammalian (e.g., human) LIGHT protein, or a variant or a fragment thereof (e.g., a LIGHT protein as described herein) and an anti-HER2 specific antibody molecule or a fragment thereof (e.g., an antibody molecule as described herein).

In embodiments, the nucleic acid encoding the anti-HER2 antibody molecule is an antibody molecule or a Fab fragment from an antibody selected from the group consisting of BIIB71F10 (SEQ ID NOs:11-14), BIIB69A09 (SEQ ID NOs:15-18); BIIB67F10 (SEQ ID NOs:19-22); BIIB67F11 (SEQ ID NOs:23-26), BIIB66A12 (SEQ ID NOs:27-30), BIIB66C01 (SEQ ID NOs:31-34), BIIB65C10 (SEQ ID NOs:35-38), BIIB65H09 (SEQ ID NOs:39-42) and BIIB65B03 (SEQ ID NOs:43-46), or a nucleic acid of PTA-10355, PTA-10356, PTA-10357, or PTA-10358, as described herein. In other embodiments, the nucleic acid encoding the anti-HER2 antibody molecule has a functional activity comparable to an antibody molecule or a Fab fragment from an antibody selected from the group consisting of BIIB71F10 (SEQ ID NOs:11-14), BIIB69A09 (SEQ ID NOs:15-18); BIIB67F10 (SEQ ID NOs:19-22); BIIB67F11 (SEQ ID NOs: 23-26), BIIB66A12 (SEQ ID NOs:27-30), BIIB66C01 (SEQ ID NOs:31-34), BIIB65C10 (SEQ ID NOs:35-38), BIIB65H09 (SEQ ID NOs:39-42) and BIIB65B03 (SEQ ID NOs:43-46), or a nucleic acid of PTA-10355, PTA-10356, PTA-10357, or PTA-10358, as described herein.

In one embodiment, the nucleic acid molecule encoding the antibody molecule of the fusion, or the anti-HER2 antibody molecule, includes one, two, three, four, five or all six CDR's from an antibody selected from the group consisting of BIIB71F10 (SEQ ID NOs:11-14), BIIB69A09 (SEQ ID NOs:15-18); BIIB67F10 (SEQ ID NOs:19-22); BIIB67F11 (SEQ ID NOs:23-26), BIIB66A12 (SEQ ID NOs:27-30), BIIB66C01 (SEQ ID NOs:31-34), BIIB65C10 (SEQ ID NOs:35-38), BIIB65H09 (SEQ ID NOs:39-42) and BIIB65B03 (SEQ ID NOs:43-46), or a nucleic acid of PTA-10355, PTA-10356, PTA-10357, or PTA-10358, or closely related CDRs, e.g., CDRs which are identical or which have at least one amino acid alteration, but not more than two, three or four alterations (e.g., substitutions (e.g., conservative substitutions), deletions, or insertions). Optionally, the nucleic acid encodes an antibody molecule that may include any CDR described herein. In embodiments, nucleic acid encodes a heavy chain immunoglobulin variable domain that includes a heavy chain CDR1, CDR2, and/or CDR3, or having a CDR that differs by fewer than 3 amino acid substitutions (e.g., conservative substitutions) from a heavy chain CDR1, CDR2, and/or CDR3 of monoclonal antibody selected from the group consisting of BIIB71F10 (SEQ ID NO:47 (CDR1), SEQ ID NO:48 (CDR2), and/or SEQ ID NO:49 (CDR3)); BIIB69A09 (SEQ ID NO:50 (CDR1), SEQ ID NO:51 (CDR2), and/or SEQ ID NO:52 (CDR3)); BIIB67F10 (SEQ ID NO:53 (CDR1), SEQ ID NO:54 (CDR2), and/or SEQ ID NO:55 (CDR3)); BIIB67F11 (SEQ ID NO:56 (CDR1), SEQ ID NO:57 (CDR2), and/or SEQ ID NO:58 (CDR3)); BIIB66A12 (SEQ ID NO:59 (CDR1), SEQ ID NO:60 (CDR2), and/or SEQ ID NO:61 (CDR3)); BIIB66C01 (SEQ ID NO:62 (CDR1), SEQ ID NO:63 (CDR2), and/or SEQ ID NO:64 (CDR3)); BIIB65C10 (SEQ ID NO:65 (CDR1), SEQ ID NO:66 (CDR2), and/or SEQ ID NO:67 (CDR3)); BIIB65H09 (SEQ ID NO:68 (CDR1), SEQ ID NO:69 (CDR2), and/or SEQ ID NO:70 (CDR3)) and BIIB65B03 (SEQ ID NO:71 (CDR1), SEQ ID NO:72 (CDR2), and/or SEQ ID NO:73 (CDR3)), or a CDR from PTA-10355, PTA-10356, PTA-10357, or PTA-10358, as described herein. In other embodiments, the nucleic acid encoding the light chain immunoglobulin variable domain comprises a light chain CDR1, CDR2, and/or CDR3, or having a CDR that differs by fewer than 3 amino acid substitutions (e.g., conservative substitutions) from a light chain CDR1, CDR2, and/or CDR3 of monoclonal antibody antibody selected from the group consisting of BIIB71F10 (SEQ ID NO:74 (CDR1), SEQ ID NO:75 (CDR2), and/or SEQ ID NO:76 (CDR3)); BIIB69A09 (SEQ ID NO:77 (CDR1), SEQ ID NO:78 (CDR2), and/or SEQ ID NO:79 (CDR3)); BIIB67F10 (SEQ ID NO:80 (CDR1), SEQ ID NO:81 (CDR2), and/or SEQ ID NO:82 (CDR3)); BIIB67F11 (SEQ ID NO:83 (CDR1), SEQ ID NO:84 (CDR2), and/or SEQ ID NO:85 (CDR3)); BIIB66A12 (SEQ ID NO:86 (CDR1), SEQ ID NO:87 (CDR2), and/or SEQ ID NO:88 (CDR3)); BIIB66C01 (SEQ ID NO:89 (CDR1), SEQ ID NO:90 (CDR2), and/or SEQ ID NO:91 (CDR3)); BIIB65C10 (SEQ ID NO:92 (CDR1), SEQ ID NO:93 (CDR2), and/or SEQ ID NO:94 (CDR3)); BIIB65H09 (SEQ ID NO:95 (CDR1), SEQ ID NO:96 (CDR2), and/or SEQ ID NO:97 (CDR3)) and BIIB65B03 (SEQ ID NO:98 (CDR1), SEQ ID NO:99 (CDR2), and/or SEQ ID NO:100 (CDR3)), or a CDR from PTA-10355, PTA-10356, PTA-10357, or PTA-10358, as described herein. The nucleotide sequence encoding the heavy chain and light chain variable domain of the BIIB71F10, BIIB69A09, BIIB67F10, BIIB67F11, BIIB66A12, BIIB66C01, BIIB65C10, BIIB65H09 or BIIB65B03 antibody molecules are described herein.

In yet another embodiment, the nucleic acid molecule encodes an antibody molecule of the fusion, or the anti-HER2 antibody molecule, that includes at least one, two, or three Chothia hypervariable loops from a heavy chain variable region of an antibody chosen from, e.g., BIIB71F10 (SEQ ID NOs:11-12), BIIB69A09 (SEQ ID NOs:15-16); BIIB67F10 (SEQ ID NOs:19-20); BIIB67F11 (SEQ ID NOs:23-24), BIIB66A12 (SEQ ID NOs:27-28), BIIB66C01 (SEQ ID NOs:31-32), BIIB65C10 (SEQ ID NOs:34-35), BIIB65H09 (SEQ ID NOs:39-40) or BIIB65B03 (SEQ ID NOs:43-44), or a nucleic acid of PTA-10355, PTA-10356, PTA-10357, or PTA-10358, as described herein. In yet another embodiment, the nucleic acid encodes an antibody molecule of the fusion, or the anti-HER2 antibody molecule, that includes at least one, two, or three hypervariable loops from a light chain variable region of an antibody chosen from, e.g., BIIB71F10 (SEQ ID NOs:13-14), BIIB69A09 (SEQ ID NOs:17-18); BIIB67F10 (SEQ ID NOs:21-22); BIIB67F11 (SEQ ID NOs:25-26), BIIB66A12 (SEQ ID NOs:29-30), BIIB66C01 (SEQ ID NOs:33-34), BIIB65C10 (SEQ ID NOs:37-38), BIIB65H09 (SEQ ID NOs:41-42) or BIIB65B03 (SEQ ID NOs:45-46), or a nucleic acid of PTA-10355, PTA-10356, PTA-10357, or PTA-10358, as described herein. In yet another embodiment, the nucleic acid encodes an antibody molecule of the fusion, or the anti-HER2 antibody molecule, that includes at least one, two, three, four, five, or six hypervariable loops from the heavy and light chain variable regions of an antibody chosen from, e.g., BIIB71F10 (SEQ ID NOs: 11-14), BIIB69A09 (SEQ ID NOs:15-18); BIIB67F10 (SEQ ID NOs:19-22); BIIB67F11 (SEQ ID NOs:23-26), BIIB66A12 (SEQ ID NOs:27-30), BIIB66C01 (SEQ ID NOs:31-34), BIIB65C10 (SEQ ID NOs:35-38), BIIB65H09 (SEQ ID NOs:39-42) or BIIB65B03 (SEQ ID NOs:43-46), or a nucleic acid of PTA-10355, PTA-10356, PTA-10357, or PTA-10358, as described herein.

In one embodiment, the nucleic acid molecule encodes an antibody molecule of the fusion, or the anti-HER2 antibody molecule, that includes all six hypervariable loops from BIIB71F10 (SEQ ID NOs:11-14), BIIB69A09 (SEQ ID NOs:15-18); BIIB67F10 (SEQ ID NOs:19-22); BIIB67F11 (SEQ ID NOs:23-26), BIIB66A12 (SEQ ID NOs:27-30), BIIB66C01 (SEQ ID NOs:31-34), BIIB65C10 (SEQ ID NOs:35-38), BIIB65H09 (SEQ ID NOs:39-42) or BIIB65B03 (SEQ ID NOs:43-46), or PTA-10355, PTA-10356, PTA-10357, or PTA-10358, or closely related hypervariable loops, e.g., hypervariable loops which are identical or which have at least one amino acid alteration, but not more than two, three or four alterations, from the sequences disclosed herein. Optionally, the nucleic acid may encode a protein including any hypervariable loop described herein.

In still another example, the nucleic acid molecule encodes an antibody molecule of the fusion, or the anti-HER2 antibody molecule, that includes at least one, two, or three hypervariable loops that have the same canonical structures as the corresponding hypervariable loop of BIIB71F10 (SEQ ID NOs:11-14), BIIB69A09 (SEQ ID NOs:15-18); BIIB67F10 (SEQ ID NOs:19-22); BIIB67F11 (SEQ ID NOs:23-26), BIIB66A12 (SEQ ID NOs:27-30), BIIB66C01 (SEQ ID NOs:31-34), BIIB65C10 (SEQ ID NOs:35-38), BIIB65H09 (SEQ ID NOs:39-42) or BIIB65B03 (SEQ ID NOs:43-46), or PTA-10355, PTA-10356, PTA-10357, or PTA-10358, e.g., the same or similar canonical structures as at least loop 1 and/or loop 2 of the heavy and/or light chain variable domains of BIIB71F10 (SEQ ID NOs:11-14), BIIB69A09 (SEQ ID NOs:15-18); BIIB67F10 (SEQ ID NOs:19-22); BIIB67F11 (SEQ ID NOs:23-26), BIIB66A12 (SEQ ID NOs:27-30), BIIB66C01 (SEQ ID NOs:31-34), BIIB65C10 (SEQ ID NOs:35-38), BIIB65H09 (SEQ ID NOs:39-42) or BIIB65B03 (SEQ ID NOs:43-46), or PTA-10355, PTA-10356, PTA-10357, or PTA-10358.

In one embodiment, the nucleic acid molecule encodes an antibody molecule of the fusion, or the anti-HER2 antibody molecule, that includes a heavy chain framework (e.g., FR1, FR2, FR3, individually, or a sequence encompassing FR1, FR2, and FR3, but excluding CDRs) that includes an amino acid sequence, which is at least 85%, 90%, 95%, 97%, 98%, 99% or higher identical to the heavy chain framework of BIIB71F10 (SEQ ID NO:11), BIIB69A09 (SEQ ID NO:15); BIIB67F10 (SEQ ID NO:19); BIIB67F11 (SEQ ID NO:23), BIIB66A12 (SEQ ID NO:27), BIIB66C01 (SEQ ID NO:31), BIIB65C10 (SEQ ID NO:35), BIIB65H09 (SEQ ID NO:39) or BIIB65B03 (SEQ ID NO:43), or PTA-10355, PTA-10356, PTA-10357, or PTA-10358. In embodiments, the heavy chain framework of the anti-HER2 antibody molecule has an amino acid sequence substantially homologous to human V segment sequence HV3-23 (SEQ ID NO:107).

In another embodiment, the nucleic acid molecule encodes a light chain framework of the antibody molecule (e.g., FR1, FR2, FR3, individually, or a sequence encompassing FR1, FR2, and FR3, but excluding CDRs) that includes, or consists essentially of, an amino acid sequence, which is at least 85%, 90%, 95%, 97%, 98%, 99% or higher identical to the light chain framework of BIIB71F10 (SEQ ID NO:13), BIIB69A09 (SEQ ID NO:17); BIIB67F10 (SEQ ID NO:21); BIIB67F11 (SEQ ID NO:25), BIIB66A12 (SEQ ID NO:29), BIIB66C01 (SEQ ID NO:33), BIIB65C10 (SEQ ID NO:37), BIIB65H09 (SEQ ID NO:41) or BIIB65B03 (SEQ ID NO:45), or PTA-10355, PTA-10356, PTA-10357, or PTA-10358. In embodiments, the heavy chain framework of the anti-HER2 antibody molecule has an amino acid sequence substantially homologous to human a VLκ I subgroup germline sequence, e.g., a VLκ consensus sequence.

In certain embodiments, the nucleic acid molecule encodes an antibody molecule of the fusion, or the anti-HER2 antibody molecule, that includes, or consists essentially of, a nucleotide sequence that hybridizes under high stringency conditions to the complement of the nucleotide sequence encoding a heavy chain variable domain of BIIB71F10 (SEQ ID NO:12; SEQ ID NO:156), BIIB69A09 (SEQ ID NO:16); BIIB67F10 (SEQ ID NO:20); BIIB67F11 (SEQ ID NO:24), BIIB66A12 (SEQ ID NO:28), BIIB66C01 (SEQ ID NO:32), BIIB65C10 (SEQ ID NO:36), BIIB65H09 (SEQ ID NO:40) or BIIB65B03 (SEQ ID NO:44), or PTA-10355, PTA-10356, PTA-10357, or PTA-10358; or includes an amino acid sequence that is at least 85%, 90%, 95%, 97%, 98%, 99% or higher identical to the amino acid sequence of the heavy chain variable domain of BIIB71F10 (SEQ ID NO:11), BIIB69A09 (SEQ ID NO:15); BIIB67F10 (SEQ ID NO:19); BIIB67F11 (SEQ ID NO:23), BIIB66A12 (SEQ ID NO:27), BIIB66C01 (SEQ ID NO:31), BIIB65C10 (SEQ ID NO:35), BIIB65H09 (SEQ ID NO:39) or BIIB65B03 (SEQ ID NO:43), or PTA-10355, PTA-10356, PTA-10357, or PTA-10358.

In other embodiments, the nucleic acid molecule encodes an antibody molecule of the fusion, or the anti-HER2 antibody molecule, that includes, or consists essentially of, a nucleotide sequence that hybridizes under high stringency conditions to the complement of the nucleotide sequence encoding a light chain variable domain of BIIB71F10 (SEQ ID NO:14), BIIB69A09 (SEQ ID NO:18); BIIB67F10 (SEQ ID NO:22); BIIB67F11 (SEQ ID NO:26), BIIB66A12 (SEQ ID NO:30), BIIB66C01 (SEQ ID NO:34), BIIB65C10 (SEQ ID NO:38), BIIB65H09 (SEQ ID NO:42) or BIIB65B03 (SEQ ID NO:46), or PTA-10355, PTA-10356, PTA-10357, or PTA-10358; or includes an amino acid sequence that is at least 80%, 85%, 90%, 95%, 97%, 98%, 99% or higher identical identical to a light chain variable domain of BIIB71F10 (SEQ ID NO:13), BIIB69A09 (SEQ ID NO:17); BIIB67F10 (SEQ ID NO:21); BIIB67F11 (SEQ ID NO:25), BIIB66A12 (SEQ ID NO:29), BIIB66C01 (SEQ ID NO:33), BIIB65C10 (SEQ ID NO:37), BIIB65H09 (SEQ ID NO:41) or BIIB65B03 (SEQ ID NO:45), or PTA-10355, PTA-10356, PTA-10357, or PTA-10358.

Exemplary nucleic acid molecules encode LIGHT/HER2 fusions that include, or consist essentially of, the amino acid sequence shown in any of 71F10 Fab-hLIGHT fusion heavy chain with the delta 4 linker (pBIIB71F10-130) (SEQ ID NO:2), 71F10 Fab-hLIGHT fusion heavy chain with the G4S delta 4 linker (pBIIB71F10-131) (SEQ ID NO:3), 71F10 Fab-hLIGHT fusion heavy chain with the $(G4S)_4$ linker (pBIIB71F10-132) (SEQ ID NO:4), or an amino sequence substantially identical thereto (e.g., a sequence at least about 85%, 90%, 95% or higher identical thereto); an amino acid sequence encoded by the nucleotide sequence shown in any of 71F10 Fab-hLIGHT fusion heavy chain with the delta 4 linker (pBIIB71F10-130) (SEQ ID NO:6), 71F10 Fab-hLIGHT fusion heavy chain with the $G_4S$ delta 4 linker (pBIIB71F10-131) (SEQ ID NO:7), 71F10 Fab-hLIGHT fusion heavy chain with the $(G_4S)_4$ linker (pBIIB71F10-132) (SEQ ID NO:8), or a nucleotide sequence substantially identical thereto (e.g., a sequence at least about 85%, 90%, 95% or higher identical thereto). In certain embodiments, the nucleic acid molecules encoding the LIGHT/HER2 fusions may also include, or consist essentially of, a second chain (genetically fused or in association with the aforesaid chains) comprising or consisting essentially of the amino acid sequence shown in human LIGHT isoform 1 (SEQ ID NO:1), or an amino sequence substantially identical thereto (e.g., a sequence at least about 85%, 90%, 95% or higher identical thereto). In embodiments, the nucleic acid molecules comprise, or consist essentially of, the nucleotide sequence shown in any of human LIGHT isoform 1 (SEQ ID NO:5), or a nucleotide sequence substantially identical thereto (e.g., a sequence at least about 85%, 90%, 95% or higher identical thereto).

In another exemplary embodiment, the nucleic acid molecules encode a LIGHT targeting molecule that comprises at least one fusion molecule of a mammalian (e.g., human) LIGHT protein, or a functional variant or a fragment thereof, and an antibody molecule that binds to CD23 (referred to herein as "LIGHT-anti-CD23 fusion"). In one embodiment, the nucleic acid molecules encoding the LIGHT-anti-CD23 fusion comprises, or consists essentially of the amino acid sequence shown in any of anti-CD23 Fab-hLIGHT fusion heavy chain with the $(G_4S)_3$ or $(G_4S)_4$ linker (pBIIB CD23-204) (SEQ ID NO:101 or 174, respectively), or an amino sequence substantially identical thereto (e.g., a sequence at least about 85%, 90%, 95% or higher identical thereto). In embodiments, the nucleic acid molecules comprise, or consist essentially of, the nucleotide sequence shown in any of anti-CD23 Fab-hLIGHT fusion heavy chain the $(G_4S)_3$ or $(G_4S)_4$ linker (pBIIB CD23-204) (SEQ ID NO:102 or 173, respectively), or a nucleotide sequence substantially identical thereto (e.g., a sequence at least about 85%, 90%, 95% or higher identical thereto). In certain embodiments, the nucleic acid molecules encoding the LIGHT/CD23 fusions may also include, or consist essentially of, a second chain (fused or in association with the aforesaid chains) comprising or consisting essentially of the amino acid sequence shown in anti-CD23 Fab-hLIGHT fusion light chain (SEQ ID NO:103), or an amino sequence substantially identical thereto (e.g., a sequence at least about 85%, 90%, 95% or higher identical thereto). In embodiments, the nucleic acid molecules comprise, or consist essentially of, the nucleotide sequence shown in any of anti-CD23 Fab-hLIGHT fusion light chain (SEQ ID NO:104), or a nucleotide sequence substantially identical thereto (e.g., a sequence at least about 85%, 90%, 95% or higher identical thereto).

In yet another embodiment, the nucleic acid molecules comprises a nucleotide sequence encoding a LIGHT targeting molecule that comprises at least one fusion molecule of a mammalian (e.g., human) LIGHT protein, or a functional variant or a fragment thereof, and an antibody molecule that binds to IGFR. In one embodiment, the nucleic acid encodes a LIGHT-anti-IGFR Fab fusion that comprises, or consists essentially of the amino acid sequence shown in any of anti-IGFR Fab-hLIGHT fusion heavy chain with the $(G_4S)_4$ linker (BIIB C06-117) (SEQ ID NO:163), or an amino sequence substantially identical thereto (e.g., a sequence at least about 85%, 90%, 95% or higher identical thereto); the nucleotide sequence encodes the anti-IGFR Fab-hLIGHT fusion heavy chain with the $(G_4S)_4$ linker (BIIB C06-117) (SEQ ID NO:162), or a nucleotide sequence substantially identical thereto (e.g., a sequence at least about 85%, 90%, 95% or higher identical thereto). In certain embodiments, the nucleic acid molecules can also include a nucleotide sequence encoding a second chain (fused or in association with the aforesaid chains) comprising or consisting essentially of the amino acid sequence shown in SEQ ID NO:168, or an amino sequence substantially identical thereto (e.g., a sequence at least about 85%, 90%, 95% or higher identical thereto); a nucleotide sequence encoding the anti-IGFR Fab-hLIGHT fusion light chain (comprising or consisting of SEQ ID NO:167), or a nucleotide sequence substantially identical thereto (e.g., a sequence at least about 85%, 90%, 95% or higher identical thereto).

In yet another aspect, the invention provides a host cell comprising one or more nucleic acid molecules encoding one or more of the LIGHT targeting molecules and/or the anti-HER2 antibody molecules disclosed herein.

In other embodiments, the invention provides vectors comprising the nucleic acid molecules described herein. In further embodiments, the nucleic acid molecules are operably associated with a promoter. In additional embodiments, the invention provides host cells comprising such vectors. In further embodiments, the invention provides vectors where the polynucleotide is operably associated with a promoter.

In additional embodiments, the invention provides a method of, or process for, producing the LIGHT targeting molecules and/or the anti-HER2 antibody molecules disclosed herein. The method includes: culturing a host cell containing a vector comprising the nucleic acid molecules described herein, and recovering said LIGHT targeting molecules and/or the anti-HER2 antibody molecules. In further embodiments, the invention provides an isolated polypeptide produced by the method.

In some embodiments, the invention provides isolated polypeptides encoded by the nucleic acid molecules described herein.

Compositions, e.g., pharmaceutical compositions, that include the LIGHT targeting molecules or the anti-HER2 antibody molecules, and a pharmaceutically-acceptable carrier, are also disclosed. It is noted that the compositions, e.g., pharmaceutical compositions, may additionally include a second therapeutic agent, e.g., a second therapeutic agent as described herein (e.g., an anti-neoplastic agent). Exemplary anti-neoplastic agents, e.g., a cytotoxic agent or a cytostatic agent, that can be used in combination with the molecules of the invention include, but are not limited to, taxoids (e.g., docetaxel, paclitaxel), doxorubicin, cyclophosphamide, gencitabine and vinorelbine.

Packaged pharmaceutical compositions that include the LIGHT targeting molecules or the anti-HER2 antibody molecules, for use in treating a hyperproliferative, e.g., neoplastic, disorder or condition described herein are also encompassed by the present invention. Optionally, the packaged pharmaceutical composition is labeled and/or contains some instructions for use in treating a hyperproliferative, e.g., neoplastic, disorder or condition described herein.

In some embodiments, the invention provides a composition comprising an isolated LIGHT targeting molecule, or an antibody heavy chain variable region encoding nucleic acid molecule and/or an isolated light chain variable region encoding nucleic acid molecule, wherein the heavy chain encoding polynucleotide and the light chain encoding polynucleotide, respectively, comprise nucleic acid molecules encoding amino acid sequences identical or substantially identical, e.g., at least 85%, 90%, 95% identical to an antibody amino acid sequences disclosed herein.

In other embodiments, the LIGHT targeting molecules, antibody molecules, compositions, nucleic acid molecules encoding one of the chains of the LIGHT targeting molecule, or the antibody molecule (e.g., a heavy or light chain variable region), further comprise a nucleic acid encoding a signal peptide fused to the nucleic acid molecule encoding the LIGHT targeting molecule, or the antibody molecule.

In some embodiments, the LIGHT targeting molecules, antibody molecules, compositions, nucleic acid molecules encoding one of the chains of the LIGHT targeting molecule, or the antibody molecule (e.g., a heavy or light chain variable region), further comprise a heavy chain constant region CH1 domain fused to the VH or VL polypeptide, further comprises a heavy chain constant region CH2 domain fused to the VH polypeptide, further comprises a heavy chain constant region CH3 domain fused to the VH polypeptide, or further comprises a heavy chain hinge region fused to the VH polypeptide. In further embodiments, the heavy chain constant region is human IgG1. In certain other embodiments, the IgG1 is mutagenized according to the Kabat numbering system.

In some embodiments, the LIGHT targeting molecules, antibody molecules, compositions, the VL encoding polynucleotide further comprises a light chain constant region domain fused to the VL polypeptide. In further embodiments, the light chain constant region is human VLκ.

In some embodiments, the LIGHT targeting molecules, antibody molecules, compositions, the framework regions of the VH and VL polypeptides are human, except for five or fewer amino acid substitutions.

In some embodiments, the VH encoding polynucleotide is contained on a first vector and the VL encoding polynucleotide is contained on a second vector. In further embodiments, the VH encoding polynucleotide is operably associated with a first promoter and the VL encoding polynucleotide is operably associated with a second promoter. In certain other embodiments, the first and second promoters are copies of the same promoter. In further embodiments, the first and second promoters are non-identical.

In various embodiments of the above-described compositions, the first vector and the second vector are contained in a single host cell, or in a separate host cells.

In another aspect, the invention features a method of selectively delivering a LIGHT-targeting molecule (e.g., a LIGHT protein, variant or fragment thereof as described herein), to a hyperproliferative cell or tissue, e.g., a neoplastic cell or tissue as described herein, thereby killing, ablating, or otherwise selectively reducing the activity of the hyperproliferative cell or tissue. The method includes contacting the hyperproliferative cell with a LIGHT-targeting molecule, e.g., a molecule as described herein. The contacting step can be performed in the presence of one or more immune cells having a LIGHT receptor, e.g., a LIGHT receptor as described herein. The method can be performed in vitro, e.g., in cultured cells, or ex-vivo, e.g., as part of a therapeutic or prophylactic protocol, in a subject (e.g., a subject having a hyperproliferative disorder or condition as described herein, or an animal model as described herein (e.g., a mouse tumor model carrying breast tumor cells, or a HER2-dependent colorectal and gastric xenograft tumor model)).

In another aspect, the invention features a method of treating or preventing (e.g., curing, suppressing, ameliorating, delaying or preventing the onset of, or preventing recurrence or relapse of) a hyperproliferative, e.g., a cancerous, condition and/or disorder. The method includes administering to a subject, e.g., a subject in need of treatment, a LIGHT-targeting molecule, or anti-HER2 antibody molecule, as described herein.

In certain embodiments, the method prevents, reduces or ameliorates the recurrence or relapse of a tumor or metastasis. The method includes administering a LIGHT-targeting molecule, or anti-HER2 antibody molecule, as described herein, to a subject, e.g., a patient that is partially or completely refractory to a standard mode of therapy (e.g., chemotherapy, antibody-based and/or surgery). For example, the patient suffers from a HER2-expressing cancer (e.g., a breast, gastric or lung cancer) and has demonstrated disease progession after surgery, chemotherapy and/or antibody therapy (e.g., trastuzumab therapy). In other embodiments, the patient is a colon cancer patient that has demonstrated disease progession after surgery, chemotherapy and/or antibody therapy (e.g., VEGF or EGFR antibody therapy). In certain embodiments, the LIGHT-targeting molecule, or anti-HER2 antibody molecule, is administered to a patient who has been treated with another mode of therapy (e.g., a standard mode of therapy) for about 10 days, one to six months, six months to a year, one to two years, and so on. In certain embodiments, the subject has developed partial or complete resistance to a first-line of therapy.

Certain embodiments relating to the in vitro or in vivo methods described herein are as follows:

In further embodiments, the hyperproliferative disorder or condition is chosen from one or more of a cancer, a neoplasm, a tumor, a malignancy, or a metastasis thereof, or a recurrent malignancy (e.g., a subject that is partially or completely refractory to a first-line of treatment).

For in vivo methods, the LIGHT-targeting molecule, or anti-HER2 antibody molecule, alone or in combination with another agent (e.g., a chemotherapeutic agent as described herein), can be administered to a subject, e.g., a mammal, suffering from a hyperproliferative condition and/or disorder, in an amount sufficient to elicit at least one LIGHT-associated biological activity, in the subject.

In some embodiments, the amount or dosage of the LIGHT-targeting molecule, or anti-HER2 antibody molecule, administered can be determined, e.g., prior to administration to the subject, by testing in vitro or ex vivo the amount of the LIGHT-targeting molecule, or anti-HER2 antibody molecule, required to decrease or inhibit one or more of hyperproliferative activities, disorders or conditions described herein. The in vivo method can, optionally, include the step(s) of identifying (e.g., evaluating, diagnosing, screening, and/or selecting) a subject at risk of having, or having, one or more symptoms associated with the disorder or condition.

In various embodiments, the targeting moiety of the LIGHT targeting molecule, or the antibody molecule, specifically binds to a cell surface protein expressed on the surface of the hyperproliferative, e.g., neoplastic, cell or tissue. The targeting moiety can bind to one or more target molecules, e.g., soluble or cell surface proteins expressed on one or more of the hyperproliferative cells or tissues described herein. For example, the targeting moiety can bind to one or more of a growth factor receptor (e.g., HER-2/neu, HER3, HER4, epidermal growth factor receptor (EGFR), insulin growth factor receptor (IGFR), Met, Ron, Cripto); a cancer-related integrin or integrin receptor (e.g., αvβ6, α6β4, laminin receptor (LAMR); and/or other antigens, such as CD23, CD20, CD16, EpCAM, Tweak receptor (FN14), PSMA, and/or VEGF, among others). Additional examples of target molecules recognized by the targeting moieties are described herein.

In further embodiments, the binding of the LIGHT targeting molecule, or the antibody molecule, to the hyperproliferative, e.g., neoplastic, cell or tissue may result in one or more of: (i) binding to one or more LIGHT-receptors (e.g., lymphotoxin β receptor (LTβR), the herpes virus entry mediator (HVEM), and/or decoy receptor 3 (DcR3)); (ii) inducing expression of one or more of chemokines or cytokines (e.g., CXCL10 (IP-10), CCL21, CXCL9, IL-5, IL-8 or TNF), chemokine or cytokine receptors (e.g., IL-10RA) adhesion molecules, and/or co-stimulatory molecules; (iii) activating T cells, e.g., lymphocytes (e.g., cytotoxic T lymphocytes), CD4- or CD8-expressing T cells, and/or regulatory T cells; (iv) recruiting T cells into a hyperproliferative, e.g., tumor, site or cell; (v) activating and/or enhancing tumor-reactive T cell proliferation; (vi) creating a lymphoid-like microenvironment, e.g., at a hyperproliferative, e.g., a tumor cell or tissue; (vi) inducing apoptosis of a hyperproliferative (e.g., tumor) cell or tissue; and/or (vii) stimulating an immune response in a subject, e.g., stimulating a subject's immune system against a hyperproliferative, e.g., a tumor or a cancerous, cell or tissue.

In embodiments where the LIGHT targeting molecule, or the antibody molecule, binds to HER2, the binding of the LIGHT targeting molecule, or the antibody molecule, to the hyperproliferative, e.g., neoplastic, cell or tissue may result in one or more of: (i) binding to HER2 with an affinity of about affinity characterized by a dissociation constant (Kd) at least of $1\times10^{-7}$ M, $1\times10^{-8}$ M, $1\times10$ M, $1\times10^{-10}$ M, $1\times10^{-11}$ M, $1\times10^{-12}$ M, $1\times10^{-13}$ M; (ii) binding substantially selective to HER2, without significant cross reactivity with other HER-family members (iii) binding to a linear or a conformational epitope on HER2 chosen from D1 epitope (corresponding to about amino acids 1 to 196 of human HER2 shown in FIG. 4), D2 epitope (corresponding to about amino acids 197 to 318 of human HER2 shown in FIG. 4), D3 epitope (corresponding to about amino acids 319 to 508 of human HER2 shown in FIG. 4), or D4 epitope (corresponding to about amino acids 508 to 630 of human HER2 shown in FIG. 4), or a combination thereof; (iii) inhibiting, blocking or reducing HER2 signaling (e.g., inhibit, block or reduce phosphorylation of one or more of HER2, AKT and/or MAP kinase; or inhibit, block or reduce homodimerization of HER2 or heterodimerization of HER2 and HER3, and/or HER2 with EGFR; (iv) inhibiting activity and/or inducing cell killing of a HER2 expressing cell in vitro (e.g., MCF7 and SKBR-3 cell) and in vivo (e.g., in an animal model (such as a mouse tumor model carrying breast tumor cells, or a HER2-dependent colorectal and gastric xenograft tumor model)), or in a human subject; (v) triggering an anti-tumor immune response in vivo, and/or (vi) inducing a prolonged reduction of tumor growth or metastasis, e.g., after prolonged monotherapy or combination therapy, or after tumor relapse is detected following another chemotherapeutic therapy (e.g., standard chemotherapy or anti-HER2 antibody therapy).

In various embodiments of the above-described methods, the LIGHT-targeting molecule, or the antibody molecule inhibits tumor cell migration. In further embodiments, the tumor cell proliferation is inhibited through the prevention or retardation of tumor spread to adjacent tissues.

In various embodiments, the hyperproliferative disease or disorder is a neoplasm located in the: prostate, colon, abdomen, bone, breast, digestive system, liver, pancreas, peritoneum, adrenal gland, parathyroid gland, pituitary gland, testicles, ovary, thymus, thyroid, eye, head, neck, central nervous system, peripheral nervous system, lymphatic system, pelvis, skin, soft tissue, spleen, thoracic region, or urogenital tract.

Exemplary hyperproliferative, e.g., cancerous or neoplastic, cells or tissues, that can be targeted with the targeting moiety, include, but are not limited to, cancers or solid tumors of the breast, lung, stomach, ovaries, prostate, pancreas, colon, colorectum, renal, bladder, liver, head, neck, brain, as well as soft-tissue malignancies, including lymphoid malignacies, leukemia and myeloma. Additional disorders that can be treated include, but are not limited to, epithelial squamous cell cancer, melanoma, brain cancer, cervical cancer, renal cancer, testicular cancer, and thyroid cancer. In embodiments, the cancer is a HER2-expressing tumor or metastatic cancer (e.g., a HER2-expressing cancer of the breast, lung or stomach).

In various embodiments, the subject is a mammal (e.g., an animal model or a human). In further embodiments, the subject is a human, e.g., a patient with one or more of the cancers described herein. In one embodiment, the subject is a patient undergoing a standard mode of therapy, e.g., a HER2-positive patient undergoing chemotherapy and/or treatment with trastuzumab, and the LIGHT-targeting molecules and/or an anti-HER2 antibody molecule are administered as a second-line of therapy. In other embodiments, the patient is a naïve patient, e.g., the LIGHT-targeting molecules and/or an anti-HER2 antibody molecule are administered as a first-line of therapy. In other embodiment, the patient is partially or completely refractory to a standard mode of therapy. For example, the patient is a breast cancer patient that has demonstrated disease progession after chemotherapy and/or trastuzumab therapy.

In other embodiments, the targeting moiety of the LIGHT targeting molecule, or the antibody molecule, is administered, alone or combination with a second agent, as a first-line of therapy to a naïve subject, e.g., a naïve patient having a HER2-expressing breast cancer. In other embodiments, the targeting moiety of the LIGHT targeting molecule, or the antibody molecule, is administered, alone or combination with a second agent, as a second-line of therapy. In other embodiment, the targeting moiety of the LIGHT targeting molecule, or the antibody molecule, is administered to a patient that is partially or completely refractory to a standard mode of therapy. For example, the patient is a breast cancer patient that has demonstrated disease progession after chemotherapy and/or trastuzumab therapy.

In another aspect, the invention features methods for detecting and/or diagnosing, a hyperproliferative disorder or condition using a LIGHT-targeting molecules and/or an anti-HER2 antibody molecule (e.g., a binding agent as described herein). The methods include: detecting the presence of a protein target, e.g., HER2, in a sample (e.g., a purified sample or in vivo). The method comprises (i) contacting the sample with the LIGHT-targeting molecule and/or the anti-HER2 antibody molecule; and (ii) detecting formation of a complex between the LIGHT-targeting molecule and/or the anti-HER2 antibody molecule and the sample, wherein formation of the complex in the sample is indicative of the presence of the protein target in the sample. In certain embodiments, the presence of the protein target is elevated or reduced in relation to a reference value, e.g., a control sample. A change, e.g., increase or decrease, in relation to the reference value is indicative of a hyperproliferative disorder or condition. In embodiments where the protein target is HER2, an elevation in the sample relative to a reference value is indicative of the hyperproliferative disorder or condition.

The LIGHT-targeting molecules and/or the anti-HER2 antibody molecules are also collectively referred to herein as "binding agents" or "binding molecules."

All publications, patent applications, patents, and other references mentioned herein are incorporated by reference in their entirety.

Other features, objects, and advantages of the invention will be apparent from the description and drawings, and from the claims.

BRIEF DESCRIPTION OF DRAWINGS

FIG. 6 discloses SEQ ID NOS 132-134, respectively, in order of appearance. A schematic representation of the 71F10 Fab-hLIGHT fusions with different linker sequences is also shown in FIG. 6.

FIG. 7 discloses SEQ ID NOS 147, 134 and 134, respectively, in order of appearance.

FIG. 21 shows that LIGHT targeting is required for its maximal activity.

FIG. 22 shows 71F10 Fab-hLIGHT can overcome tumor resistance to anti-Her2 therapies.

FIG. 24 depicts a schematic representation of dimeric form of 71F10 Fab-hLIGHT fusion protein. Amino acid residues 215-225 and 233-257 of SEQ ID NO:179 (top) and amino acid residues 215-257 of SEQ ID NO:179 (bottom) are depicted.

Like reference symbols in the various drawings indicate like elements.

BRIEF DESCRIPTION OF TABLES

TABLE 1 depicts a summary of the binding activity of Fabs to HER2 measured by flow cytometry.

TABLE 2 depicts a summary of the binding activity of LIGHT fusion proteins.

TABLE 3 depicts examples of pro-inflammatory genes in HT29 cells that are effected by treatment with BIIB71F10-130 as measured by quantitative reverse transcriptase PCR.

DETAILED DESCRIPTION

Figure 3:
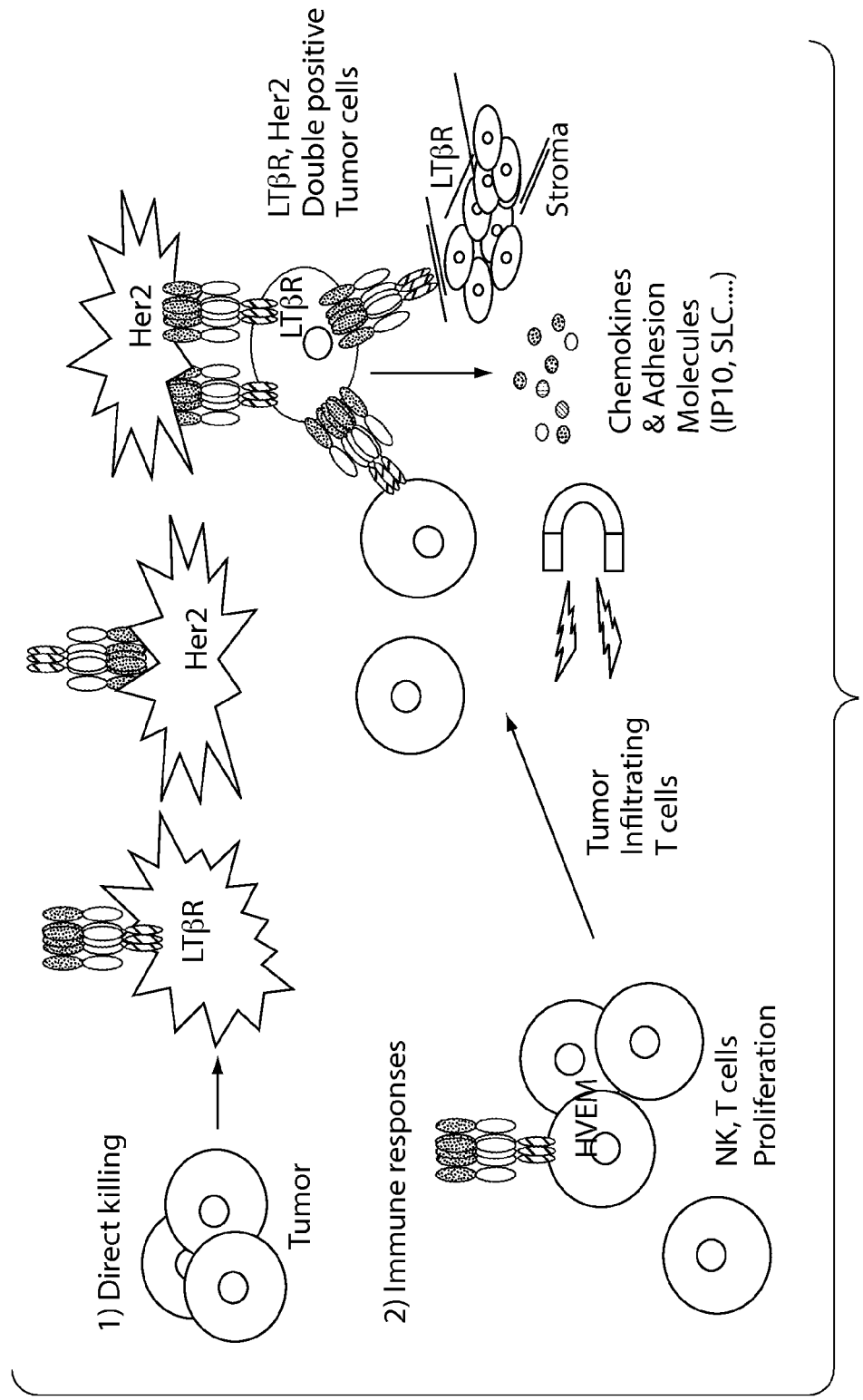
FIG. 3 depicts a schematic representation of antibody-directed tumor targeting.

The present invention is based, at least in part, on the generation of LIGHT-targeting molecules that are selectively delivered to a hyperproliferative, e.g., cancerous, cell or tissue, thereby eliciting an anti-tumor response, including tumor cell killing and/or anti-tumor immunity. In certain embodiments, the LIGHT-targeting molecules include at least one LIGHT fusion molecule that comprises a LIGHT moiety (e.g., a LIGHT protein, or a functional variant or a fragment thereof), and a targeting moiety (e.g., a binding agent, such as an antibody molecule) that interacts, e.g., binds to, a cancer protein (e.g., a cell surface protein expressed on a cancer cell or tumor), thereby delivering the LIGHT moiety in close proximity to the hyperproliferative cell or tissue. Without being bound by theory and as depicted in FIG. 3, it is believed that the LIGHT targeting molecules of the invention exert one or more of the following activities upon binding to one of its receptors, lymphotoxin β receptor (LTβR) and the herpes virus entry mediator (HVEM), exerting one or more of the following LIGHT-associated activities: i) inducing expression of one or more of chemokines or cytokines (e.g., CXCL10 (IP-10), CCL21, CXCL9, IL-5, IL-8 or TNF), chemokine or cytokine receptors (e.g., IL-10RA) adhesion molecules, and/or co-stimulatory molecules; (ii) activating T cells, e.g., lymphocytes (e.g., cytotoxic T lymphocytes), CD4- or CD8-expressing T cells, and/or regulatory T cells; (iii) recruiting T cells into a hyperproliferative, e.g., tumor, site or cell; (iv) activating and/or enhancing tumor-reactive T cell proliferation; (v) creating a lymphoid-like microenvironment, e.g., at a hyperproliferative, e.g., a tumor cell or tissue; (vi) inducing apoptosis of a hyperproliferative (e.g., tumor) cell or tissue; and/or (vii) stimulating an immune response in a subject, e.g., stimulating a subject's immune system against a hyperproliferative, e.g., a tumor or a cancerous, cell or tissue.

In one exemplary embodiment, the LIGHT targeting molecules comprises at least one fusion molecule of a mammalian (e.g., human) LIGHT protein, or a functional variant or a fragment thereof, and an antibody molecule that binds to HER2 (referred to herein as "LIGHT-anti-HER2 fusion"). Without being bound by theory, the LIGHT-anti-HER2 fusions are believed to trigger dual anti-cancer effects by inducing tumor cell killing mediated by the anti-HER2 antibody molecule, as well as stimulating localized LIGHT-mediated anti-tumor immunity. Thus, the present invention provides, in part, LIGHT-targeting molecules (e.g., LIGHT fusion molecules), antibody molecules against HER2, and methods for treating various hyperproliferative, e.g., neoplastic diseases, including cancer and metastasis using the same.

In order that the present invention may be more readily understood, certain terms are first defined. Additional definitions are set forth throughout the detailed description.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

The terms "proteins" and "polypeptides" are used interchangeably herein.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The term "LIGHT protein" and similar terms ("polypeptides," "peptides" and "proteins" are used interchangeably herein) refer to a member of the TNF superfamily from any species (typically of mammalian, e.g., murine, or human or non-human primate origin), as well as functional variants thereof (including mutants, fragments and peptidomimetic forms) that retain a LIGHT-associated activity (e.g., which is capable of interacting with, e.g., binding to, a LIGHT receptor (typically of mammalian, e.g., murine or human LIGHT receptor chosen from lymphotoxin β receptor (LTβR) (Crowe et al. (1994) *Science* 264 707-10, Browning et al. (1997) *J Immunol* 159: 3288-98); the herpes virus entry mediator (HVEM) (Montgomery et al. (1996) *Cell* 87(3): 427-36), and/or decoy receptor 3 (DcR3) (Yu et al. (1999) *J. Biol. Chem.* 274 13733-6). Also encompassed are soluble forms of LIGHT, e.g., soluble forms encompassing the extracellular domain of LIGHT or functional variants thereof. Typically, LIGHT has a biological activity as described herein and one of the following features: (i) an amino acid sequence of a naturally occurring mammalian LIGHT polypeptide or a fragment thereof (e.g., a mature LIGHT), e.g., an amino acid sequence of human LIGHT isoform 1 (SEQ ID NO:1) or human LIGHT isoform 2 (SEQ ID NO:111) or mouse LIGHT (SEQ ID NO:113) or a fragment thereof (e.g., about amino acids 93 to 240 of human LIGHT isoform 1 (corresponding to a portion of the human LIGHT extracellular domain shown as SEQ ID NO:1), about amino acids 253 to 400 of 71F10 Fab-hLIGHT fusion heavy chain with the delta 4 linker (pBIIB71F10-130) (corresponding to the portion of the LIGHT extracellular domain fused to anti-HER2 antibody molecule shown as SEQ ID NO:2), about amino acids 258 to 405 of 71F10 Fab-hLIGHT fusion heavy chain with the G$_4$S delta 4 linker (pBIIB71F10-131) (corresponding to the portion of the LIGHT extracellular domain fused to anti-HER2 antibody molecule shown as SEQ ID NO:3), about amino acids 245 to 392 of 71F10 Fab-hLIGHT fusion heavy chain with the (G$_4$S)$_4$ linker (pBIIB71F10-132) (corresponding to the portion of the LIGHT extracellular domain fused to anti-HER2 antibody molecule shown as SEQ ID NO:4), or (ii) an amino sequence substantially identical thereto (e.g., a sequence at least about 85%, 90%, 95% or higher identical thereto); (iii) an amino acid sequence encoded by the nucleotide sequence from: about nucleotides 277 to 720 of, human LIGHT isoform 1 (nucleotide sequence corresponding to a portion of the human LIGHT extracellular domain shown as SEQ ID NO:5), human LIGHT isoform 2 (SEQ ID NO:112), mouse LIGHT (SEQ ID NO:114), about nucleotides 757 to 1200 of 71F10 Fab-hLIGHT fusion heavy chain with the delta 4 linker (pBIIB71F10-130) (nucleotide sequence corresponding to the portion of the LIGHT extracellular domain fused to anti-HER2 antibody molecule shown as SEQ ID NO:6), about nucleotides 772 to 1215 of 71F10 Fab-hLIGHT fusion heavy chain with the G$_4$S delta 4 linker (pBIIB71F10-131) (nucleotide sequence corresponding to the portion of the LIGHT extracellular domain fused to anti-HER2 antibody molecule shown as SEQ ID NO:7), about nucleotides 733 to 1176 of 71F10 Fab-hLIGHT fusion heavy chain with the (G$_4$S)$_4$ linker (pBIIB71F10-132) (nucleotide sequence corresponding to the portion of the LIGHT extracellular domain fused to anti-HER2 antibody molecule shown as SEQ ID NO:8), or (iv) an amino acid sequence encoded by a nucleotide sequence substantially identical thereto (e.g., a sequence at least about 85%, 90%, 95% or higher identical thereto); or (v) an amino acid sequence encoded by a nucleotide sequence degenerate to a naturally occurring LIGHT nucleotide sequence or a fragment thereof, e.g., an amino acid sequence of human LIGHT isoform 1 (SEQ ID NO:1) or a fragment thereof; or (vi) a nucleotide sequence that hybridizes to one of the foregoing nucleotide sequence sequences under stringent conditions, e.g., highly stringent conditions.

The phrase "a biological activity of" a LIGHT refers to one or more of the biological activities associated with LIGHT, including but not limited to: (i) binding to one or more LIGHT-receptors (e.g., lymphotoxin β receptor (LTβR), the herpes virus entry mediator (HVEM), and/or decoy receptor 3 (DcR3)); (ii) inducing expression of one or more of chemokines or cytokines (e.g., CXCL10 (IP-10), CCL21, CXCL9, IL-5, IL-8 or TNF), chemokine or cytokine receptors (e.g., IL-10RA) adhesion molecules, and/or co-stimulatory molecules; (iii) activating T cells, e.g., lymphocytes (e.g., cytotoxic T lymphocytes), CD4- or CD8-expressing T cells, and/or regulatory T cells; (iv) recruiting T cells into a hyperproliferative, e.g., tumor, site or cell; (v) activating and/or enhancing tumor-reactive T cell proliferation; (vi) creating a lymphoid-like microenvironment, e.g., at a hyperproliferative, e.g., a tumor cell or tissue; (vii) inducing apoptosis of a hyperproliferative (e.g., tumor) cell or tissue; and/or (viii) stimulating an immune response in a subject, e.g., stimulating a subject's immune system against a hyperproliferative, e.g., a tumor or a cancerous, cell or tissue.

The methods and compositions of the present invention encompass LIGHT targeting molecules, antibody molecules and nucleic acids having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 85%, 90%. 91%, 92%, 93%, 94%, 95%, 96%, 97%, 98% or 99% identity to a reference sequence.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 85%, 90%. 91%, 92%, 93%, 94%, 95%, 96%, 97%, 98% or 99% identity to a reference sequence Also included as polypeptides of the present invention are fragments, derivatives, analogs, or variants of the foregoing polypeptides, and any combination thereof. The terms "fragment," "variant," "derivative" and "analog" when referring to LIGHT proteins, LIGHT targeting molecules, antibody molecules of the present invention include any polypeptides which retain at least some of the functional properties of the corresponding native antibody or polypeptide. Fragments of polypeptides of the present invention include proteolytic fragments, as well as deletion fragments, in addition to specific antibody fragments discussed elsewhere herein. Variants of the polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of the fragments of the present invention are polypeptides which have been altered so as to exhibit additional features not found on the native polypeptide. Examples include fusion proteins. As used herein a "derivative" of a polypeptide refers to a subject polypeptide having one or more residues chemically derivatized by reaction of a functional side group. Also included as "derivatives" are those polypeptides which contain one or more naturally occurring amino acid derivatives of the twenty standard amino acids.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes can be at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences. The comparison of sequences and determination of percent identity between two sequences can be accomplished using a mathematical algorithm. The percent identity between two amino acid sequences can be determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS*, 4:11-17) which has been incorporated into the ALIGN program (version 2.0), using a PAM120 weight residue table, a gap length penalty of 12 and a gap penalty of 4. The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to a nucleic acid (SEQ ID NO:1) molecules of the invention. BLAST protein searches can be performed with the XBLAST program, score=50, wordlength=3 to obtain amino acid sequences homologous to a protein (SEQ ID NO:1) protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley & Sons, N.Y. (1989), 6.3.1-6.3.6. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5M sodium phosphate, 7% SDS at 65° C., followed by one or more washes at 0.2×SSC, 1% SDS at 65° C. Very high stringency conditions (4) are the preferred conditions and the ones that should be used unless otherwise specified.

It is understood that the LIGHT targeting molecules of the present invention may have additional conservative or nonessential amino acid substitutions, which do not have a substantial effect on their functions. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Various aspects of the invention are described in further detail below.

I. LIGHT Targeting Molecules

In one aspect, the invention features a LIGHT targeting molecule that includes at least one LIGHT moiety (e.g., a LIGHT protein, or a functional variant or a fragment thereof as described herein), and at least one targeting moiety (e.g., a binding agent, such as an antibody molecule) that interacts, e.g., binds to, a surface protein on a hyperproliferative cell (e.g., a cell surface protein expressed on a cancer or tumor cell or tissue), thereby delivering the LIGHT moiety to the hyperproliferative cell or tissue. In embodiments, the LIGHT molecule is functionally linked (e.g., by chemical coupling, genetic or polypeptide fusion, non-covalent association or otherwise) to the targeting moiety. For example, the LIGHT molecule can be fused, with or without a linking group, to the targeting moiety as a genetic or a polypeptide fusion. In other embodiments, the LIGHT molecule is covalently attached to the antibody molecule via a reactive group with or without a linking group (e.g., a biocompatible polymer). The LIGHT targeting molecule can be a monomer, dimer, trimer, tetramer, pentamer, or more of at least one LIGHT moiety and at least one targeting moiety. For example, the LIGHT targeting molecule may comprise at least one, two, three, four or five LIGHT fusion molecules, each one comprising at least one LIGHT moiety and at least one targeting moiety. In one embodiment, the LIGHT targeting molecule comprises, or consists essentially of, three LIGHT fusion molecules, each one comprising, or consisting essentially of, one LIGHT moiety (e.g., a LIGHT moiety as described herein) and one targeting moiety (e.g., a targeting moiety as described herein).

As used herein, a "fusion protein" refers to a protein containing two or more operably associated, e.g., linked, moieties, e.g., protein moieties. Typically, the moieties are covalently associated. The moieties can be directly associated, or connected via a spacer or linker (e.g., a linking group as described herein).

In other embodiments, the targeting moiety directs the LIGHT targeting moiety to a desired site, e.g., a hyperproliferative, e.g., cancerous, cell or tissue, such that the LIGHT moiety induces one or more LIGHT-associated activities (e.g., one or more of the LIGHT-associated activities as described herein) against the desired site (e.g., the hyperproliferative, e.g., cancerous, cell or tissue). Exemplary hyperproliferative, e.g., cancerous, cells or tissues, that can be targeted with the targeting moiety, include, but are not limited to, cancers or solid tumors of the breast, lung, stomach, ovaries, prostate, pancreas, colon, colorectum, renal, bladder, liver, head, neck, brain, as well as soft-tissue malignancies, including lymphoid malignacies, leukemia and myeloma. The targeting moiety can bind to one or more cell surface proteins expressed on one or more of the hyperproliferative cells or tissues described herein. For example, the targeting moiety, e.g., an antibody molecule as described herein, can bind to one or more of a growth factor receptor (e.g., HER-2/neu, HER3, HER4, epidermal growth factor receptor (EGFR), insulin growth factor receptor (IGFR), Met, Ron, Cripto); a cancer-related integrin or integrin receptor (e.g., αvβ6, α6β4, laminin receptor (LAMR); and/or CD23, CD20, CD16, EpCAM and/or Tweak receptor (FN14). Each one of the selected targets is described in more detail herein.

Epidermal growth factor receptor: The nucleotide acid sequences of human EGFR genomic DNA and mRNA are disclosed e.g., in Ullrich A et al., *Nature* 309:418-425 (1984) (isoform 1); Ilekis J. V., et al. (1995) *Mol. Reprod. Dev.* 41:149-156 (isoform 2); Reiter J. L. and Maihle N. J. *Nucleic Acids Res.* 24:4050-4056 (1996) (isoform 2); Ilekis J. V. et al., *Gynecol. Oncol.* 65:36-41 (1997) (isoform 2); and Reiter J. L., et al., *Genomics* 71:1-20 (2001) (isoforms 3 and 4). The protein sequences of human EGFR and its phosphorylation and ubiquitination sites are disclosed e.g., in Heisermann G. J. and Gill G. N. *J. Biol. Chem.* 263:13152-13158 (1988); Zhang Z. and Henzel W. J. *Protein Sci.* 13:2819-2824 (2004); Russo M. W. et al., *J. Biol. Chem.* 260:5205-5208 (1985); Huang F. et al, *Mol. Cell.* 21:737-748 (2006); and Abe Y. et al., *J. Biol. Chem.* 273:11150-11157 (1998). The nucleotide acid and protein sequences of mouse EGFR mRNA are disclosed in e.g., Avivi A. et al., *Oncogene* 7:1957-1962 (1992); Paria B. C. et al., *Proc. Natl. Acad. Sci. U.S.A.* 90:55-59 (1993); Luetteke N. C. et al., *Genes Dev.* 8:399-413 (1994); and Avivi A. et al., *Oncogene* 6:673-676 (1991). Human EGFR is ubiquitously expressed. Isoform 2 is also expressed in ovarian cancers. Mutations in this gene are associated with lung cancer. EGFR phosphorylates MUC1 in breast cancer cells and increases the interaction of MUC1 with C-SRC and CTNNB1/beta-catenin.

Insulin-like growth factor 1: The nucleotide acid sequences of human IGF1R genomic DNA and mRNA are disclosed e.g., in Ullrich A. et al., *EMBO J.* 5:2503-2512 (1986); Abbot A. M. et al., *J. Biol. Chem.* 267:10759-10763 (1992); The MGC Project Team, *Genome Res.* 14:2121-2127 (2004); Cooke D. W. et al., *Biochem. Biophys. Res. Commun.* 177:1113-1120 (1991); and Lee S.-T., et al., *Oncogene* 8:3403-3410 (1993). The protein sequences of human IGF1R are disclosed e.g., Ullrich A. et al., *EMBO J.* 5:2503-2512 (1986). The nucleotide acid and protein sequences of mouse IGF1R mRNA are disclosed in e.g., Wada J. et al., *Proc. Natl. Acad. Sci. U.S.A.* 90:10360-10364 (1993); and Wilks A. F. et al., *Gene* 85:67-74 (1989). Human IGF1R is expressed in various tissues. Defects in IGF1R may be a cause in some cases of resistance to insulin-like growth factor 1 (IGF1 resistance). IGF1 resistance is a growth deficiency disorder characterized by intrauterine growth retardation and poor postnatal growth accompanied with increased plasma IGF1.

HER3: The nucleotide acid and protein sequences of human HER3 are disclosed e.g., in Kraus M. H. et al., *Proc. Natl. Acad. Sci. U.S.A.* 86:9193-9197 (1989) (isoform 1); Plowman G. D. et al., *Proc. Natl. Acad. Sci. U.S.A.* 87:4905-4909 (1990) (isoform 1); Katoh M. et al., *Biochem. Biophys. Res. Commun.* 192:1189-1197 (1993) (isoform 2); and The MGC Project Team, *Genome Res.* 14:2121-2127 (2004) (isoform 1). The nucleotide acid and protein sequences of mouse HER3 are disclosed e.g., in The MGC Project Team, *Genome Res.* 14:2121-2127 (2004); and Moscoso L. M. et al., *Dev. Biol.* 172:158-169 (1995). Human HER3 is expressed in epithelial tissues and brain. It is overexpressed in a subset of human mammary tumors. Defects in HER3 are the cause of lethal congenital contracture syndrome type 2 (LCCS2); also called Israeli Bedouin multiple contracture syndrome type A. LCCS2 is an autosomal recessive neurogenic form of a neonatally lethal arthrogryposis that is associated with atrophy of the anterior horn of the spinal cord.

HER4: The nucleotide acid and protein sequences of human HER4 are disclosed e.g., in Plowman G. D., et al., *Proc. Natl. Acad. Sci. U.S.A.* 90:1746-1750 (1993) (isoform JM-A); Elenius K. et al., *J. Biol. Chem.* 272:26761-26768 (1997) (isoforms JM-A and JM-B); and The MGC Project Team, *Genome Res.* 14:2121-2127 (2004) (isoform JM-A). The nucleotide acid and protein sequences of mouse HER4 are disclosed e.g., in Carninci P. et al., *Science* 309:1559-1563 (2005); Elenius K. et al., *J. Biol. Chem.* 272:26761-26768 (1997); Moscoso L. M. et al., *Dev. Biol.* 172:158-169 (1995). Human HER4 is expressed at highest levels in brain, heart, kidney, in addition to skeletal muscle, parathyroid, cerebellum, pituitary, spleen, testis and breast; and lower levels in thymus, lung, salivary gland, and pancreas. Mutations in this gene have been associated with cancer.

MET: Met proto-oncogene (hepatocyte growth factor receptor) (MET) is also known in the art as HGFR, AUTS9, RCCP2 and c-Met. The nucleotide acid and protein sequences of human MET are disclosed e.g., in Park M. et al., *Proc. Natl. Acad. Sci. U.S.A.* 84:6379-6383 (1987) (isoform 2); Hillier L. W. et al., *Nature* 424:157-164 (2003); Chan A. M.-L. et al., *Oncogene* 1:229-233 (1987). Lee S.-T. et al., *Oncogene* 8:3403-3410 (1993); and Dean M. et al., *Nature* 318:385-388 (1985). The nucleotide acid and protein sequences of mouse MET are disclosed e.g., in Chan A. M.-L. et al., *Oncogene* 2:593-599 (1988); Wilks A. F. *Gene* 85:67-74 (1989); and Weidner K. M. et al., *J. Cell Biol.* 121:145-154 (1993). Activation of MET after rearrangement with the TPR gene produces an oncogenic protein. Defects in MET may be associated with gastric cancer. Defects in MET are a cause of hepatocellular carcinoma (HCC) and a cause of hereditary papillary renal carcinoma (HPRC) also known as papillary renal cell carcinoma 2 (RCCP2). HPRC is a form of inherited kidney cancer characterized by a predisposition to develop multiple, bilateral papillary renal tumors. The pattern of inheritance is consistent with autosomal dominant transmission with reduced penetrance. Genetic variations in MET may be associated with susceptibility to autism type 1B (AUTS1B).

RON: The nucleotide acid and protein sequences of human RON are disclosed e.g., in Ronsin C. et al., *Oncogene* 8:1195-1202 (1993); and Collesi C. et al., *Mol. Cell. Biol.* 16:5518-5526 (1996). The nucleotide acid and protein sequences of mouse RON are disclosed e.g., in Iwama A. et al., *Blood* 83:3160-3169 (1994); Waltz S. E. et al., *Oncogene* 16:27-42 (1998); and Persons D. A. et al., *Nat. Genet.* 23:159-165 (1999). RON is expressed in keratinocytes and lung. It confers susceptibility to friend virus induced erythroleukemia in mice.

Cripto: The nucleotide acid and protein sequences of human Cripto are disclosed e.g., in Ciccodicola A. et al., *EMBO J.* 8:1987-1991 (1989); Dono R. et al., *Am. J. Hum. Genet.* 49:555-565 (1991); Zhang Z. and Henzel W. J. *Protein Sci.* 13:2819-2824 (2004); Foley S. F. et al., Eur. J. Biochem. 270:3610-3618 (2003). The nucleotide acid and protein sequences of mouse Cripto are disclosed e.g., in. Dono R. et al., *Development* 118:1157-1168 (1993); and Liguori G. et al., *Mamm. Genome* 7:344-348 (1996). Cripto is preferentially expressed in gastric and colorectal carcinomas than in their normal counterparts. In mice, it is expressed at low level in specific organs of the adult animal such as spleen, heart, lung and brain. Examples of antibody molecules that bind to Cripto are described in e.g., U.S. Patent Appl. Publ. No.: 200810166341A1.

VEGFR: The nucleotide acid and protein sequences of human VEGFR are disclosed e.g., in Shibuya M. et al., *Oncogene* 5:519-524 (1990) (isoform Flt1); Kendall R. L. and Thomas K. A. *Proc. Natl. Acad. Sci. U.S.A.* 90:10705-10709 (1993) (isoform SFLT1); The MGC Project Team, *Genome Res.* 14:2121-2127 (2004) (isoform sFlt1); Matsushime H. et al., *Jpn. J. Cancer Res.* 78:655-661 (1987) (isoform Flt1); and Ito N. et al., *J. Biol. Chem.* 273:23410-23418 (1998). The nucleotide acid and protein sequences of mouse VEGFR are disclosed e.g., in Finnerty H. et al., *Oncogene* 8:2293-2298 (1993); Choi K. et al., *Oncogene* 9:1261-1266 (1994); and Kondo K. et al., *Gene* 208:297-305 (1998). VEGFR is mostly expressed in normal lung, but also in placenta, liver, kidney, heart and brain tissues. It is specifically expressed in most of the vascular endothelial cells, and also expressed in peripheral blood monocytes. It is not expressed in tumor cell lines. Isoform sFlt1 is strongly expressed in placenta.

Integrin αvβ6: Integrins are cell surface receptors that interact with the extracellular matrix (ECM) and mediate various intracellular signals. There are many types of integrin, and many cells have multiple types on their surface. Integrins are obligate heterodimers containing two distinct chains, called the α (alpha) and β (beta) subunits. In mammals, 19 α and 8 β subunits have been characterized. The nucleotide and protein sequences of human integrin αv are disclosed e.g., in Suzuki S. et al., *J. Biol. Chem.* 262:14080-14085 (1987); Sims M. A., *Cytogenet. Cell Genet.* 89:268-271 (2000); Hillier L. W. et al., *Nature* 434:724-731 (2005); The MGC Project Team, *Genome Res.* 14:2121-2127 (2004); Donahue J. P. et al., *Biochim. Biophys. Acta* 1219:228-232 (1994); Suzuki S. et al., *Proc. Natl. Acad. Sci. U.S.A.* 83:8614-8618 (1986); Cheresh D. A. et al., *Cell* 57:59-69 (1989). The nucleotide and protein sequences of mouse integrin av are disclosed e.g., in Almeida J. Submitted (APR-2008) to the EMBL/GenBank/DDBJ databases. The nucleotide and protein sequences of human integrin β6 are disclosed e.g., in Sheppard D. et al., *J. Biol. Chem.* 265: 11502-11507 (1990); Hillier L. W., *Nature* 434:724-731 (2005); The MGC Project Team, *Genome Res.* 14:2121-2127 (2004); Jiang W.-M. et al., *Int. Immunol.* 4:1031-1040 (1992). The nucleotide and protein sequences of mouse integrin β6 are disclosed e.g., in Arend L. J. et al., *J. Am. Soc. Nephrol.* 11:2297-2305 (2000); Carninci P. et al., *Science* 309:1559-1563 (2005); The MGC Project Team, *Genome Res.* 14:2121-2127 (2004).

Integrin αvβ6 is mostly distributed in proliferating epithelia, e.g. lung and liver. Functions of integrin αvβ6 are disclosed in e.g., Jovanović J. et al., *Biochem Soc Trans.* 36(Pt 2):257-262 (2008); Wipff P. J. and Hinz B. Eur *J Cell Biol.* 87:601-615 (2008); Bates R. C. *Future Oncol.* 1:821-8 (2005); Thomas G. J. et al., *J Oral Pathol Med.* 35:1-10 (2006); Sheppard D. *Cancer Metastasis Rev.* 24:395-402 (2005); Bates R. C. and Mercurio A. M. *Cancer Biol Ther.* 4:365-370 (2005); Keski-Oja J. et al., *Trends Cell Biol.* 14:657-659 (2004); Sheppard D. *Curr Opin Cell Biol.* 16:552-557 (2004); Wada J. et al., *Nephrol Dial Transplant.* 17:75-77 (2002); Thomas G. J. and Speight P. M. *Crit. Rev Oral Biol Med.* 12:479-498 (2001); and Imhof B. A. et al., *Curr Top Microbiol Immunol.* 213:195-203 (1996).

Integrin α6β4: The nucleotide and protein sequences of human integrin α6 are disclosed e.g., in Hogervorst F. et al., *Eur. J. Biochem.* 199:425-433 (1991); Starr L. et al., BioTechniques 13:612-618 (1992); Tamura R. N. et al., *Proc. Natl. Acad. Sci. U.S.A.* 88:10183-10187 (1991); Ziober B. L. et al., *J. Biol. Chem.* 268:26773-26783 (1993); Shaw L. M. et al., *J. Biol. Chem.* 268:11401-11408 (1993); and Delwel G. O. et al., *Cell Adhes. Commun.* 3:143-161 (1995). The nucleotide and protein sequences of mouse integrin α6 are disclosed e.g., in Carninci P. et al., *Science* 309:1559-1563 (2005). The nucleotide and protein sequences of human integrin β4 are disclosed e.g., in Suzuki S, and Naitoh Y. EMBO J. 9:757-763 (1990); Hogervorst F. et al., *EMBO J.* 9:765-770 (1990); and Tamura R. N. et al., *J. Cell Biol.* 111:1593-1604 (1990). The nucleotide and protein sequences of mouse integrin β4 are disclosed e.g., in Brown J. Submitted (APR-2008) to the EMBL/GenBank/DDBJ database.

Integrin α6β4 is mostly expressed in epithelial tissues and endothelial and Schwann cells. Expression of α6β4 is increased in many epithelial tumors and it activates several key signaling molecules in carcinoma cells, including activating the phosphatidylinositol 3-kinase/Akt pathway (Bon G. et al., *Breast Cancer Res.* 9:203 (2007); Wilhelmsen K, A. et al., *Mol Cell Biol.* 26:2877-86 (2006)).

LAMR: Ribosomal protein SA (LAMR) It is also known in the art as RPSA, LRP, p40, 67LR, 37LRP, LAMBR and LAMR1. Laminins, a family of extracellular matrix glycoproteins, are the major noncollagenous constituent of basement membranes. The nucleotide and protein sequences of human LAMR are disclosed e.g., in Yow H. et al., *Proc. Natl. Acad. Sci. U.S.A.* 85:6394-6398 (1988); van den Ouweland A. M. W. et al., *Nucleic Acids Res.* 17:3829-3843 (1989); Satoh K. et al., *Cancer Lett.* 62:199-203 (1992); Jackers P. et al., *Oncogene* 13:495-503 (1996); The MGC Project Team, *Genome Res.* 14:2121-2127 (2004); Siyanova E. Y. et al., *Dokl. Biochem.* 313:227-231 (1990); Vladimirov S, N. et al., *Eur. J. Biochem.* 239:144-149 (1996); Selvamurugan N. and Eliceiri G. L. et al., *Genomics* 30:400-401 (1995); and Wewer U. M. et al., *Proc. Natl. Acad. Sci. U.S.A.* 83:7137-7141 (1986). The nucleotide and protein sequences of mouse LAMR are disclosed e.g., Rao C. N. et al., *Biochemistry* 28:7476-7486 (1989); Makrides S. et al., *Nucleic Acids Res.* 16:2349-2349 (1988); Coggin J. H. Jr. et al., *Anticancer Res.* 19:5535-5542 (1999); Carninci P. et al., *Science* 309:1559-1563 (2005); and The MGC Project Team, *Genome Res.* 14:2121-2127 (2004). It has been observed that the level of the laminin receptor transcript is higher in colon carcinoma tissue and lung cancer cell line than their normal counterparts. Also, there is a correlation between the upregulation of this polypeptide in cancer cells and their invasive and metastatic phenotype.

CD23: Fc fragment of IgE, low affinity II, receptor for (CD23) It is also known in the art as FCER2, FCE2, CD23A, IGEBF and CLEC4J. The human leukocyte differentiation antigen CD23 (FCE2) is a key molecule for B-cell activation and growth. It is the low-affinity receptor for IgE. The truncated molecule can be secreted, then functioning as a potent mitogenic growth factor. The nucleotide acid and protein sequences of human CD23 are disclosed e.g., in Ikuta K. et al., *Proc. Natl. Acad. Sci. U.S.A.* 84:819-823 (1987); Kikutani H. et al., *Cell* 47:657-665 (1986); Luedin C. et al., *EMBO J.* 6:109-114 (1987); The MGC Project Team, *Genome Res.* 14:2121-2127 (2004); Rose K. et al., *Biochem. J.* 286:819-824 (1992); and Yokota A. et al., *Cell* 55:611-618 (1988). The nucleotide acid and protein sequences of mouse CD23 are disclosed e.g., in Bettler B. et al., *Proc. Natl. Acad. Sci. U.S.A.* 86:7566-7570 (1989); Gollnick S. O. et al., *J. Immunol.* 144: 1974-1982 (1990); and Kondo H. et al., *Int. Arch. Allergy Immunol.* 105:38-48 (1994). Anti-CD23 antibodies that can be used as targeting moieties are described, e.g., in U.S. Pat. Nos. 7,332,163 and 7,223,392.

CD20: Membrane-spanning 4-domains, subfamily A, member 1 (CD20) is also known in the art as MS4A1, B1, S7, Bp35, MS4A2, LEU-16 and MGC3969. CD20 encodes a member of the membrane-spanning 4A gene family. The nucleotide acid and protein sequences of human CD20 are disclosed e.g., in Stamenkovic I. and Seed B. *J. Exp. Med.* 167:1975-1980 (1988); Tedder T. F. et al., *Proc. Natl. Acad. Sci. U.S.A.* 85:208-212 (1988); Einfeld D. A. et al., *EMBO J.* 7:711-717 (1988); Tedder T. F. et al., *J. Immunol.* 142:2560-2568 (1989); Taylor T. D. et al., *Nature* 440:497-500 (2006); and The MGC Project Team, *Genome Res.* 14:2121-2127 (2004). The nucleotide acid and protein sequences of mouse CD20 are disclosed e.g., in Tedder T. F. et al., *J. Immunol.* 141:4388-4394 (1988); Carninci P. et al., *Science* 309:1559-1563 (2005); and The MGC Project Team, *Genome Res.* 14:2121-2127 (2004). CD20 is expressed on B-cells. This gene encodes a B-lymphocyte surface molecule which plays a role in the development and differentiation of B-cells into plasma cells.

CD16: Fc fragment of IgG, low affinity IIIa or IIIb, receptor (CD16) It is also know in the art as FCGR3A, FCGR3B, FCG3, CD16A, FCGR3, IGFR3, FCR-10, FCRIII, FCGRIII and FCRIIIA The nucleotide acid and protein sequences of human CD16a and CD16b are disclosed e.g., in The MGC Project Team, *Genome Res.* 14:2121-2127 (2004); and Scallon B. J. et al., *Proc. Natl. Acad. Sci. U.S.A.* 86:5079-5083 (1989). The nucleotide acid and protein sequences of human CD16b are disclosed e.g., in Ravetch J. V. and Perussia B. *J. Exp. Med.* 170:481-497 (1989); Simmons D. and Seed B. *Nature* 333:568-570 (1988); Simmons D. and Seed B. *Nature* 340:662-662 (1989); Peltz G. A. et al., *Proc. Natl. Acad. Sci. U.S.A.* 86:1013-1017 (1989); Scallon B. J. et al., *Proc. Natl. Acad. Sci. U.S.A.* 86:5079-5083 (1989); Bertrand G. et al., *Tissue Antigens* 64:119-131 (2004); and Gessner J. E. et al., *J. Biol. Chem.* 270:1350-1361 (1995). The nucleotide acid and protein sequences of mouse CD16 are disclosed e.g., Bonnerot C. et al., *Mol. Immunol.* 29: 353-361 (1992); and Kulczycki A. Jr. et al., *Proc. Natl. Acad. Sci. U.S.A.* 87: 2856-2860 (1990). The receptor encoded by FCGR3A is expressed on natural killer (NK) cells as an integral membrane glycoprotein anchored through a transmembrane peptide, whereas FCGR3B is expressed on polymorphonuclear neutrophils (PMN) where the receptor is anchored through a phosphatidylinositol (PI) linkage. Mutations in this gene have been linked to susceptibility to recurrent viral infections, susceptibility to systemic lupus erythematosus, and alloimmune neonatal neutropenia. The more active FCGR3B*01 allele has been associated with severe renal disease in certain systemic vasculitides.

EpCAM: Tumor-associated calcium signal transducer 1 (EpCAM) It is also known in the art as TACSTD1, EGP, KSA, M4S1, MK-1, CD326, EGP40, MIC18, TROP1, Ep-CAM, hEGP-2, C017-1A and GA733-2. This 9-exon gene encodes a carcinoma-associated antigen and is a member of a family that includes at least two type I membrane proteins. The nucleotide acid and protein sequences of human EpCAM are disclosed e.g., in Stranad J. et al., *Cancer Res.* 49:314-317 (1989); Simon B. et al., *Proc. Natl. Acad. Sci. U.S.A.* 87:2755-2759 (1990); Perez M. S, and Walker L. E. *J. Immunol.* 142:3662-3667 (1989); Szala S. et al., *Proc. Natl. Acad. Sci. U.S.A.* 87:3542-3546 (1990); The MGC Project Team, *Genome Res.* 14:2121-2127 (2004); Linnenbach A. J. et al., *Proc. Natl. Acad. Sci. U.S.A.* 86:27-31 (1989); and Chong J. M. and Speicher D. W. *J. Biol. Chem.* 276:5804-5813 (2001). The nucleotide acid and protein sequences of mouse EpCAM are disclosed e.g., in The MGC Project Team, *Genome Res.* 14:2121-2127 (2004); and Carninci P. et al., *Science* 309: 1559-1563 (2005). This antigen is expressed on most normal epithelial cells and gastrointestinal carcinomas and functions as a homotypic calcium-independent cell adhesion molecule.

FN14: Tumor necrosis factor receptor superfamily, member 12A (FN14) It is also known in the art as TNFRSF12A, CD266 and TWEAKR. It is a receptor for TNFSF12/TWEAK. The nucleotide and protein sequences of human FN14 are disclosed e.g., in Feng S.-L. Y. et al., *Am. J. Pathol.* 156:1253-1261 (2000); and The MGC Project Team, *Genome Res.* 14:2121-2127 (2004). The nucleotide and protein sequences of mouse FN14 are disclosed e.g., in Meighan-Mantha R. L. et al., *J. Biol. Chem.* 274:33166-33176 (1999); Carninci P., *Science* 309:1559-1563 (2005); and The MGC Project Team, *Genome Res.* 14:2121-2127 (2004). The unprocessed precursor of human FN14 is about 129 amino acids in length and about 13911 Da in molecular weight. The unprocessed precursor of mouse FN14 is about 129 amino acids in length and about 13641 Da in molecular weight. Human FN14 is highly expressed in heart, placenta and kidney; and moderately expression in lung, skeletal muscle and pancreas. Mouse FN14 is highly expressed in fetal heart, intestine, kidney, liver, lung and skin, and in adult heart and ovary; and moderately expression in adult kidney, lung and skin.

The targeting moiety, e.g., an antibody molecule as described herein, can also bind to one or more of the following: a tyrosine-protein kinase receptor (e.g., TYRO3 (tyrosine-protein kinase receptor TYRO3, also known as tyrosine-protein kinase RSE, SKY, DTK, or byk, Mark M. R. et al., *J. Biol. Chem.* 269:10720-10728 (1994)); AXL (also know as tyrosine-protein kinase receptor UFO; O'Bryan J. P. et al., *Mol. Cell. Biol.* 11:5016-5031 (1991)); DDR1 (epithelial discoidin domain-containing receptor 1, also known as tyrosine kinase DDR, discoidin receptor tyrosine kinase, tyrosine-protein kinase CAK, cell adhesion kinase, TRK E, protein-tyrosine kinase RTK 6, HGK2, CD167 antigen-like family member A, mammary carcinoma kinase 10 (MCK-10), or CD167a; Perez J. L. et al., *Oncogene* 9:211-219 (1994)); DDR2 (discoidin domain-containing receptor 2, also known as receptor protein-tyrosine kinase TKT, tyrosine-protein kinase TYRO10, neurotrophic tyrosine kinase, receptor-related 3, CD167 antigen-like family member B, or CD167b; Ichikawa O. et al., *EMBO J.* 26:4168-4176 (2007)); ALK (ALK tyrosine kinase receptor, also known as anaplastic lymphoma kinase or CD246; Simonitsch I. et al., *FASEB J.* 15:1416-1418 (2001)); CSF1R (macrophage colony-stimulating factor 1 receptor, also known as Fms proto-oncogene, c-fms, or CD115; Hampe A. et al., *Oncogene Res.* 4:9-17 (1989))); a growth factor receptor (e.g., FGFR1 (basic fibroblast growth factor receptor 1, also known as bFGF-R, Fms-like tyrosine kinase 2, c-fgr, or CD331; Dionne C. A. et al., *EMBO J.* 9:2685-2692 (1990)); FGFR2 (fibroblast growth factor receptor 2, also known as keratinocyte growth factor receptor 2 or CD332; Hattori Y. et al., *Proc. Natl. Acad. Sci. U.S.A.* 87:5983-5987 (1990))); a growth factor (e.g., PDGF1 (also known as platelet-derived growth factor subunit A, platelet-derived growth factor A chain, or platelet-derived growth factor alpha polypeptide; Bonthron D. T. et. al., *Proc. Natl. Acad. Sci. U.S.A.* 85:1492-1496 (1988)); PDGF2 (also known as platelet-derived growth factor subunit B, platelet-derived growth factor B chain, platelet-derived growth factor beta polypeptide, or c-sis; Josephs S. F. et al., *Science* 225: 636-639 (1984))); an apoptosis protein (e.g., a Netrin, e.g., Netrin-1 (Meyerhardt J. A. et al., *Cell Growth Differ.* 10:35-42 (1999), or Netrin-4 (also known as Beta-netrin or Hepar-derived netrin-like protein; Koch M. et al., *J. Cell Biol.* 151: 221-234 (2000))); a tyrosine kinase (e.g., MER (Proto-oncogene tyrosine-protein kinase MER, also known as C-mer or Receptor tyrosine kinase MerTK; Graham D. K. et al., *Cell Growth Differ.* 5:647-657 (1994))); a hormone receptor (e.g., PRL-R (Prolactin receptor; Boutin J.-M. et al., *Mol. Endocrinol.* 3:1455-1461 (1989)); GH receptor (growth hormone receptor, also known as somatotropin receptor, GH-binding protein, GHBP, or Serum-binding protein; Leung D. W. et al., *Nature* 330:537-543 (1987))); a signal transduction protein (e.g., ephrin, e.g., ephrin A (e.g., ephrin A1, ephrin A2, ephrin A3, ephrin A4, ephrin A5; Holzman L. B. et al., *Mol. Cell. Biol.* 10 (11): 5830-5838 (1990)) and ephrin B (e.g., ephrin B1, ephrin B2, ephrin B3; Fletcher F. A. et al. *Genomics* 25 (1): 334-335 (1995)); PD-L1 (programmed cell death ligand 1, also known as B7-H1 or CD274; Dong H. et al., *Nat. Med.* 5:1365-1369 (1999)); neuropilin (e.g., NRP1 (Neuropilin-1, also known as Vascular endothelial cell growth factor 165 receptor or CD304; He Z. and Tessier-Lavigne M. *Cell* 90:739-751 (1997)); NRP2 (Neuropilin-2, also known as vascular endothelial cell growth factor 165 receptor 2; Chen H. et al., *Neuron* 19:547-559 (1997)); or Semaphorin (SEMA, e.g., SEMA3, SEMA4, SEMAS, SEMA6, or SEMA7; Flannery E. and Duman-Scheel M. *Curr Drug Targets.* 10:611-619 (2009))); a cell adhesion molecule (e.g., Mesothelin (MSLN, also known as Pre-pro-megakaryocyte-potentiating factor, CAK1 antigen, or Megakaryocyte-potentiating factor (MPF); Chang K. and Pastan I. *Proc. Natl. Acad. Sci. U.S.A.* 93:136-140 (1996)); Nectin, (e.g, Nectin 1, Nectin 2, Nectin 3, Nectin 4, Nectin-like protein 1, Nectin-like protein 2, Nectin-like protein 3, or Nectin-like protein 4; Takai Y. et al., *Nat. Rev. Mol. Cell Biol.* 9:603-615 (2008)); CEA (Carcinoembryonic antigen-related cell adhesion molecule, e.g., CEAS; Schrewe H. et al., *Mol. Cell. Biol.* 10:2738-2748 (1990); CEACAM6 (Carcinoembryonic antigen-related cell adhesion molecule 6, also known as Normal cross-reacting antigen, Non-specific crossreacting antigen, or CD66c; Barnett T. et al., *Genomics* 3:59-66 (1988))); a chemokine receptor (e.g., CCR4 (C-C chemokine receptor type 4, also known as C-C CKR-4, CC-CKR-4, K5-5, or CD194; Power C. A. et al., *J. Biol. Chem.* 270:19495-19500 (1995)); CXCR7 (C-X-C chemokine receptor type 7, also known as CXC-R7, G-protein coupled receptor RDC1 homolog, RDC-1, Chemokine orphan receptor 1, or G-protein coupled receptor 159; Sreedharan S. P. et al., *Proc. Natl. Acad. Sci. U.S.A.* 88:4986-4990 (1991))); a G-protein coupled receptor (e.g., GPR49 (Leucine-rich repeat-containing G-protein coupled receptor 5, also known as Orphan G-protein coupled receptor HG38, G-protein coupled receptor 49, or G-protein coupled receptor 67; McDonald T. et al., *Biochem. Biophys. Res. Commun.* 247: 266-270 (1998)); SIT receptor (Sphingosine 1-phosphate receptor, also known as Endothelial differentiation G-protein coupled receptor; e.g., S1P1, S1P2, S1P3, S1P4, S1P5; Hla T. and Maciag T. *J. Biol. Chem.* 265:9308-9313 (1990))); an angiogenesis factor receptor (e.g., TIE2 (Angiopoietin-1 receptor, TEK, Tunica interna endothelial cell kinase, p140 TEK, or CD202b; Ziegler S. F. et al., *Oncogene* 8:663-670 (1993))); a membrane-bound mucin (e.g., MUC1 (also known as PEM, PEMT, Episialin, EMA, H23AG, PUM, or CD227; Lan M. S. et al., *J. Biol. Chem.* 265:15294-15299 (1990)), MUC2 (also known as Intestinal mucin-2; Gum J. R. Jr. et. al., *J. Biol. Chem.* 269:2440-2446 (1994)), MUC3 (also known as Intestinal mucin-3; Hillier L. W. et al., *Nature* 424:157-164 (2003)), MUC4 (also known as Pancreatic adenocarcinoma mucin, Testis mucin, ASGP, or Tracheobronchial mucin; Moniaux N. et al., *Eur. J. Biochem.* 267: 4536-4544 (2000)), MUC5AC (also known as TBM, Major airway glycoprotein, Gastric mucin, or LeB; Escande F. et al., *Biochem. J.* 358:763-772 (2001)), and MUC 16 (also known as CA-125; O'Brien T. J. et al., *Tumor Biol.* 23:154-169 (2002))); a tumor marker (e.g., Endosialin (also known as Tumor endothelial marker 1 or CD248; a C-type lectin-like protein; St Croix B. et al., *Science* 289:1197-1202 (2000)); PSMA (Prostate specific membrane antigen, also known as PSA, Kallikrein-3, Semenogelase, Seminin, or P-30 antigen; Lundwall A. and Lilja H. *FEBS Lett.* 214:317-322 (1987)); TAG-72 (Tumor associated glycoprotein 72; a protein/sugar complex found on the surface of many cancer cells, including breast, colon, and pancreatic cells; Alles A. J. et al., *Ann Surg.* 219(2): 131-134 (1994)); KIM-1 (Kidney injury molecule-1, also known as T-cell immunoglobulin and mucin-containing molecule (Tim-1) or Hepatitis A virus cellular receptor 1 (HAVCR1); Feigelstock D. et al., *J. Virol.* 72:6621-6628 (1998))); a cell surface marker on melanoma (e.g., MART-1 (Melanoma antigen recognized by T-cells 1, also known Melan-A protein, Antigen SK29-AA, or Antigen LB39-AA; Kawakami Y. et al., *Proc. Natl. Acad. Sci. U.S.A.* 91:3515-3519 (1994)); gp100 (Melanocyte lineage-specific antigen GP100, also known as Melanocyte protein Pmel 17, Silver locus protein homolog, ME20-M, ME20-S, or 95 kDa melanocyte-specific secreted glycoprotein; Adema G. J. et al., *J. Biol. Chem.* 269:20126-20133 (1994)); TRP-1 (Tyrosinase-related protein 1, also known as DHICA oxidase, Catalase B, Glycoprotein 75, or Melanoma antigen gp75; Cohen T. et al., *Nucleic Acids Res.* 18:2807-2807 (1990)); TRP-2 (Tyrosinase-related protein 2, also known as DCT, DT, or L-dopachrome Delta-isomerase; Yokoyama K. et al., *Biochim. Biophys. Acta* 1217:317-321 (1994))); or a heat shock protein (e.g., GRP78 (78 kDa glucose-regulated protein, also known as Heat shock 70 kDa protein 5, BiP, or Endoplasmic reticulum lumenal Ca(2+)-binding protein grp78; Corrigall V. M. et al., *J. Immunol.* 166:1492-1498 (2001))).

The fusion proteins may additionally include a linker sequence joining the first moiety, e.g., the LIGHT moiety, to the second moiety, e.g., the targeting moiety. The linking group can be any linking group apparent to those of skill in the art. For example, the fusion protein can include a peptide linker, e.g., a peptide linker of about 5 to 50, more preferably, 10 to 35, or 15 to 33 amino acids in length; the peptide linker is about 20, 28 or 33 amino acids in length. Each of the amino acids in the peptide linker is selected from the group consisting of Gly, Ser, Asn, Thr and Ala; the peptide linker includes a Gly-Ser element. In other embodiments, the fusion protein includes a peptide linker and the peptide linker includes a sequence having the formula (Gly-Gly-Gly-Gly-Ser)y wherein y is 1, 2, 3, 4, 5, 6, 7, or 8 (SEQ ID NO:149). In one embodiment, the linking group includes or consists of polyglycine, polyserine, polylysine, polyglutamate, polyisoleucine, or polyarginine residues, or a combination thereof. For example, the polyglycine or polyserine linkers can include at least five, ten, fifteen or twenty glycine and serine residues in the following configuration, (Gly)$_4$-Ser (SEQ ID NO: 145), in one, two, three, four, five or more repeats, e.g., four repeats of (Gly)$_4$-Ser (SEQ ID NO: 134). In other embodiments, linking group may include one or more amino acid residues (e.g., at least 10 to 35, 15 to 30, or about 20 to 26 amino acid residues) from the extracellular domain of LIGHT or a mutated form thereof, e.g., from about amino acids 61 to 92 of human LIGHT isoform 1 (SEQ ID NO:1), about amino acids 225 to 252 of 71F10 Fab-hLIGHT fusion heavy chain with the delta 4 linker (pBIIB71F10-130) (SEQ ID NO:2), about amino acids 230 to 257 of 71F10 Fab-hLIGHT fusion heavy chain with the G4S delta 4 linker (pBIIB71F10-131) (SEQ ID NO:3), or an amino acid sequence substantially identical thereto; or an amino acid sequence encoded by the nucleotide sequence from about nucleotides 181 to 276 of human LIGHT isoform 1 (SEQ ID NO:5), about nucleotides 673 to 756 of 71F10 Fab-hLIGHT fusion heavy chain with the delta 4 linker (pBIIB71F10-130) (SEQ ID NO:6), about nucleotides 688 to 771 of 71F10 Fab-hLIGHT fusion heavy chain with the $G_4S$ delta 4 linker (pBIIB71F10-131) (SEQ ID NO:7), or a nucleotide sequence substantially identical thereto (e.g., a sequence at least about 85%, 90%, 95% or higher identical thereto). Alternatively, the linking group may include a combination of one or more $(Gly)_4$-Ser (SEQ ID NO: 146) repeats and one or more amino acid residues (e.g., at least 10 to 35, 15 to 30, or about 20 to 26 amino acid residues) from the extracellular domain of LIGHT or a mutated form thereof, e.g., from about amino acids 61 to 92 of human LIGHT isoform 1 (SEQ ID NO:1), about amino acids 225 to 252 of 71F10 Fab-hLIGHT fusion heavy chain with the delta 4 linker (pBIIB71F10-130) (SEQ ID NO:2), about amino acids 230 to 257 of 71F10 Fab-hLIGHT fusion heavy chain with the $G_4S$ delta 4 linker (pBIIB71F10-131) (SEQ ID NO:3), or an amino acid sequence substantially identical thereto; or an amino acid sequence encoded by the nucleotide sequence from about nucleotides 181 to 276 of human LIGHT isoform 1 (SEQ ID NO:5), about nucleotides 673 to 756 of 71F10 Fab-hLIGHT fusion heavy chain with the delta 4 linker (pBIIB71F10-130) (SEQ ID NO:6), about nucleotides 688 to 771 of 71F10 Fab-hLIGHT fusion heavy chain with the $G_4S$ delta 4 linker (pBIIB71F10-131) (SEQ ID NO:7), or a nucleotide sequence substantially identical thereto (e.g., a sequence at least about 85%, 90%, 95% or higher identical thereto).

The amino acid and nucleotide sequences of 71F10 Fab-hLIGHT fusion heavy chain with the delta 4 linker (pBIIB71F10-130) are shown as SEQ ID NOs:2 and 6, respectively. The amino acid and nucleotide sequences corresponding to heavy chain of 71F10 Fab are shown starting from the N-terminus; followed by amino acids corresponding to the linking group (about amino acids 225 to 252); followed by the amino acids corresponding to human LIGHT extracellular domain (amino acids 253 to 400). The physical and chemical parameters of 71F10 Fab-Δ4huLIGHT are as follows: Extinction coefficient=1.62; pI=8.7; MW=66 kDa (x3=198 kDa); AA number=614).

The amino acid and nucleotide sequences of 71F10 Fab-hLIGHT fusion heavy chain with the $G_4S$ (SEQ ID NO:147) delta 4 linker (pBIIB71F10-131) are shown as SEQ ID NOs:3 and 7, respectively. The amino acid and nucleotide sequences corresponding to heavy chain of 71F10 Fab are shown starting from the N-terminus; followed by amino acids corresponding to the linking group (amino acids 225 to 257); followed by the amino acids corresponding to human LIGHT extracellular domain (amino acids 258 to 405). The physical and chemical parameters of 71F10 Fab-$G_4S$-Δ4huLIGHT are as follows: Extinction coefficient=1.61; pI=8.7; MW=66 kDa (x3=198 kDa); AA number=619).

The amino acid and nucleotide sequences of 71F10 Fab-hLIGHT fusion heavy chain with the $(G_4S)_4$ (SEQ ID NO:134) linker (pBIIB71F10-132) are shown as SEQ ID NOs:4 and 8, respectively. The amino acid and nucleotide sequences corresponding to heavy chain of 71F10 Fab are shown starting from the N-terminus; followed by amino acids corresponding to the linking group (amino acids 225 to 244); followed by the amino acids corresponding to human LIGHT extracellular domain (amino acids 245 to 392). The physical and chemical parameters of 71F10 Fab-$(G_4S)_4$-Δ4huLIGHT are as follows: Extinction coefficient=1.5; pI=8.7; MW=64 kDa (x3=198 kDa); AA number=606).

In other embodiments, additional amino acid sequences can be added to the N- or C-terminus of the fusion protein to facilitate expression, detection and/or isolation or purification. For example, fusion protein may be linked to one or more additional moieties, e.g., GST, His6 tag (SEQ ID NO:150), FLAG tag. For example, the fusion protein may additionally be linked to a GST fusion protein in which the fusion protein sequences are fused to the C-terminus of the GST (i.e., glutathione S-transferase) sequences. Such fusion proteins can facilitate the purification of the fusion proteins.

In another embodiment, the fusion protein includes a heterologous signal sequence (i.e., a polypeptide sequence that is not present in a polypeptide encoded by a LIGHT nucleic acid) at its N-terminus. For example, the native LIGHT signal sequence can be removed and replaced with a signal sequence from another protein. In certain host cells (e.g., mammalian host cells), expression and/or secretion of fusion protein can be increased through use of a heterologous signal sequence. A fusion protein of the invention can be produced by standard recombinant DNA techniques (see, for example, Ausubel et al. (eds.) *Current Protocols in Molecular Biology*, John Wiley & Sons, 1992). Moreover, many expression vectors are commercially available that encode a fusion moiety (e.g., an Fc region of an immunoglobulin heavy chain). A nucleic acid can be cloned into such an expression vector such that the fusion moiety is linked in-frame to the immunoglobulin protein.

In some embodiments, fusion polypeptides exist as oligomers, such as dimers or trimers of a single contiguous polypeptides, or two or more non-contiguous polypeptides.

In other embodiments, the LIGHT or the targeting moiety is provided as a variant polypeptide having a mutation in the naturally-occurring sequence (wild type) that results in one or more higher affinity binding, increased stability, e.g., more resistant to proteolysis (relative to the non-mutated sequence), among others.

In other embodiments, additional amino acid sequences can be added to the N- or C-terminus of the fusion protein to facilitate expression, steric flexibility, detection and/or isolation or purification. The second polypeptide is preferably soluble. In some embodiments, the second polypeptide enhances the half-life, (e.g., the serum half-life) of the linked polypeptide. In some embodiments, the second polypeptide includes a sequence that facilitates association of the fusion polypeptide with a second polypeptide. In embodiments, the second polypeptide includes at least a region of an immunoglobulin polypeptide. Immunoglobulin fusion polypeptides are known in the art and are described in, e.g., U.S. Pat. Nos. 5,516,964; 5,225,538; 5,428,130; 5,514,582; 5,714,147; and 5,455,165.

It will be understood that the antibody molecules and soluble LIGHT or fusion proteins described herein can be functionally linked (e.g., by chemical coupling, genetic fusion, non-covalent association or otherwise) to one or more other molecular entities, such as an antibody (e.g., a bispecific or a multispecific antibody), toxins, radioisotopes, cytotoxic or cytostatic agents, among others.

Exemplary LIGHT targeting molecules include a LIGHT/HER2 fusion, e.g., a LIGHT/HER2 fusion as described herein. LIGHT/HER2 fusions include, or consist essentially of, the amino acid sequence shown in any of 71F10 Fab-hLIGHT fusion heavy chain with the delta 4 linker (pBIIB71F10-130) (SEQ ID NO: 2), 71F10 Fab-hLIGHT fusion heavy chain with the $G_4S$ delta 4 linker (pBIIB71F10-131) (SEQ ID NO:3), 71F10 Fab-hLIGHT fusion heavy chain with the (G4S)4 linker (pBIIB71F10-132) (SEQ ID NO:4), or an amino sequence substantially identical thereto (e.g., a sequence at least about 85%, 90%, 95% or higher identical thereto); an amino acid sequence encoded by the nucleotide sequence shown in any of 71F10 Fab-hLIGHT fusion heavy chain with the delta 4 linker (pBIIB71F10-130) (SEQ ID NO:6), 71F10 Fab-hLIGHT fusion heavy chain with the $G_4S$ delta 4 linker (pBIIB71F10-131) (SEQ ID NO:7), 71F10 Fab-hLIGHT fusion heavy chain with the $(G_4S)_4$ linker (pBIIB71F10-132) (SEQ ID NO:8), or a nucleotide sequence substantially identical thereto (e.g., a sequence at least about 85%, 90%, 95% or higher identical thereto). In certain embodiments, the LIGHT/HER2 fusions may also include, or consist essentially of, a second chain (fused or in association with the aforesaid chains) comprising or consisting essentially of the amino acid sequence shown as SEQ ID NO:109, or an amino sequence substantially identical thereto (e.g., a sequence at least about 85%, 90%, 95% or higher identical thereto); an amino acid sequence encoded by the nucleotide sequence shown in any of SEQ ID NO:110, or a nucleotide sequence substantially identical thereto (e.g., a sequence at least about 85%, 90%, 95% or higher identical thereto).

In another exemplary embodiment, the LIGHT targeting molecule comprises at least one fusion molecule of a mammalian (e.g., human) LIGHT protein, or a functional variant or a fragment thereof, and an antibody molecule that binds to CD23 (referred to herein as "LIGHT-anti-CD23 fusion"). In one embodiment, the LIGHT-anti-CD23 fusion comprises, or consists essentially of the amino acid sequence shown in any of anti-CD23 Fab-hLIGHT fusion heavy chain with the $(G_3S)_3$ or $(G_4S)_4$ linker (pBIIB CD23-204) (SEQ ID NO:101 or 174), or an amino sequence substantially identical thereto (e.g., a sequence at least about 85%, 90%, 95% or higher identical thereto); an amino acid sequence encoded by the nucleotide sequence shown in any of anti-CD23 Fab-hLIGHT fusion heavy chain with the $(G_3S)_3$ or $(G_4S)_4$ linker (pBIIB CD23-204) (SEQ ID NO:102 or 173), or a nucleotide sequence substantially identical thereto (e.g., a sequence at least about 85%, 90%, 95% or higher identical thereto). In certain embodiments, the LIGHT/CD23 fusions may also include, or consist essentially of, a second chain (fused or in association with the aforesaid chains) comprising or consisting essentially of the amino acid sequence shown in anti-CD23 Fab-hLIGHT fusion light chain (SEQ ID NO:103), or an amino sequence substantially identical thereto (e.g., a sequence at least about 85%, 90%, 95% or higher identical thereto); an amino acid sequence encoded by the nucleotide sequence shown in any of anti-CD23 Fab-hLIGHT fusion light chain (SEQ ID NO:104), or a nucleotide sequence substantially identical thereto (e.g., a sequence at least about 85%, 90%, 95% or higher identical thereto).

In yet another exemplary embodiment, the LIGHT targeting molecule comprises at least one fusion molecule of a mammalian (e.g., human) LIGHT protein, or a functional variant or a fragment thereof, and an antibody molecule that binds to insulin growth factor receptor (referred to herein as "LIGHT-anti-IGFR Fab fusion"). In one embodiment, the LIGHT-anti-IGFR Fab fusion comprises, or consists essentially of the amino acid sequence shown in any of anti-IGFR Fab-hLIGHT fusion heavy chain with the $(G_4S)_4$ linker (BIIB C06-117) (SEQ ID NO:163), or an amino sequence substantially identical thereto (e.g., a sequence at least about 85%, 90%, 95% or higher identical thereto); an amino acid sequence encoded by the nucleotide sequence shown in any of anti-IGFR Fab-hLIGHT fusion heavy chain with the $(G_4S)_4$ linker (BIIB C06-117) (SEQ ID NO:162), or a nucleotide sequence substantially identical thereto (e.g., a sequence at least about 85%, 90%, 95% or higher identical thereto). In certain embodiments, the LIGHT/IGFR fusions may also include, or consist essentially of, a second chain (fused or in association with the aforesaid chains) comprising or consisting essentially of the amino acid sequence shown in SEQ ID NO:168, or an amino sequence substantially identical thereto (e.g., a sequence at least about 85%, 90%, 95% or higher identical thereto); an amino acid sequence encoded by the nucleotide sequence shown in any of anti-IGFR Fab-hLIGHT fusion light chain (SEQ ID NO:167), or a nucleotide sequence substantially identical thereto (e.g., a sequence at least about 85%, 90%, 95% or higher identical thereto).

Antibody Molecules

In certain embodiments, the targeting moiety is an antibody molecule against a selected hyperproliferative cell surface protein, e.g., a hyperproliferative, e.g., cancerous, cell or tissue, such that the LIGHT moiety induces one or more LIGHT-associated activities (e.g., one or more of the LIGHT-associated activities as described herein) against the desired site (e.g., the hyperproliferative, e.g., cancerous, cell or tissue). In other embodiments, novel antibody molecules against HER2 are disclosed. Exemplary hyperproliferative, e.g., cancerous, cells or tissues, that can be targeted with the targeting moiety, include, but are not limited to, cancers or solid tumors of the breast, lung, stomach, ovaries, prostate, pancreas, colon, colorectum, renal, bladder, liver, head, neck, brain, as well as soft-tissue malignancies, including lymphoid malignacies, leukemia and myeloma. The targeting moiety can bind to one or more cell surface proteins expressed on one or more of the hyperproliferative cells or tissues described herein. For example, the targeting moiety, e.g., an antibody molecule as described herein, can bind to one or more of a growth factor receptor (e.g., HER-2/neu, HER3, HER4, epidermal growth factor receptor (EGFR), insulin growth factor receptor (IGFR), Met, Ron, Cripto); a cancer-related integrin or integrin receptor (e.g., αvβ6, α6β4, laminin receptor (LAMR); and/or CD23, CD20, CD16, EpCAM and/or Tweak receptor (FN14). Each one of the selected targets is described in more detail herein.

In one embodiment, the antibody molecule binds to HER2 polypeptide (e.g., to a linear or a conformation epitope on HER2 chosen from epitope D1, epitope D2, epitope D3, or epitope D4, or a combination thereof, e.g., epitope D1-D2 or epitope D1-D3. In other specific embodiments, the antibody molecule binds to CD23 or IGFR.

In one embodiment, the antibody molecule binds to HER2 and is an antibody molecule or a Fab fragment from an antibody selected from the group consisting of BIIB71F10 (SEQ ID NOs:11-14), BIIB69A09 (SEQ ID NOs:15-18); BIIB67F10 (SEQ ID NOs:19-22); BIIB67F11 (SEQ ID NOs: 23-26), BIIB66A12 (SEQ ID NOs:27-30), BIIB66C01 (SEQ ID NOs:31-33), BIIB65C10 (SEQ ID NOs:34-38), BIIB65H09 (SEQ ID NOs:39-42) and BIIB65B03 (SEQ ID NOs:43-46) (also referred to herein as 71F10, 69A09; 67F10; 67F11, 67F12, 66A12, 66C01, 65C10, 65H09 and 65B03), or the antibody molecule expressed by PTA-10355, PTA-10356, PTA-10357, or PTA-10358. In other embodiments, the anti-HER2 antibody molecule has a functional activity comparable to an antibody molecule or a Fab fragment from an antibody selected from the group consisting of BIIB71F10, BIIB69A09; BIIB67F10; BIIB67F11, BIIB66A12, BIIB66C01, BIIB65C10, BIIB65H09 and BIIB65B03, or the antibody molecule expressed by PTA-10355, PTA-10356, PTA-10357, or PTA-10358. The anti-HER2 antibody molecule can cross-react with HER2 from one or more species chosen from human, mouse, rat, or cyno origin.

The anti-HER2 antibody molecule can bind to HER2 with an EC50 in the range of about 1 to 120 nM, about 1 to 100 nM, 1 to 80 nM, about 1 to 70 nM, about 1 to 60 nM, about 1 to 40 nM, about 1 to 30 nM, about 1 to 20 nM, about 1 to 15 nM, about 1 to 12 nM, about 1 to 5 nM, about 1 to 2 nM, or about 1 to 1 nM. In other embodiments, the anti-HER2 antibody molecule inhibits or reduces one or more HER2-associated biological activities with an $IC_{50}$ of about 50 nM to 5 pM, typically about 100 to 250 pM or less, e.g., better inhibition. For example, the anti-HER2 antibody molecule inhibit, block or reduce HER2 signaling with an $IC_{50}$ of about 50 nM to 5 pM, typically about 100 to 250 pM or less, e.g., better inhibition (e.g., inhibit, block or reduce phosphorylation of one or more of HER2, AKT or MAP kinase; or inhibit, block or reduce homodimerization of HER2 or heterodimerization of HER2 and HER3, or HER2 with EGFR; internalize with a slow kinetics estimated to be less than or equal to the rate of internalization for control anti-HER2 antibody, which is $8e^{-6} s^{-1}$ in SKBR-3 cells and $2.1e^{-5} s^{-1}$ in BT-474 cells; inhibit activity and/or induce cell killing of a HER2 expressing cell in vitro (e.g., MCF7 and SKBR-3 cell) and in vivo. In one embodiment, the anti-HER2 antibody molecule associates with HER2 with kinetics in the range of $10^4$ to $10^7$ $M^{-1} s^{-1}$, typically $10^5$ to $10^6$ $M^{-1} s^{-1}$. In one embodiment, the anti-HER2 antibody molecule binds to human HER2 with a kD of 0.1-100 nM. In yet another embodiment, the anti-HER2 antibody molecule has dissociation kinetics in the range of $10^{-2}$ to $10^{-6}$ $s^{-1}$, typically $10^{-2}$ to $10^5$ $s^{-1}$. In one embodiment, the anti-HER2 antibody molecule binds to HER2, e.g., human HER2, with an affinity and/or kinetics similar (e.g., within a factor 20, 10, or 5) to a monoclonal antibody selected from the group consisting of BIIB71F10, BIIB69A09; BIIB67F10; BIIB67F11, BIIB66A12, BIIB66C01, BIIB65C10, BIIB65H09 and BIIB65B03, or the antibody molecule expressed by PTA-10355, PTA-10356, PTA-10357, or PTA-10358. The affinity and binding kinetics of the anti-HER2 antibody molecule can be tested using, e.g., biosensor technology (BIACORE™).

As used herein, the term "antibody molecule" refers to a protein comprising at least one immunoglobulin variable domain sequence. The term antibody molecule includes, for example, full-length, mature antibodies and antigen-binding fragments of an antibody. For example, an antibody molecule can include a heavy (H) chain variable domain sequence (abbreviated herein as VH), and a light (L) chain variable domain sequence (abbreviated herein as VL). In another example, an antibody molecule includes two heavy (H) chain variable domain sequences and two light (L) chain variable domain sequence, thereby forming two antigen binding sites, such as Fab, Fab', $F(ab')_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The antibodies of the present invention can be monoclonal or polyclonal. The antibody can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda.

Examples of antigen-binding fragments include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

In embodiments, the antibody molecule is a monoclonal or single specificity antibody, or an antigen-binding fragment thereof (e.g., an Fab, $F(ab')_2$, Fv, a single chain Fv fragment, or a camelid variant) that binds to a hyperproliferative cell surface protein, e.g., a mammalian (e.g., human, hyperproliferative cell surface protein (or a functional variant thereof)). In embodiments, the antibody molecule binds to one or more epitopes located on the extracellular domain of the hyperproliferative cell surface protein (e.g., a hyperproliferative cell surface protein as described herein). Typically, the antibody molecule is a human, humanized, chimeric, camelid, or in vitro generated antibody to a human hyperproliferative cell surface protein (or functional fragment thereof). Typically, the antibody inhibits, reduces or neutralizes one or more activities of hyperproliferative cell surface protein (e.g., one or more biological activities of HER2 as described herein).

Antibodies of the present invention can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in *Camelidae* species, for example in camel, llama, dromedary, alpaca and guanaco. Other species besides *Camelidae* may produce heavy chain antibodies naturally devoid of light chain; such VHHs are within the scope of the invention.

Antibodies of the present invention can also be Affibody molecule scaffolds, e.g., as described in Lee et al. (2008) *Clin Cancer Res* 14(12):3840-3849; Ahlgren et al. (2009) *J. Nucl. Med.* 50:781-789).

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

The term "antigen-binding site" refers to the part of an antibody molecule that comprises determinants that form an interface that binds to the antigen, e.g., HER2, or an epitope thereof. With respect to proteins (or protein mimetics), the antigen-binding site typically includes one or more loops (of at least four amino acids or amino acid mimics) that form an interface that binds to the antigen, e.g., HER2, or an epitope thereof. Typically, the antigen-binding site of an antibody molecule includes at least one or two CDRs, or more typically at least three, four, five or six CDRs.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

As indicated above, the variable region allows the antibody to selectively recognize and specifically bind epitopes on antigens. That is, the VL domain and VH domain, or subset of the complementarity determining regions (CDRs), of an antibody combine to form the variable region that defines a three dimensional antigen binding site. This quaternary antibody structure forms the antigen binding site present at the end of each arm of the Y. More specifically, the antigen binding site is defined by three CDRs on each of the VH and VL chains. In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., Nature 363:446-448 (1993).

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The exact residue numbers which encompass a particular CDR will vary depending on the sequence and size of the CDR. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196: 901-917 (1987), which are incorporated herein by reference in their entireties).

Antibodies or antigen-binding fragments, variants, or derivatives thereof of the invention include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VL or VH domain, fragments produced by a Fab expression library, and anti-idiotypic (anti-Id) antibodies (including, e.g., anti-Id antibodies to antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibody fragments, including single-chain antibodies, may comprise the variable region(s) alone or in combination with the entirety or a portion of the following: hinge region, CH1, CH2, and CH3 domains. Additionally included in the invention are antigen-binding fragments comprising any combination of variable region(s) with a hinge region, CH1, CH2, and CH3 domains. Antibodies or immunospecific fragments thereof of the present invention may be from any animal origin including birds and mammals. The antibodies can be human, murine, donkey, rabbit, goat, guinea pig, camel, llama, horse, or chicken antibodies. In another embodiment, the variable region may be condricthoid in origin (e.g., from sharks). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "heavy chain portion" includes amino acid sequences derived from an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. In certain antibody molecules disclosed herein, the heavy chain portions of one polypeptide chain of a multimer are identical to those on a second polypeptide chain of the multimer. Alternatively, heavy chain portion-containing monomers of the invention are not identical. For example, each monomer may comprise a different target binding site, forming, for example, a bispecific antibody. The heavy chain portions of a binding polypeptide for use in the diagnostic and treatment methods disclosed herein may be derived from different immunoglobulin molecules. For example, a heavy chain portion of a polypeptide may comprise a CH1 domain derived from an IgG1 molecule and a hinge region derived from an IgG3 molecule. In another example, a heavy chain portion can comprise a hinge region derived, in part, from an IgG1 molecule and, in part, from an IgG3 molecule. In another example, a heavy chain portion can comprise a chimeric hinge derived, in part, from an IgG1 molecule and, in part, from an IgG4 molecule.

As used herein, the term "light chain portion" includes amino acid sequences derived from an immunoglobulin light chain. Preferably, the light chain portion comprises at least one of a VL or CL domain.

Antibody molecules disclosed herein may be described or specified in terms of the epitope(s) or portion(s) of an antigen, e.g., a target polypeptide (e.g., HER2, CD23) that they recognize or specifically bind. The portion of a target polypeptide which specifically interacts with the antigen binding domain of an antibody is an "epitope," or an "antigenic determinant." A target polypeptide may comprise a single epitope, but typically comprises at least two epitopes, and can include any number of epitopes, depending on the size, conformation, and type of antigen. Furthermore, it should be noted that an "epitope" on a target polypeptide may be or include non-polypeptide elements, e.g., an "epitope may include a carbohydrate side chain. The minimum size of a peptide or polypeptide epitope for an antibody is thought to be about four to five amino acids. Peptide or polypeptide epitopes preferably contain at least seven, more preferably at least nine and most preferably between at least about 15 to about 30 amino acids. Since a CDR can recognize an antigenic peptide or polypeptide in its tertiary form, the amino acids comprising an epitope need not be contiguous, and in some cases, may not even be on the same peptide chain. In the present invention, peptide or polypeptide epitope recognized by antibodies of the present invention contains a sequence of at least 4, at least 5, at least 6, at least 7, more preferably at least 8, at least 9, at least 10, at least 15, at least 20, at least 25, or between about 15 to about 30 contiguous or non-contiguous amino acids.

By "specifically binds," it is generally meant that an antibody binds to an epitope via its antigen binding domain, and that the binding entails some complementarity between the antigen binding domain and the epitope. According to this definition, an antibody is said to "specifically bind" to an epitope when it binds to that epitope, via its antigen binding domain more readily than it would bind to a random, unrelated epitope. The term "specificity" is used herein to qualify the relative affinity by which a certain antibody binds to a certain epitope.

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

By way of non-limiting example, an antibody may be considered to bind a first epitope preferentially if it binds said first epitope with a dissociation constant ($K_D$) that is less than the antibody's $K_D$ for the second epitope. In another non-limiting example, an antibody may be considered to bind a first antigen preferentially if it binds the first epitope with an affinity that is at least one order of magnitude less than the antibody's $K_D$ for the second epitope. In another non-limiting example, an antibody may be considered to bind a first epitope preferentially if it binds the first epitope with an affinity that is at least two orders of magnitude less than the antibody's $K_D$ for the second epitope.

In another non-limiting example, an antibody molecule may be considered to bind a first epitope preferentially if it binds the first epitope with an off rate (k(off)) that is less than the antibody's k(off) for the second epitope. In another non-limiting example, an antibody may be considered to bind a first epitope preferentially if it binds the first epitope with an affinity that is at least one order of magnitude less than the antibody's k(off) for the second epitope. In another non-limiting example, an antibody may be considered to bind a first epitope preferentially if it binds the first epitope with an affinity that is at least two orders of magnitude less than the antibody's k(off) for the second epitope.

An antibody molecule disclosed herein may be said to bind a target polypeptide disclosed herein or a fragment or variant thereof with an off rate (k(off)) of less than or equal to $5\times10^{-2}$ sec$^{-1}$, $10^{-2}$ sec$^{-1}$, $5\times10^{-3}$ sec$^{-1}$ or $10^{-3}$ sec$^{-1}$. More preferably, an antibody of the invention may be said to bind a target polypeptide disclosed herein or a fragment or variant thereof with an off rate (k(off)) less than or equal to $5\times10^{-4}$ sec$^{-1}$, $10^{-4}$ sec$^{-1}$, $5\times10^{-5}$ sec$^{-1}$, or $10$ sec$^{-1}$ $5\times10^{-6}$ sec$^{-1}$, $10^{-6}$ sec$^{1}$, $5\times10^{-7}$ sec$^{-1}$ or $10^{-7}$ sec$^{-1}$.

An antibody molecule disclosed herein may be said to bind a target polypeptide disclosed herein or a fragment or variant thereof with an on rate (k(on)) of greater than or equal to $10^{3} M^{-1}$ sec$^{-1}$, $5\times10^{3}$ $M^{-1}$ sec$^{-1}$, $10^{4} M^{-1}$ sec$^{-1}$ or $5\times10^{4}$ $M^{-1}$ sec$^{-1}$. An antibody molecule of the invention may be said to bind a target polypeptide disclosed herein or a fragment or variant thereof with an on rate (k(on)) greater than or equal to $10^{5} M^{-1}$ sec$^{-1}$, $5\times10^{5}$ $M^{-1}$ sec$^{-1}$, $10^{6} M^{-1}$ sec$^{-1}$, or $5\times10^{6} M^{-1}$ sec$^{-1}$ or $10^{7}$ $M^{-1}$ sec$^{-1}$.

An antibody molecule is said to competitively inhibit binding of a reference antibody to a given epitope if it preferentially binds to that epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

Antibody molecules of the invention may also be described or specified in terms of their cross-reactivity. As used herein, the term "cross-reactivity" refers to the ability of an antibody, specific for one antigen, to react with a second antigen; a measure of relatedness between two different antigenic substances. Thus, an antibody is cross reactive if it binds to an epitope other than the one that induced its formation. The cross reactive epitope generally contains many of the same complementary structural features as the inducing epitope, and in some cases, may actually fit better than the original. For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody may be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope.

An antibody may be deemed "highly specific" for a certain epitope, if it does not bind any other analog, ortholog, or homolog of that epitope.

Antibody molecules of the invention may also be described or specified in terms of their binding affinity to a polypeptide of the invention. Typical binding affinities include those with a dissociation constant or Kd less than $5 \times 10^{-2}$ M, $10^{-2}$ M, $5 \times 10^{-3}$M, $10^{-3}$M, $5 \times 10^{-4}$M, $10^{-4}$M, $5 \times 10^{-5}$M, $10^{-5}$M, $5 \times 10^{-6}$M, $10^{-6}$M, $5 \times 10^{-7}$M, $10^{-7}$M, $5 \times 10^{-8}$M, $10^{-8}$ M, $5 \times 10^{-9}$M, $10^{-9}$M, $5 \times 10^{-10}$M, $M^{-10}$ M, $5 \times 10^{-11}$M, $10^{-11}$M, $5 \times 10^{-12}$M, $10^{-12}$M, $5 \times 10^{-13}$M, $10^{-13}$ M, $5 \times 10^{-14}$ M, $10^{-14}$ M, $5 \times 10^{-15}$ M, or $10^{-15}$ M.

Antibody molecules of the invention may be "multispecific," e.g., bispecific, trispecific or of greater multispecificity, meaning that it recognizes and binds to two or more different epitopes present on one or more different antigens (e.g., proteins) at the same time. Thus, whether an antibody molecule is "monospecific" or "multispecific," e.g., "bispecific," refers to the number of different epitopes with which a binding polypeptide reacts. Multispecific antibodies may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in an antibody, binding polypeptide or antibody. Each binding domain specifically binds one epitope. When an antibody, binding polypeptide or antibody comprises more than one binding domain, each binding domain may specifically bind the same epitope, for an antibody with two binding domains, termed "bivalent monospecific," or to different epitopes, for an antibody with two binding domains, termed "bivalent bispecific." An antibody may also be bispecific and bivalent for each specificity (termed "bispecific tetravalent antibodies"). In another embodiment, tetravalent minibodies or domain deleted antibodies can be made.

Bispecific bivalent antibodies, and methods of making them, are described, for instance in U.S. Pat. Nos. 5,731,168; 5,807,706; 5,821,333; and U.S. Appl. Publ. Nos. 2003/020734 and 2002/0155537, the disclosures of all of which are incorporated by reference herein. Bispecific tetravalent antibodies, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

The antibody molecule can be a polyclonal or a monoclonal antibody. In other embodiments, the antibody can be recombinantly produced, e.g., produced by phage display or by combinatorial methods. Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J. 12:725-734; Hawkins et al. (1992) J Mol Biol 226:889-896; Clackson et al. (1991) Nature 352:624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982, the contents of all of which are incorporated by reference herein).

In one embodiment, the antibody molecule is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Method of producing rodent antibodies are known in the art. Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368:856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

An antibody molecule can be one in which the variable region, or a portion thereof, e.g., the CDRs, are generated in a non-human organism, e.g., a rat or mouse. Chimeric, CDR-grafted, and humanized antibodies are within the invention. Antibodies generated in a non-human organism, e.g., a rat or mouse, and then modified, e.g., in the variable framework or constant region, to decrease antigenicity in a human are within the invention. Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 Science 240:1041-1043); Liu et al. (1987) PNAS 84:3439-3443; Liu et al., 1987, J. Immunol. 139:3521-3526; Sun et al. (1987) PNAS 84:214-218; Nishimura et al., 1987, Canc. Res. 47:999-1005; Wood et al. (1985) Nature 314:446-449; and Shaw et al., 1988, J. Natl Cancer Inst. 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding of the humanized antibody. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody molecule can be humanized by methods known in the art. Humanized antibodies can be generated by replacing sequences of the Fv variable region which are not directly involved in antigen binding with equivalent sequences from human Fv variable regions. General methods for generating humanized antibodies are provided by Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762. Humanized or CDR-grafted antibodies can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:1534; Beidler et al. 1988 *J. Immunol.* 141: 4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibodies in which specific amino acids have been substituted, deleted or added. Preferred humanized antibodies have amino acid substitutions in the framework region, such as to improve binding to the antigen. For example, a humanized antibody will have framework residues identical to the donor framework residue or to another amino acid other than the recipient framework residue. To generate such antibodies, a selected, small number of acceptor framework residues of the humanized immunoglobulin chain can be replaced by the corresponding donor amino acids. Preferred locations of the substitutions include amino acid residues adjacent to the CDR, or which are capable of interacting with a CDR (see e.g., U.S. Pat. No. 5,585,089). Criteria for selecting amino acids from the donor are described in U.S. Pat. No. 5,585,089, e.g., columns 12-16 of U.S. Pat. No. 5,585,089, the e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

In one embodiment, an antibody can be made by immunizing with purified target cell antigen, or a fragment thereof, e.g., a fragment described herein, membrane associated antigen, tissue, e.g., crude tissue preparations, whole cells, preferably living cells, lysed cells, or cell fractions, e.g., membrane fractions.

The antibody molecule can be a single chain antibody. A single-chain antibody (scFv) may be engineered (see, for example, Colcher, D. et al. (1999) *Ann N Y Acad Sci* 880:263-80; and Reiter, Y. (1996) *Clin Cancer Res* 2:245-52). The single chain antibody can be dimerized or multimerized to generate multivalent antibodies having specificities for different epitopes of the same target.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

An antibody molecule can be used to isolate target proteins by standard techniques, such as affinity chromatography or immunoprecipitation. Moreover, an antibody molecule can be used to detect a target protein (e.g., in a cellular lysate or cell supernatant). Antibody molecules can be used diagnostically to monitor protein levels in tissue as part of a clinical testing procedure, e.g., to determine the efficacy of a given treatment regimen. Detection can be facilitated by coupling (e.g., physically linking) the antibody to a detectable substance (e.g., antibody labeling). Examples of detectable substances include, but are not limited to, various enzymes, prosthetic groups, fluorescent materials, luminescent materials, bioluminescent materials, chemiluminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

One of the ways in which an antibody molecule can be detectably labeled is by linking the same to an enzyme and using the linked product in an enzyme immunoassay (EIA) (Voller, A., "The Enzyme Linked Immunosorbent Assay (ELISA)" Microbiological Associates Quarterly Publication, Walkersville, Md., *Diagnostic Horizons* 2:1-7 (1978)); Voller et al., *J. Clin. Pathol.* 31:507-520 (1978); Butler, J. E., *Meth. Enzymol.* 73:482-523 (1981); Maggio, E. (ed.), *Enzyme Immunoassay*, CRC Press, Boca Raton, Fla., (1980); Ishikawa, E. et al., (eds.), *Enzyme Immunoassay*, Kgaku Shoin, Tokyo (1981). Detection may also be accomplished using any of a variety of other immunoassays. For example, by radioactively labeling the antibody molecule, it is possible to detect the antibody through the use of a radioimmunoas say (RIA) (see, for example, Weintraub, B., *Principles of Radioimmunoassays, Seventh Training Course on Radioligand Assay Techniques*, The Endocrine Society, (March, 1986)).

Techniques for conjugating various moieties to an antibody molecules are known, see, e.g., Amon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. (1985); Hellstrom et al., "Antibodies For Drug Delivery", in *Controlled Drug Delivery* (2nd Ed.), Robinson et al. (eds.), Marcel Dekker, Inc., pp. 623-53 (1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), Academic Press pp. 303-16 (1985), and Thorpe et al., "The Preparation And Cytotoxic Properties Of Antibody-Toxin Conjugates", *Immunol. Rev.* 62:119-58 (1982).

In particular, binding molecules, e.g., binding polypeptides (LIGHT targeting molecules and/or anti-HER2 antibody molecules) for use in the diagnostic and treatment methods disclosed herein may be conjugated to cytotoxins (such as radioisotopes, cytotoxic drugs, or toxins) therapeutic agents, cytostatic agents, biological toxins, prodrugs, peptides, proteins, enzymes, viruses, lipids, biological response modifiers, pharmaceutical agents, immunologically active ligands (e.g., lymphokines or other antibodies wherein the resulting molecule binds to both the neoplastic cell and an effector cell such as a T cell), or PEG. In another embodiment, a binding molecule, e.g., a binding polypeptide, for use in the diagnostic and treatment methods disclosed herein can be conjugated to a molecule that decreases vascularization of tumors. In other embodiments, the disclosed compositions may comprise binding molecules, e.g., binding polypeptides, coupled to drugs or prodrugs. Still other embodiments of the present invention comprise the use of binding molecules, e.g., binding polypeptides, conjugated to specific biotoxins or their cytotoxic fragments such as ricin, gelonin, pseudomonas exotoxin or diphtheria toxin. The selection of which conjugated or unconjugated binding molecule to use will depend on the type and stage of cancer, use of adjunct treatment (e.g., chemotherapy or external radiation) and patient condition. It will be appreciated that one skilled in the art could readily make such a selection in view of the teachings herein.

It will be appreciated that anti-tumor antibodies labeled with isotopes have been used successfully to destroy cells in solid tumors as well as lymphomas/leukemias in animal models, and in some cases in humans. Exemplary radioisotopes include: $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re.

It will also be appreciated that, in accordance with the teachings herein, binding molecules may be conjugated to different radiolabels for diagnostic and therapeutic purposes. To this end the aforementioned U.S. Pat. Nos. 6,682,134, 6,399,061, and 5,843,439 disclose radiolabeled therapeutic conjugates for diagnostic "imaging" of tumors before administration of therapeutic antibody.

Additional preferred agents for conjugation to antibody molecules are cytotoxic drugs, particularly those which are used for cancer therapy. As used herein, "a cytotoxin or cytotoxic agent" means any agent that is detrimental to the growth and proliferation of cells and may act to reduce, inhibit or destroy a cell or malignancy. Exemplary cytotoxins include, but are not limited to, radionuclides, biotoxins, enzymatically active toxins, cytostatic or cytotoxic therapeutic agents, prodrugs, immunologically active ligands and biological response modifiers such as cytokines. Any cytotoxin that acts to retard or slow the growth of immunoreactive cells or malignant cells is within the scope of the present invention. Exemplary cytotoxins include, in general, cytostatic agents, alkylating agents, anti-metabolites, anti-proliferative agents, tubulin binding agents, hormones and hormone antagonists, and the like. Other classes of cytotoxic agents include, for example, the maytansinoid family of drugs, the anthracycline family of drugs, the vinca drugs, the mitomycins, the bleomycins, the cytotoxic nucleosides, the pteridine family of drugs, diynenes, and the podophyllotoxins.

In certain embodiments, a moiety that enhances the stability or efficacy of an antibody molecule can be conjugated. For example, in one embodiment, PEG can be conjugated to the binding molecules of the invention to increase their half-life in vivo. Leong, S. R., et al., *Cytokine* 16:106 (2001); *Adv. in Drug Deliv. Rev.* 54:531 (2002); or Weir et al., *Biochem. Soc. Transactions* 30:512 (2002).

Nucleic Acids Encoding LIGHT Targeting and Antibody Molecules

The present invention also provides for nucleic acid molecules encoding LIGHT targeting and antibody molecules of the invention.

In one embodiment, the present invention provides an isolated polynucleotide comprising, consisting essentially of, or consisting of a nucleic acid encoding an immunoglobulin heavy chain variable region (VH), where at least one of the CDRs of the heavy chain variable region or at least two of the VH-CDRs of the heavy chain variable region are at least 80%, 85%, 90% or 95% identical to reference heavy chain VH-CDR1, VH-CDR2, or VH-CDR3 amino acid sequences from monoclonal HER2 antibodies disclosed herein. Alternatively, the VH-CDR1, VH-CDR2, and VH-CDR3 regions of the VH are at least 80%, 85%, 90% or 95% identical to reference heavy chain VH-CDR1, VH-CDR2, and VH-CDR3 amino acid sequences from monoclonal HER2 antibodies disclosed herein. Thus, according to this embodiment a heavy chain variable region of the invention has VH-CDR1, VH-CDR2, or VH-CDR3 polypeptide sequences related to the polypeptide sequences shown in SEQ ID NOs:47-70.

In certain embodiments, the nucleic acid molecule encodes an antibody molecule of the fusion, or the anti-HER2 antibody molecule, that includes, or consists essentially of, a nucleotide sequence that hybridizes under high stringency conditions to the complement of the nucleotide sequence encoding a heavy chain variable domain of BIIB71F10 (SEQ ID NO:12; SEQ ID NO:156), BIIB69A09 (SEQ ID NO:16); BIIB67F10 (SEQ ID NO:20); BIIB67F11 (SEQ ID NO:24), BIIB66A12 (SEQ ID NO:28), BIIB66C01 (SEQ ID NO:32), BIIB65C10 (SEQ ID NO:36), BIIB65H09 (SEQ ID NO:40) or BIIB65B03 (SEQ ID NO:44), or the heavy chain variable domain of the antibody molecule expressed by PTA-10355, PTA-10356, PTA-10357, or PTA-10358; or includes an amino acid sequence that is at least 85%, 90%, 95%, 97%, 98%, 99% or higher identical identical to the amino acid sequence of the heavy chain variable domain of BIIB71F10 (SEQ ID NO:11), BIIB69A09 (SEQ ID NO:15); BIIB67F10 (SEQ ID NO:19); BIIB67F11 (SEQ ID NO:23), BIIB66A12 (SEQ ID NO:27), BIIB66C01 (SEQ ID NO:31), BIIB65C10 (SEQ ID NO:35), BIIB65H09 (SEQ ID NO:39) or BIIB65B03 (SEQ ID NO:43), or the heavy chain variable domain of the antibody molecule expressed by PTA-10355, PTA-10356, PTA-10357, or PTA-10358.

In other embodiments, the nucleic acid molecule encodes an antibody molecule of the fusion, or the anti-HER2 antibody molecule, that includes, or consists essentially of, a nucleotide sequence that hybridizes under high stringency conditions to the complement of the nucleotide sequence encoding a light chain variable domain of BIIB71F10 (SEQ ID NO:14), BIIB69A09 (SEQ ID NO:18); BIIB67F10 (SEQ ID NO:22); BIIB67F11 (SEQ ID NO:26), BIIB66A12 (SEQ ID NO:30), BIIB66C01 (SEQ ID NO:34), BIIB65C10 (SEQ ID NO:38), BIIB65H09 (SEQ ID NO:42) or BIIB65B03 (SEQ ID NO:46), or the light chain variable domain of the antibody molecule expressed by PTA-10355, PTA-10356, PTA-10357, or PTA-10358; or includes an amino acid sequence that is at least 80%, 85%, 90%, 95%, 97%, 98%, 99% or higher identical to a light chain variable domain of BIIB71F10 (SEQ ID NO:13), BIIB69A09 (SEQ ID NO:17); BIIB67F10 (SEQ ID NO:21); BIIB67F11 (SEQ ID NO:25), BIIB66A12 (SEQ ID NO:29), BIIB66C01 (SEQ ID NO:33), BIIB65C10 (SEQ ID NO:37), BIIB65H09 (SEQ ID NO:41) or BIIB65B03 (SEQ ID NO:45), or the light chain variable domain of the antibody molecule expressed by PTA-10355, PTA-10356, PTA-10357, or PTA-10358.

Exemplary nucleic acid molecules encode LIGHT/HER2 fusions that include, or consist essentially of, the amino acid sequence shown in any of SEQ ID NO:2, SEQ ID NO:3, SEQ ID NO:4, or an amino sequence substantially identical thereto (e.g., a sequence at least about 85%, 90%, 95% or higher identical thereto); an amino acid sequence encoded by the nucleotide sequence shown in any of SEQ ID NO:6, SEQ ID NO:7, SEQ ID NO:8, or a nucleotide sequence substantially identical thereto (e.g., a sequence at least about 85%, 90%, 95% or higher identical thereto). In certain embodiments, the nucleic acid molecules encoding the LIGHT/HER2 fusions may also include, or consist essentially of, a second chain (genetically fused or in association with the aforesaid chains) comprising or consisting essentially of the amino acid sequence shown in SEQ ID NO:1, or an amino sequence substantially identical thereto (e.g., a sequence at least about 85%, 90%, 95% or higher identical thereto). In embodiments, the nucleic acid molecules comprise, or consist essentially of, the nucleotide sequence shown in any of SEQ ID NO:5, or a nucleotide sequence substantially identical thereto (e.g., a sequence at least about 85%, 90%, 95% or higher identical thereto).

In another exemplary embodiment, the nucleic acid molecules encode a LIGHT targeting molecule that comprises at least one fusion molecule of a mammalian (e.g., human) LIGHT protein, or a functional variant or a fragment thereof, and an antibody molecule that binds to CD23 or IGFR. In one embodiment, the nucleic acid molecules encoding the LIGHT-anti-CD23 or the LIGHT-anti-IGFR fusion comprises, or consists essentially of the amino acid sequence shown in any of SEQ ID NO:101, 174, 163, or an amino sequence substantially identical thereto (e.g., a sequence at least about 85%, 90%, 95% or higher identical thereto). In embodiments, the nucleic acid molecules comprise, or consist essentially of, the nucleotide sequence shown in any of SEQ ID NO:102, 173, 162, or a nucleotide sequence substantially identical thereto (e.g., a sequence at least about 85%, 90%, 95% or higher identical thereto). In certain embodiments, the nucleic acid molecules encoding the LIGHT/CD23 fusions may also include, or consist essentially of, a second chain (fused or in association with the aforesaid chains) comprising or consisting essentially of the amino acid sequence shown in SEQ ID NO:103 or 168, or an amino sequence substantially identical thereto (e.g., a sequence at least about 85%, 90%, 95% or higher identical thereto). In embodiments, the nucleic acid molecules comprise, or consist essentially of, the nucleotide sequence shown in any of SEQ ID NO:104 or 167, or a nucleotide sequence substantially identical thereto (e.g., a sequence at least about 85%, 90%, 95% or higher identical thereto).

Recombinant Expression Vectors, Host Cells and Genetically Engineered Cells

The invention also includes a nucleic acid which encodes the targeting molecules and/or antibody molecules described herein. Also included are vectors which include the nucleic acid and cells transformed with the nucleic acid, particularly cells which are useful for producing an antibody, e.g., mammalian cells, e.g. CHO or lymphatic cells. The invention also includes cell lines (e.g., recombinant host cells, hybridomas), which make an antibody molecule as described herein, and method of using said cells to make antibody molecules.

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein.

The recombinant expression vectors of the invention can be designed for expression of proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified recombinant proteins can be activity assays, (e.g., direct assays or competitive assays described in detail below), or to generate antibodies specific for proteins. In a preferred embodiment, a fusion protein expressed in a retroviral expression vector of the present invention can be used to infect bone marrow cells which are subsequently transplanted into irradiated recipients. The pathology of the subject recipient is then examined after sufficient time has passed (e.g., six weeks).

To maximize recombinant protein expression in *E. coli* is to express the protein in a host bacterium with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

The expression vector can be a yeast expression vector, a vector for expression in insect cells, e.g., a baculovirus expression vector or a vector suitable for expression in mammalian cells. When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983). In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a nucleic acid molecule within a recombinant expression vector or a nucleic acid molecule containing sequences which allow it to homologously recombine into a specific site of the host cell's genome. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, a protein can be expressed in bacterial cells (such as *E. coli*), insect cells, yeast or mammalian cells (such as Chinese hamster ovary cells (CHO) or COS cells e.g., COS-7 cells, CV-1 origin SV40 cells; Gluzman (1981) *Cell* 23:175-182). Other suitable host cells are known to those skilled in the art.

A host cell of the invention can be used to produce (i.e., express) a protein. Accordingly, the invention further provides methods for producing a protein using the host cells of the invention. In one embodiment, the method includes culturing the host cell of the invention (into which a recombinant expression vector encoding a protein has been introduced) in a suitable medium such that a protein is produced. In another embodiment, the method further includes isolating a protein from the medium or the host cell.

Inhibition of Hyperproliferative Activity

The invention provides methods of treating or preventing (e.g., curing, suppressing, ameliorating, delaying or preventing the onset of, or preventing recurrence or relapse of) a hyperproliferative, e.g., neoplastic condition and/or disorder, in a subject. The method includes administering to the subject a LIGHT targeting molecule or an anti-HER2 antibody molecule as described herein, in an amount sufficient to inhibit or reduce one or more biological activities in the hyperproliferative, e.g., neoplastic cell or tissue, thereby treating or preventing the disorder or condition.

Figure 22:
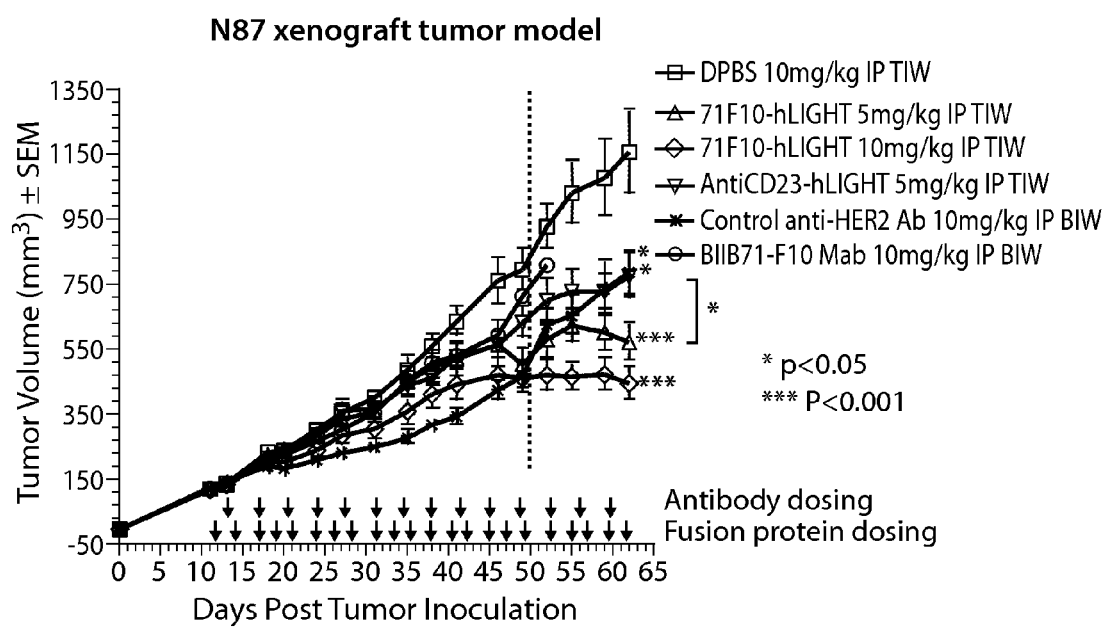
FIG. 22 depicts the potent anti-tumor activity of 71F10 Fab-hLIGHT in N87 xenograft tumor model.

In certain embodiments, the method prevents, reduces or ameliorates the recurrence or relapse of a tumor or metastasis. The method includes administering a LIGHT-targeting molecule, or anti-HER2 antibody molecule, as described herein, to a subject, e.g., a patient that is partially or completely refractory to a standard mode of therapy (e.g., chemotherapy, antibody-based and/or surgery). For example, the patient suffers from a HER2-expressing cancer (e.g., a breast, gastric or lung cancer) and has demonstrated disease progression after surgery, chemotherapy and/or antibody therapy (e.g., trastuzumab therapy). In this regard, the majority of the patients with metastatic breast cancer who initially respond to trastuzumab demonstrate disease progression within one year of treatment initiation (Nahta, R. et al. (2006) *Nature Clinical Practice Vol.* 3 (5):269-280). The LIGHT-anti-HER2 molecules of the invention can be used to treat the trastuzumab-refractory patient population. The LIGHT-anti-HER2 molecules of the invention have been shown to excert a prolonged inhibition of anti-tumor activity (beyond the inhibition detected with anti-HER2 antibodies) (FIG. 22), thus, expanding the therapeutic and prophylactic uses of these molecules.

In other embodiments, the patient is a colon cancer patient that has demonstrated disease progression after surgery, chemotherapy and/or antibody therapy (e.g., VEGF or EGFR antibody therapy). In certain embodiments, the LIGHT-targeting molecule, or anti-HER2 antibody molecule, is administered to a patient who has been treated with another mode of therapy (e.g., a standard mode of therapy) for about 10 days, one to six months, six months to a year, one to two years, and so on. In certain embodiments, the subject has developed partial or complete resistance to a first-line of therapy.

In some embodiments, the amount or dosage of the LIGHT-targeting molecule, or anti-HER2 antibody molecule, administered can be determined, e.g., prior to administration to the subject, by testing in vitro or ex vivo the amount of the LIGHT-targeting molecule, or anti-HER2 antibody molecule, required to decrease or inhibit one or more of hyperproliferative activities, disorders or conditions described herein. The in vivo method can, optionally, include the step(s) of identifying (e.g., evaluating, diagnosing, screening, and/or selecting) a subject at risk of having, or having, one or more symptoms associated with the disorder or condition.

In various embodiments of the above-described methods, the antibody or fragment thereof inhibits tumor cell migration. In further embodiments, the tumor cell proliferation is inhibited through the prevention or retardation of tumor spread to adjacent tissues.

In further embodiments, the hyperproliferative disorder or condition is chosen from one or more of a cancer, a neoplasm, a tumor, a malignancy, or a metastasis thereof, or a recurrent malignancy (e.g., a subject that is partially or completely refractory to a first-line of treatment).

In embodiments, the targeting moiety of the LIGHT targeting molecule, or the antibody molecule, is administered, alone or combination with a second agent, as a first-line of therapy to a naïve subject, e.g., a naïve patient having a HER2-expressing breast cancer. In other embodiments, the targeting moiety of the LIGHT targeting molecule, or the antibody molecule, is administered, alone or combination with a second agent, as a second-line of therapy. In other embodiment, the targeting moiety of the LIGHT targeting molecule, or the antibody molecule, is administered to a patient that is partially or completely refractory to a standard mode of therapy. For example, the patient is a breast cancer patient that has demonstrated disease progession after chemotherapy and/or trastuzumab therapy.

As used herein, the terms "treat" or "treatment" refer to both therapeutic treatment and prophylactic or preventative measures, wherein the object is to prevent or slow down (lessen) an undesired physiological change or disorder, such as the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, and so on.

As used herein, phrases such as "a subject that would benefit from administration of a binding molecule" and "an animal in need of treatment" includes subjects, such as mammalian subjects, that would benefit from administration of a binding molecule used, e.g., for detection of an antigen recognized by a binding molecule (e.g., for a diagnostic procedure) and/or from treatment, i.e., palliation or prevention of a disease such as cancer, with a binding molecule which specifically binds a given target protein. As described in more detail herein, the binding molecule can be used in unconjugated form or can be conjugated, e.g., to a drug, prodrug, or an isotope.

In various embodiments, the subject is a mammal (e.g., an animal model or a human). In further embodiments, the subject is a human, e.g., a patient with one or more of the cancers or neoplastic conditions described herein. In one embodiment, the subject is a patient undergoing a standard mode of therapy, e.g., a HER2-positive patient undergoing chemotherapy and/or treatment with trastuzumab, and the LIGHT-targeting molecules and/or an anti-HER2 antibody molecule are administered as a second-line of therapy. In other embodiments, the patient is a naïve patient, e.g., the LIGHT-targeting molecules and/or an anti-HER2 antibody molecule are administered as a first-line of therapy. In other embodiment, the patient is partially or completely refractory to a standard mode of therapy. For example, the patient is a breast cancer patient that has demonstrated disease progession after chemotherapy and/or trastuzumab therapy.

By "hyperproliferative disease or disorder" is meant all neoplastic cell growth and proliferation, whether malignant or benign, including all transformed cells and tissues and all cancerous cells and tissues. Hyperproliferative diseases or disorders include, but are not limited to, precancerous lesions, abnormal cell growths, benign tumors, malignant tumors, and "cancer." In certain embodiments of the present invention, the hyperproliferative disease or disorder, e.g., the precancerous lesion, abnormal cell growth, benign tumor, malignant tumor, or "cancer" comprises cells which express, over-express, or abnormally express a target cell antigen.

Additional examples of hyperproliferative diseases, disorders, and/or conditions include, but are not limited to neoplasms, whether benign or malignant, located in the: prostate, colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital tract. Such neoplasms, in certain embodiments, express, over-express, or abnormally express a target cell antigen.

Other hyperproliferative disorders include, but are not limited to: hypergammaglobulinemia, lymphoproliferative disorders, paraproteinemias, purpura, sarcoidosis, Sezary Syndrome, Waldenstron's macroglobulinemia, Gaucher's Disease, histiocytosis, and any other hyperproliferative disease, besides neoplasia, located in an organ system listed above. In certain embodiments of the present invention the diseases involve cells which express, over-express, or abnormally express a target cell antigen.

As used herein, the terms "tumor" or "tumor tissue" refer to an abnormal mass of tissue that results from excessive cell division, in certain cases tissue comprising cells which express, over-express, or abnormally express a hyperproliferative cell protein. A tumor or tumor tissue comprises "tumor cells" which are neoplastic cells with abnormal growth properties and no useful bodily function. Tumors, tumor tissue and tumor cells may be benign or malignant.

As used herein, the term "malignancy" refers to a non-benign tumor or a cancer. As used herein, the term "cancer" connotes a type of hyperproliferative disease which includes a malignancy characterized by deregulated or uncontrolled cell growth. Examples of cancer include, but are not limited to, carcinoma, lymphoma, blastoma, sarcoma, and leukemia or lymphoid malignancies. More particular examples of such cancers are noted below and include: squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulval cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). Cancers conducive to treatment methods of the present invention involves cells which express, over-express, or abnormally express a target cell antigen.

The method of the present invention may be used to treat premalignant conditions and to prevent progression to a neoplastic or neoplastic state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, *Basic Pathology*, 2d Ed., W. B. Saunders Co., Philadelphia, pp. 68-79 (1976). Such conditions in which cells begin to express, over-express, or abnormally express a target cell antigen, are particularly treatable by the methods of the present invention.

Additional pre-neoplastic disorders which can be treated by the method of the invention include, but are not limited to, benign dysproliferative disorders (e.g., benign tumors, fibrocystic conditions, tissue hypertrophy, intestinal polyps, colon polyps, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed herein.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, menangioma, melanoma, neuroblastoma, and retinoblastoma.

Several assay systems, cell lines and animal models are known in the art for evaluating the effects of the LIGHT targeting agents and anti-HER2 antibody molecules described herein. For example, cell lines expressing different levels of one or more of HER2, LTβR and HVEM can be used. Exemplary human cell lines expressing high levels of HER2 include, but are not limited to, BT474, SKBR3, N87 and SKOV3. Exemplary cell lines expressing moderate levels of HER2 include rat Tubo and human HT29. Exemplary cell lines expressing low or undetectable levels of HER2 include human MCF7, MDA-MB-231, MDA-MB-468, as well as mouse TSA and 4T1. Examples of cell lines that express LIGHT receptors include HT29, N87 and WiDr (which express high levels of LTβR); BT474, SKBR3, MCF7, MDA-MB-231, MDA-MB-468, SKOV3 and Tubo (all of which express moderate levels of LTβR); and mouse TSA and 4T1 (which express low levels of LTβR). Cell lines expressing moderate levels of HVEM include MCF7, MDA-MB-231 and HT29. Xenograft animal models for testing the molecules of the invention are described in the Examples below.

Pharmaceutical Compositions, Dosages, Modes of Administration

The molecules (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

When a therapeutically effective amount of a molecule of the invention is administered by intravenous, cutaneous or subcutaneous injection, binding agent will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to binding agent an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

For administration by inhalation, the molecules of the invention are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. For repeated administrations over several days or longer, depending on the condition, the treatment is repeated until a desired suppression of disease symptoms occurs. However, other dosage regimens may be useful. The progress of this therapy is easily monitored by conventional techniques and assays, including, for example, radiographic tumor imaging. Ultimately the attending physician will decide on the appropriate duration of intravenous therapy using the pharmaceutical composition of the present invention.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

The dosage and frequency of administration can vary depending on whether the treatment is prophylactic or therapeutic. In prophylactic applications, compositions comprising antibodies or a cocktail thereof are administered to a patient not already in the disease state or in a pre-disease state to enhance the patient's resistance. Such an amount is defined to be a "prophylactic effective dose." In this use, the precise amounts again depend upon the patient's state of health and general immunity, but generally range from 0.1 to 25 mg per dose, especially 0.5 to 2.5 mg per dose. A relatively low dosage is administered at relatively infrequent intervals over a long period of time. Some patients continue to receive treatment for the rest of their lives.

In therapeutic applications, a relatively high dosage (e.g., from about 1 to 400 mg/kg of binding molecule, e.g., antibody per dose, with dosages of from 5 to 25 mg being more commonly used for radioimmunoconjugates and higher doses for cytotoxin-drug conjugated molecules) at relatively short intervals is sometimes required until progression of the disease is reduced or terminated, and preferably until the patient shows partial or complete amelioration of symptoms of disease. Thereafter, the patent can be administered a prophylactic regime.

In one embodiment, a subject can be treated with a nucleic acid molecule encoding a LIGHT targeting molecule or an antibody molecule (collectively referred to herein as "binding molecules" or "molecules") (e.g., in a vector). Doses for nucleic acids encoding polypeptides range from about 10 ng to 1 g, 100 ng to 100 mg, 1 µg to 10 mg, or 30-300 µg DNA per patient. Doses for infectious viral vectors vary from 10-100, or more, virions per dose.

Therapeutic agents can be administered by parenteral, topical, intravenous, oral, subcutaneous, intraarterial, intracranial, intraperitoneal, intranasal or intramuscular means for prophylactic and/or therapeutic treatment. In some methods, agents are injected directly into a particular tissue where cancer-expressing cells have accumulated, for example intracranial injection. Intramuscular injection or intravenous infusions are preferred for administration of antibody. In some methods, particular therapeutic antibodies are injected directly into the cranium. In some methods, antibodies are administered as a sustained release composition or device, such as a Medipad® device.

Molecules of the invention can optionally be administered in combination with other agents that are effective in treating the disorder or condition in need of treatment (e.g., prophylactic or therapeutic). The LIGHT-targeting molecule, or anti-HER2 antibody molecule, alone or in combination with another agent (e.g., a chemotherapeutic agent as described herein), can be administered to a subject, e.g., a mammal, suffering from a hyperproliferative condition and/or disorder, in an amount sufficient to elicit at least one LIGHT-associated biological activity, in the subject.

While a great deal of clinical experience has been gained with $^{131}$I and $^{90}$Y, other radiolabels are known in the art and have been used for similar purposes. Still other radioisotopes are used for imaging. For example, additional radioisotopes which are compatible with the scope of the instant invention include, but are not limited to, $^{123}$I, $^{125}$I, $^{32}$P, $^{57}$Co, $^{64}$Cu, $^{67}$Cu, $^{77}$Br, $^{81}$Rb, $^{81}$Kr, $^{87}$Sr, $^{113}$In, $^{127}$Cs, $^{129}$Cs, $^{132}$I, $^{197}$Hg, $^{203}$Pb, $^{206}$Bi, $^{177}$Lu, $^{186}$Re, $^{212}$Pb, $^{212}$Bi, 47Sc, $^{105}$Rh, $^{109}$Pd, $^{153}$Sm, $^{188}$Re, $^{199}$Au, $^{225}$Ac, $^{211}$At, and $^{213}$Bi. In this respect alpha, gamma and beta emitters are all compatible with in the instant invention. Further, in view of the instant disclosure it is submitted that one skilled in the art could readily determine which radionuclides are compatible with a selected course of treatment without undue experimentation. To this end, additional radionuclides which have already been used in clinical diagnosis include $^{125}$I, $^{123}$I, $^{99}$Tc, $^{43}$K, $^{52}$Fe, $^{67}$Ga, $^{68}$Ga, as well as $^{111}$In. Antibodies have also been labeled with a variety of radionuclides for potential use in targeted immunotherapy (Peirersz et al. *Immunol. Cell Biol.* 65: 111-125 (1987)). These radionuclides include $^{188}$Re and $^{186}$Re as well as $^{199}$Au and $^{67}$Cu to a lesser extent. U.S. Pat. No. 5,460,785 provides additional data regarding such radioisotopes and is incorporated herein by reference.

While molecules of the invention may be administered as described immediately above, it must be emphasized that in other embodiments conjugated and unconjugated binding molecules may be administered to otherwise healthy patients as a first line therapeutic agent.

However, selected embodiments of the invention comprise the administration of molecules of the invention to patients or in combination or conjunction with one or more adjunct therapies such as radiotherapy or chemotherapy (i.e. a combined therapeutic regimen). As used herein, the administration of binding molecules of the invention in conjunction or combination with an adjunct therapy means the sequential, simultaneous, coextensive, concurrent, concomitant or contemporaneous administration or application of the therapy and the disclosed binding molecules. Those skilled in the art will appreciate that the administration or application of the various components of the combined therapeutic regimen may be timed to enhance the overall effectiveness of the treatment. For example, chemotherapeutic agents could be administered in standard courses of treatment followed within a few weeks by radioimmunoconjugates described herein. Conversely, cytotoxin-conjugated binding molecules could be administered intravenously followed by tumor localized external beam radiation. In yet other embodiments, binding molecules may be administered concurrently with one or more selected chemotherapeutic agents in a single office visit. A skilled artisan (e.g. an experienced oncologist) would be readily be able to discern effective combined therapeutic regimens without undue experimentation based on the selected adjunct therapy and the teachings of the instant specification.

In this regard it will be appreciated that the combination of a binding molecule (with or without cytotoxin) and the chemotherapeutic agent may be administered in any order and within any time frame that provides a therapeutic benefit to the patient. That is, the chemotherapeutic agent and binding molecule may be administered in any order or concurrently. In selected embodiments, binding molecules of the present invention will be administered to patients that have previously undergone chemotherapy. In yet other embodiments, binding molecules of the present invention will be administered substantially simultaneously or concurrently with the chemotherapeutic treatment. For example, the patient may be given the binding molecule while undergoing a course of chemotherapy. In preferred embodiments the binding molecule will be administered within 1 year of any chemotherapeutic agent or treatment. In other preferred embodiments the polypeptide will be administered within 10, 8, 6, 4, or 2 months of any chemotherapeutic agent or treatment. In still other preferred embodiments the binding molecule will be administered within 4, 3, 2 or 1 week of any chemotherapeutic agent or treatment. In yet other embodiments the binding molecule will be administered within 5, 4, 3, 2 or 1 days of the selected chemotherapeutic agent or treatment. It will further be appreciated that the two agents or treatments may be administered to the patient within a matter of hours or minutes (i.e. substantially simultaneously).

With respect to these aspects of the invention, exemplary chemotherapeutic agents that are compatible with the instant invention include alkylating agents, vinca alkaloids (e.g., vincristine and vinblastine), procarbazine, methotrexate and prednisone. The four-drug combination MOPP (mechlethamine (nitrogen mustard), vincristine (Oncovin), procarbazine and prednisone) is very effective in treating various types of lymphoma and comprises a preferred embodiment of the present invention. In MOPP-resistant patients, ABVD (e.g., adriamycin, bleomycin, vinblastine and dacarbazine), Ch1VPP (chlorambucil, vinblastine, procarbazine and prednisone), CABS (lomustine, doxorubicin, bleomycin and streptozotocin), MOPP plus ABVD, MOPP plus ABV (doxorubicin, bleomycin and vinblastine) or BCVPP (carmustine, cyclophosphamide, vinblastine, procarbazine and prednisone) combinations can be used. Arnold S. Freedman and Lee M. Nadler, *Malignant Lymphomas*, in Harrison's Principles of Internal Medicine 1774-1788 (Kurt J. Isselbacher et al., eds., 13$^{th}$ ed. 1994) and V. T. DeVita et al., (1997) and the references cited therein for standard dosing and scheduling. These therapies can be used unchanged, or altered as needed for a particular patient, in combination with one or more antibodies or immunospecific fragments thereof of the present invention.

For patients with intermediate- and high-grade malignancies, who fail to achieve remission or relapse, salvage therapy is used. Salvage therapies employ drugs such as cytosine arabinoside, cisplatin, carboplatin, etoposide and ifosfamide given alone or in combination. In relapsed or aggressive forms of certain neoplastic disorders the following protocols are often used: IMVP-16 (ifosfamide, methotrexate and etoposide), MIME (methyl-gag, ifosfamide, methotrexate and etoposide), DHAP (dexamethasone, high dose cytarabine and cisplatin), ESHAP (etoposide, methylpredisolone, HD cytarabine, cisplatin), CEPP(B) (cyclophosphamide, etoposide, procarbazine, prednisone and bleomycin) and CAMP (lomustine, mitoxantrone, cytarabine and prednisone) each with well known dosing rates and schedules.

The amount of chemotherapeutic agent to be used in combination with the binding molecules of the present invention may vary by subject or may be administered according to what is known in the art. See for example, Bruce A Chabner et al., Antineoplastic Agents, in Goodman & Gilman's The Pharmacological Basis of Therapeutics 1233-1287 (Joel G. Hardman et al., eds., 9$^{th}$ ed. (1996)).

In another embodiment, a binding molecule of the present invention is administered in conjunction with a biologic. Biologics useful in the treatment of cancers are known in the art and a binding molecule of the invention may be administered, for example, in conjunction with such known biologics. For example, the FDA has approved the following biologics for the treatment of breast cancer: Herceptin® (trastuzumab, Genentech Inc., South San Francisco, Calif.; a humanized monoclonal antibody that has anti-tumor activity in HER2-positive breast cancer); Faslodex® (fulvestrant, AstraZeneca Pharmaceuticals, LP, Wilmington, Del.; an estrogen-receptor antagonist used to treat breast cancer); Arimidex® (anastrozole, AstraZeneca Pharmaceuticals, LP; a nonsteroidal aromatase inhibitor which blocks aromatase, an enzyme needed to make estrogen); Aromasin® (exemestane, Pfizer Inc., New York, N.Y.; an irreversible, steroidal aromatase inactivator used in the treatment of breast cancer); Femara® (letrozole, Novartis Pharmaceuticals, East Hanover, N.J.; a nonsteroidal aromatase inhibitor approved by the FDA to treat breast cancer); and Nolvadex® (tamoxifen, AstraZeneca Pharmaceuticals, LP; a nonsteroidal antiestrogen approved by the FDA to treat breast cancer). Other biologics with which the binding molecules of the invention may be combined include: Avastin® (bevacizumab, Genentech Inc.; the first FDA-approved therapy designed to inhibit angiogenesis); and Zevalin® (ibritumomab tiuxetan, Biogen Idec, Cambridge, Mass.; a radiolabeled monoclonal antibody currently approved for the treatment of B-cell lymphomas).

In addition, the FDA has approved the following biologics for the treatment of colorectal cancer: Avastin®; Erbitux® (cetuximab, ImClone Systems Inc., New York, N.Y., and Bristol-Myers Squibb, New York, N.Y.; is a monoclonal antibody directed against the epidermal growth factor receptor (EGFR)); Gleevec® (imatinib mesylate; a protein kinase inhibitor); and Ergamisol® (levamisole hydrochloride, Janssen Pharmaceutica Products, LP, Titusville, N.J.; an immunomodulator approved by the FDA in 1990 as an adjuvant treatment in combination with 5-fluorouracil after surgical resection in patients with Dukes' Stage C colon cancer).

For use in treatment of Non-Hodgkin's Lymphomas currently approved therapies include: Bexxar® (tositumomab and iodine I-131 tositumomab, GlaxoSmithKline, Research Triangle Park, N.C.; a multi-step treatment involving a mouse monoclonal antibody (tositumomab) linked to a radioactive molecule (iodine I-131)); Intron® A (interferon alfa-2b, Schering Corporation, Kenilworth, N.J.; a type of interferon approved for the treatment of follicular non-Hodgkin's lymphoma in conjunction with anthracycline-containing combination chemotherapy (e.g., cyclophosphamide, doxorubicin, vincristine, and prednisone [CHOP])); Rituxan® (rituximab, Genentech Inc., South San Francisco, Calif., and Biogen Idec, Cambridge, Mass.; a monoclonal antibody approved for the treatment of non-Hodgkin's lymphoma; Ontak® (denileukin diftitox, Ligand Pharmaceuticals Inc., San Diego, Calif.; a fusion protein consisting of a fragment of diphtheria toxin genetically fused to interleukin-2); and Zevalin® (ibritumomab tiuxetan, Biogen Idec; a radiolabeled monoclonal antibody approved by the FDA for the treatment of B-cell non-Hodgkin's lymphomas).

For treatment of Leukemia, exemplary biologics which may be used in combination with the binding molecules of the invention include Gleevec®; Campath®-1H (alemtuzumab, Berlex Laboratories, Richmond, Calif.; a type of monoclonal antibody used in the treatment of chronic Lymphocytic leukemia). In addition, Genasense (oblimersen, Genta Corporation, Berkley Heights, N.J.; a BCL-2 antisense therapy under development to treat leukemia may be used (e.g., alone or in combination with one or more chemotherapy drugs, such as fludarabine and cyclophosphamide) may be administered with the claimed binding molecules.

For the treatment of lung cancer, exemplary biologics include Tarceva® (erlotinib HCL, OSI Pharmaceuticals Inc., Melville, N.Y.; a small molecule designed to target the human epidermal growth factor receptor 1 (HER1) pathway).

For the treatment of multiple myeloma, exemplary biologics include Velcade® Velcade (bortezomib, Millennium Pharmaceuticals, Cambridge Mass.; a proteasome inhibitor). Additional biologics include Thalidomid® (thalidomide, Clegene Corporation, Warren, N.J.; an immunomodulatory agent and appears to have multiple actions, including the ability to inhibit the growth and survival of myeloma cells and anti-angiogenesis).

Other exemplary biologics include the MOAB IMC-C225, developed by ImClone Systems, Inc., New York, N.Y.

Diagnostic or Prognostic Methods Using Binding Molecules and Nucleic Acid Amplification Assays Binding molecules can be used for diagnostic purposes to detect, diagnose, or monitor diseases, disorders, and/or conditions associated with the aberrant expression and/or activity of a target cell antigen, e.g., HER2 or CD23. Expression of these targets may be in tumor tissue and other neoplastic conditions. Binding molecules are useful for diagnosis, treatment, prevention and/or prognosis of hyperproliferative disorders in mammals, preferably humans. Exemplary disorders are disclosed herein. Thus, the invention provides a diagnostic method useful during diagnosis of a cancers and other hyperproliferative disorders, which involves measuring the expression level of target protein or transcript in tissue or other cells or body fluid from an individual and comparing the measured expression level with a standard target expression levels in normal tissue or body fluid, whereby an increase in the expression level compared to the standard is indicative of a disorder.

One embodiment provides a method of detecting the presence of abnormal hyperproliferative cells, e.g., precancerous or cancerous cells, in a fluid or tissue sample, comprising assaying for the expression of the target in tissue or body fluid samples of an individual and comparing the presence or level of target expression in the sample with the presence or level of target expression in a panel of standard tissue or body fluid samples, where detection of target expression or an increase in target expression over the standards is indicative of aberrant hyperproliferative cell growth.

More specifically, the present invention provides a method of detecting the presence of abnormal hyperproliferative cells in a body fluid or tissue sample, comprising (a) assaying for the expression of target in tissue or body fluid samples of an individual using target-specific antibody molecules of the present invention, and (b) comparing the presence or level of target expression in the sample with a the presence or level of target expression in a panel of standard tissue or body fluid samples, whereby detection of target expression or an increase in target expression over the standards is indicative of aberrant hyperproliferative cell growth.

With respect to cancer, the presence of a relatively high amount of target protein in biopsied tissue from an individual may indicate the presence of a tumor or other malignant growth, may indicate a predisposition for the development of such malignancies or tumors, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Target-specific antibody molecules of the present invention can be used to assay protein levels in a biological sample using classical immunohistological methods known to those of skill in the art (e.g., see Jalkanen, et al., *J. Cell. Biol.* 101:976-985 (1985); Jalkanen, et al., *J. Cell Biol.* 105:3087-3096 (1987)). Other antibody-based methods useful for detecting protein expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{112}$In) and technetium ($^{99}$Tc); luminescent labels, such as luminol; and fluorescent labels, such as fluorescein and rhodamine, and biotin. Suitable assays are described in more detail elsewhere herein.

One aspect of the invention is a method for the in vivo detection or diagnosis of a hyperproliferative disease or disorder associated with aberrant expression of the target in a subject, preferably a mammal and most preferably a human. In one embodiment, diagnosis comprises: a) administering (for example, parenterally, subcutaneously, or intraperitoneally) to a subject an effective amount of a labeled antibody or fragment thereof of the present invention, which specifically binds to target; b) waiting for a time interval following the administering for permitting the labeled binding molecule to preferentially concentrate at sites in the subject where target is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of target. Background level can be determined by various methods including comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of, e.g., $^{99}$Tc. The labeled binding molecule, e.g., antibody or antibody fragment, will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: *The Radiochemical Detection of Cancer*, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 7 to 10 days.

Presence of the labeled molecule can be detected in the patient using methods known in the art for in vivo scanning. These methods depend upon the type of label used Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography. Antibody labels or markers for in vivo imaging of target expression include those detectable by X-radiography, nuclear magnetic resonance imaging (NMR), MRI, CAT-scans or electron spin resonance imaging (ESR). In a related embodiment to those described above, monitoring of an already diagnosed disease or disorder is carried out by repeating any one of the methods for diagnosing the disease or disorder, for example, one month after initial diagnosis, six months after initial diagnosis, one year after initial diagnosis, etc.

Where a diagnosis of a disorder, including diagnosis of a tumor, has already been made according to conventional methods, detection methods as disclosed herein are useful as a prognostic indicator, whereby patients continuing to exhibiting enhanced target expression will experience a worse clinical outcome relative to patients whose expression level decreases nearer the standard level.

By "assaying the expression level of the tumor associated target polypeptide" is intended qualitatively or quantitatively measuring or estimating the level of target polypeptide in a first biological sample either directly (e.g., by determining or estimating absolute protein level) or relatively (e.g., by comparing to the cancer associated polypeptide level in a second biological sample). Preferably, target polypeptide expression level in the first biological sample is measured or estimated and compared to a standard target polypeptide level, the standard being taken from a second biological sample obtained from an individual not having the disorder or being determined by averaging levels from a population of individuals not having the disorder. As will be appreciated in the art, once the "standard" target polypeptide level is known, it can be used repeatedly as a standard for comparison.

By "biological sample" is intended any biological sample obtained from an individual, cell line, tissue culture, or other source of cells potentially expressing target. As indicated, biological samples include body fluids (such as sera, plasma, urine, synovial fluid and spinal fluid), and other tissue sources which contain cells potentially expressing target. Methods for obtaining tissue biopsies and body fluids from mammals are well known in the art.

In an additional embodiment, antibodies, or immunospecific fragments of antibodies directed to a conformational epitope of target may be used to quantitatively or qualitatively detect the presence of target gene products or conserved variants or peptide fragments thereof. This can be accomplished, for example, by immunofluoresence techniques employing a fluorescently labeled antibody coupled with light microscopic, flow cytometric, or fluorimetric detection.

Cancers that may be diagnosed, and/or prognosed using the methods described above include but are not limited to, stomach cancer, renal cancer, brain cancer, bladder cancer, colon cancer, lung cancer, breast cancer, pancreatic cancer, ovarian cancer, and prostate cancer.

Immunoassays

Target-specific antibodies or immunospecific fragments thereof disclosed herein may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, *Current Protocols in Molecular Biology*, John Wiley & Sons, Inc., New York, Vol. 1 (1994), which is incorporated by reference herein in its entirety). Exemplary immunoassays are described briefly below (but are not intended by way of limitation).

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}$H or $^{125}$I) with the antibody of interest in the presence of increasing amounts of unlabeled antigen, and the detection of the antibody bound to the labeled antigen. The affinity of the antibody of interest for a particular antigen and the binding off-rates can be determined from the data by Scatchard plot analysis. Competition with a second antibody can also be determined using radioimmunoassays. In this case, the antigen is incubated with antibody of interest is conjugated to a labeled compound (e.g., $^3$H or $^{125}$I) in the presence of increasing amounts of an unlabeled second antibody.

Target-specific antibodies may, additionally, be employed histologically, as in immunofluorescence, immunoelectron microscopy or non-immunological assays, for in situ detection of cancer antigen gene products or conserved variants or peptide fragments thereof. In situ detection may be accomplished by removing a histological specimen from a patient, and applying thereto a labeled target-specific antibody or fragment thereof, preferably applied by overlaying the labeled antibody (or fragment) onto a biological sample.

Surface plasmon resonance (SPR) as performed on BIAcore offers a number of advantages over conventional methods of measuring the affinity of antibody-antigen interactions: (i) no requirement to label either antibody or antigen; (ii) antibodies do not need to be purified in advance, cell culture supernatant can be used directly; (iii) real-time measurements, allowing rapid semi-quantitative comparison of different monoclonal antibody interactions, are enabled and are sufficient for many evaluation purposes; (iv) biospecific surface can be regenerated so that a series of different monoclonal antibodies can easily be compared under identical conditions; (v) analytical procedures are fully automated, and extensive series of measurements can be performed without user intervention. BIAapplications Handbook, version AB (reprinted 1998), BIACORE code No. BR-1001-86; BIAtechnology Handbook, version AB (reprinted 1998), BIACORE code No. BR-1001-84.

Epitope specificity is an important characteristic of a monoclonal antibody. Epitope mapping with BIAcore, in contrast to conventional techniques using radioimmunoassay, ELISA or other surface adsorption methods, does not require labeling or purified antibodies, and allows multi-site specificity tests using a sequence of several monoclonal antibodies. Additionally, large numbers of analyses can be processed automatically.

Peptide inhibition is another technique used for epitope mapping. This method can complement pair-wise antibody binding studies, and can relate functional epitopes to structural features when the primary sequence of the antigen is known. Peptides or antigen fragments are tested for inhibition of binding of different MAbs to immobilized antigen. Peptides which interfere with binding of a given MAb are assumed to be structurally related to the epitope defined by that MAb.

The Examples that follow are set forth to aid in the understanding of the inventions but are not intended to, and should not be construed to limit its scope in any way.

EXAMPLES

Example 1

Selection of hHER2/ErbB2 Specific Fabs from Phage Libraries

Recombinant human HER2 ectodomain was used to screen a human naïve phagemid Fab library containing 3.5×10$^{10}$ unique clones (Nat Biotechnol. 2005 March; 23(3):344-8.) Biotinylated hHer2-Fc protein was captured on steptavidin-coated magnetic beads prior to incubation with the phage library. Selections were performed as described previously, with depletion on hEGFR-Fc to eliminate Fc specific binders as well as EGFR cross-reactive binders (Nat Biotechnol. 2005 March; 23(3):344-8). After 3 rounds of panning, the 479 by gene III stump was removed by M/u/digestion, and the vector was religated for soluble Fab expression in TG1 cells. ELISA analysis of 920 clones yielded 224 positive clones, containing 79 unique sequences. Unique clones were purified and binding was reconfirmed at a single concentration to recombinant human hHER2 ectodomain by ELISA as well as by FACS on CHO cells stably transfected with full-length human HER2 (see below for cell line construction). Based on binding data, 24 unique clones (65A03, 65B03, 65C10, 65H09, 66A12, 66C01, 67A02, 67C12, 67F10, 67F11, 68B11, 68D03, 69A09, 69E02, 69F02, 70C01, 70C08, 70D11, 71A03, 71A06, 71F08, 71F10, 71H02 and 72H10) were selected for further analysis.

Example 2

Binding Activity of Fabs to hHER2/ErbB2 Measured by Flow Cytometry

The ability of Fabs to bind to the wild type hHER2/ErbB2 was determined by flow cytometry using CHO cell line stably transfected with hHER2/ErbB2.

CHO cells (Chinese Hamster Ovary cells) stably transfected with hHER2 expression vector and selected in G418 containing medium. G418 resistant clones were pooled and split 24 hours prior to the setup of the assay to obtain 70% confluent monolayer. Routinely, CHO cell line was maintained within 20 passages. Cells were lifted with cell dissociation buffer (Gibco catalog #13151-014), counted, washed and adjusted to 1×10$^6$ cells/ml and one ml of cells were then added to each tube (12×75 mm tube Falcon catalog #352054). Cells were pelleted and supernatant removed by centrifugation at 1200 rpm for 5 min and 100 µl of diluted antibodies were then added to the cell pellet. Purified Fabs were tested at a starting concentration of either 210 or 60 µg/ml with 1:3 dilutions in FACS buffer, down to 0.001 µg/ml. FACS buffer used throughout the assay was PBS (without Ca$^{++}$/Mg$^{++}$) containing 1% BSA (Sigma catalog #A-7906) and 0.1% Sodium Azide (Sigma catalog #S2002). Samples were allowed to incubate on ice for 1 hour and 15 minutes then were washed with 2 ml FACS buffer and centrifuged at 1200 rpm for 5 minutes at 4° C. The supernatant was aspirated and 100 µl of the secondary detection antibody was added to each corresponding tube in FACS buffer. Samples were then incubated for 30 minutes on ice, in the dark. Cells were washed as described above, then, re-suspended in 250 µl FACS buffer per tube/sample.

Cell bound Fabs were detected using FITC-conjugated affinity-purified F(ab')$_2$ Fragment specific goat anti-human-IgG (Jackson ImmunoResearch Lab catalog #109-096-006; used at 5 µg/ml), while positive murine control antibody was detected using the F(ab')$_2$ FITC conjugated goat anti-mouse IgG (H+L) (Jackson ImmunoResearch, catalog#115-096-062; used at 5 µg/ml). Cells were stained for live cell determination with Propidium Iodide staining solution (PI for dead cell exclusion; BD Pharmingen catalog #51-66211E or 556463; use at 1:500 final in FACS buffer). Samples were run on the FACSCalibur instrument (Becton Dickinson) with 10,000 live events collected per sample. Data analysis was done using GraphPad Prism version 4.0 software (www.graphpad.com) (GraphPad Software, Inc., 11452 El Camino Real, #215, San Diego, Calif. 92130 USA).

Once samples have been run and geometric means determined, antibody concentration (X axis) vs. geometric mean (Y axis) was graphed to the log10, using Graphpad Prism (Prism Graph) graphing program. Data sets were then transformed (X value data set=antibody concentration) to X=Log (X) and graphed using a nonlinear regression curve fit, Sigmoidal dose-response. EC50 values and R2 values were generated using the Prism Graph software.

24 Fabs identified from the screening in Example 1 were tested at multiple concentrations by FACS on human HER2-CHO cells and untransfected CHO cells to confirm specificity (data not shown and Table 1)

12 Fabs (65B03, 65C10, 65H09, 66A12, 66C01, 67A02, 67C12, 67F10, 67F11, 69A09, 71A06 and 71F10) showed good binding activity to wild type HER2/ErbB expressed on CHO cells. The Fabs were tested on the MDA-MB-468 tumor cell line (EGFR+, HER2−); no binding was detected, demonstrating that these Fabs are specific to HER2. A full titration was performed on MCF7 and SKBR3 tumor cell lines, and human Her2-CHO and murine Her2-CHO cell lines in order to calculate an approximate EC50 (data not shown, see summary in Table 1). The 12 Fabs were also tested on CHO cells stably transfected with full-length murine HER2 and cyno HER2; One Fab (71F10) was found to bind murine HER2 and nine were found to bind to cyno HER2 (Table 1).

Example 3

Binding Activity of Fabs to Human and Mouse HER2/ErbB2 Measured by ELISA

The ability of Fabs to bind to the wild type hHER2/ErbB2 and mHER2/ErbB2 was determined by Enzyme-Linked ImmunoSorbent Assay (ELISA).

96 well microtiter Immulon II plates (Fisher, Cat# 14245-61) were coated with 100 ul/well of 2 ug/ml unlabeled Gt-anti-hu IgG or unlabeled Gt-anti-hu Kappa (SouthernBiotech, Cat# 2040-01; 2060-01) in Na2CO3/NaHCO3 buffer, pH 9.5 overnight at 4° C. and dumped coating buffer out of plate. In the next step, 100 ul dilution buffer (0.5% nonfat dry milk in PBS plus 0.01% thimerosal) and 100 ul individual supernatant or purified protein in dilution buffer were added to duplicate wells and incubated for 1 h at 37° C. After washing with tap water, 100 ul of a ⅟₁₀,₀₀₀ dilution in dilution buffer of Gt-anti-hu Kappa-HRP (SouthernBiotech, Cat# 2060-05) was added to the wells and incubated for 1 h at 37° C. After washing, 100 ul/well of a HRPO Substrate combined TMB Peroxidase Substrate/Peroxidase Solution B (Kirdgaard and Perry Labs, Cat. 50-76-00) was added. The reaction was stopped with 100 ul of 2M $H_2SO_4$ after 5 to 10 min. The OD was measured at 450 nm and 540 nm using a Molecular Devices plate reader and binding curves were generated.

Twenty two of the twenty four Fabs showed moderate/strong binding activity to wild type hHER2/ErbB2 (data not shown and Table 1). Only Fab 71F10 showed moderate/strong binding activity to wild type mHER2/ErbB2 (data not shown and Table 1).

Example 4

Antibody Cross-reactivity

The Cynomolgus Monkey HER2 cDNA was amplified by RT-PCR from kidney mRNA of Cynomologous monkey kidney (BioChain Institute, Inc, Hayward, Calif.). PCR primers are: for cyno HER2 extracellular domain forward primer, GAGCCATGGGGCCGGAGCCGCAGTGAGCACCATG (SEQ ID NO:159); reverse primer, TCGGGGCTTCTGCGGACTTGGCCTTCTGGTTCAC (SEQ ID NO:160); for the intracelluar domain: forward primer: GCCCAACCAGGCGCAGATGCGGATCCT-GAAAGAG (SEQ ID NO:161); reverse primer: CCAGATC-CAAGCACCTTCACCTTCCTCAGCTCCG (SEQ ID NO:162). The amplified PCR products were cloned into a TA cloning vector, pCR2.1 (Invitrogen) and sequenced. The full length cyno HER2 cDNA was assembled at the BsmB I site from both extracellular and intracellular domain sequences. The plamid is termed pCR2.1cynoHER2.

To express cyno HER2 in cell lines, the HER2 cDNA was digested from pCR2.1cynoHER2 using NotI and HindIII and cloned into a lentiviral vector plasmid under the control of the hCMV promoter. Lentiviral vector was produced and the culture supernatant was used to transduce HEK 293 cells.

To establish a CHO cell line that expresses mouse HER2, a mouse HER2 coding sequence was PCR amplified from a plasmid containing mouse HER2 cDNA (MGC:62447 IMAGE:570). PCR primers: forward primer: CATGGCG-GCCGCCCGGAGCCGCAGTGATCATC (SEQ ID NO:163); and reverse primer: CGATGCGGCCGCGGAT-GTCTGCACATGTGACC (SEQ ID NO:164). The PCR product was inserted into a mammalian expression vector pV90. The resultant plasmid was termed pKJS462.21. pKJS462.21 DNA was transfected into DG44-1 CHO cells and selected for stable integration by culturing in alpha minus MEM with 10% dialyzed FBS (Hyclone#SH30079.03). The bulk stable population was subcloned and a single clone expressing high levels of HER2, termed, 3G11B, was selected for Fab cross reactivity analysis for mHer2 using FACS. This cell line was generally referred as CHO/mHer2.

Cross reactivity to rat Her2 was analyzed by FACS analysis using Tubo cancer cells (derived from rat HER2 transgenic mouse).

Lentiviral Vector Plasmid Construction pLenti6/TR from Invitrogen kit, V480-20, was modified by replacing the Tet Repressor gene with a multiple cloning site to bridge the BamH1 to EcoR1 sites. Sense oligo GATC-CCCGGGTACCGGTCGGCGCGCCTC-GAGATATCTTAATTAAG (SEQ ID NO:115) was annealed to antisense AATTCTTAATTAAGATATCTCGAG-GCGCGCCGACCGGTACCCGGG (SEQ ID NO:116) and ligated into the BamH1/EcoR1 digested backbone. This plasmid (CK072) contains a multiple cloning site downstream of the CMV promoter with SV40 promoter driving a blasticidin resistance marker. The cynomolgus monkey HER2 gene was PCRed in two pieces for sequencing using oligos GAGC-CATGGGGCCGGAGCCGCAGTGAGCACCATG (SEQ ID NO:117) and antisense CCAGATCCAAGC-ACCT-TCACCTTCCTCAGCTCCG (SEQ ID NO:118) for the extracellular portion and GCCCAACCAGGCGCAGAT-GCGGATCCTGAAAGAG (SEQ ID NO:119) and antisense TCGGGGCTTCTGCGGACTTGGCCTTCTGGTTCAC (SEQ ID NO:120) for the intracellular portion. The PCR products were TA-TOPO cloned into pCR2.1 (Invitrogen K4500-01) and sequenced. Finally, the consensus cyno Her2 sequences were assembled from extracellular and intracellular plasmids (joined at the BsmB1 site), excised with SpeI/XbaI digestion, and ligated into the downstream XbaI site of CK072 described above. The resulting lentiviral vector plasmid (CK090.18) was used to generate vector for overexpressing cyno HER2 in target cell lines.

Vector Production and Transduction

293FT cells (Invitrogen #R700-07) were co-transfection with the Invitrogen Virapower packaging mix (K4975-00)

and lentiviral vector plasmid CK90.18 described above, following the manufacturer's instructions for Lipofectamine 2000 (Invitrogen #11668-019). Culture supernatant was harvested 48 hours later, cellular debris pelleted at 1250 g for ten minutes, and the clarified supernatant was 0.45u filtered. Supernatants were applied to HEK293 cells in order to varify the ability of the vector to deliver the cyno Her2 transgene. Stably transduced HEK 293 cells showed high level expression of the trangene in a portion of a mixed population of positive and negative cells.

Cross Reactivity Test

A pool population of transduced and untransduced HEK293 cells were treated to the various Fabs and stained with FITC conjugated secondary antibodies for viewing as follows. Briefly, HEK 293 cells expressing cynoHer2 were plated in CC2-coated 8-well chamber slides (Nunc #154941) and allowed to attach overnight in the incubator (5% CO2, 37° C.). The growth medium was replaced with 50 to 75 ul of the Dyax Fabs (10 mg/ml) and these were allowed to bind for 90 minutes at 4oC. Cells were rinsed with dilution buffer (PBS with 10% FBS) and then fixed for 20 minutes at room temperature with 4% formaldehyde in PBS. The fixed cells were rinsed and incubated with secondary conjugated antibodies for 45 minutes at 4° C. The secondary antibody solution was a 50:50 mix of FITC conjugated goat anti human kappa chain and goat anti human IgG F(ab')2 specfic fragment (Sigma #F3761 and Jackson Immun. #109-096-097 respectively). The wells were rinsed with dilution buffer to get rid of unbound antibodies before viewing in the Zeiss Axiovert fluorescent microscope.

Results: Nine out of twelve Fabs selected for testing showed cross-reactivity with cynoHER2 (Table 1). One Fab, 71-F10, showed moderate binding cross-reactivity to mHER2/ErbB2 (Table 1) was confirmed in this assay. 71F10 also showed cross-reactivity with rat HER2 (data not shown).

Example 5

HER2/ErbB2 Fab Epitope Mapping

Figure 4:
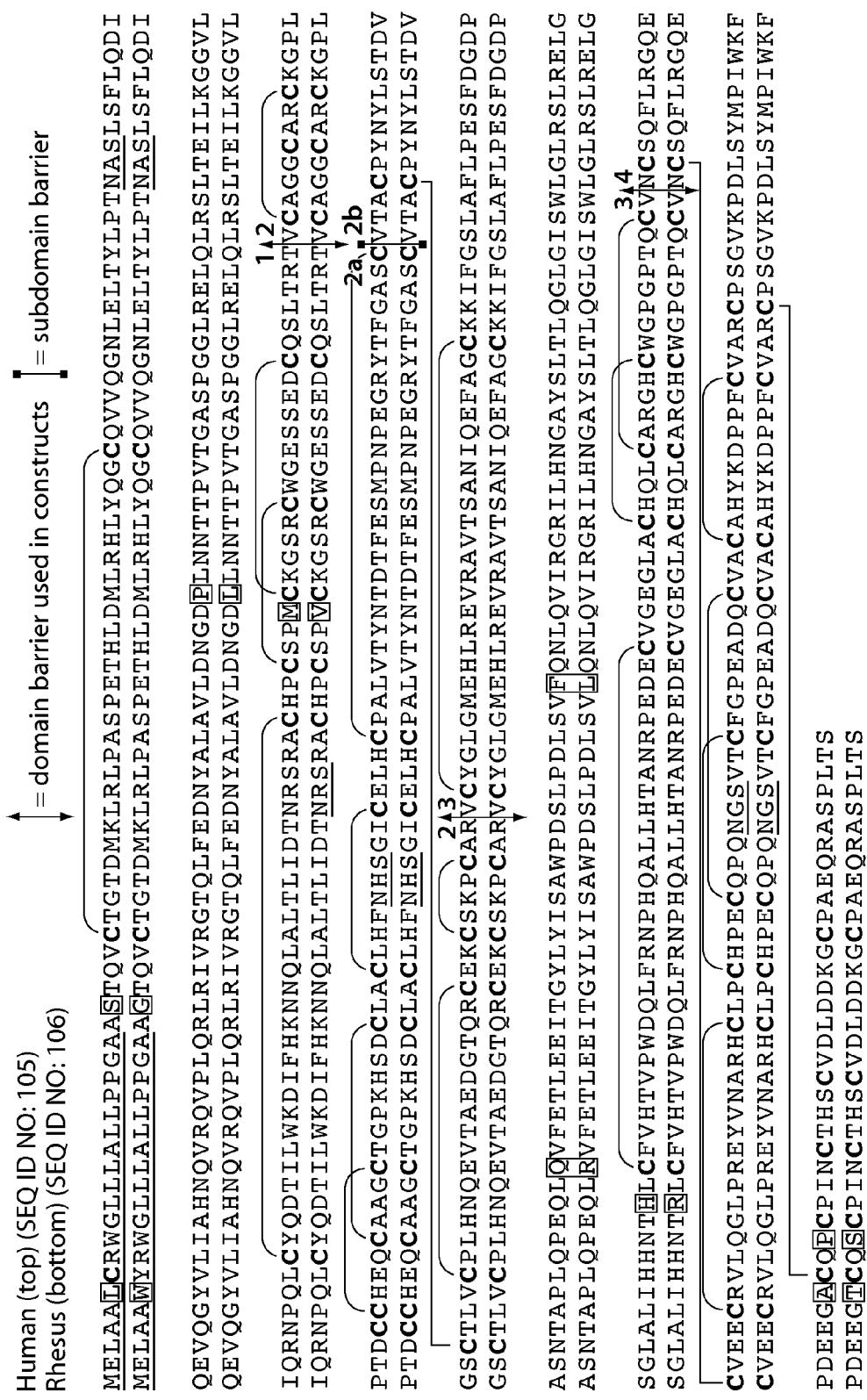
FIG. 4 depicts the amino acid sequences of human (SEQ ID NO:105) and rhesus (SEQ ID NO:106) ErbB2 extracellular domain with cysteine pairing.

Amino acid sequences of human ErbB2 ECD (SEQ ID NO:105) and Rhesus ErbB2 ECD (SEQ ID NO:106) are shown in FIG. 4 with cysteine pairing. Residues different between human and rhesus are highlighted. Potential N-glycosylation sites are underlined.

Human ErbB2-encoding DNA fragments were obtained by PCR from pLXSN-HER2. ErbB2-Fc vectors for expression in CHO cells were generated by cloning each ErbB2 DNA fragment (residues Thr1-Thr196 (Domain 1), Thr1-Arg318 (Domains 1-2), Thr1-Asn508 (Domains 1-3) or Thr1-Asn630 (Domains 1-4) of human HER2/ErbB2 ECD) in frame with a huIgG1-Fc into the PV90 vector. The protein constructs are denoted MR066 (Domain 1), MR067 (Domain 1-2), MR068 (Domain 1-3) and MR069 (full length ECD).

Proteins were transiently expressed in 293E mammalian cells. After 4 days of culture at 37° C., the cell supernatants were harvested, filtered and purified on Protein A Sepharose. Protein was eluted from column with 25 mM $H_3PO_4$/NaOH, 0.1 M NaCl, pH 2.8 and neutralized immediately with ½0th volume 0.5 M sodium phosphate, pH 8.6. Protein was evaluated for purity and degree of aggregation by SDS-PAGE and analytical SEC. Protein concentration was determined by UV absorbance using the sequence-predicted extinction coefficient at 280 nm for each protein.

Figure 5:
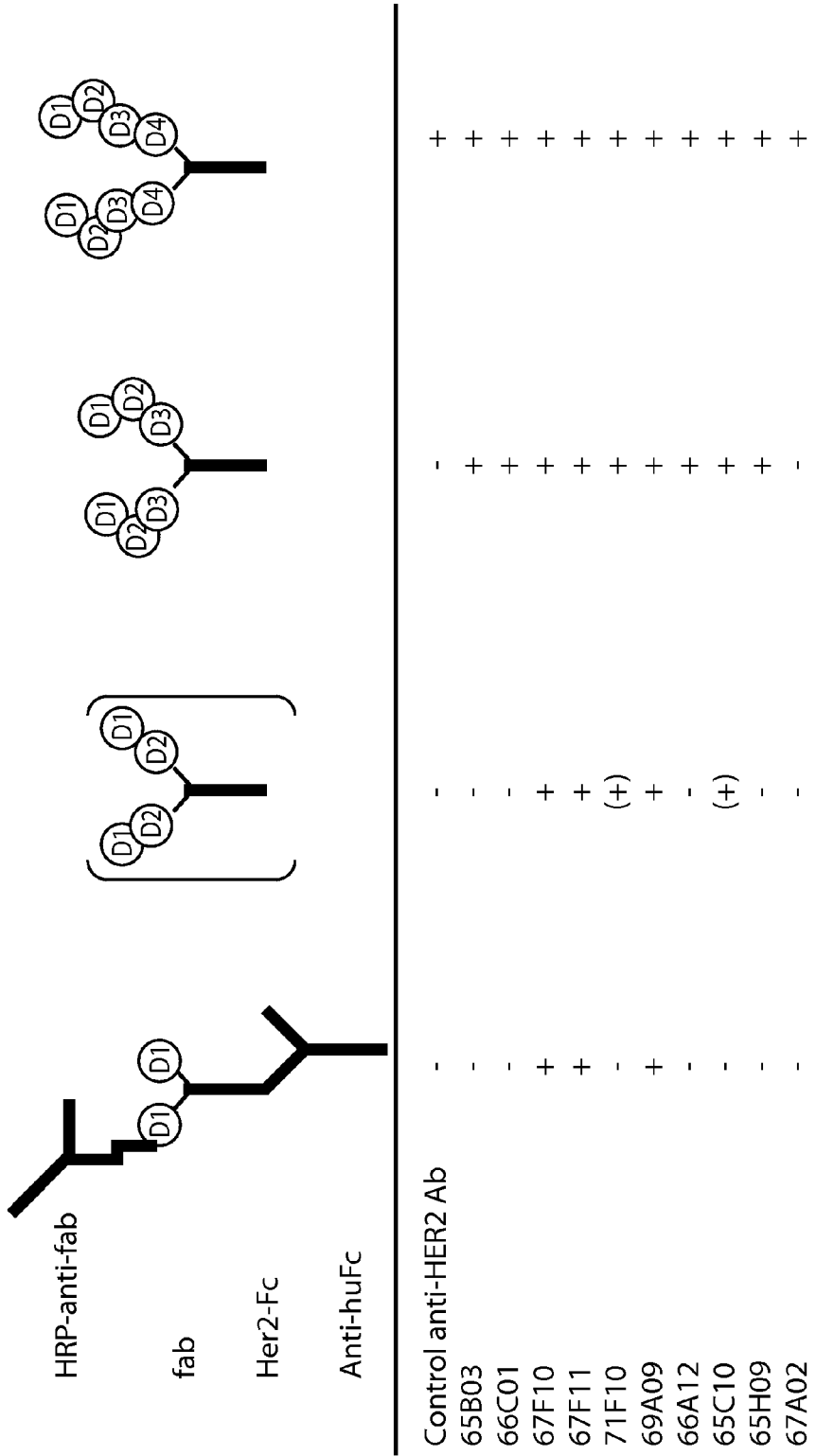
FIG. 5 depicts the domain mapping of human anti-HER2Fabs.

The ability of 65B03, 66C01, 67F10, 67F11, 71F10, 69A09, 66A12, 65C10, 65H09 and 67A02 Fabs and control anti-HER2 antibody to bind MR066, MR067, MR068 and MR069, was determined by ELISA. Nunc Maxisorp ELISA plates were coated with 5 ug/ml rabbit pAbs anti-human Fc gamma in PBS overnight at 4 degrees. Plates were washed one time with PBST (PBS, 0.05% tween 20) and blocked with 1% BSA in PBS for one hour at room temperature. Plates were washed one time with PBST and incubated with 1 ug/ml HER2-Fc fusion protein for one hour. Plates were washed three times with PBST and dilutions of Fab (four 5-fold serial dilutions, starting at 1 ug/ml) in block were added and incubated for ninety minutes. Plates were washed three times with PBST and incubated with 1:2,000 HRP-labelled goat anti-human kappa (Southern Biotech cat#2060-05) and HRP-labelled goat anti-human lambda (Southern Biotech cat#2070-05) in block for one hour at room temperature. Plates were washed three times with PBST, developed with TMB solution for 5 minutes, and stopped with equal volume 1 $NH_2SO_4$. Absorbance values were read at 450 nm. The results are shown in FIG. 5.

Example 6

Construction of 71F10 Fab-hLIGHT Fusions with Delta4; G4Sdelta4 (SEQ ID NO: 147) and $(G4S)_4$ (SEQ ID NO: 134) Linkers The protein sequences of the 71F10 mature heavy chain variable domain (VH) and Light chain variable domain (VL) are shown in SEQ ID NO:11 and 13, respectively. The CDRs, (complementarity determining regions, based upon the Kabat designations) of 71F10 heavy chain and light chain are shown in SEQ ID NOs:47-49 and 74-76, respectively. Alignment of partial amino acid sequences between 71F10 VH (residues 1-97 of SEQ ID NO:11) and HV3-23 VH (residues 1-97 of SEQ ID NO:107) shows 93% (91/97) identities and 95% (93/97) positives (parameters: Length=98, Score=186 bits (471), and Expect=3e-050). HV3-23 refers to the human germline HV3-23 sequence with Genbank accession number M99660. Nucleotide sequences of 71F10 VH and VL are shown in SEQ ID NOs:156 and 14, respectively. The nucleotide sequence of 71F10 VH (SEQ ID NO:156) is codon-optimized for mammalian cell expression. The amino acid and nucleotide sequences of HV3-23 VH are shown in SEQ ID NOs:107 and 108, respectively.

The scheme of 71F10 Fab-hLIGHT construction is described as follows.

71F10 VL region was synthesized by PCR amplification using the oligonucleotide primers described in 110-F1 (SEQ ID NO:121), C06-5' (SEQ ID NO:122) and 039-VLR (SEQ ID NO:123). The 5' VL PCR primers consisted of a forward primer 110-F1 (SEQ ID NO:121) including a Not I restriction endonuclease site (GCGGCCGC (SEQ ID NO:180)) followed by sequences encoding a partial Light chain signal peptide and an internal forward primer C06-5' (SEQ ID NO:122) encoding a partial Light chain signal peptide followed by sequences complementary to the amino terminus of 71F10 VL. The 3' VL PCR primer 039-VLR (SEQ ID NO:123) included a BsiW I restriction endonuclease site (CGTACG (SEQ ID NO:181)) and sequences encoding the carboxyl terminus of 71F10 VL. The 71F10 VL region was amplified in two sequential PCR reactions through the common overlapping sequences encoding the Light chain signal peptide using these three PCR primers from plasmid DNA CPG169 containing the 71F10VL. The 71F10 VL gene fragment was cloned into the Not I/Bsiw I digested the modified pV100 vector which contained a BsiW I site at the amino terminus of the human kappa domain. Correct sequences were confirmed by DNA sequence analysis.

71F10 VH region was recoded by replacing with the consensus codons from human immunoglobulin VH database without change in polypeptide sequence and eliminating the putative cryptic splice donor and acceptor sites by synonymous codon exchange. The recoded 71F10 VH region was synthesized by assembly PCR amplification using the oligonucleotide primers described in VH-FR1-F (SEQ ID NO:124), VH-FR2-R (SEQ ID NO:125), VH-FR3-F (SEQ ID NO:126), 71F10VH-CDR1-F (SEQ ID NO:127), 71F10VH-CDR2-F (SEQ ID NO:128), 71F10VH-CDR3+FR4-R (SEQ ID NO:129), VH-pV90-F (SEQ ID NO:130), and VH-pV90-R (SEQ ID NO:131). In the first PCR step, two sets of three oligodeoxynucleotides (oligos) were annealed and elongated to produce a half-length product. The 5' half of the recoded 71F10 VH was generated by PCR using the forward 5' primer VH-FR1-F (SEQ ID NO:124) which consists of nucleotide sequences encoding the 71F10 VH framwork1 region and the forward 5' primer 71F10VH-CDR1-F (SEQ ID NO:125) which consists of nucleotide sequences encoding the 71F10 VH CDR1 region and the reverse 3' primer VH-FR2-R (SEQ ID NO:126) which consists of nucleotide sequences encoding the 71F10 VH framework 2 region. The 3' half of the recoded 71F10 VH was generated by PCR using the forward 5' primer 71F10VH-CDR2-F (SEQ ID NO:127) which consists of nucleotide sequences encoding the 71F10 VH CDR2 region and the forward 5' primer DyaxVH-FR3-F (SEQ ID NO:128) which consists of nucleotide sequences encoding the 71F10 VH framework 3 region and the reverse 3' primer 71F10VH-CDR3+FR4-R (SEQ ID NO:129) which consists of nucleotide sequences encoding the 71F10 VH CDR3 and framework 4 regions. In the second PCR step, the full-length recoded 71F10 VH gene sequence is selectively amplified from two mixtures of first PCR step using primers specific for the desired full-length product. The 5' forward primer, VH-pV90-F (SEQ ID NO:130) which contained a unique Mlu I restriction endonuclease site (ACGCGT (SEQ ID NO:160)) followed by sequences encoding the last three amino acids of the heavy chain signal peptide followed by sequences complementary to the amino terminus of the recoded 71F10 VH and the 3' reverse primer, VH-pV90-R (SEQ ID NO:131) which contained a Nhe I site (GCTAGC (SEQ ID NO:182)) and sequence encoding complementary to the carboxyl terminus of the recoded 71F10 VH. The recoded 71F10 VH gene fragment was cloned into the Mlu I/NheI digested the modified pV90 vector which contained a synthetic heavy-chain leader sequence and a Mlu I site followed by a BamH I site at the amino terminus of the IgG1 CH1 domain. Correct sequences were confirmed by DNA sequence analysis.

Three different linkers (SEQ ID NOs:132-134) were used to connect the 71F10 Fab heavy chain to the amino terminus of the huLIGHT and the amino acid sequences of these linkers are shown in Delta 4 (SEQ ID NO:132), G4Sdelta4 (SEQ ID NO:133), and (G4S)$_4$ (SEQ ID NO:134). The optimal linker length was determined as follow:

1. The initial 3D structure of Fab was built through homology modeling using Modeller 9 based on crystal structure of human IgG(pdb: 1 HZH). Five pairs of Cysteines were constrained to form disulfide bond. The 3D LIGHT/LTbR structure was constructed based on crystal structure of TNFbeta/TNF-R p55(pdb: 1TNR).

2. Trimeric Fab structure was constructed with C3 symmetry using in-house program.

3. Energetic analysis was carried out by changing distance between trimeric Fab and LIGHT/LTbR with C3 axis aligned. d is the distance between the one point (intersection point of Fab axis and C3 axis) and closed point (intersection of surface and C3 axis) of LIGHT/LTbR. The vdW interaction energy was calculated with each structure. 25A is the minimum distance; otherwise there will be significant repulsion between trimeric Fab and LIGHT; The interaction energy is zero beyond 40A. In our model for linker optimization, 40A was chosen as the starting geometry.

4. Four different linkers were constructed and evaluated using Modeller: (G4S)$_2$ (SEQ ID NO: 151), (G4S)$_4$ (SEQ ID NO: 134), delta4 (natural LIGHT linker), G4S+delta (SEQ ID NO: 147). The results indicate that (G4S)$_2$ (SEQ ID NO: 151) is too short while the other three are linkers of appropriate length.

The 71F10 Fab-hLIGHT fusion heavy chains were constructed in the PCR reactions using the 5' forward+3' reverse PCR primers and internal overlapping PCR primer sets encoding three different linkers from plasmid DNAs N5KG1 containing the huIgG1 and pABF046 containing the huLIGHT. The oligonucleotide primers were described as MB-04F (SEQ ID NO:135), 130-R1 (SEQ ID NO:136), 130-F2 (SEQ ID NO:137), 130-R2 (SEQ ID NO:138), 131-R2 (SEQ ID NO:139), 132-F2 (SEQ ID NO:140), and 132-R2 (SEQ ID NO:141). Briefly, the 5' forward primer, MB-04F (SEQ ID NO:135) which included an Age I site (ACCGGT (SEQ ID NO:161)) followed by sequences complementary to the IgG1 CH1 region. The 3' reverse primer, 130-R1 (SEQ ID NO:136) which contained a BamH I site (GGATCC (SEQ ID NO:177)) and sequence encoding complementary to the carboxyl terminus of huLIGHT. The 5' forward primers, 130-F2 (SEQ ID NO:137) and 132-F2 (SEQ ID NO:138) of the internal overlapping PCR primer sets included the three partial linkers followed by sequences complementary to the amino terminus huLIGHT. The 3' reverse primers, 130-R2 (SEQ ID NO:139), 131-R2 (SEQ ID NO:140), and 132-R2 (SEQ ID NO:141) of the internal overlapping PCR primer sets contained sequences encoding a partial IgG1 hinge followed by the three partial linkers. The PCR fragments were then finally assembled in a second PCR reaction using sequences encoding the overlapping three linkers and digested with the Age I and BamH I restriction endonucleases and ligated into the Age I/BamH I digested 71F10 IgG1 heavy chain vector. This resulted in fusion products of the 71F10 Fab heavy chain to the amino terminus of the huLIGHT. Correct sequences were confirmed by DNA sequence analysis.

The 71F10 light chain vector (pBIIB71F10-129) was commonly used in the 71F10Fab-hLIGHT fusions and the DNA (SEQ ID NO:110) and amino acid (SEQ ID NO:109) are disclosed herein. Heavy chain DNA and amino acid sequences for the 71F10Fab-hLIGHT fusions (pBIIB71F10-130, pBIIB71F10-131, and pBIIB71F10-132) and their physical and chemical parameters are described herein as SEQ ID NOs:2-4 and 6-8, respectively.

The 71F10 agly IgG heavy-chain (pBIIB71F10-137) was constructed using QuikChange Multi Site-Directed Mutagenesis Kit (Stratagene Cat# 200513) using the 71F10 IgG heavy-chain (pBIIB71F10-134) as a template. A threonine amino acid was changed to an alanine amino acid at position 299 (kabat number) in CH2 domain by primer 137-F which contains a desired mutation. DNA and amino acid sequences for the 71F10 IgG heavy-chain (pBIIB71F10-134) are shown in SEQ ID NO:157 and 158, respectively. DNA and amino acid sequences for the 71F10 agly IgG heavy-chain (pBIIB71F10-137) are shown in SEQ ID NOs:153 and 154, respectively. The 71F10 light chain vector (pBIIB71F10-129) was common used in the 71F10 IgG and 71F10 agly IgG antibodies.

The oligonucleotide (forward 5' PCR primer 137-F) used for Site-Directed Mutagenesis of the 71F10 agly IgG heavy-chain is 5'-GAGGAGCAGTACAACAGC GCCTACCGTGTGGTCAGCGTC-3' (SEQ ID NO:155) which includes a desired point mutation codon (underlined).

Example 7

Construction of Anti-CD23 Fab-hLIGHT Fusion, BIIB CD23-204

Anti-CD23 VH region was synthesized by PCR amplification using the oligonucleotide primers described in 204-F (SEQ ID NO:142) and DyaxVH-pV90-R (SEQ ID NO:143). The 5' forward primer, 204-F (SEQ ID NO:142) which contains a unique Mlu I restriction endonuclease site (ACGCGT (SEQ ID NO:160) followed by sequences encoding the last three amino acids of the heavy chain signal peptide followed by sequences complementary to the amino terminus of the anti-CD23 VH. The 3' reverse primer, DyaxVH-pV90-R (SEQ ID NO:143) which contained a Nhe I site (GCTAGC (SEQ ID NO:182) and sequence encoding complementary to the carboxyl terminus of the anti-CD23 VH. The anti-CD23 VH region was amplified in a PCR reaction from plasmid DNA pBIIB CD23-121 containing the anti-CD23 VH gene. The anti-CD23 VH gene fragment was cloned into the Mlu I/Nhe I digested the pBIIB71F10-132. Correct sequences were confirmed by DNA sequence analysis. The resultant vector is termed pBIIBCD23-204. The anti-CD23 light chain vector (pBIIBCD23-178) was used in the anti-CD23Fab-hLIGHT fusion. DNA and amino acid sequences for the light chain of the anti-CD23 Fab-hLIGHT fusion are shown in SEQ ID NOs:104 and 103, respectively. DNA and amino acid sequences for the heavy chain of the anti-CD23 Fab-hLIGHT fusion (pBIIBCD23-204) are shown in SEQ ID NOs:173 and 174, respectively. The amino acid and nucleotide sequences corresponding to heavy chain of 71F10 Fab are shown starting from the N-terminus; followed by amino acids corresponding to the linking group (amino acids 224 to 243); followed by the amino acids corresponding to human LIGHT extracellular domain (amino acids 244 to 391).

A second anti-CD23Fab-hLIGHT fusion was also made with a $(G_4S)_3$ (SEQ ID NO: 148) linker for evaluation (data not shown). DNA and amino acid sequences for the light chain of the anti-CD23 Fab-hLIGHT fusion with a $(G_4S)_3$ linker are shown in SEQ ID NOs:104 and 103, respectively. DNA and amino acid sequences for the heavy chain of the anti-CD23 FAb-hLIGHT fusion with a $(G_4S)_3$ linker are shown as SEQ ID NOs:102 and 101, respectively. The amino acid and nucleotide sequences corresponding to heavy chain of 71F10 Fab are shown starting from the N-terminus; followed by amino acids corresponding to the linking group (amino acids 222 to 236); followed by the amino acids corresponding to human LIGHT extracellular domain (amino acids 237 to 384).

Example 8

Expression of 71F10 Fab-hLIGHT Fusions in CHO Cells

Figure 6:
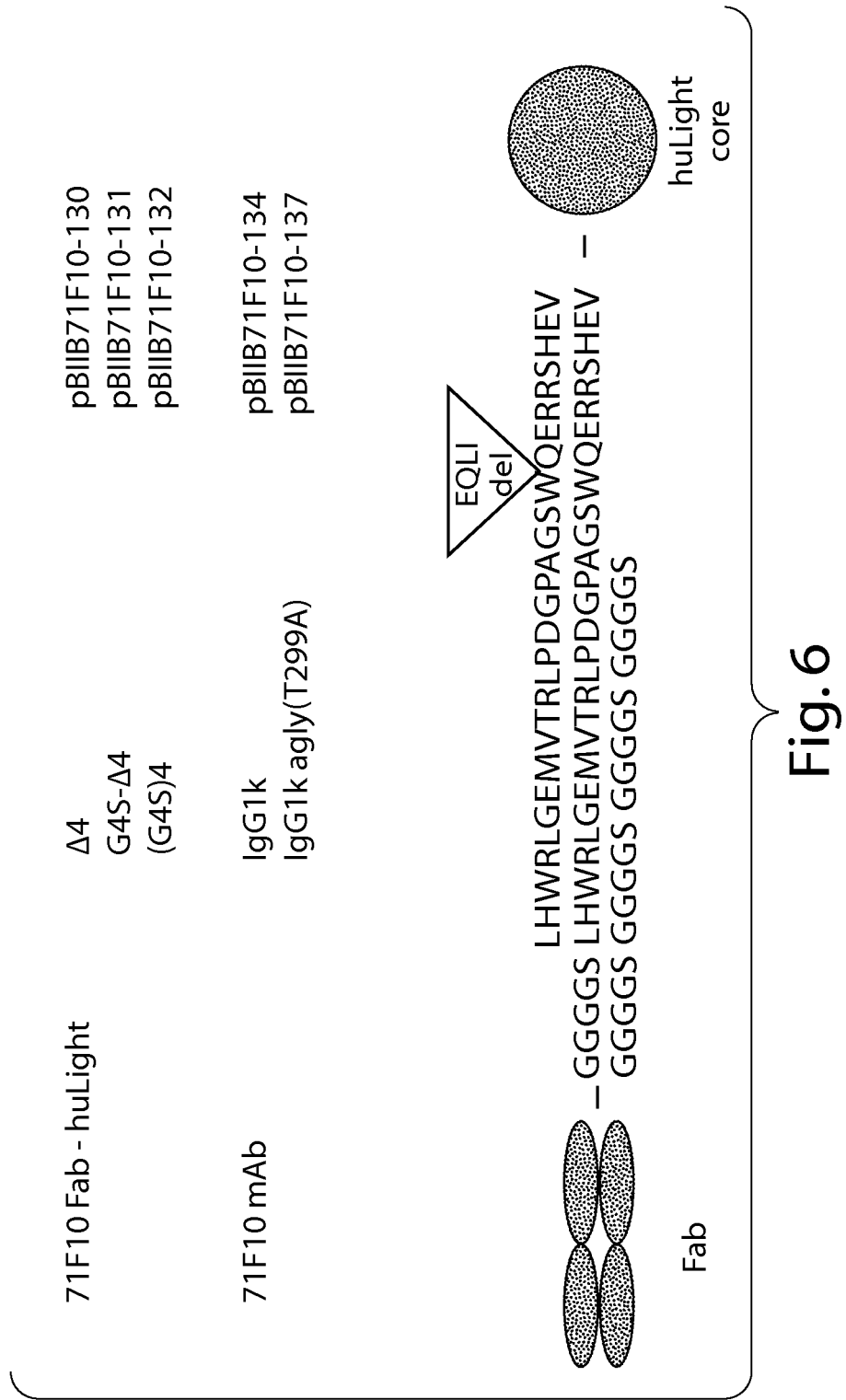
FIG. 6 depicts a summary of 71F10 Fab-hLIGHT constructs used for expression.

A summary of 71F10 constructs used for expression is shown in FIG. 6.

Transient Expression of 71F10 Fab-hLIGHT in CHO Cells

The host DG44 suspension cells were maintained in CD-CHO (25%) and DMEM/F12 (75%), and two identical transfections were carried out. For each transfection, the cells were seeded at $7.5 \times 10^5$ cells/well in a six-well plates and cultured for 24 hours; then the cells were transfected with 1 µg of pBIIB71F10-129 (Light chain in pV100) and 1 µg of pBIIB71F10-130, pBIIB71F10-131, pBIIB71F10-132, pBIIB71F10-134 or pBIIB71F10-137 (heavy chain in pV90) using FuGENE transfection reagent (Roche) according to the manufacturing protocol. The RR399 vector which contains the 71F10 IgG1 agly heavy chain with original VH sequence was used as a control in CHO cell expression. 48 hour later, the supernatant was harvested and the titer was determined by Octet (ForteBio) with a surrogate standard according to quantitation method from manufacturing protocol. The titers of 71F10Fab/Hlight fusions from transcient transfection are 0.06 ug/ml (pBIIB71F10-137), 1.6 ug/ml (pBIIB71F10-134), 0.9 ug/ml (pBIIB71F10-130), 0.2 ug/ml (pBIIB71F10-131), and 1.0 ug/ml (pBIIB71F10-132).

Stable Expression of 71F10 Fab-hLIGHT in CHO Cells

The host DG44 suspension cells were maintained in CHO-SSFMII (Invitrogen), and two identical transfections were carried out. For each transfection, the cells were seeded at $7.5 \times 10^5$ cells/well in a six-well plates and cultured for 24 hours; then the cells were transfected with 1 µg of pBIIB71F10-129 (Light chain in pV100) and 1 µg of pBIIB71F10-130, pBIIB71F10-131, pBIIB71F10-132, pBIIB71F10-134 or pBIIB71F10-137 (heavy chain in pV90) using FuGENE transfection reagent (Roche) according to the manufacturing protocol. 48 hour later, cells from two transfections were combined and splited into three T-75 flasks that each contained 15 ml CHO-SSFMII supplemented with 400 µg/ml of genticin (Invitrogen). After two or three week selection, the cells either sorted or as an unsorted pool were scaled up in CHO-SSFMII with 400 µg/ml of genticin and later in BCM16 with 400 µg/ml of genticin for production run. In the end of the run, the supernatant was harvested and the titer was determined by Octet (ForteBio) with a surrogate standard.

Octet Assay

Analysis of Fab-LIGHT fusions by biolayer interferometry (Octet QK System, ForteBio, Inc. Menlo Park, Calif.). Anti-human Fc-specific biosensors (Fortebio SKU 18-0001) were hydrated in OB (1×PBS supplemented with 1 mg/ml BSA, 0.05% NaN₃, and 0.02% TWEEN 20) for at least five minutes prior to assays. For each assay, the respective receptor Fc fusion was diluted to 10 µg/ml in OB and allowed to bind to the biosensors for five minutes. The sensors were then incubated in the indicated culture supernatant for an additional five minutes, and subsequently transferred to fresh wells containing. As a control, the behavior of the 71F10 FAb (10 µg/ml in OB) was also examined in this assay. Dissociation constants ($k_d$) were calculated using software provided by the manufacturer and off-rates compared to the $k_d$ of the 71F10 Fab.

Example 9

Purification of 71F10 Fab-hLIGHT Fusion Proteins

The fusion protein produced in CHO cells were purified and characterized by methods described below.

Protein A Capture: Pre-equilibrate the Protein A column with 1×PBS (equilibration buffer) at 100-150 cm/hr with 3 column volumes. Load the supernatant at 150 cm/hr with a maximum of 10 mg of 71F10 Fab-hLIGHT per milliliter of resin. After loading, wash the column with 5 column volumes of equilibration buffer. Then, step elute in an upflow direction with 100 mM Glycine, pH 3.0. Collect desired fractions and titrate to neutral pH with 2M Tris base. Dialyze collected fractions against 1×PBS and concentrate material to prepare for the size exclusion step.

SUPERDEX(r) 200 (Size Exclusion) aggregate removal step involved equilibration of SUPERDEX(r) 200 with 1×PBS with 1.5 column volumes at a flow rate of 36 cm/hr followed by loading of protein and collecting desired fractions.

Identity testing performed as follows

1). Intact mass analysis by mass spectrometry where molecular mass measurements were performed on an electrospray mass spectrometer (ESI-MSD). Prior to analysis, the sample was reduced to remove disulfide bonds. The deconvoluted mass spectrum represents the masses of the heavy and Light chains.

2). N-terminal sequence analysis was performed by Edman degradation using an ABI protein sequencer equipped with an on-line PTH analyzer. The sequences for the initial amino acids of the Light chain and heavy chain were identified.

3). Peptide mapping with mass spectrometric analysis: tryptic or/and EndoLysC peptide maps were performed to obtain complete sequence coverage by analysis of the LC/MS data generated from each peptide. In addition, determination of sites and amounts of oxidation and deamidation were detected.

Purity testing was performed by; 1) SDS-Page or CE-SDS: Reduced and non-reduced samples, this technique is used to measure antibody fragmentation, aggregation and impurities, 2) SEC-HPLC with LS and RI technique was used to measure aggregation and fragmentation and LIGHT scattering determines the molar mass of sample components. 3) SDS gel or capillary IEF method was used to determine the isoelectric focusing pattern and pI distribution of charge isoforms that can result from C- and N-terminal heterogeneity and/or deamidation.

Finally, endotoxin concentrations were measured by the *Limulus* amoebocyte lysate (LAL) kinetic turbidometric method.

Example 10

Binding Activity of 71F10 Fab-hLIGHT Fusion Proteins

The concentration of 71F10 Fab-Light fusion proteins and the 71F10 mAb expressed transiently by 293E cells was quantified by ELISA, using purified 71F10 Fab as a standard. Wells of 96-well plates were coated by incubation overnight at 4-8° C. with goat antibodies against human kappa chain (80 ul/well of a 5 ug/ml solution in PBS). Wells were emptied, filled completely with a solution of PBS with 1% BSA (blocking buffer) and incubated at room temperature for 1 hour. Wells were emptied, washed twice PBS containing 0.05% Tween 20 (PBST) and filled with the samples (80 ul/well of 3× dilution series of the standard and supernatants in blocking buffer) prepared in another 96-well plate. After a 2-hour incubation at room temperature, the wells were emptied, washed three times with PBST and filled with a solution of HRP-conjugated goat pAbs anti-human kappa chain (80 ul/well of a 2000-fold dilution in blocking buffer). After 1-hour incubation, the wells were emptied and filled with a solution of HRP substrate prepared freshly. The color was left to develop for 3 minutes and was stopped by addition of an equal volume of 1N $H_2SO_4$. Absorbance was measured at 450 nm using a Plate Reader (SpectraMax, Molecular Devices). The data was processed and graphs were created using Soft-Max Pro software.

A similar ELISA format was used to compare the binding of control anti-HER2 antibody, control anti-HER2 antibody Fab, 71F10 Fab, 71F10 mAb and 71F10 Fab-Light fusion proteins to human (FIG. 7) or murine (FIG. 8) HER2-Fc. control anti-HER2 antibody was obtained from Pharmaceuticals Buyers International, Inc. The Fab of control anti-HER2 antibody was prepared by limited papain digestion and purified using standard technology. Human and murine HER2-Fc (homodimeric fusion proteins consisting of the extracellular domain of HER2 and the Fc fragment of human IgG1) were obtained from R&D Systems. The ELISA was done using the same protocol as described before with the exception that the wells were coated with murine or human HER2-Fc instead of goat anti-human kappa antibodies.

Example 11

Characterization of 71F10 Fab-hLIGHT Trimer

Figure 9:
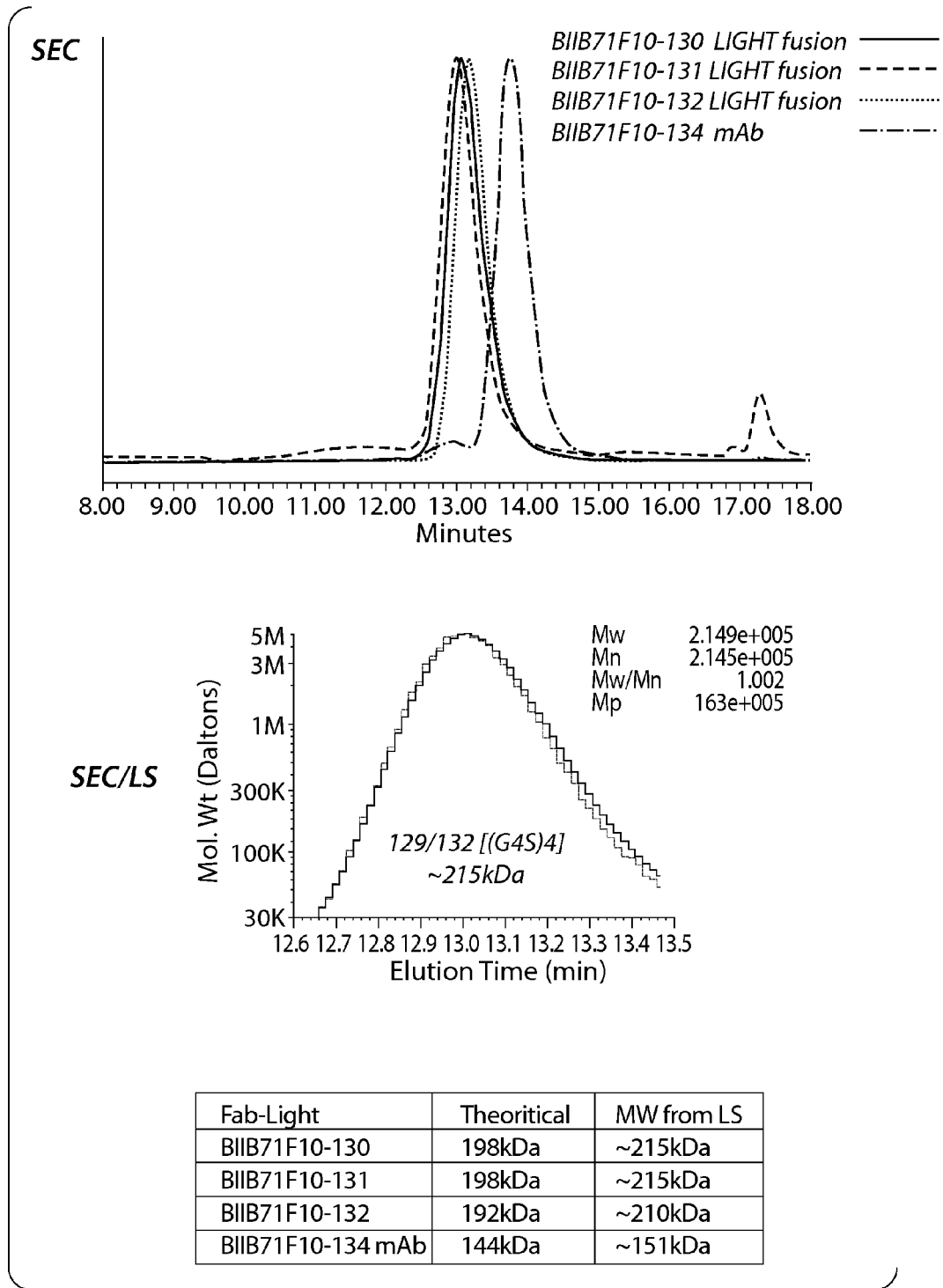
FIG. 9 depicts the demonstration of 71F10 Fab-hLIGHT trimer with expected Molecular Weight. SEC/LS analysis of 71F10 Fab-hLIGHT fusion proteins.

The Fab, the mAb and Fab-Light fusion proteins were purified by chromatography on protein A Sepharose and Size Exclusion to isolate material substantially devoid of aggregates. The purified proteins were quantified by UV absorbance at 280 nm using the sequence-predicted extinction coefficient. Purity was evaluated by SDS-PAGE and size-exclusion HPLC. The molecular mass was measured by SEC/static light scattering analysis using a BioSeptember 3000 column (Phenomenex) in PBS with a Waters Alliance HPLC instrument coupled to a refractive index detector (Waters) and light scattering detector (PD2000, Precision Detectors). The average molecular masses were determined using the Precision Detector software (FIG. 9).

Example 12

SEC/LS Analysis of 71F10 Fab-hLIGHT/shuLTBR Complex

Soluble human LTBR (shuLTBR) was prepared by limited proteolytic digestion of human LTBR-Ig and purified by chromatography on protein A Sepharose and Fractogel TMAE. 71F10 Fab-$(G_4S)_4$-LIGHT (SEQ ID NO: 134) was incubated overnight at 4-8° C. with a 5-fold molar excess of shuLTBR. Controls with each protein were also included. The samples were analyzed by SEC using a BioSeptember 3000 column (Phenomenex) in PBS with a Waters Alliance HPLC instrument. Results show the formation of a higher molecular weight complex, demonstrating that Fab-Light is capable of binding the receptor (data not shown). The precision of the light scattering analysis data did not allow calculation of the exact stoechiometry which was 2 or 3 shuLTBR for 1 Fab-Light trimer.

Example 13

Figure 7:
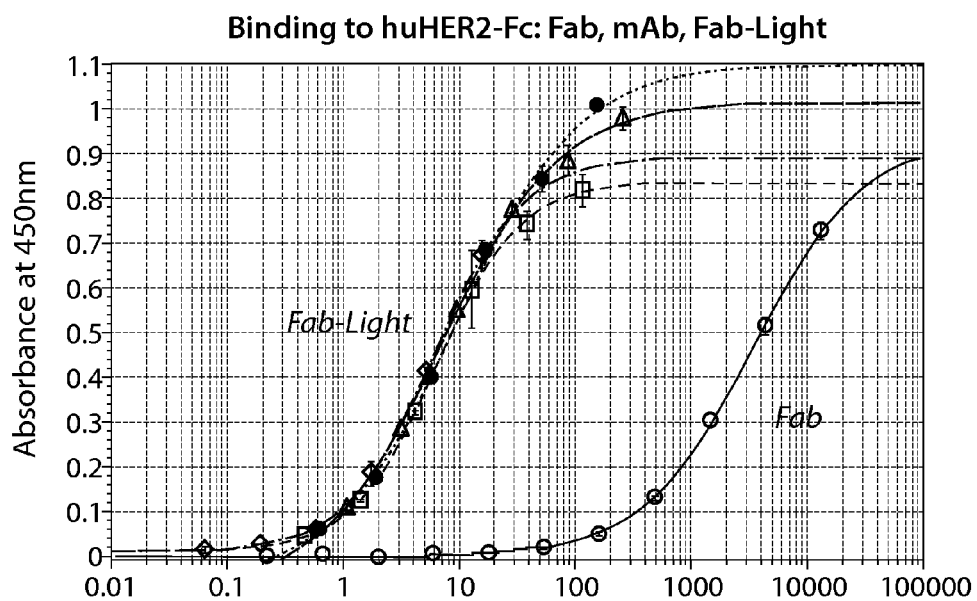
FIG. 7 depicts the binding of 71F10 Fab-hLIGHT to human HER2-Fc measured by quantitation ELISA.
Figure 8:
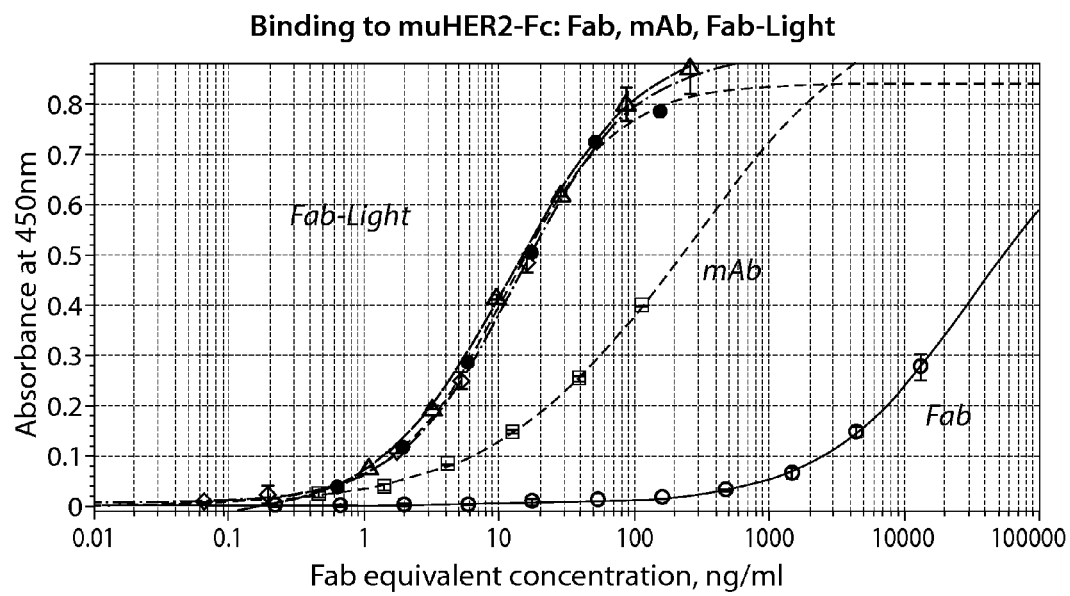
FIG. 8 depicts the binding of 71F10 Fab-hLIGHT to murine HER2-Fc measured by quantitation ELISA.

Binding of Purified LIGHT Fusion Protein, BIIB71F10-132, to Receptors Measured by ELISA The binding of 71F10 Fab or BIIB71F10-132 LIGHT fusion protein (dilution series) to human or murine HER2-Fc was tested by ELISA. Human and murine ErbB2-Fc were obtained from R&D Systems. Wells of 96-well plates were coated with 2 ug/ml or 0.2 ug/ml of human or murine HER2-Fc by incubation overnight at 4-8° C. with either of these six proteins (80 ul/well of a 0.2 or 2 ug/ml solution in PBS). Wells were emptied, filled completely with a solution of PBS with 1% BSA (blocking buffer) and incubated at room temperature for 1 hour. Wells were emptied, washed twice PBS containing 0.05% Tween 20 (PBST) and filled with the samples (80 ul/well of 3× dilution series of the standard and supernatants in blocking buffer) prepared in another 96-well plate. After a 2-hour incubation at room temperature, the wells were emptied, washed three times with PBST and filled with a solution of HRP-conjugated goat pAbs anti-human kappa chain (80 ul/well of a 2000-fold dilution in blocking buffer). After 1-hour incubation, the wells were emptied and filled with a solution of HRP substrate prepared freshly. The color was left to develop for 3 minutes and was stopped by addition of an equal volume of 1N $H_2SO_4$. Absorbance was measured at 450 nm using a Plate Reader (SpectraMax, Molecular Devices). The data was processed and graphs were created using SoftMax Pro software. Results demonstrated that the HER2 binding activity of the LIGHT fusion is HER2 receptor density dependent, i.e. higher affinity when HER2 antigen is abundantly presented on the coated plate (2 ug/ml). Results are shown in FIGS. 7 and 8.

Figure 10A:
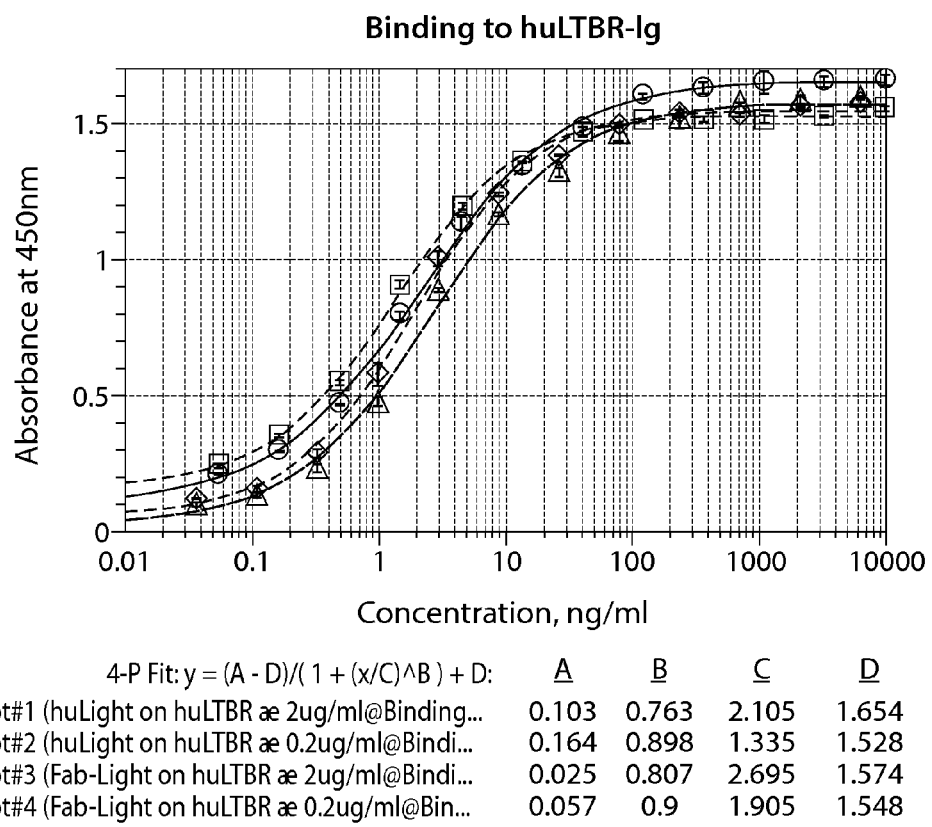
FIG. 10 depicts the binding of purified 71F10 Fab-hLIGHT to human (A) and murine (B) LTβR-Ig.
Figure 10B:
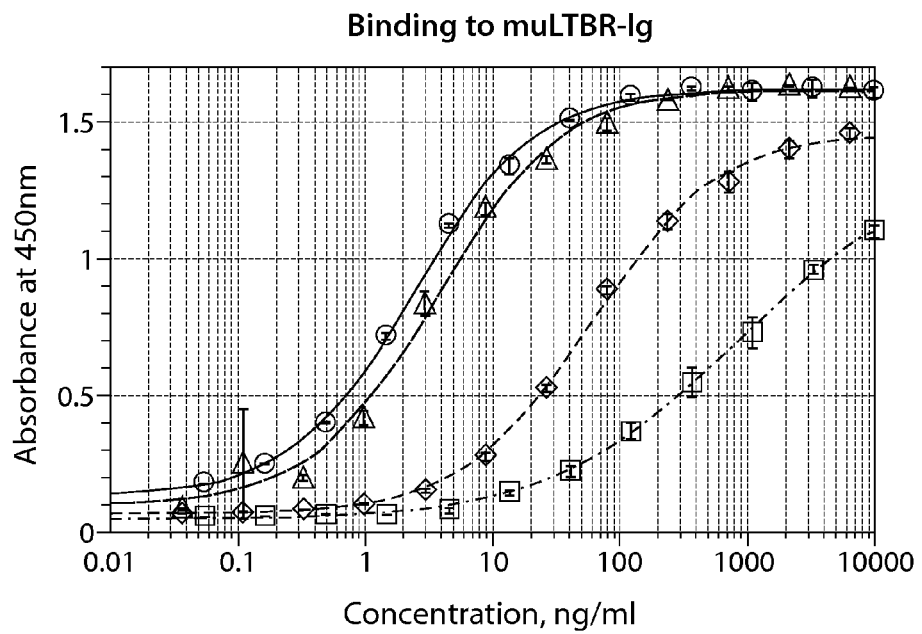

The binding of Flag-huLIGHT (control) or BIIB71F10-132 LIGHT fusion (dilution series) to human or murine LTBR-Ig was tested by ELISA (FIGS. 10A and 10B and Table 2) using the protocol described above except that plates were coated with 2 ug/ml or 0.2 ug/ml of human or murine LTBR-Ig; and HRP-conjugated anti-Flag mAb or goat anti-human kappa pAb was used. Human and murine LTBR-Ig were expressed and purified in house. At high receptor density, 71F10 Fab-hLIGHT showed high affinity to both hLTbR and mLTbR. At low receptor density, 71F10 Fab-hLIGHT showed high affinity to hLTbR and moderate affinity to mLTbR.

Figure 11A:
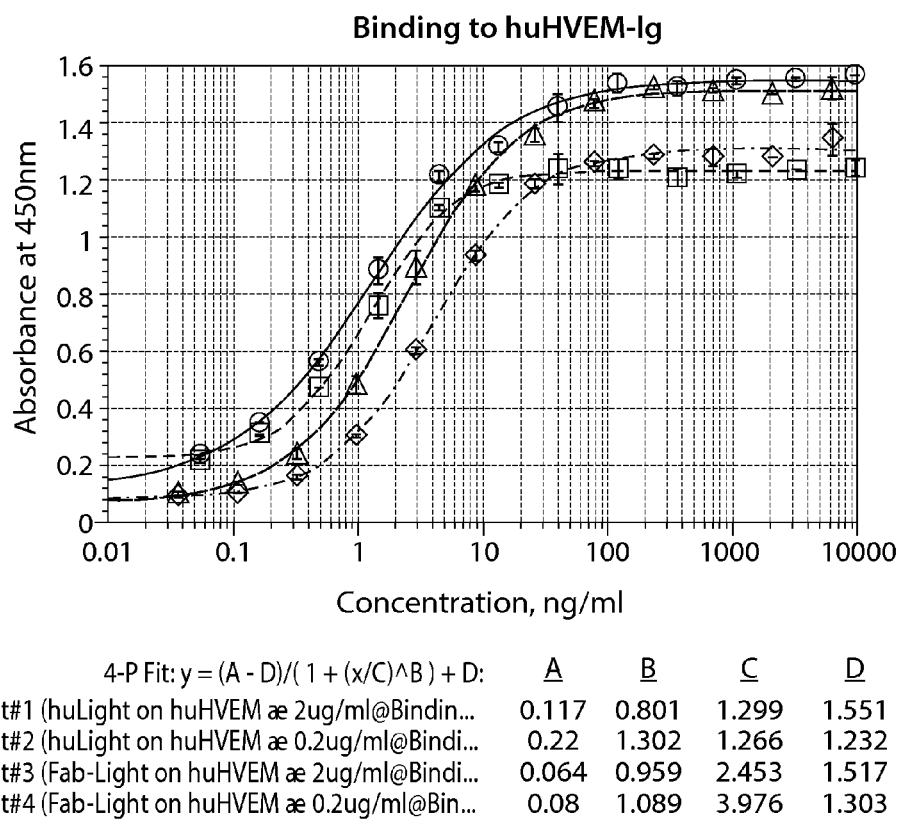
FIG. 11 depicts the binding of purified 71F10 Fab-hLIGHT to human (A) and murine (B) HVEM-Ig.
Figure 11B:
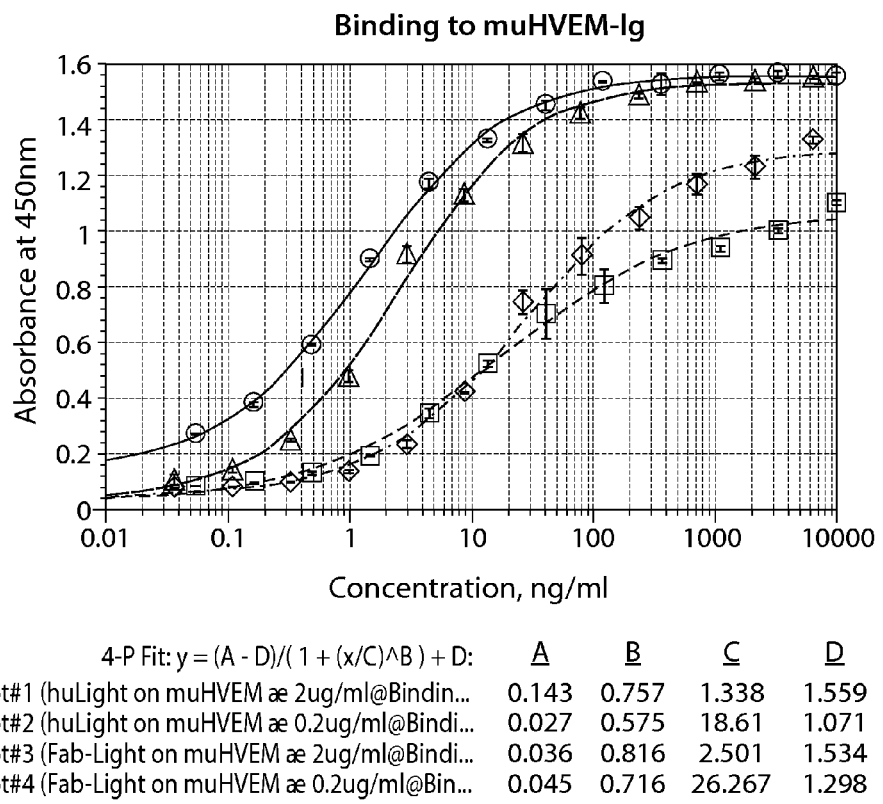

The binding of Flag-huLIGHT (control) or BIIB71F10-132 (dilution series) to human or murine HVEM-Ig (Herpes virus entry mediator-Ig) was tested by ELISA (FIGS. 11A and 11B and Table 2) using the protocol described above except that plates were coated with 2 ug/ml or 0.2 ug/ml of human or murine LTBR-Ig; and HRP-conjugated anti-Flag mAb or goat anti-human kappa pAb was used. Human and murine HVEM-Ig were expressed and purified in house.

Binding activity of 71F10-hLIGHT fusion proteins is summarized in Table 2.

Example 14

LIGHT Fusion Proteins Bind to High Her2 Expressing SKBR3 Cells

Methods: SK-BR-3 cell line was obtained from the American Type Culture Collection (Rockville, Md.). Cells were cultured in McCoy's 5a medium supplemented with 10% heat-inactivated fetal bovine serum (FBS) and 1.5 mM L-glutamine. PE-conjugated goat anti-mouse F(ab')2 specific antibody was purchased from Jackson ImmunoResearch (West Grove, Pa.). SK-BR-3 cells were exposed to various concentrations of 71F10-LIGHT fusion proteins (BIIB71F10-130, BIIB71F10-131 and BIIB71F10-132). Control anti-HER2 Fab, 71F10 Fab and 71F10 IgG (BIIB71F10-134) were used as controls. Samples were washed in FACS buffer (PBS containing 5% FBS and 0.02% sodium azide), and counterstained with PE-conjugated goat anti-mouse F(ab')2 specific antibody. Cells were finally washed and resuspended in FACS buffer with 1% paraformaldehyde. Fixed samples were subjected to analysis on a FACScan flow microfluorometer (Becton Dickinson, Sunnyvale, Calif.).

Figure 12:
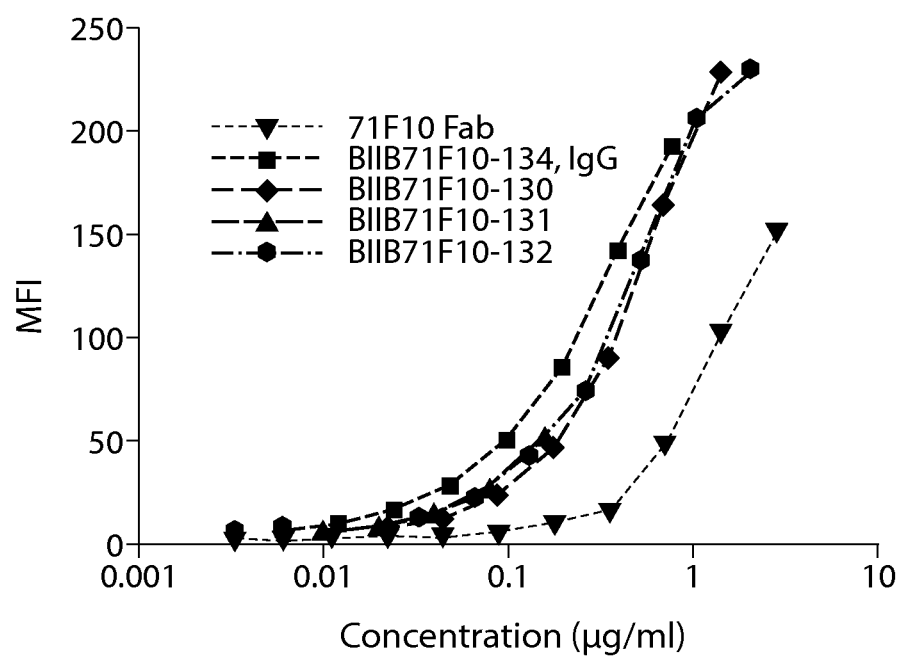
FIG. 12 depicts the binding of 71F10 Fab-hLIGHT to SKBR3 cells.

Results: Trimeric 71F10 Fab-hLIGHT showed significantly higher binding activity to SKBR3 cells than that of 71F10 Fab, presumably due to increased avidity (FIG. 12).

Example 15

Binding of hLIGHT Fusion Proteins to CHO/hHER2 Cells can be Blocked by Either LTbR-Ig or HER2-Fc Methods: Original CHO cell line was obtained from the American Type Culture Collection and modified to express hHER2 as described in Example 4. Clone KS19 that expresses high levels of HER2 was chosen for the experiments. KS19 cells were cultured in DMEM supplemented with 10% heat-inactivated FBS in 6 well culture plates. KS19 cells were exposed to BIIB71F10-130, BIIB71F10-131, BIIB71F10-132 and BIIB71F10-MAB at a concentration of 0.2 nM for 1 h. In separate groups, fusion proteins and BIIB71F10-MAB were pre-incubated with hLTbR-Ig (20 mg/ml) or HER2-Fc (20 mg/ml). Mouse anti-LTbR mAb (AC H16), hLIGHT, and 71F10 Fab were used as controls (data not shown). Samples were washed in FACS buffer, and counterstained with PE-conjugated goat anti-mouse F(ab')2 specific antibody. Cells were finally washed and subjected to analysis on a FACScan flow microfluorometer.

Figure 13:
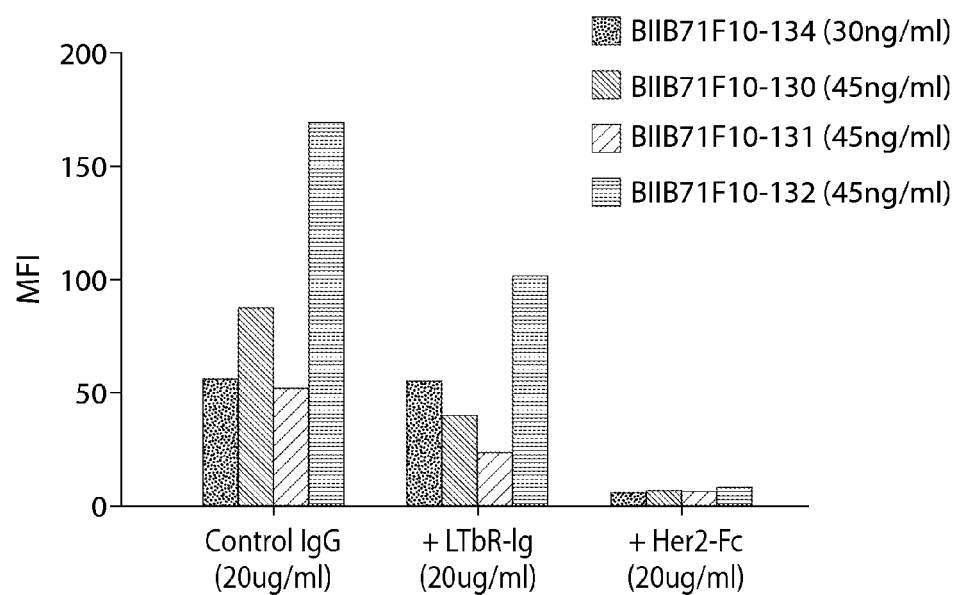
FIG. 13 depicts the block of binding of 71F10-LIGHT to CHO/hHER2 cells by either LTβR-Ig or HER2-Fc

Results: 71F10-hLIGHT fusion proteins binding to CHO/hHER2 cells can be blocked by either LTbR-Ig or HER2-Fc (FIG. 13). These results suggested that both LIGHT and HER2 specific Fab are capable of binding to their receptors on the CHO cell surface. The binding is specific and can be competed by its receptor fusion proteins, i.e. LTbR-Ig or HER2-Fc proteins. The level of blocking effect depends on the receptor numbers on the cell surface. It appears that hHER2 receptor is much more aboudant than LTbR on KS10 cells.

Example 16

Figure 14:
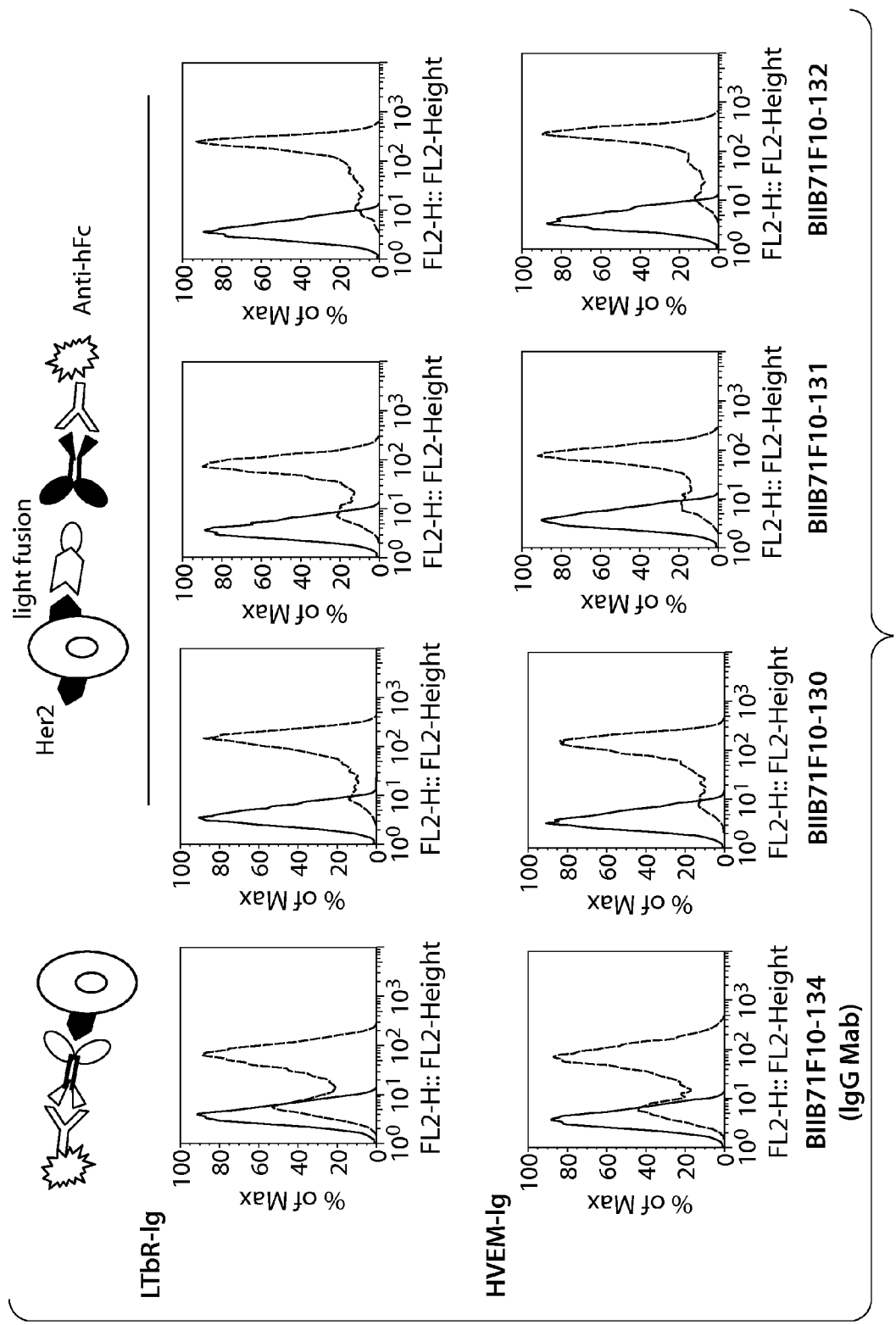
FIG. 14 depicts the detection of functional hLIGHT sites using LTβR-Ig and HVEM-Ig fusions.

LIGHT Fusion Proteins can Simultaneously Engage Both HER2 and hLIGHT Receptors, LTbR and HVEM, on Cell Surface Methods: KS19 cells were exposed to BIIB71F10-130, BIIB71F10-131, BIIB71F10-132 and BIIB71F10-134, IgG at a concentration of 0.2 nM for 1 h at 4° C. After washed with FACS buffer, groups of cell were incubated with FACS buffer alone, hLTbR-Ig (20 ug/ml) or HVEM-Fc (20 ug/ml) for 30 min and then washed again. For group incubated with FACS buffer, cells were counterstained with PE-conjugated goat anti-mouse F(ab')2 specific antibody; for groups contacted with hLTbR-Ig or HER2-Fc, cells were staining with PE-conjugated goat anti-human Fc specific antibody (Jackson ImmunoResearch) for 30 min. Cells were finally washed and fixed in FACS buffer with 1% paraformaldehyde. Samples were subjected to analysis on a FACScan flow microfluorometer (FIG. 14).

Results: Both ends (71F10 Fab and LIGHT) of three fusion proteins are functional simultaneously, with 71F10 Fab site recognizing HER2 and LIGHT end binding to LTβR-Ig or HVEM-Ig.

Example 17

In Vitro Enhancement of T Cell Proliferation by 71F10 Fab-hLIGHT Fusion Proteins Methods: Flat-bottom 96-well plates were pre-coated with sub-optimal concentration of anti-CD3 mAb (0.25 mg/well)

at 4° C. overnight. Nylon wool column-purified T cells isolated from naïve Balb/c mice were subsequently cultured in the presented of various concentrations of hLIGHT, BIIB71F10-134 IgG and 71F10-LIGHT fusion proteins (BIIB71F10-130, BIIB71F10-131 and BIIB71F10-132) at 37° C. for 72 h. Anti-CD28 mAb was used as a control. [$^3$H]TdR (1 uCi/well) was added for the last 18 h. Plates were harvested using a Tomtec Harvester Mach III M cell harvester (Hamden, Conn.), and the radioactivity was measured using a MicroBeta liquid scintillation and luminescence counter (Wallac, Turku, Finland). Augmentation of T cell proliferation was determined by plotting the percentage of [$^3$H]TdR incorporation compared with cells treated with anti-CD3 mAb alone that were taken as 100%.

Figure 15:
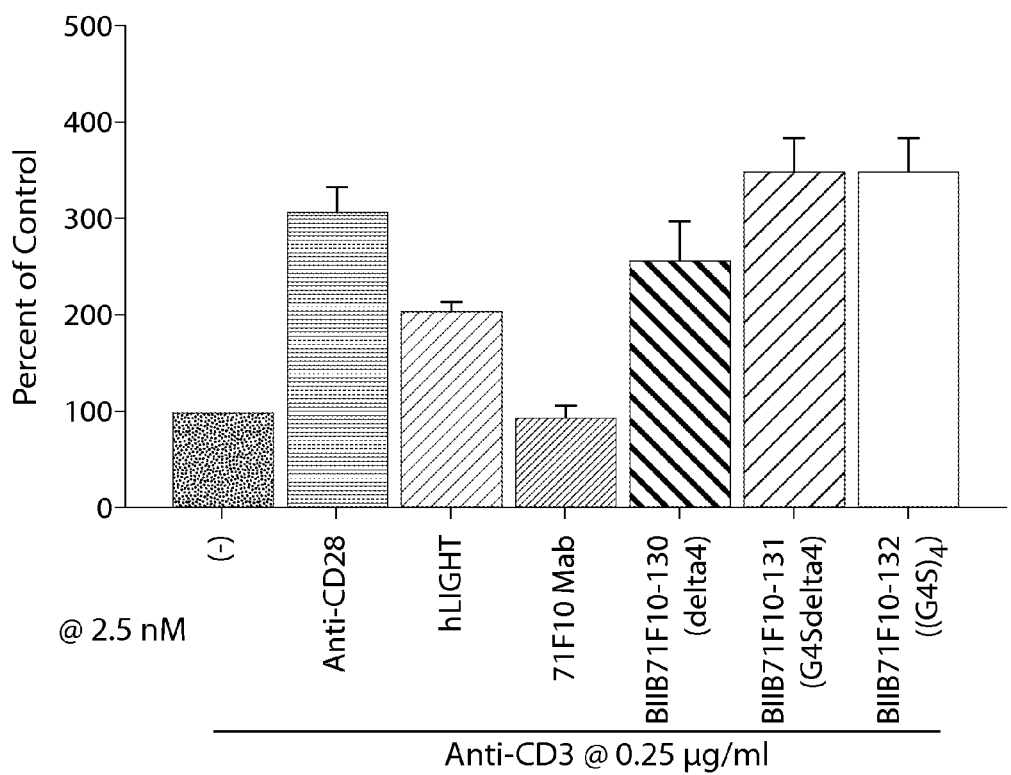
FIG. 15 depicts the enhancement of T cell proliferation by 71F10 Fab-hLIGHT.

Results: hLIGHT fusion proteins enhanced primary mouse T cell proliferation in the presence of sub-optimal anti-CD3 antibody (FIG. 15). These results suggest that the fusion proteins remain as active co-stimulatory molecule for T cell proliferation. In the absence of anti-CD3, LIGHT fusion proteins showed no activity on T cell proliferation.

Example 18

Inhibition of Tumor Cell Growth by 71F10 Fab-hLIGHT Fusion Proteins

SKBR3 Tumor Cell Growth Inhibition by Recombinant Hlight Proteins

Methods: Human breast cancer cell line, SKBR-3, cells were seeded in flat-bottom 96-well plates at $1.0 \times 10^4$ cells/well in McCoy's 5a and allowed to adhere overnight. The cells were then treated with various concentrations of hLIGHT. As control groups, hLIGHT were pre-incubated with hLTβR-Ig (20 ug/ml) to block LIGHT binding activity to LTbR on tumor cell surface. An agonistic anti-LTβR mAb (CBE11) and control anti-HER2 antibody were used as controls. The plates were incubated for 72 h and then pulsed for 6 h with [3H]TdR (1 µCi/well). Plates were harvested and [3H]TdR incorporation was then measured.

Figure 16:
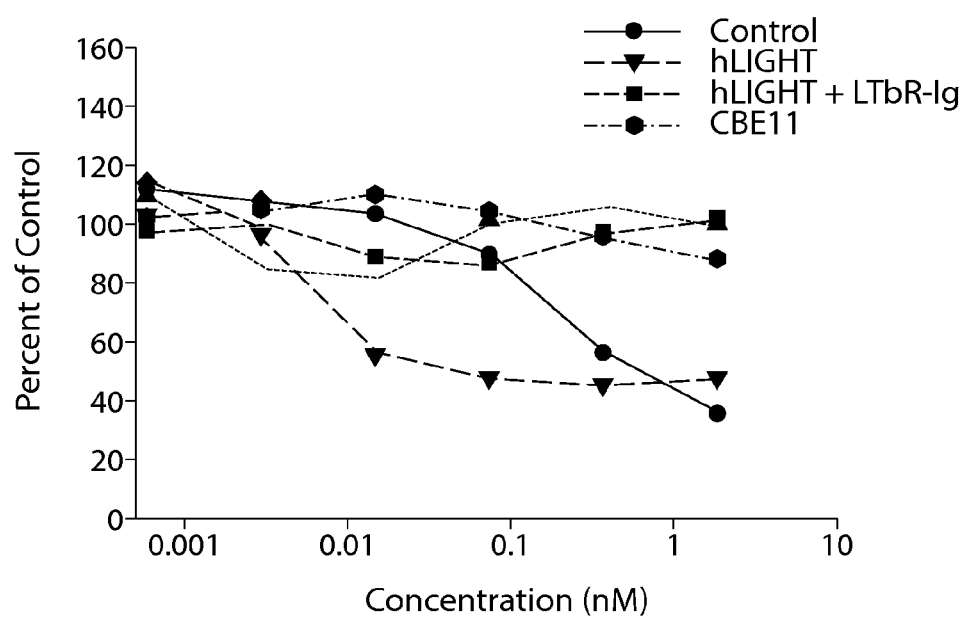
FIG. 16 depicts the growth inhibition of SKBR-3 cells by recombinant hLIGHT.

Results: Treatment with recombinant hLIGHT proteins lead to growth inhibition of SKBR-3 cells. The inhibitory effects of hLIGHT can be specifically blocked by the addition of LTbR-Fc—suggesting that this inhibitory activity depends on hLIGHT/LTbR interaction. In contrast, the agonistic antibody CBE11 did not show any inhibition any the tested concentrations and control anti-HER2 antibody demonstrated growth inhibition at higher antibody concentrations (>2 nM) (FIG. 16).

SKBR-3 Cell Growth Inhibition by hLIGHT Fusion Proteins

The growth inhibitory activity of three LIGHT fusion proteins were tested on SKBR-3 cells following the procedure described in above section. In brief, SK-BR-3 cells were seeded in flat-bottom 96-well plates ($1.0 \times 10^4$/well) overnight. The cells were then treated with increasing concentration of BIIB71F10-130, -131, -132 and -134 (BIIB71F10 mAb control). Again control anti-HER2 antibody was used. The plates were incubated for 72 h at 37° C. in a 5% CO2 incubator and then pulsed with [3H]TdR for 6 h. Plates were harvested and measured using a MicroBeta liquid scintillation and luminescence counter.

Figure 17:
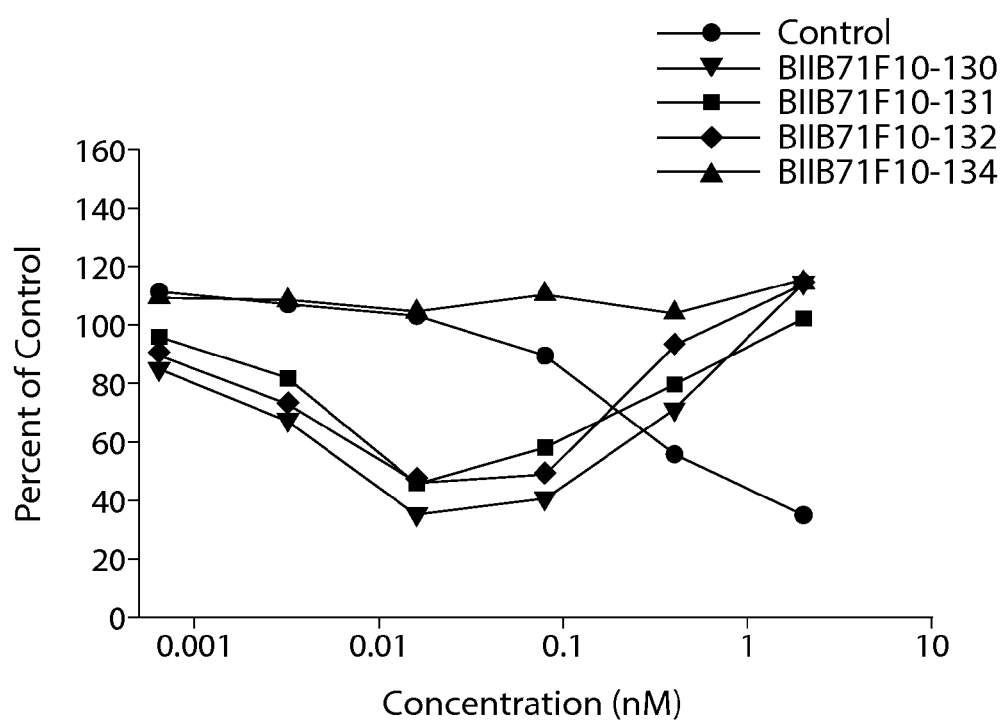
FIG. 17 depicts the "U shaped" growth inhibition curve (SKBR3 cells) shown by 71F10 Fab-hLIGHT fusion proteins.

Results indicated that all three hLIGHT fusion proteins showed potent inhibitory activity of SKBR-3 cell growth. However, unlike seen in hLIGHT where inhibition correlated with hLIGHT concentration (above), all three LIGHT fusion proteins only inhibited cell growth at lower concentrations and lost their inhibitory activity at higher concentrations. This pattern of growth inhibition was described as "U" shaped cell growth inhibition (FIG. 17). It was hypothesized that this is the balancing result of LIGHT induced inhibition and trimeric Fab triggered resistance or growth promoton of these cells. It was also noted that the control antibody or BIIB71F10-134 mAb (IgG) showed neither growth promoting nor inhibitory effect.

Mechanism of Action Study of LIGHT Fusion Proteins in SKBR-3 Cells

Figure 18:
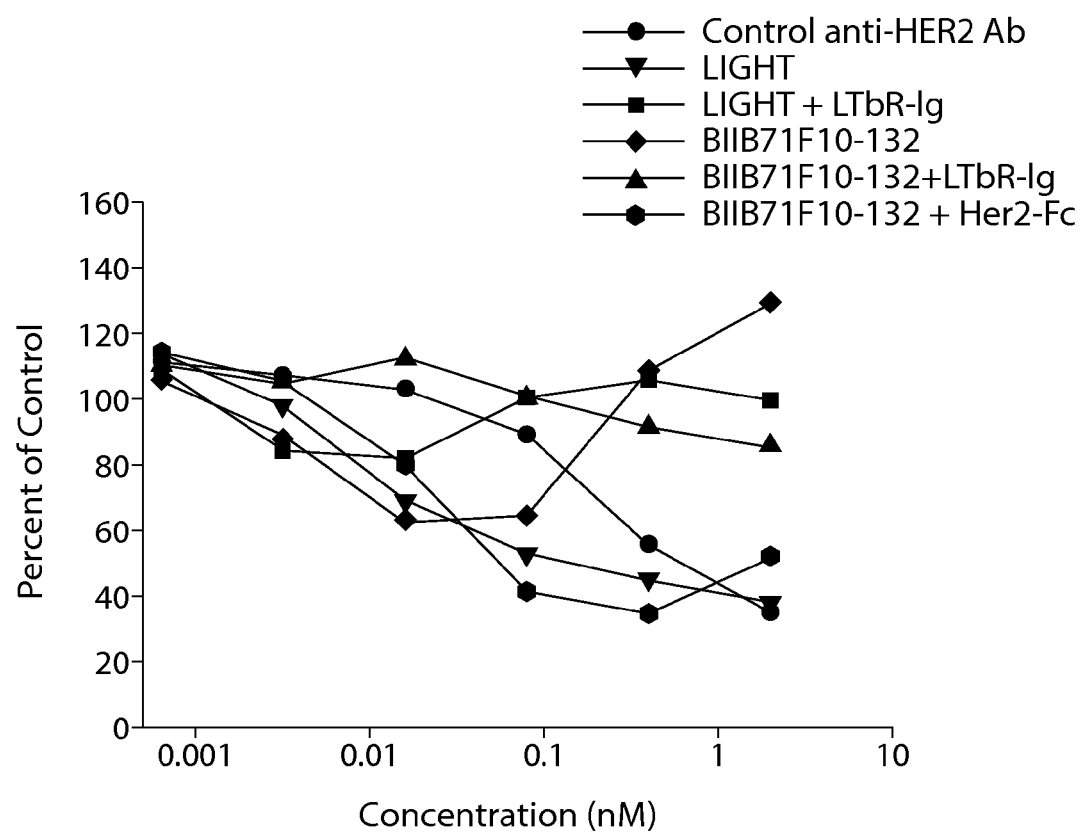
FIG. 18 depicts the LIGHT activity-dependent growth inhibition of SKBR-3 cells by 71F10 Fab-hLIGHT fusion proteins.

SKBR-3 cell growth inhibition experiment was setup following procedure described above. The treatment employed only one fusion protein, BIIB71F10-132. In addition to BIIB71F10-132 LIGHT fusion protein treatment, BIIB71F10-132 was also pre-incubated with LTbR-Ig (20 ug/ml) or Her2-Fc (20 ug/ml) respectively at RT for 30 min, then were used for treatment. Again, control anti-HER2 antibody and recombinant hLIGHT was used as additional control. Results were shown in FIG. 18. Again BIIB71F10-132 treatment alone showed "U" shaped inhibition curve (FIG. 17). In contrast, blockade of Her2 binding activity of the LIGHT fusion protein by preincubation with Her2-Fc abrogated the tail of "U" shape curve, i.e. suppressed the growth promoting signal from trimeric Fab and showed similar growth inhibition as seen with hLIGHT. Whereas blockade of LIGHT function by LTβR-Fc completely blocked the inhibitory activity of the LIGHT fusion protein—suggesting the inhibitory effect was LIGHT/LTβR interaction dependent.

hLIGHT Fusion Proteins Growth Inhibition of BT474 Cells

BT474 cells, at a concentration of $0.1 \times 10^6$ cells/ml in RPMI1640 with 10% FBS, were plated (100 µl/well) in flat-bottom 96-well plates and allowed to adhere overnight. The cells were then treated with 200 µl of different concentrations of BIIB71F10-132 alone, 71F10 mAb alone, hLIGHT alone, various concentrations of 71F10 mAb mixed with hLIGHT (200 nM) or 71F10 mAb (2.5 nM) in combination with different concentration of hLIGHT (200, 20, 2, 0.2 and 0.02 nM). Control anti-HER2 antibody was used. The plates were incubated for 72 h and then pulsed for 6 h with [3H]TdR. The radioactivity was measured using a MicroBeta liquid scintillation and luminescence counter.

Figure 19:
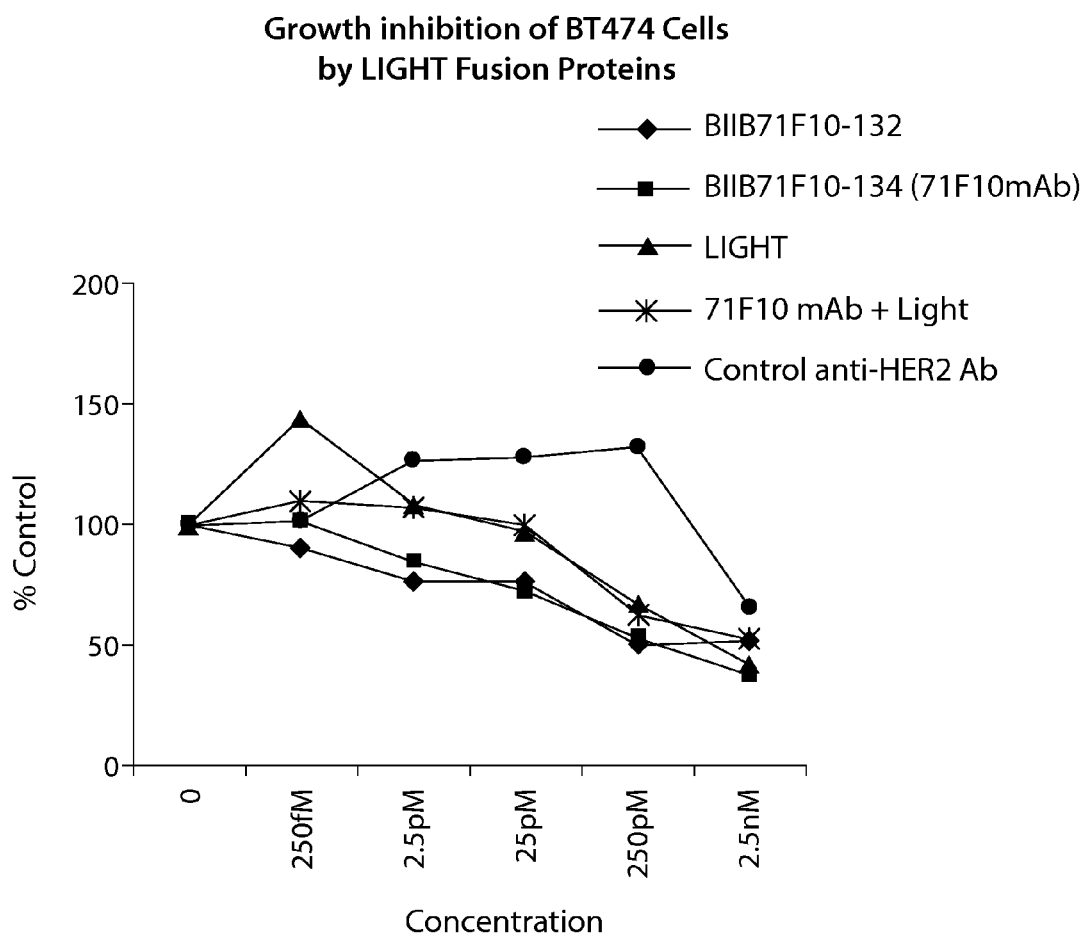
FIG. 19 depicts the growth inhibition of BT-474 cells by 71F10-hLIGHT.

Results: 71F10 Fab-hLIGHT fusion proteins, hLIGHT as well as BIIB71F10-134 (71F10 mAb) all showed potent growth inhibition in breast cancer line—BT474 cells (FIG. 19). When the targeting mAb, 71F10 mab was added together with hLIGHT, no significant synergy was observed in these cells. In comparison with the SKBR-3 cells results, no "U" shaped growth inhibition curve was observed. These results suggest that different cell line respond very differently to LIGHT fusion protein treatment.

Example 19

Internalization of 71F10-hLIGHT Fusion Proteins

Internalization Assay (Fabs)

SKBR3 cells were plated in CC2-coated 8-well chamber slides (Nunc #154941) and allowed to attach over night in the incubator (5% CO$_2$, 37° C.). The growth medium was replaced with 50 ul to 75 ul of the Dyax Fabs (10 ug/ml) and they were allowed to bind for 15 minutes at 4oC. Santa Cruz anti human Neu monoclonal antibody (9G6), Sc-08 was used as a positive control since it rapidly internalizes upon cross-linking with a secondary antibody. One set of slides was moved to 37° C. for one hour. The SC08-treated wells were changed to solution containing Alexa Fluor 488-conjugated goat anti-mouse IgG antibody (Invitrogen A-11029) and 37°

C. incubation continued for one additional hour. Wells were washed with dilution buffer (PBS with 10% FBS). Cells were fixed for 10 minutes at room temperature with 4% formaldehyde in PBS. Slides were washed with dilution buffer. Cells were permeabilized with 0.2% Triton X in PBS at room temperature for 15 minutes. Slides were washed and then incubated for 45 minutes at 4oC with a 50:50 mix of FITC conjugated goat anti human kappa chain and goat anti human IgG F(ab')2 specific fragment (Sigma #F3761 and Jackson Immun. #109-096-097 respectively). Slides were washed with dilution buffer, the chambers removed, and Vectashield with DAPI (Vector Laboratories #H-1200) was added before coverslipping. Stacks of images were captured using the Leica Confocal microscope and ones that focus on a central plain were selected for the figures.

Binding Assay

SKBR3 cells were plated in CC2-coated 8-well chamber slides (Nunc #154941) and allowed to attach over night in the incubator (5% $CO_2$, 37° C.). One well was treated with Adenoviral vector delivering the murine LIGHT gene for a positive control. The next day, the growth medium was replaced with 100 ml of test antibodies (10 mg/ml) and they were allowed to bind for one hour at 4oC. Cells were washed with dilution buffer (PBS with 10% FBS) and 100 ml LTβR-human Fc fusion was added and let bind for one hour at 4° C. Cells were washed and then the slides were incubated with FITC-conjugated goat anti human Fc (gamma) fragment specific antibody (Jackson Immun. #109-096-098) for one hour at 4° C. Slides were washed with dilution buffer, the chambers removed, and Vectashield with DAPI (Vector Laboratories #H-1200) was added before coverslipping. Stacks of images were captured using the Leica Confocal microscope and ones that focus on a central plain were selected for the figures.

Results: 71F10-hLIGHT fusion proteins display functional hLIGHT on tumor cell surface (data not shown).

Internalization Assay (Fab-LIGHT Fusion Proteins)

Methods: Similar to above procedure of binding assay, SKBR3 and BT474 cells were plated in CC2-coated 8-well chamber slides (Nunc #154941) and allowed to attach over night in the incubator (5% $CO_2$, 37° C.). The growth medium was replaced with 0.1 ml of the treatment antibodies (1 ug/ml SC08 and 100 nM fusions and control anti-HER2 antibody) and let bind for 15 minutes at 4° C. Santa Cruz anti human Neu monoclonal antibody (9G6), Sc-08 was used as a positive control since it rapidly internalizes upon cross-linking with a secondary antibody. One set of slides was moved to 37° C. for 90 minutes. The SC08-treated wells were changed to solution containing Alexa Fluor 488-conjugated goat anti-mouse IgG antibody (Invitrogen A-11029) and 37° C. incubation continued for 30 minutes more. Wells were washed with dilution buffer (PBS with 10% FBS). Cells were fixed for 10 minutes at room temperature with 4% formaldehyde in PBS. Slides were washed with dilution buffer. Cells were permeabilized with 0.2% Triton X in PBS at room temperature for 15 minutes. Slides were washed and then incubated for 45 minutes at 4° C. with a 50:50 mix of FITC conjugated goat anti human kappa chain and goat anti human IgG F(ab')2 specific fragment (Sigma #F3761 and Jackson Immun. #109-096-097 respectively). Slides were washed with dilution buffer, the chambers removed, and Vectashield with DAPI (Vector Laboratories #H-1200) was added before coverslipping. Stacks of images were captured using the Leica Confocal microscope and ones that focus on a central plain were selected.

Results: None of the 71F10 Fab-hLIGHT fusion proteins (BIIB71F10-130, BIIB71F10-131, BIIB71F10-132) showed internalization (Confocal Microscopy on SKBR3) under experimental conditions.

Example 20

Induction of Proinflammatory Genes by hLIGHT Fusion Proteins

Quantitative PCR Analysis of Proinflammatory Genes Induced by LIGHT Fusion Proteins Methods: HT29 cells were seeded in a 6-well plate to be approximately 80% confluent at time of treatment. 24 hours later, they were refed with fresh media or fresh media with 4 nM BIIB71F10-130 and allowed to incubate for 24 hours more. At the time of harvest, the cells were estimated at 1E6/well. The RNA was isolated using Qiagen RNeasy mini extraction kit (#74104) according to the manufacturer's instructions including a Dnase treatment to remove any genomic contamination. First strand cDNA synthesis was performed using a kit from SuperArray Bioscience Corporation (#C-03). QPCR was done using SuperArray "Human Inflammatory Cytokines and Receptors" 96-well array plates (#PAHS-011), the RT Sybr Green PCR Master Mix (SuperArray #PA-012) and cycled according to manufacturer's recommendations on an ABI 7300 real time PCR cycler. Data from the thermocycler were entered into the "RT2 PCR Array Data Analysis Software" that SuperArray supplies with the arrays. Briefly, after the data are normalized for controls of the various steps of sample preparation (reverse transcription and PCR) as well as a panel of five housekeeping genes, they are presented as treated divided by untreated data that manifests as a "fold change" in gene expression.

Results: Treatment of HT29 cells with LIGHT fusion #130 led to a significant change in the expression of pro-inflammatory chemokines and cytokines. Most of the 84 genes assayed were upregulated and a few were down-regulated when we compare the treated to the untreated transcripts. This indicates that when the LIGHT end of the fusion molecule engages the LTbR, it initiates an alteration of gene expression to a pro-inflammatory state. A sampling of genes that show a high fold change is presented in Table 3.

Stimulatory Effect of LIGHT Fusion Proteins on IP-10 and IL-8 Secretion

Methods: HT29 cells were plated at $3 \times 10^4$ per well in a 96-well plate and allowed to attach overnight. The cells were refed with dilutions of reagents in media containing 100 u/ml IFNg (total volume of 100 ul/well). 24 hours later the supernatants were collected and spun to pellet cellular debris. The clarified supernatants were stored overnight on ice. The R+D Systems Quantikine ELISA kits for Human CXCL8/IL-8 (#D8000C) and Human IP-10 (#DIP100) were used according to the manufacturer's instructions. Samples were diluted a total of 1:90 for the IL-8 ELISA and 1:30 for the IP-10 ELISA. Data above are plotted in ng/ml of IP-10 or IL-8 over the molar treatment concentrations.

Figure 20:
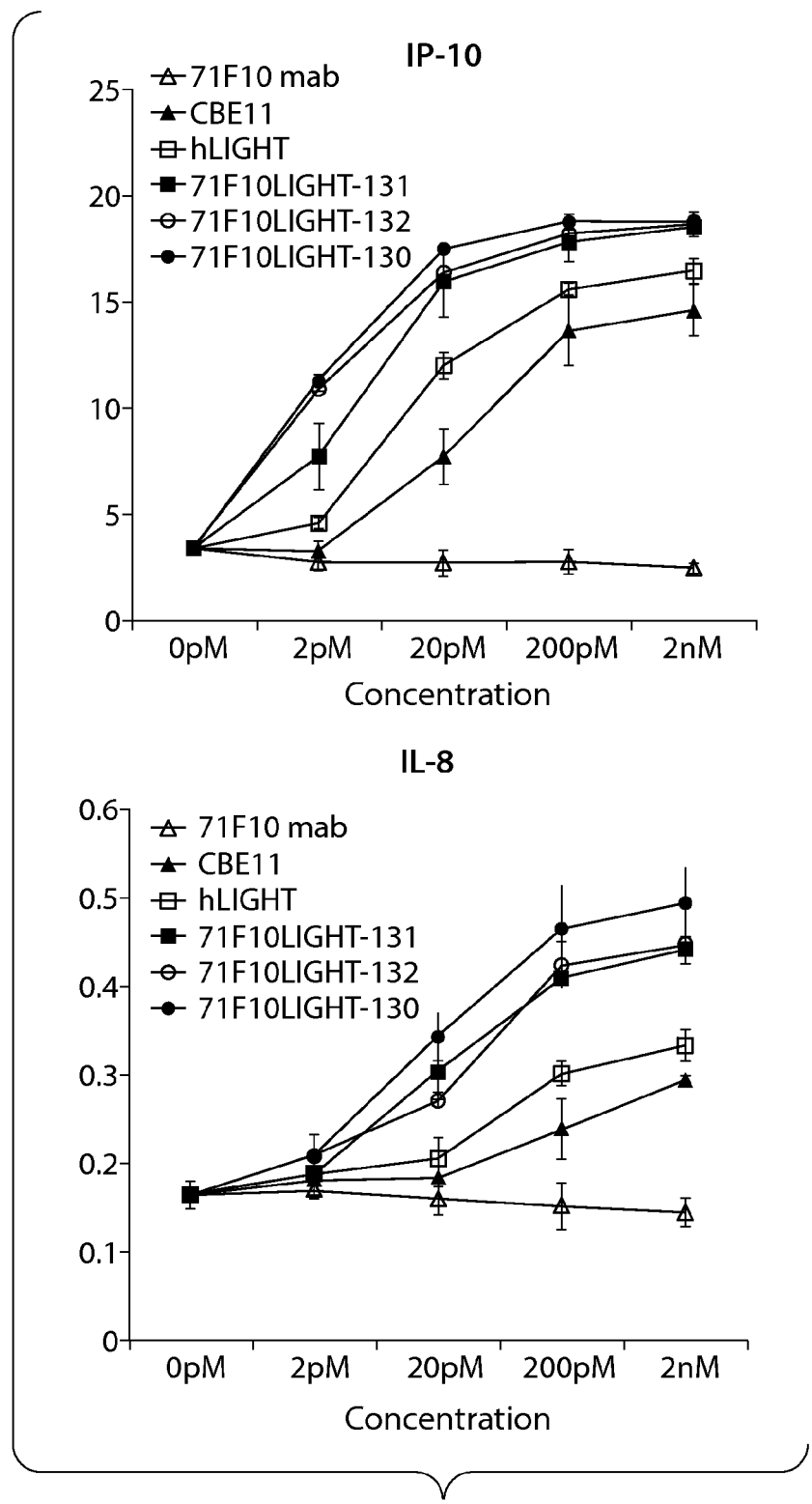
FIG. 20 depicts the stimulation of IP-10, IL-8 secretion in HT29 cells by 71F10 Fab-hLIGHT fusion proteins.

Results: 71F10 Fab-hLIGHT fusion proteins stimulate IP-10 and IL-8 secretion in HT29 cells (FIG. 20).

Example 21

HER2 Signaling Analysis of Anti-Her2 Fabs, mAbs and LIGHT Fusion Proteins

Effect of on Phosphorylation of HER2, Akt and MAPK

Methods: $5 \times 10^5$ MCF7, SKBR3, BT474 or N87 cells/well were plated in 6-well plates in 1 mL volume. After 24 hrs 1 mL 200 nM solution of indicated reagent (Fab, mAb, control anti-HER2 antibody or LIGHT fusion proteins) was added to wells to give 2 mL of 100 nM solution. After desirable incubation time (1, 6, 24 or 72 hours), media were removed and cells were washed 1× with PBS. Cells lysed with 500 uL RIPA buffer (20 mM MOPS pH 7.0, 150 mM Sodium Chloride, 1% NP40, 1% Deoxycholate, 0.1% SDS) containing protease and phosphatase inhibitors (Mini-complete and PhosStop, respectively, Roche Applied Bioscience cat#11836153001 and 04906837001, respectively). Lysates collected in microcentrifuge tubes and stored at 4° C. Total protein concentrations determined using Micro BCA Protein Assay kit (Pierce cat#23235). 10 ug of total protein loaded per well on NuPAGE® Novex 4-12% Bis-Tris Gel (Invitrogen cat#. Gels run with NuPAGE® MOPS SDS Running Buffer (Invitrogen cat#NP0001) for 1 hr at 200V. Gels blotted onto PVDF membranes (Invitrogen cat#LC2002) using transfer buffer (12.5 mM Tris, 96 mM Glycine, 20% Methanol) run at 30V for 1 hr. Membranes rinse in TBS-T (1× Tris-buffered with 0.1% Tween20) and block in StartingBlock T20 (TBS) Blocking Buffer (Pierece cat#37543) for 1 hr at R/T with gentle shaking. Primary antibodies (Her2 (#2242), phospho-Her2 (#2249), Akt (#4691), phosphoAkt (#4060), MAPK (#4695), phosphoMAPK (#4370) all from Cell Signaling Technology, Beverly, Mass.) added to blocking buffer. Blots incubated with antibodies overnight at 4° C. with gentle shaking. Blot was washed thoroughly in TBS-T. HRP-conjugated donkey anti-rabbit IgG (H+L) (JacksonImmuno cat#711-035-152) secondary antibody was added in blocking buffer at a concentration of 1:10000. Blots incubated at R/T for one hour with gentle shaking. After incubation blots were thoroughly washed with TBS-T and ECL Plus reagent (GE Healthcare Life Science cat#RPN2132) was added as per instructions. Blots were exposed to X-ray film (Kodak BioMax XAR cat#165-1454) and developed. Alternatively, blots were incubated with detecting antibodies overnight at 4° C. with gentle shaking. Blots were washed thoroughly in TBS-T. Goat anti-mouse IgG (H+L), DyLight 680 conjugated (Pierce cat#35518) and goat anti-rabbit IgG (H+L), DyLight 800 conjugated (Pierce cat#35571) secondary antibodies were added to blocking buffer at a concentration of 1:10000 in one container and incubated for one hour at R/T with gentle shaking. Blots were then washed thoroughly with TBS-T. Blots visualized on Licor Odyssey Infrared Scanner.

Results:

None of the anti-HER2 Fabs appears to induce HER2, MAP kinase and AKT phosphorylation as observed at 6 or 72 hours compared to control anti-HER2 antibody (data not shown).

After converting to full antibody, BIIB71F10-134, showed weak agonistic activity in activating MAP kinase in the absence of Heregulin in MCF7 cells (mAb concentration 1-100 nM). No significant in total or phosphorylated Her2 and Akt was detected after BIIB71F10-134 treatment. LIGHT fusion protein, BIIB71F10-132, treatment also induced MAP kinase phosphorylation in the absence of Heregulin in MCF7 cells. Induction of MAP kinase phosphrylation can be detected from 2.5 pM to 200 nM of BIIB71F10-132 fusion protein treatment (data not shown). Similar MAP kinase activation was also detected in SKBR3 cells, but at much lower levels (data not shown).

Furthermore, MAP kinase activation by BIIB71F10-132 fusion protein in MCF7 is presumably through the trimerization of HER2 upon LIGHT fusion treatment. This MAP kinase activation is not a result of LIGHT pathway activation because blockage of LIGHT function by LTbR-Ig of the fusion protein produced identical results as observed in LIGHT fusion treatment alone. These results suggest that trimeric 71F10 appears to be agonistic and is able to activate HER2 signal transduction under current experimental conditions.

Effect on HER2 Heterodimerization with HER3

Methods: $5 \times 10^5$ MCF7, SKBR3 or N87 cells were plated in 6-well plates. After 24 hrs testing reagents (Fab, full antibodies, or LIGHT fusion proteins) were added at 50 nM and cells were incubated with them for one or 72 hrs. After antibody incubation heregulin beta (100 ng/mL) was added to media and cells were incubated for an additional 30 min. Cells were washed 1× with PBS and lysed with 250 uL of RIPA buffer (20 mM MOPS pH 7.0, 150 mM Sodium Chloride, 1% NP40, 1% Deoxycholate, 0.1% SDS) containing protease and phosphatase inhibitors (Mini-complete and PhosStop, respectively, Roche Applied Bioscience cat#11836153001 and 04906837001, respectively). Lysates were collected in microcentrifuge tubes and stored at 4° C. 100 uL of lysate was added to 900 uL of RIPA buffer not containing protease and phosphotase inhibitors. 1 ug of rabbit anti-HER3 (Santa Cruz Biotechnology cat#sc-285) added to each sample, along with 25 uL of Protein A sepharose (GE Healthcare cat#17-5280-01). Mixtures were rocked overnight at 4° C. After overnight incubation sepharose beads were pelleted by centrifugation at 3000 rpm for one minute. The supernatant was removed by aspiration and the pellet washed with 500 uL PBS. This procedure was repeated two more times. After the final supernatant was removed 30 uL of 5×SDS sample reducing buffer (11.5% SDS, 50% Glycerol, 0.3M Tris, 0.025% Phenol Red, 25% beta-mercaptoethanol) was added to pellet, pellet disrupted and heated to 95° C. for five minutes. The sample was then centrifuged at 14000 rpm for 3 minutes and the supernatant loaded on a NuPAGE® Novex 4-12% Bis-Tris Gel (Invitrogen). Gels were run with NuPAGE® MOPS SDS Running Buffer (Invitrogen cat#NP0001) for 1 hr at 200V. Gels were blotted onto PVDF membranes (Invitrogen cat#LC2002) using transfer buffer (12.5 mM Tris, 96 mM Glycine, 20% Methanol) run at 30V for 1 hr. Membranes were rinsed in TBS-T (1× Tris-buffered with 0.1% Tween20) and blocked in StartingBlock T20 (TBS) Blocking Buffer (Pierce cat#37543) for 1 hr at R/T with gentle shaking. A rabbit-anti Human HER2 antibody (Cell Signal Technologies cat#2242) was added to the blocking buffer. Blots incubated with antibody overnight at 4° C. with gentle shaking. Blots were washed thoroughly in TBS-T. HRP-conjugated donkey anti-rabbit IgG (H+L) (JacksonImmuno cat#711-035-152) secondary antibody was added in blocking buffer at a concentration of 1:20000. Blots were incubated at R/T for one hour with gentle shaking. After incubation blots were thoroughly washed with TBS-T and ECL Plus reagent (GE Healthcare Life Science cat#RPN2132) was added as per instructions. Blots were exposed to X-ray film (Kodak BioMax XAR cat#165-1454) and developed.

Results:

Fab 65H09 appears to increase heterodimerization with HER3 in the absence of Heregulin, but that effect is abrogated by Heregulin treatment. This can be explained by that 65H09 binding site at Her2 overlaps with the interaction site of Heregulin to HER2. Since Heregulin has higher affinity than Fab 65H09, the facilitation effect of 65H09 to HER2/HER3 heterodimerization was eliminated. All other Fabs show no effect on HER2/HER3 heterodimerization (data not shown).

It appears that Fab 71F10 decreased HER2/HER3 heterodimerization at 1 hour in the presence of HER3 ligand Heregulin in N87 cells. But the effect is not replicated in SKBR3 cells (data not shown). The effect of LIGHT fusion proteins on Her2/Her3 heterodimerization remain to be tested using the same procedure described above.

Effect of Fabs on HER2 Heterodimerization with EGFR

Methods: $5 \times 10^5$ MCF7, SKBR3 or B87 cells were plated in 6-well plates. After 24 hrs antibodies were added at 50 nM and cells were incubated with them for one or 72 hrs. After antibody incubation human epidermal growth factor (100 ng/mL) was added and cells were incubated for an additional 30 min. Cells were washed 1× with PBS and lysed with 250 uL of RIPA buffer (20 mM MOPS pH 7.0, 150 mM Sodium Chloride, 1% NP40, 1% Deoxycholate, 0.1% SDS) containing protease and phosphatase inhibitors (Mini-complete and PhosStop, respectively, Roche Applied Bioscience cat#11836153001 and 04906837001, respectively). Lysates were collected in microcentrifuge tubes and stored at 4° C. 100 uL of lysate was added to 900 uL of RIPA buffer not containing protease and phosphotase inhibitors. 1 ug of mouse anti human EGFR (BD Bioscinces Pharmingen cat#610016) added to each sample, along with 25 uL of Protein A sepharose (GE Healthcare cat#17-5280-01). Mixtures were rocked overnight at 4° C. After overnight incubation sepharose beads were pelleted by centrifugation at 3000 rpm for one minute. The supernatant was removed by aspiration and the pellet washed with 500 uL PBS. This procedure was repeated two more times. 30 uL of 5×SDS sample reducing buffer (11.5% SDS, 50% Glycerol, 0.3M Tris, 0.025% Phenol Red, 25% beta-mercaptoethanol) was added to pellet, pellet disrupted and heated to 95° C. for five minutes. The sample was then centrifuged at 14000 rpm for 3 minutes and the supernatant loaded on a NuPAGE® Novex 4-12% Bis-Tris Gel (Invitrogen). Gels were run with NuPAGE® MOPS SDS Running Buffer (Invitrogen cat#NP0001) for 1 hr at 200V. Gels were blotted onto PVDF membranes (Invitrogen cat#LC2002) using transfer buffer (12.5 mM Tris, 96 mM Glycine, 20% Methanol) run at 30V for 1 hr. Membranes were rinsed in TBS-T (1× Tris-buffered with 0.1% Tween20) and blocked in StartingBlock T20 (TBS) Blocking Buffer (Pierce cat#37543) for 1 hr at R/T with gentle shaking. A rabbit anti Human HER2 antibody (Cell Signal Technologies cat#2242) was added to the blocking buffer. Blots incubated with antibody overnight at 4° C. with gentle shaking. Blots were washed thoroughly in TBS-T. HRP-conjugated donkey anti-rabbit IgG (H+L) (JacksonImmuno cat#711-035-152) secondary antibody was added in blocking buffer at a concentration of 1:20000. Blots were incubated at R/T for one hour with gentle shaking. After incubation blots were thoroughly washed with TBS-T and ECL Plus reagent (GE Healthcare Life Science cat#RPN2132) was added as per instructions. Blots were exposed to X-ray film (Kodak BioMax XAR cat#165-1454) and developed.

Results:

Results indicated that Fab 66A12 facilitates EGFR/HER2 heterodimerization in SKBR3 cells, whereas all other Fabs show no activity. Similarly control anti-HER2 antibody Fab was also able to facilitate EGFR/HER2 heterodimerization as observed in 66A12 (data not shown). The effect of LIGHT fusion proteins on EGFR/HER2 heterodimerization remain to be evaluated using the same procedure.

Example 22

Tumor Models for Evaluation of LIGHT Fusion Activity Against Primary Tumor and Metastasis LIGHT fusion protein potential display its anti-tumor activity through the combination of HER2 pathway blockade and activation of LTβR pathway. Therefore LTβR and HER2 double positive tumor models are desirable for testing LIGHT fusion proteins. These tumor models include human tumor cell lines such as BT474, SKBR-3, MCF7, MDA-MB-231, MDA-MB-468, N87, SKOV3, HT29, WiDr; and mouse breast tumor cell lines Tubo, TSA and 4T1 cells.

BT474, MCF7, MDA-MB-231, MDA-MB-468 human breast tumor cell lines, N87 human gastric cancer cell line, and SKOV3 human ovarian cancer cell line were cultured in RPMI 1640 with 10% fetal bovine serum in a humidified atmosphere of 5% $CO_2$ at 37° C. SKBR3 human breast tumor cell line, HT29, Widr human colon adenocarcinoma were cultured in McCoy's 5a medium containing 1.5 mM L-glutamine, and 10% fetal bovine serum. Mouse mammary gland tumor cell lines Tubo, TSA and 4T1 were cultured in DMEM supplied with 10% fetal bovine serum. Medium was changed every 3 days. Cells were removed from culture flasks for passage by washing once with PBS, followed by a 5-min incubation with 0.5 mM EDTA and 0.05% trypsin at PH 7.4. Their viability was determined by microscopic examination of cells stained by 0.1% trypan blue. Viable cells were inoculated into mice in a volume of 0.1 ml of PBS.

To establish xenograft models of LTβR and HER2 double positive tumor, female athymic nude (nu/nu) BALB/c mice, 6-8 weeks of age, were inoculated subcutaneously into the right flank skin with $2×10^6$ viable cultured human tumor cells in 0.1 ml of PBS. Mice with established s.c. tumors were evaluated by perpendicular bidimensional tumor measurements twice weekly with a Vernier caliper. Mice were euthanized and scored as dead from lethal tumor progression when the s.c. tumor diameter exceeded 14 mm. Tumor volume was calculated using the formula, $V=xy^2/2$. where x and y are the two perpendicular diameters (length and width). Because MCF7 tumors do not grow without estradiol, all mice inoculated with MCF7 tumors received s.c. 17β-estradiol pellet (Innovative Research of America, Sarasota, Fla.) implants 7 days prior to tumor inoculation.

To establish syngeneic models, female Balb/c ($H-2K^d$) mice, were inoculated subcutaneously into the right flank skin with $0.5×10^6$ viable cultured mouse tumor cells (Tubo, TSA or 4T1) in 0.1 ml of PBS. Tumor volume was calculated as described above.

LIGHT fusion protein can also be tested in engineered tumor cell lines to over express human or mouse Her2 such as MCF7/hHer2, 4T1/mHer2, TSA/mHer2. The overexpression of Her2 in these cells attempts to mimic the Her2 overexpression in human breast cancer and made it more feasible to test anti-HER2 LIGHT fusion proteins tumor targeting capability. These modified cell lines will be grown in the same culture medium of their parental cell lines but including selection drugs such as G418 and Blasticydin.

Example 23

In Vivo Inhibition of Tumor Growth Using Combination Therapy

Method: The efficacy of LIGHT fusion protein in inhibiting tumor growth in combination with chemotherapeutic agents (e.g., Docetaxel, Paclitaxel, Doxcirubicin, Cyclophosphamide, Fluorouracil (5FU), Gemcitabine and Vinorelbine) can be tested in a xenograft model (e.g., BT474 or MCF model) or a model of primary tumor segments. The efficacy of LIGHT-Fab fusion protein administered intraperitoneally (i.p.) two times per week at 30 mg/kg for 7 weeks or one time per week at 60 mg/kg for 5 weeks can be evaluated in combination with gemcitabine administered according to the current standard of care (i.e., 80 mg/kg every 3 days for 4 weeks). Gemcitabine alone, LIGHT-Fab fusion protein alone, and sham injections of the delivery vehicle alone can be administered as negative controls. Tumor volume at the start of the therapy was approximately 200 $mm^3$. Primary tumor regression, hLIGHT fusion accumulation in tumors, infiltrating lymphocytes, CD4, CD8, Tregs and tumor re-challenge can be evaluated.

Example 24

Antitumor Activity of Fab-LIGHT Fusion Proteins in Xenograft Tumor Models

LIGHT fusion protein is believed to display its antitumor activity at least in part through the combination of tumor cell target inhibition (e.g. HER2) and activation of LIGHT receptors (namely LTβR and HVEM) on tumor cell surface. Therefore both HER2 and LIGHT receptor(s) double positive tumor models can be used for testing LIGHT fusion proteins. As examples, HT29 and N87 xenograft tumor models were selected for testing LIGHT fusion protein antitumor activity in vivo.

HT29, a tumor cell line derived from human colorectal adenocarcinoma, was purchased from ATCC (cat# HTB-38) and passaged afterwards. These cells express HER2 at medium levels (IHC score 2+) as determined by Western blot and immunohistochemical staining (data not shown). HT29 cells also express both LTβR and HVEM receptors for LIGHT. The growth of HT29 cells is not HER2 dependent although these cells do express HER2. For example, these cells do not exhibit growth arrest after anti-HER2 antibody treatment (data not shown). Therefore the antitumor activity of 71-F10-hLIGHT fusion proteins is mainly dependent on the LIGHT-directed killing activity to the tumor cells as shown by in vitro proliferation assays (data not shown). In contrast, N87 is a tumor cell line derived from human gastric carcinoma (ATCC, #CRL5822) and forms subcutaneous tumors in SCID mice. N87 cells over-express HER2 to high levels (IHC score 3+) and respond to anti-HER2 antibody treatment, which lead to growth arrest and cell death (data not shown). Therefore, blocking of HER2 and cell growth arrest/cell death triggered by LIGHT can contribute to 71F10-hLIGHT antitumor activity.

Both nu/nu athymic female mice and SCID female mice were obtained from Charles River Laboratories (Wilmington, Mass.) at 6-8 weeks of age. $2\times10^6$ (HT-29) and $5\times10^6$ (N87) tumor cells were inoculated subcutaneously in the right flank of nu/nu and SCID mice, respectively. Mice with established tumors (50-200 mm3) were selected for study (N=7 to 10 per treatment group). Tumor dimensions were measured using calipers and tumor volumes were calculated using the equation for an ellipsoid sphere $(L \times W^2)/2 = mm^3$, where L and W refer to the larger and smaller dimensions collected at each measurement. The test fusion proteins or antibodies were formulated and administered intravenously (IV) or via the intraperitoneal cavity (IP) at a dose volume of 6 mL/kg. The vehicle alone was administered to control groups. Animals were dosed three days per week (TIW—Monday, Wednesday, Friday) for six to eight consecutive weeks. For monoclonal antibodies, the treatment was twice a week (BIW—Monday and Thursday). Animals were weighed and the tumors were measured twice per week. Mice were followed until tumor volumes in the control group reached approximately 1000 mm$^3$ and were sacrificed by $CO_2$ euthanasia. The mean tumor volumes of each group were calculated. The change in mean treated tumor volume was divided by the change in mean control tumor volume, multiplied by 100 and subtracted from 100% to give the tumor growth inhibition for each group. Statistical analysis was performed using the standard T-test and using GraphPad Prism© Software.

Example 25

Figure 21:
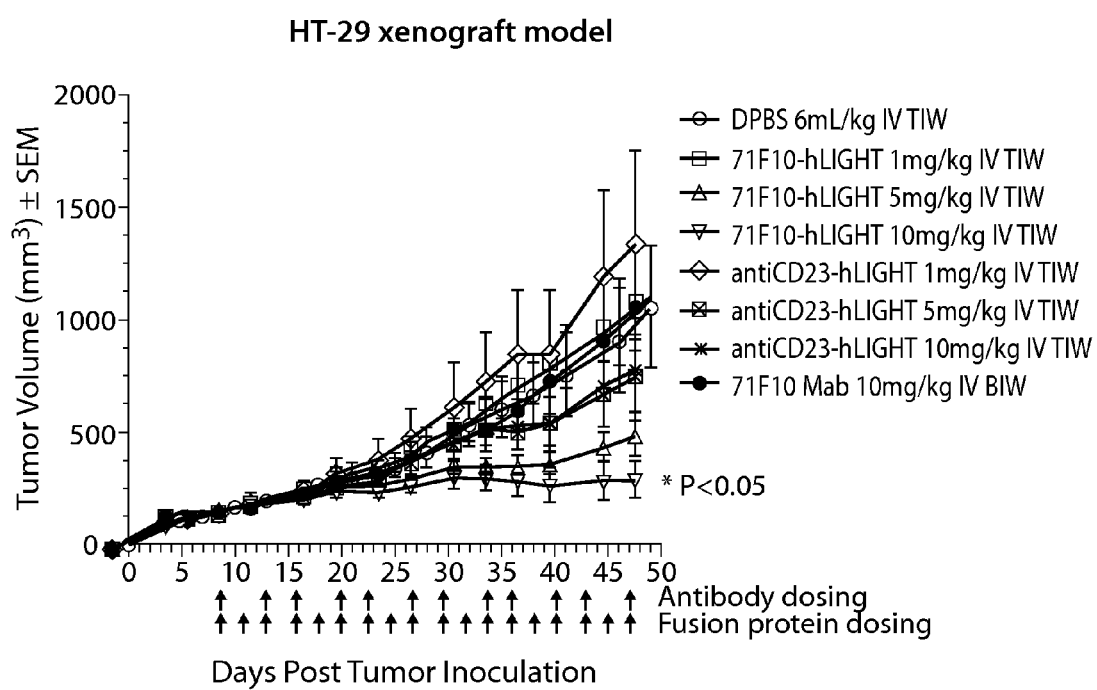
FIG. 21 depicts the suppression of HT29 tumor growth by 71F10 Fab-hLIGHT fusion proteins.

The Anti-HER2-LIGHT Fusion Protein Demonstrated Potent Anti-Tumor Activity in HT29 Xenograft Model Results of 71F10-hLIGHT activity in HT29 tumor model is summarized as FIG. 21. Significant antitumor activity of 71F10-hLIGHT was shown in 10 mg/kg 71F10-hLIGHT fusion protein treatment group (p<0.05). The T/C (treated group vs. control group) value is less than 42% (data not shown). Although not reaching statistical significance, the 1 mg/kg and 5 mg/kg groups also showed clear anti-tumor activity in a dose dependent manner compared to the control groups. No difference was observed between IP vs IV delivery of 71F10-hLIGHT proteins for anti-tumor efficacy (data not shown). In contrast, the anti-HER2 monoclonal antibody BIIB71-F10 treatment alone did not show any antitumor effect. As discussed in Example 24, the growth of HT29 cells is not HER2-dependent although these cells do express HER2, which might contribute the lack of efficacy in the BIIB-71F10 Mab treatment. Furthermore, these results showed that the antitumor efficacy of HT29 tumors is from the LIGHT side of the 71F10-LIGHT fusion molecule since no activity was observed from 71F10 Mab treatment. The direct killing activity of LIGHT was further demonstrated in the control fusion molecule, anti-CD23-hLIGHT treatment groups. CD23 is not expressed on HT29 cells and therefore no "targeting effect" should be expected from its treatment. Only mild anti-tumor activity was detected in 5 and 10 mg/kg anti-CD23-hLIGHT groups, but there was no dose dependency (i.e. 5 and 10 mg/kg data overlapped) for its efficacy. These results suggested that free LIGHT fusion molecule in circulation is probably sufficient to induce tumor growth arrest.

HER2-targeted 71F10-hLIGHT showed much more potent anti-tumor activity than that of the non-targeted anti-CD23-hLIGHT control molecule. The weaker anti-tumor activity of anti-CD23-hLIGHT is not due to reagent difference in quality or pharmacokinetic difference since both 71F10-hLIGHT and anti-CD23-hLIGHT have equal potency as shown by in vitro killing assays using HT29 cells and identical PK values (data not shown). Therefore, the more potent activity of 71F10-hLIGHT can result from the necessity of targeting LIGHT to tumor cells for its maximal anti-tumor activity. These results provided additional evidence to support the role of LIGHT/LTβR/HVEM receptor oligomerization on cell surface in obtaining maximal signaling strength of TNF family members.

Example 26

The Anti-HER2-LIGHT Fusion Protein Demonstrated Potent Anti-tumor Activity in HER2-dependent N87 Xenograft Tumor Model To test the synergy between anti-HER2 therapy and LIGHT-directed killing activity, N87 tumor model was employed in this experiment. As mentioned above, N87 cells over-express HER2 to high levels (IHC score 3+) and respond to anti-HER2 antibody such as control anti-HER2 antibody treatment that results in cell growth rest and cell death (data not shown). N87 tumors were grown on the flank of SCID mice and treated when tumor size reached 50-200 mm$^3$. The treatments were similar to those used in Example 25, but included Trastuzumab or control anti-HER2 antibody (Roch/Genentech). The results were summarized in FIG. 22. 71F10-hLIGHT demonstrated significant (p<0.001) anti-tumor activity and suppressed tumor growth (T/C<40%) in a dose dependent manner. Similar to the observations from Example 25, anti-CD23-hLIGHT was less efficacious than 71F10-hLIGHT at the same dose (5 mg/kg) and showed significant efficacy in N87 models (p<0.02). The targeting antibody alone, BIIB71-F10 (without the LIGHT moiety) did not reach statistical significance in reducing tumor growth (note BIIB71-F10 antibody does not cross block with control anti-HER2 antibody). Control anti-HER2 antibody treatment showed significant growth retardation throughout the course of treatments (p<0.02). However, N87 tumors treated with control anti-HER2 antibody relapsed and resumed growth at Day 50. In contrast, tumors treated with 71F10-hLIGHT showed continued growth inhibition and even trend of tumor regression. These observations underscore some of the molecular and cellular differences between anti-HER2 antibody and anti-HER2-LIGHT fusion molecules in their respective anti-tumor activity. For example, aside from the mechanisms involving the blocking of HER2 receptor and cell growth arrest and death triggered by LIGHT, LIGHT may have stimulated the innate cells such as NK cells and macrophage to assist tumor cell killing. This mechanism is consistent with the known biological function of LIGHT and the observation that there was a slight delay in tumor response to 71F10-hLIGHT fusion protein treatment. The involvement of innate immune cells in anti-tumor activity can be further investigated by immunohistochemical staining of tumor sections and cell depletion experiments. Regardless the mechanism of action, 71F10-hLIGHT fusion protein displayed differences in treating HER2-dependent tumors compared to anti-HER2 antibodies, and offers an alternative therapy to overcome resistance to anti-HER2 antibody therapies.

Example 27

LIGHT Fusion Treatment Stimulates Host Anti-tumor Immune Responses

LIGHT is a potent co-stimulatory molecule for T cell activity, therefore targeting LIGHT to tumor tissue via Fab-LIGHT evokes host anti-tumor responses and reduces or eradicates tumor metastasis. The immune responses can be tested in immune competent animals. Syngeneic mouse tumor models, such as mouse breast tumor cells TSA, 4T1 and Tubo (Her2+) cells can be employed. Briefly, tumor cells can be prepared as single cell suspension. $1-5\times10^5$ tumor cells can be inoculated at the right flank of Balb/c mice. When the s.c. tumor area is established and reaches 50-100 $mm^3$, animals can be treated with 71F10-hLIGHT fusion protein and controls at various doses and schedules for two weeks. At the end of the treatment and two weeks post treatment, tumor tissues and draining lymph nodes can be harvested to analyze immune cells infiltration, i.e. tumor residing CD4, CD8, NK cells and macrophages. For histology analyses lymphoid-like structure in tumor tissues can be examined and intratumoral levels of SLC (CCL21) can be determined for lymphocytes trafficking. The draining lymph nodes and lung tissues can be collected at one month after treatment for metastasis analyses. The fusion protein treatment group can have increased number of tumor infiltrating lymphocytes, upregulation of cytokines/adhesion molecules and result in reduced metastatic tumors.

The effect of LIGHT fusion protein induced-immunity in protecting animals from tumor rechallenge can also be determined. Both primary growth of re-challenged tumor and metastasis can be monitored.

Example 28

Construction of Anti-IGFR Fab-LIGHT Fusion Protein, C06-hLIGHT

Monoclonal antibody C06 VH region was synthesized by PCR amplification using the oligonucleotide primers described as DyaxVH-pV90-F (SEQ ID NOs:157), 256-R (SEQ ID NO:158), and 165-R2 (SEQ ID NO:159). The 5' forward primer, DyaxVH-pV90-F which contains a unique Mlu I restriction endonuclease site (ACGCGT (SEQ ID NO:160) followed by sequences encoding the last three amino acids of the heavy chain signal peptide followed by sequences complementary to the amino terminus of the recoded C06 VH. The 3' reverse primers consisted of an internal reverse primer, 256-R encoding the carboxyl terminus of C06 VH and a second reverse primer 165-R2 encoding a partial human IgG1 CH1 domain and an Age I site (AC-CGGT (SEQ ID NO:161)). The recoded C06 VH region was amplified in two sequential PCR reactions through the common overlapping sequences encoding the human IgG1 CH1 domain using these three PCR primers from plasmid DNA pBIIBC06-030 containing the recoded Dyax anti-IGF1R C06 VH gene. The C06 VH gene fragment was cloned into the Mlu I/Age I digested the pBIIB71F10-132. Correct sequences were confirmed by DNA sequencing. Heavy chain DNA and amino acid sequences for the C06Fab-hLIGHT fusion (pBI-IBC06-256) are shown as SEQ ID NOs:162 and 163, respectively. The amino acid and nucleotide sequences corresponding to heavy chain of C06Fab are shown starting from the N-terminus; followed by amino acids corresponding to the linking group (amino acids 226 to 245); followed by the amino acids corresponding to human LIGHT extracellular domain (amino acids 246 to 393). The amino acid sequences for C06 VH CDRs 1-3 are shown in SEQ ID NOs:164-166, respectively.

The C06 light chain vector (pBIIBC06-117) was used in the C06Fab-hLIGHT fusion and DNA and amino acid sequences are shown as SEQ ID NOs:167 and 168, respectively. The amino acid sequences for C06 VL CDRs 1-3 are shown in SEQ ID NOs:169-171, respectively.

Figure 23A:
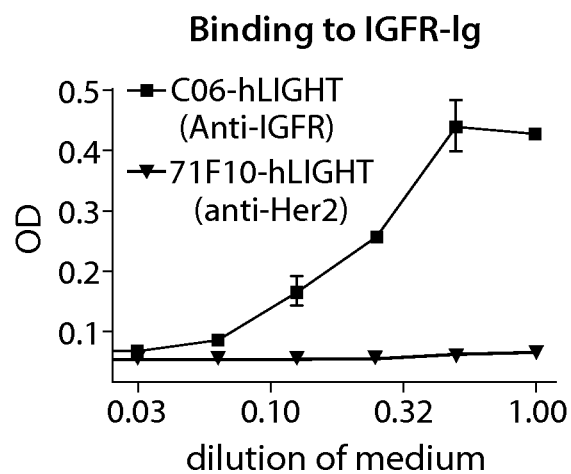
FIG. 23A depicts the binding of anti-IGFR C06 Fab-hLIGHT fusion protein to IGFR-Ig as measured by ELISA.
Figure 23B:
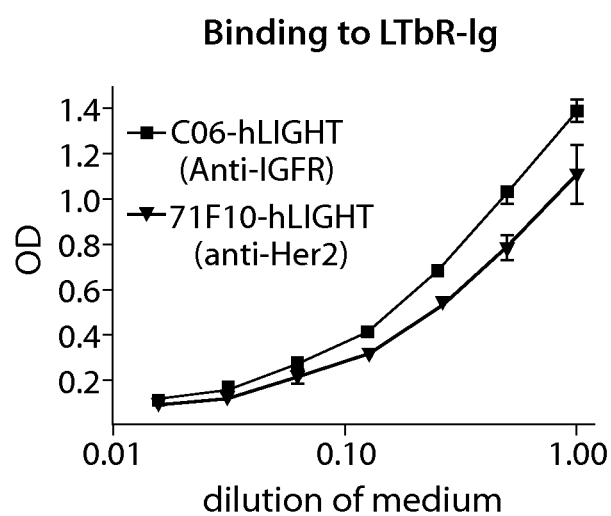
FIG. 23B depicts the binding of anti-IGFR C06 Fab-hLIGHT fusion protein to LTβR-Ig as measured by ELISA.

C06-hLIGHT fusion protein was produced by transient transfection of CHO cells as described in Example 8. The protein titer in the medium was determined by Octet (Forte-Bio) and used for ELISA assay to assess binding activities to IGFR and LIGHT receptor LTβR. Anti-HER271F10-hLIGHT was used as a control. Results were summarized in FIGS. 23A and 23B. C06-hLIGHT showed specific binding to both IGFR (FIG. 23A) and LTβR (FIG. 23B) and demonstrated its bi-functional activity.

Example 29

Construction of Dimeric Form of Fab-LIGHT Fusion Protein

Dimeric form of Fab-LIGHT fusion protein was generated by including the full CH1 hinge region of IgG1. Dimer is stabilized by the formation of double disulfide bonds. The human IgG1 hinge sequence which contains two cysteine residues for interchain disulfide bonds formation was inserted in front of the $(G4S)_4$ linker region of in 71F10-hLIGHT fusion heavy chain (FIG. 24). The 71F10 Fab-hLIGHT dimeric fusion heavy chain was constructed in the PCR reaction using the 5' forward plus 3' reverse PCR primers and an internal overlapping PCR primer set encoding the human IgG1 hinge sequence from plasmid DNAs containing the human IgG1 and hLIGHT. The primer sequences were shown as MB-04F (SEQ ID NO:135), 130-R1 (SEQ ID NO:136), 255-mF (SEQ ID NO:175) and 255-mR (SEQ ID NO:176). Briefly, the 5' forward primer, MB-04F that has an AgeI site (ACCGGT (SEQ ID NO161)) followed by sequences complementary to the IgG1 CH1 region. The 3' reverse primer, 130-R1 which contained a BamH I site (GGATCC (SEQ ID NO:177)) and sequence encoding complementary to the carboxyl terminus of hLIGHT. The 5' forward primer, 255-mF and the 3' reverse primer 255-mR of the internal overlapping PCR primer set included the sequences encoding the human IgG1 hinge region followed by the partial (G4S)$_4$ linker. The PCR fragments were assembled together in a second PCR reaction using sequences encoding the overlapping the huIgG1 hinge and (G4S)$_4$ linker sequence. The final PCR products were digested with the Age I and BamH I and ligated into the Age I/BamH I digested pBIIB71F10-134 vector which contains the BIIB71-F10 IgG1 heavy chain sequence. DNA sequences of the construct were confirmed by DNA sequencing. Heavy chain DNA and amino acid sequences for the 71F10 Fab-hLIGHT dimeric fusion (pBIIB71F10-255) are shown as SEQ ID NOs:178 and 179, respectively. The amino acid and nucleotide sequences corresponding to heavy chain of 71F10 Fab are shown starting from the N-terminus; followed by amino acids corresponding to the CH1 hinge region of IgG1 (amino acids 225 to 232 of SEQ ID NO:172); followed by amino acids corresponding to the linking group (amino acids 233 to 252 of SEQ ID NO:172); followed by the amino acids corresponding to human LIGHT extracellular domain (amino acids 253 to 400 of SEQ ID NO:172).

The 71F10 light chain vector (pBIIB71F10-129) was used in the 71F10 Fab-hLIGHT dimeric fusion and DNA and amino acid sequences are shown as SEQ ID NOs:110 and 109, respectively.

Figure 1:
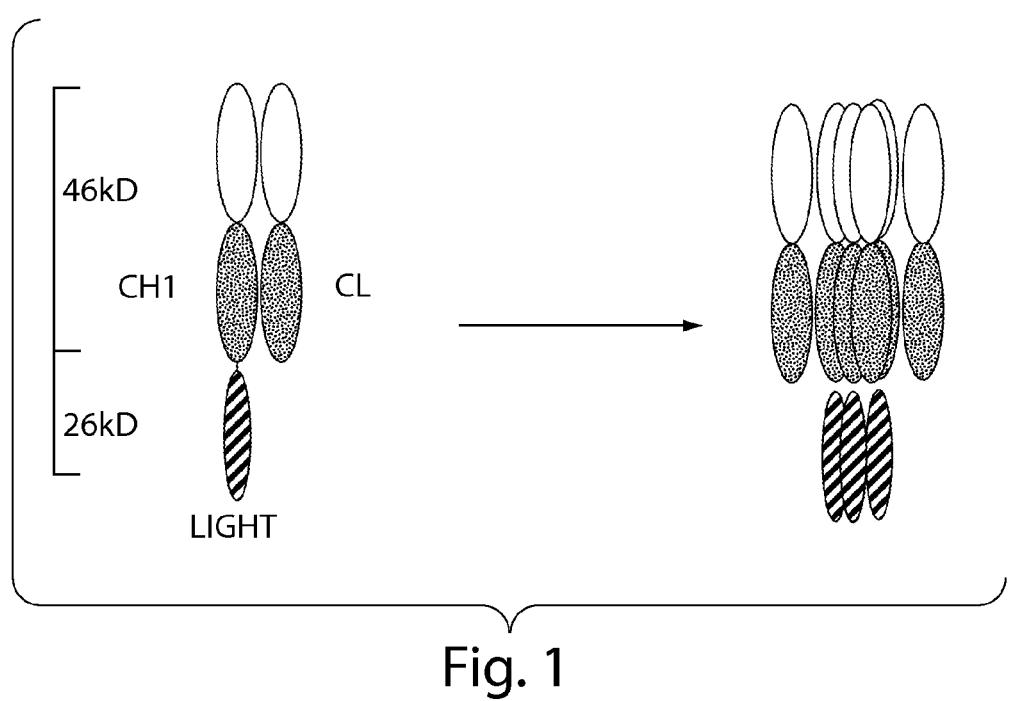
FIG. 1 depicts a schematic representation of LIGHT-Fab design.
Figure 2:
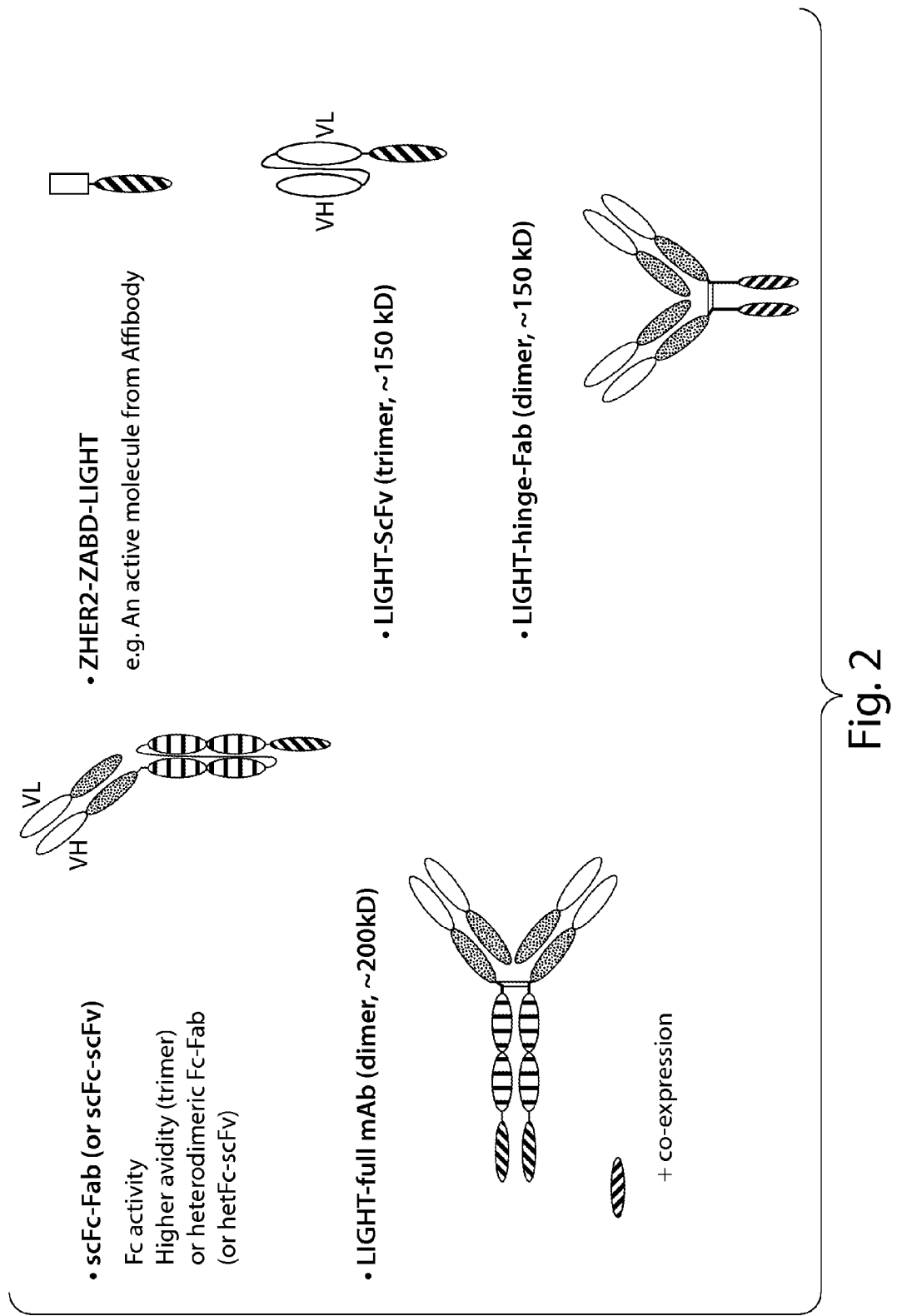
FIG. 2 depicts a schematic representation of LIGHT fusion protein design alternatives.
Figure 25A:
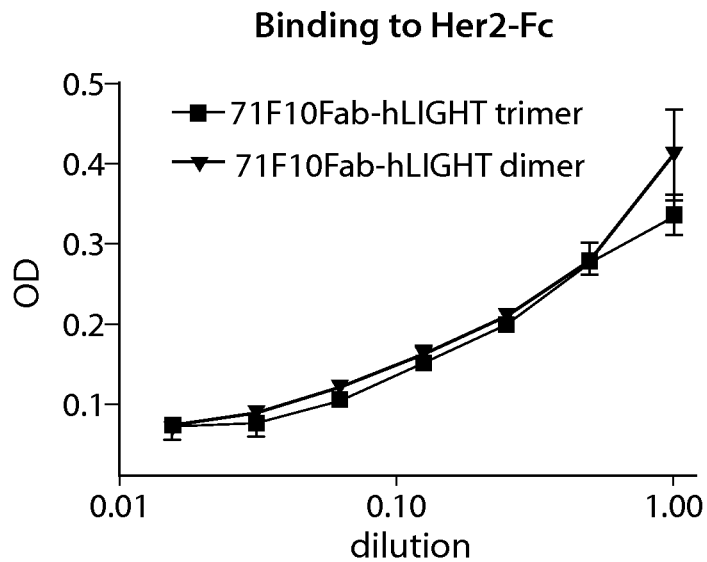
FIG. 25A depicts the binding of the dimeric form of 71F10 Fab-hLIGHT to HER2-Fc as shown by ELISA.
Figure 25B:
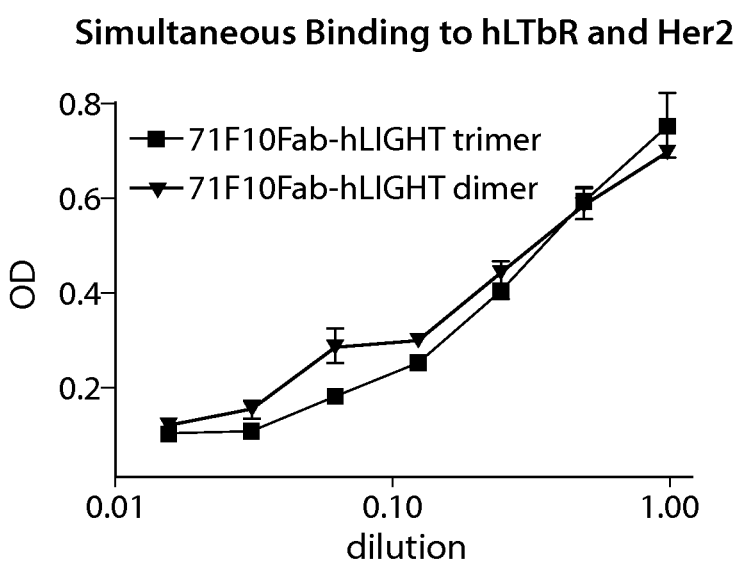
FIG. 25B depicts the simultaneous binding of the dimeric form of 71F10 Fab-LIGHT to hLTβR and HER2 as shown by ELISA.

Dimeric 71F10 Fab-hLIGHT fusion protein was produced by transient transfection of CHO cells with pBIIB71F10-255 vector as described in Example 8. The protein titer in the medium was determined by Octet (ForteBio) and used for ELISA assay to assess binding activities to HER2 target and LIGHT receptor LTβR. AntiHer2 71F10-hLIGHT was used as a control. Results were summarized in FIGS. 25A and 25B. In FIG. 25A, 2-fold serial dilution of medium was added to the plates coated with 2 ug/ml rhErbB2-Fc, and binding was detected by goat-anti-human kappa-HRP (1:10000). In FIG. 25B, 2-fold serial dilution of medium was added to the plates coated with 2 ug/ml hHER2-Fc, and binding was detected by streptavidin-HRP (1:4000) after incubation with 1 ug/ml of Biotin-hLTβR-Fc. C06-hLIGHT showed specific binding to both IGFR (FIG. 25A) and LTβR (FIG. 25B) and demonstrated its bi-functional activity.

Deposits

CHO cells expressing the following Fab-LIGHT fusions were deposited on behalf of Biogen IDEC Inc., 14 Cambridge Center, Cambridge, Mass. 02142, with the Amercian Type Tissue Culture Collection (ATCC®) on Sep. 24, 2009 pursuant to the requirements of the Budapest Treaty:

| ATCC ® Patent Deposit Designation | |
|---|---|
| CHO cells: 71F10 fablight #1 | PTA-10355 |
| CHO cells: 65H09 fablight 5F6 | PTA-10356 |
| CHO cells: 67F11 fablight #4 | PTA-10357 |
| CHO cells: 65C10 fablight sorted pool | PTA-10358 |

Equivalents

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

TABLE 1

| Antibody | human Her2 CHO FACS EC50 (nM) | murine Her2 CHO FACS Binding | cyno Her2 CHO FACS Binding |
|---|---|---|---|
| BIIB65-B03 | 15 | no | yes |
| BIIB65-C10 | 6 | no | yes |
| BIIB65-H09 | 20 | no | yes |
| BIIB66-A12 | 60 | no | yes |
| BIIB66-C01 | 12 | no | yes |
| BIIB67-A02 | 100 | no | no |
| BIIB67-C12 | n.d. | no | no |
| BIIB67-F10 | 2 | no | yes |
| BIIB67-F11 | 7 | no | yes |
| BIIB69-A09 | 2 | no | yes |
| BIIB71-A06 | 6 | no | no |
| BIIB71-F10 | 60 | yes | yes |

TABLE 2

Binding activity summary of LIGHT fusion proteins

| Construct Name | ELISA EC50 (nM) | | | FACS EC50 (nM) | | | Octet Kinetic off-rates ($k_d$), x ~1e−4 sec$^{-1}$ | | |
|---|---|---|---|---|---|---|---|---|---|
| | Her2 | LTbR | HVEM | Her2 | LTbR | HVEM | Her2 | LTbR | HVEM |
| BIIB71F10 Mab | 0.07 | ND | ND | 2 | | | ND | ND | ND |
| BIIB71F10-130 | 0.05 | 0.01 | 0.01 | 0.5 | 0.2 | 0.5 | 1.12 | 1.68 | 1.22 |
| BIIB71F10-131 | 0.05 | 0.01 | 0.01 | 0.5 | 0.2 | 0.5 | 3.07 | 1.83 | ND |
| BIIB71F10-132 | 0.05 | 0.01 | 0.01 | 0.5 | 0.2 | 0.5 | 1.17 | 1.97 | 1.60 |
| BIIBCD23-121 | ND | ND | ND | ND | ND | ND | | 0.83 | 2.82 |

ND—not determined

TABLE 3

Examples of pro-inflammatory genes in HT29 cells that are effected by treatment with BIIB71F10-130 as measured by quantitative reverse transcriptase PCR

| Gene | Fold Difference Test Sample/ Control Sample |
|---|---|
| CCL2 (MCP-1) | 1.05E+03 |
| CCL21 | 5.46E+02 |
| CCL5 (RANTES) | 1.22E+03 |
| CCL7 (MCP-3) | −5.27E+02 |
| CCR4 | 1.65E+03 |
| CXCL10 (IP-10) | 5.27E+03 |
| CXCL11 (I-TAC/IP9) | 1.73E+03 |
| CXCL2 | 1.13E+03 |
| CXCL3 | 1.09E+03 |
| CXCL5 (ENA-78/LIX) | 1.81E+03 |
| CXCL9 | 6.75E+02 |
| IFNA2 | 1.93E+02 |
| IL10RA | 3.44E+03 |
| IL5 | 9.40E+02 |
| IL8 | 3.73E+02 |
| LTB | 2.91E+03 |
| TNF | 7.37E+03 |

What is claimed is:

1. A LIGHT-targeting molecule, comprising an extracellular domain of a human LIGHT protein or fragment thereof, and a targeting antibody molecule that binds to HER2, wherein the targeting antibody molecule comprises a heavy chain variable ($V_H$) amino acid sequence comprising the amino acid sequence of CDR1 (SEQ ID NO:47), CDR2 (SEQ ID NO:48) and CDR3 (SEQ ID NO:49) and a light chain variable ($V_L$) amino acid sequence comprising the amino acid sequence of CDR1 (SEQ ID NO:74), CDR2 (SEQ ID NO:75) and CDR3 (SEQ ID NO:76), and wherein the targeting antibody molecule is linked to the extracellular domain of the human LIGHT protein or fragment thereof.

2. The LIGHT-targeting molecule of claim 1, wherein the $V_H$ is linked to a heavy chain constant region ($C_H$), which is linked, with or without a linking group (L), to the extracellular domain of the human LIGHT protein or fragment thereof.

3. The LIGHT-targeting molecule of claim 1, which comprises a dimer or a trimer of the extracellular domain of the human LIGHT protein or fragment thereof and the targeting antibody molecule.

4. The LIGHT-targeting molecule of claim 3, wherein the extracellular domain of the LIGHT protein or fragment thereof has one or more LIGHT-associated activities chosen from: (i) binding to one or more LIGHT-receptors; (ii) inducing expression of one or more of chemokines or cytokines, chemokine or cytokine receptors, adhesion molecules, or co-stimulatory molecules; (iii) activating T cells; (iv) recruiting T cells into a tumor, cell or tissue; (v) activating or enhancing tumor-reactive T cell proliferation; (vi) creating a lymphoid-like microenvironment at a tumor cell or tissue; (vii) inducing apoptosis of a tumor cell or tissue; or (viii) stimulating an immune response in a subject.

5. The LIGHT-targeting molecule of claim 4, wherein the extracellular domain of the human LIGHT protein or fragment thereof comprises amino acids 93 to 240 of SEQ ID NO:1 (human LIGHT isoform 1), or an amino sequence at least 90% identical thereto.

6. The LIGHT-targeting molecule of claim 1, which comprises a linker comprising one, two, three, four or five $(G_4S)_4$ (SEQ ID NO:134) repeats.

7. The LIGHT-targeting molecule of claim 6, comprising a heavy chain having the amino acid sequence of SEQ ID NO:4 and a light chain having the amino acid sequence of SEQ ID NO:109, or an amino acid sequence at least 90% identical to SEQ ID NO:4 or SEQ ID NO:109.

8. The LIGHT-targeting molecule of claim 1, wherein the $V_H$ amino acid sequence comprises the amino acid sequence of SEQ ID NO:11, or an amino acid sequence at least 90% identical thereto.

9. The LIGHT-targeting molecule of claim 1, wherein the $V_L$ amino acid sequence comprises the amino acid sequence of SEQ ID NO:13, or an amino acid sequence at least 90% identical thereto.

10. The LIGHT-targeting molecule of claim 1, wherein the $V_H$ amino acid sequence comprises the amino acid sequence of SEQ ID NO:11, or an amino acid sequence at least 90% identical thereto, and wherein the $V_L$ amino acid sequence comprises the amino acid sequence of SEQ ID NO:13, or an amino acid sequence at least 90% identical thereto.

11. The LIGHT-targeting molecule of claim 1, wherein the $V_H$ amino acid sequence comprises the amino acid sequence of SEQ ID NO:11.

12. The LIGHT-targeting molecule of claim 1, wherein the $V_L$ amino acid sequence comprises the amino acid sequence of SEQ ID NO:13.

13. The LIGHT-targeting molecule of claim 1, wherein the $V_H$ amino acid sequence comprises the amino acid sequence of SEQ ID NO:11, and wherein the $V_L$ amino acid sequence comprises the amino acid sequence of SEQ ID NO:13.

14. The LIGHT-targeting molecule of claim 1, wherein the extracellular domain of the LIGHT protein comprises amino acids 93 to 240 of SEQ ID NO:1.

15. A pharmaceutical composition comprising the LIGHT-targeting molecule of claim 7 and a pharmaceutically acceptable carrier.

16. A LIGHT-targeting molecule, comprising an extracellular domain of a human LIGHT protein, and a Fab fragment that binds to HER2, wherein the Fab fragment comprises:

a heavy chain variable ($V_H$) domain comprising the amino acid sequence of SEQ ID NO:11; and a light chain variable ($V_L$) domain comprising the amino acid sequence of SEQ ID NO:13;

and wherein the $V_H$ domain is linked to a heavy chain constant region 1 ($C_{H1}$) which is linked to the extracellular domain of a human LIGHT protein comprising amino acids 93 to 240 of SEQ ID NO:1.

17. The LIGHT-targeting molecule of claim 16, further comprising a linking group which links the $C_{H1}$ to the extracellular domain of a human LIGHT protein.

18. The LIGHT-targeting molecule of claim 17, wherein the linking group comprises one, two, three, four or five $(G_45)_4$ (SEQ ID NO:134) repeats.

19. The LIGHT-targeting molecule of claim 17, wherein the linking group comprises amino acids 61 to 92 of SEQ ID NO:1.

20. A LIGHT-targeting molecule, comprising an extracellular domain of a human LIGHT protein, and a Fab fragment that binds HER2, wherein the Fab fragment comprises:

the amino acid sequence of SEQ ID NO:4; and the amino acid sequence of SEQ ID NO:109;

and wherein the Fab fragment is linked with a linking group to the extracellular domain of a human LIGHT protein comprising amino acids 93 to 240 of SEQ ID NO:1.

21. The LIGHT-targeting molecule of claim 20, wherein the linking group comprises one, two, three, four or five $(G_45)_4$ (SEQ ID NO:134) repeats.

22. The LIGHT-targeting molecule of claim 20, wherein the linking group comprises amino acids 61 to 92 of SEQ ID NO:1.

\* \* \* \* \*

SEQUENCE LISTING

```
<160> NUMBER OF SEQ ID NOS: 182

<210> SEQ ID NO 1
<211> LENGTH: 240
<212> TYPE: PRT
<213> ORGANISM: Homo sapiens

<400> SEQUENCE: 1

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```

```
<210> SEQ ID NO 2
<211> LENGTH: 350
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2
```

| | | | | | | | | | | | | | | |
|---|---|---|---|---|---|---|---|---|---|---|---|---|---|---|
| Ile | Ser | Ser | Ser | Gly | Gly | Leu | Thr | Trp | Tyr | Ala | Asp | Ser | Val | Lys | Gly |
| 1 | | | | 5 | | | | | 10 | | | | | 15 | |

Arg Phe Thr Ile Ser Arg Asp Asn Ser Lys Asn Thr Leu Tyr Leu Gln
                20                  25                  30

Met Asn Ser Leu Arg Ala Glu Asp Thr Ala Val Tyr Tyr Cys Ala Ser
             35                  40                  45

Pro Pro Gly Ile Ala Val Ala Arg Asp Tyr Trp Gly Gln Gly Thr Leu
     50                  55                  60

Val Thr Val Ser Ser Ala Ser Thr Lys Gly Pro Ser Val Phe Pro Leu
65                  70                  75                  80

Ala Pro Ser Ser Lys Ser Thr Ser Gly Gly Thr Ala Ala Leu Gly Cys
                85                  90                  95

Leu Val Lys Asp Tyr Phe Pro Glu Pro Val Thr Val Ser Trp Asn Ser
            100                 105                 110

Gly Ala Leu Thr Ser Gly Val His Thr Phe Pro Ala Val Leu Gln Ser
        115                 120                 125

Ser Gly Leu Tyr Ser Leu Ser Ser Val Val Thr Val Pro Ser Ser Ser
    130                 135                 140

Leu Gly Thr Gln Thr Tyr Ile Cys Asn Val Asn His Lys Pro Ser Asn
145                 150                 155                 160

Thr Lys Val Asp Lys Lys Val Glu Pro Lys Ser Cys Asp Lys Leu His
                165                 170                 175

Trp Arg Leu Gly Glu Met Val Thr Arg Leu Pro Asp Gly Pro Ala Gly
            180                 185                 190

Ser Trp Gln Glu Arg Arg Ser His Glu Val Asn Pro Ala Ala His Leu
        195                 200                 205

Thr Gly Ala Asn Ser Ser Leu Thr Gly Ser Gly Gly Pro Leu Leu Trp
    210                 215                 220

Glu Thr Gln Leu Gly Leu Ala Phe Leu Arg Gly Leu Ser Tyr His Asp
225                 230                 235                 240

Gly Ala Leu Val Val Thr Lys Ala Gly Tyr Tyr Tyr Ile Tyr Ser Lys
                245                 250                 255

Val Gln Leu Gly Gly Val Gly Cys Pro Leu Gly Leu Ala Ser Thr Ile
            260                 265                 270

Thr His Gly Leu Tyr Lys Arg Thr Pro Arg Tyr Pro Glu Glu Leu Glu
        275                 280                 285

Leu Leu Val Ser Gln Gln Ser Pro Cys Gly Arg Ala Thr Ser Ser Ser
    290                 295                 300

Arg Val Trp Trp Asp Ser Ser Phe Leu Gly Gly Val Val His Leu Glu
305                 310                 315                 320

Ala Gly Glu Glu Val Val Arg Val Leu Asp Glu Arg Leu Val Arg
                325                 330                 335

Leu Arg Asp Gly Thr Arg Ser Tyr Phe Gly Ala Phe Met Val
            340                 345                 350

```
<210> SEQ ID NO 3
<211> LENGTH: 405
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 3

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Val Trp Val Arg Gln Ala Pro Gly Lys Gly Leu Glu Trp Val
        35                  40                  45

Ser Ser Ile Ser Ser Ser Gly Gly Leu Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gly Ile Ala Val Ala Arg Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Gly Gly Gly Gly Ser Leu His Trp Arg Leu Gly Glu Met Val Thr Arg
225                 230                 235                 240

Leu Pro Asp Gly Pro Ala Gly Ser Trp Gln Glu Arg Arg Ser His Glu
                245                 250                 255

Val Asn Pro Ala Ala His Leu Thr Gly Ala Asn Ser Ser Leu Thr Gly
            260                 265                 270

Ser Gly Gly Pro Leu Leu Trp Glu Thr Gln Leu Gly Leu Ala Phe Leu
        275                 280                 285

Arg Gly Leu Ser Tyr His Asp Gly Ala Leu Val Val Thr Lys Ala Gly
    290                 295                 300

Tyr Tyr Tyr Ile Tyr Ser Lys Val Gln Leu Gly Gly Val Gly Cys Pro
305                 310                 315                 320

Leu Gly Leu Ala Ser Thr Ile Thr His Gly Leu Tyr Lys Arg Thr Pro
                325                 330                 335

Arg Tyr Pro Glu Glu Leu Glu Leu Leu Val Ser Gln Gln Ser Pro Cys
            340                 345                 350

Gly Arg Ala Thr Ser Ser Ser Arg Val Trp Trp Asp Ser Ser Phe Leu
        355                 360                 365

Gly Gly Val Val His Leu Glu Ala Gly Glu Glu Val Val Val Arg Val
    370                 375                 380

Leu Asp Glu Arg Leu Val Arg Leu Arg Asp Gly Thr Arg Ser Tyr Phe
```

```
                385                 390                 395                 400

Gly Ala Phe Met Val
                405

<210> SEQ ID NO 4
<211> LENGTH: 392
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Val Trp Val Arg Gln Ala Pro Gly Lys Gly Leu Glu Trp Val
        35                  40                  45

Ser Ser Ile Ser Ser Ser Gly Gly Leu Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gly Ile Ala Val Ala Arg Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Gly Gly Gly Gly Ser Gly Gly Gly Ser Gly Gly Gly Gly Ser Gly
225                 230                 235                 240

Gly Gly Gly Ser Asn Pro Ala Ala His Leu Thr Gly Ala Asn Ser Ser
                245                 250                 255

Leu Thr Gly Ser Gly Gly Pro Leu Leu Trp Glu Thr Gln Leu Gly Leu
            260                 265                 270

Ala Phe Leu Arg Gly Leu Ser Tyr His Asp Gly Ala Leu Val Val Thr
        275                 280                 285

Lys Ala Gly Tyr Tyr Tyr Ile Tyr Ser Lys Val Gln Leu Gly Gly Val
    290                 295                 300

Gly Cys Pro Leu Gly Leu Ala Ser Thr Ile Thr His Gly Leu Tyr Lys
305                 310                 315                 320

Arg Thr Pro Arg Tyr Pro Glu Glu Leu Glu Leu Leu Val Ser Gln Gln
                325                 330                 335

Ser Pro Cys Gly Arg Ala Thr Ser Ser Ser Arg Val Trp Trp Asp Ser
```

```
                340                 345                 350
Ser Phe Leu Gly Gly Val Val His Leu Glu Ala Gly Glu Val Val
            355                 360                 365

Val Arg Val Leu Asp Glu Arg Leu Val Arg Leu Arg Asp Gly Thr Arg
    370                 375                 380

Ser Tyr Phe Gly Ala Phe Met Val
385                 390

<210> SEQ ID NO 5
<211> LENGTH: 723
<212> TYPE: DNA
<213> ORGANISM: Homo sapiens

<400> SEQUENCE: 5
atggaggaga gtgtcgtacg gccctcagtg tttgtggtgg atggacagac cgacatccca      60
ttcacgaggc tgggacgaag ccaccggaga cagtcgtgca gtgtggcccg ggtgggtctg     120
ggtctcttgc tgttgctgat gggggccggg ctggccgtcc aaggctggtt cctcctgcag     180
ctgcactggc gtctaggaga gatggtcacc cgcctgcctg acggacctgc aggctcctgg     240
gagcagctga tacaagagcg aaggtctcac gaggtcaacc cagcagcgca tctcacaggg     300
gccaactcca gcttgaccgg cagcgggggg ccgctgttat gggagactca gctgggcctg     360
gccttcctga ggggcctcag ctaccacgat ggggcccttg tggtcaccaa agctggctac     420
tactacatct actccaaggt gcagctgggc ggtgtgggct gcccgctggg cctggccagc     480
accatcaccc acgcctcta caagcgcaca ccccgctacc ccgaggagct ggagctgttg     540
gtcagccagc agtcaccctg cggacgggcc accagcagct cccgggtctg gtgggacagc     600
agcttcctgg gtggtgtggt acacctggag gctggggaga aggtggtcgt ccgtgtgctg     660
gatgaacgcc tggttcgact gcgtgatggt accggtctt acttcggggc tttcatggtg     720
tga                                                                    723

<210> SEQ ID NO 6
<211> LENGTH: 1203
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
gaggtgcagc tgttggagtc tgggggaggc ttggtccagc ctggggggtc cctgagactc      60
tcctgtgcag cctctggatt caccttcagt agctatggca tggtctgggt ccgccaggct     120
ccagggaagg gctggagtg gtctcatcc attagttctt ctggtggcct gacatggtac       180
gcagactccg tgaagggccg attcaccatc tccagagaca attccaagaa cacgctgtat     240
ctgcaaatga acagcctgag agccgaggac acggccgtgt attactgtgc gagccccccc     300
ggtattgccg ttgctcggga ctactgggc cagggaaccc tggtcaccgt ctcctcagct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcactg cgcgtctagg agatggtca cccgcctgcc tgacggacct     720
```

```
gcaggctcct ggcaagagcg aaggtctcac gaggtcaacc cagcagcgca tctcacaggg    780
gccaactcca gcttgaccgg cagcggggggg ccgctgttat gggagactca gctgggcctg   840
gccttcctga ggggcctcag ctaccacgat ggggcccttg tggtcaccaa agctggctac    900
tactacatct actccaaggt gcagctgggc ggtgtgggct gcccgctggg cctggccagc    960
accatcaccc acggcctcta caagcgcaca ccccgctacc ccgaggagct ggagctgttg   1020
gtcagccagc agtcaccctg cggacgggcc accagcagct cccgggtctg gtgggacagc   1080
agcttcctgg gtggtgtggt acacctggag gctggggagg aggtggtcgt ccgtgtgctg   1140
gatgaacgcc tggttcgact gcgtgatggt acccggtctt acttcggggc tttcatggtg   1200
tga                                                                  1203

<210> SEQ ID NO 7
<211> LENGTH: 1218
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gaggtgcagc tgttggagtc tgggggaggc ttggtccagc ctggggggtc cctgagactc     60
tcctgtgcag cctctggatt caccttcagt agctatggca tggtctgggt ccgccaggct    120
ccagggaagg ggctggagtg ggtctcatcc attagttctt ctggtggcct gacatggtac    180
gcagactccg tgaagggccg attcaccatc tccagagaca attccaagaa cacgctgtat    240
ctgcaaatga acagcctgag agccgaggac acggccgtgt attactgtgc gagcccccc    300 ggtattgccg ttgctcggga ctactgggc cagggaaccc tggtcaccgt ctcctcagct    360
agcaccaagg gcccatcggt cttccccctg gcaccctcct ccaagagcac ctctggggc    420 acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aggcggtgg agggtccctg cactggcgtc taggagagat ggtcacccgc    720
ctgcctgacg gacctgcagg ctcctggcaa gagcgaaggt ctcacgaggt caacccagca    780
gcgcatctca caggggccaa ctccagcttg accggcagcg ggggccgct gttatgggag    840 actcagctgg gcctggcctt cctgaggggc ctcagctacc acgatggggc ccttgtggtc    900
accaaagctg gctactacta catctactcc aaggtgcagc tgggcggtgt gggctgcccg    960
ctgggcctgg ccagcaccat cacccacggc tctacaagc gcacaccccg ctaccccgag   1020
gagctggagc tgttggtcag ccagcagtca ccctgcggac gggccaccag cagctcccgg   1080
gtctggtggg acagcagctt cctgggtggt gtggtacacc tggaggctgg ggaggaggtg   1140
gtcgtccgtg tgctggatga acgcctggtt cgactgcgtg atggtacccg gtcttacttc   1200
ggggctttca tggtgtga                                                 1218

<210> SEQ ID NO 8
<211> LENGTH: 1179
<212> TYPE: DNA
<213> ORGANISM: Artificial Sequence
<220> FEATURE:
<223> OTHER INFORMATION: Description of Artificial Sequence: Synthetic
      polynucleotide
```

-continued

```
<400> SEQUENCE: 8
gaggtgcagc tgttggagtc tgggggaggc ttggtccagc ctggggggtc cctgagactc    60
tcctgtgcag cctctggatt caccttcagt agctatggca tggtctgggt ccgccaggct   120
ccagggaagg ggctggagtg ggtctcatcc attagttctt ctggtggcct gacatggtac   180
gcagactccg tgaagggccg attcaccatc tccagagaca attccaagaa cacgctgtat   240
ctgcaaatga acagcctgag agccgaggac acggccgtgt attactgtgc gagcccccc    300 ggtattgccg ttgctcggga ctactggggc cagggaaccc tggtcaccgt ctcctcagct   360
agcaccaagg gcccatcggt cttccccctg gcaccctcct ccaagagcac ctctgggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagaaagt tgagcccaaa   660
tcttgtgaca aggcggtgg agggtccggt gggggcggat ctggggggg cgggtccggt   720 ggtggtggta gtaacccagc agcgcatctc acaggggcca actccagctt gaccggcagc   780
ggggggccgc tgttatggga gactcagctg gcctggcct tcctgagggg cctcagctac   840
cacgatgggg cccttgtggt caccaaagct ggctactact acatctactc caaggtgcag   900
ctgggcggtg tgggctgccc gctgggcctg gccagcacca tcacccacgg cctctacaag   960
cgcacacccc gctaccccga ggagctggag ctgttggtca gccagcagtc accctgcgga  1020
cgggccacca gcagctcccg ggtctggtgg acagcagct tcctgggtgg tgtggtacac  1080
ctggaggctg gggaggaggt ggtcgtccgt gtgctggatg aacgcctggt tcgactgcgt  1140
gatggtaccc ggtcttactt cggggctttc atggtgtga                         1179

<210> SEQ ID NO 9
<211> LENGTH: 4
<212> TYPE: PRT
<213> ORGANISM: Homo sapiens

<400> SEQUENCE: 9

Glu Gln Leu Ile
1

<210> SEQ ID NO 10
<211> LENGTH: 4
<212> TYPE: PRT
<213> ORGANISM: Mus sp.

<400> SEQUENCE: 10

Glu Lys Leu Ile
1

<210> SEQ ID NO 11
<211> LENGTH: 119
<212> TYPE: PRT
<213> ORGANISM: Homo sapiens

<400> SEQUENCE: 11

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Val Trp Val Arg Gln Ala Pro Gly Lys Gly Leu Glu Trp Val
        35                  40                  45
```

Ser Ser Ile Ser Ser Ser Gly Gly Leu Thr Trp Tyr Ala Asp Ser Val
       50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gly Ile Ala Val Ala Arg Asp Tyr Trp Gly Gln Gly
            100                 105                 110

Thr Leu Val Thr Val Ser Ser
        115

<210> SEQ ID NO 12
<211> LENGTH: 357
<212> TYPE: DNA
<213> ORGANISM: Homo sapiens

<400> SEQUENCE: 12
gaagttcaat tgttagagtc tggtggcggt cttgttcagc ctggtggttc tttacgtctt      60
tcttgcgctg cttccggatt cactttctct tcttacggta tggtttgggt cgccaagct     120 cctggtaaag gtttggagtg ggtttcttct atctcttctt ctggtggcct tacttggtat     180
gctgactccg ttaaaggtcg cttcactatc tctagagaca actctaagaa tactctctac     240
ttgcagatga acagcttaag ggctgaggac acggccgtgt attactgtgc gagccctccg     300
ggtatagcag tggcccggga ctactggggc cagggcaccc tggtcaccgt ctcaagc        357

<210> SEQ ID NO 13
<211> LENGTH: 107
<212> TYPE: PRT
<213> ORGANISM: Homo sapiens

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Leu Leu
                85                  90                  95

Thr Phe Gly Gly Gly Thr Lys Val Glu Ile Lys
            100                 105

<210> SEQ ID NO 14
<211> LENGTH: 321
<212> TYPE: DNA
<213> ORGANISM: Homo sapiens

<400> SEQUENCE: 14
gacatccaga tgacccagtc tccatcctcc ctgtctgcat ctgtaggaga cagagtcacc      60
atcacttgcc gggcgagtca gggcattagc aattatttag cctggtatca gcagaaacca     120
gggaaagttc ctaagctcct gatctatgct gcatccactt tgcaatcagg ggtcccatct     180
cggttcagtg gcagtggatc tgggacagat ttcactctca ccatcagcag cctgcagcct     240

```
gaagatgttg caacttatta ctgtcaaaag tataacagtg ccctcctcac tttcggcgga   300
gggaccaagg tggagatcaa a                                             321

<210> SEQ ID NO 15
<211> LENGTH: 125
<212> TYPE: PRT
<213> ORGANISM: Homo sapiens

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Asn Met Trp Trp Val Arg Gln Ala Pro Gly Lys Gly Leu Glu Trp Val
        35                  40                  45

Ser Val Ile Arg Ser Ser Gly Gly Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Asn Ser Gly Tyr Ser Tyr Trp Asp Tyr Tyr Tyr Gly Met
            100                 105                 110

Asp Val Trp Gly Gln Gly Thr Thr Val Thr Val Ser Ser
        115                 120                 125

<210> SEQ ID NO 16
<211> LENGTH: 375
<212> TYPE: DNA
<213> ORGANISM: Homo sapiens

<400> SEQUENCE: 16
gaagttcaat tgttagagtc tggtggcggt cttgttcagc ctggtggttc tttacgtctt   60
tcttgcgctg cttccggatt cactttctct cgttacaata tgtggtgggt tcgccaagct  120
cctggtaaag gtttggagtg ggtttctgtt atccgttctt ctggtggcta tactggttat  180
gctgactccg ttaaaggtcg cttcactatc tctagagaca actctaagaa tactctctac  240
ttgcagatga acagcttaag ggctgaggac acggccgtat attactgtgc gagatggaat  300
agtggataca gctactggga ctactactac ggtatggacg tctggggcca agggaccacg  360
gtcaccgtct caagc                                                   375

<210> SEQ ID NO 17
<211> LENGTH: 107
<212> TYPE: PRT
<213> ORGANISM: Homo sapiens

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Gln Gln Phe Asn Thr Tyr Pro Ile
                    85                  90                  95

Thr Phe Gly Pro Gly Thr Lys Val Asp Ile Lys
            100                 105

<210> SEQ ID NO 18
<211> LENGTH: 321
<212> TYPE: DNA
<213> ORGANISM: Homo sapiens

<400> SEQUENCE: 18
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag cctgcagcct     240
gaagattttg caacttatta ctgtcaacaa tttaatactt acccgattac tttcggccct     300
gggaccaaag tggatatcaa a                                                321

<210> SEQ ID NO 19
<211> LENGTH: 116
<212> TYPE: PRT
<213> ORGANISM: Homo sapiens

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Pro Tyr
            20                  25                  30

Met Met Val Trp Val Arg Gln Ala Pro Gly Lys Gly Leu Glu Trp Val
        35                  40                  45

Ser Trp Ile Ser Pro Ser Gly Gly Tyr Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Tyr Gly Thr Tyr Pro Leu Thr Tyr Trp Gly Gln Gly Thr Leu Val
            100                 105                 110

Thr Val Ser Ser
        115

<210> SEQ ID NO 20
<211> LENGTH: 348
<212> TYPE: DNA
<213> ORGANISM: Homo sapiens

<400> SEQUENCE: 20
gaagttcaat tgttagagtc tggtggcggt cttgttcagc ctggtggttc tttacgtctt      60
tcttgcgctg cttccggatt cactttctct ccttacatga tggtttgggt tcgccaagct     120
cctggtaaag gtttggagtg gtttcttgg atctctcctt ctggtggcta tactttttat      180
gctgactccg ttaaaggtcg cttcactatc tctagagaca actctaagaa tactctctac     240
ttgcagatga acagcttaag ggctgaggac acgccgtgt attactgtgc atatgggacc      300
tacccgctta catactgggg ccaggaacc ctggtcaccg tctcaagc                    348
```

<210> SEQ ID NO 21
<211> LENGTH: 106
<212> TYPE: PRT
<213> ORGANISM: Homo sapiens

<400> SEQUENCE: 21

```
Gln Ser Glu Leu Thr Gln Thr Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Ser Trp Phe Gln Leu Lys Pro Gly Gln Ser Pro Leu Leu Val Ile Tyr
        35                  40                  45

Gln Asp Ser Lys Trp Pro Ser Gly Ile Pro Glu Arg Phe Ser Gly Ser
    50                  55                  60

Asn Ser Gly Asn Thr Ala Thr Leu Thr Ile Ser Gly Thr Gln Ala Thr
65                  70                  75                  80

Asp Glu Ala Asp Tyr Tyr Cys Gln Val Trp Asp Ile Ser His Val Val
                85                  90                  95

Phe Gly Gly Gly Thr Lys Leu Thr Val Leu
            100                 105
```

<210> SEQ ID NO 22
<211> LENGTH: 318
<212> TYPE: DNA
<213> ORGANISM: Homo sapiens

<400> SEQUENCE: 22

```
cagagcgaat tgactcagac accctcagtg tccgtgtccc caggacagac agccagcatc      60
acctgttctg gagataaaat tggggataag tatgtttcct ggttccagct gaagccaggc     120
cagtcccctc ttttggtcat ctatcaagat agtaagtggc cctcagggat ccctgagcga     180
ttctctggct ccaattctgg gaacacagcc actctgacca tcagcgggac ccaggctacg     240
gatgaggctg actactattg tcaggtgtgg gacatcagcc atgtggtatt cggcggaggg     300
accaagctga ccgtccta                                                    318
```

<210> SEQ ID NO 23
<211> LENGTH: 130
<212> TYPE: PRT
<213> ORGANISM: Homo sapiens

<400> SEQUENCE: 23

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Tyr Met Met Trp Val Arg Gln Ala Pro Gly Lys Gly Leu Glu Trp Val
        35                  40                  45

Ser Val Ile Gly Ser Ser Gly Gly Met Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Pro Thr Gly Tyr Tyr Asp Ser Ser Gly Trp Val Tyr
            100                 105                 110

Ser Tyr Tyr Gly Ile Asp Val Trp Gly Gln Gly Thr Thr Val Thr Val
        115                 120                 125
```

Ser Ser
    130

<210> SEQ ID NO 24
<211> LENGTH: 390
<212> TYPE: DNA
<213> ORGANISM: Homo sapiens

<400> SEQUENCE: 24
gaagttcaat tgttagagtc tggtggcggt cttgttcagc ctggtggttc tttacgtctt      60
tcttgcgctg cttccggatt cactttctct aattactata tgatgtgggt tcgccaagct     120
cctggtaaag gtttggagtg ggtttctgtt atcggttctt ctggtggcat gactaattat     180
gctgactccg ttaaaggtcg cttcactatc tctagagaca actctaagaa tactctctac     240
ttgcagatga acagcttaag ggctgaggac acggccgtgt attactgtgc gagaggctac     300
ccgacaggtt actatgatag tagtggctgg gtctactcct actacggtat cgacgtctgg     360
ggccaaggga ccacggtcac cgtctcaagc                                      390

<210> SEQ ID NO 25
<211> LENGTH: 107
<212> TYPE: PRT
<213> ORGANISM: Homo sapiens

<400> SEQUENCE: 25

Asp Ile Gln Met Thr Gln Ser Pro Ser Ser Leu Ser Ala Ser Ile Gly
1               5                   10                  15

Asp Arg Val Thr Ile Thr Cys Gln Ala Ser Gln Asp Thr Asp Asn Arg
            20                  25                  30

Leu His Trp Tyr Gln Gln Lys Ser Gly Arg Ala Pro Lys Leu Leu Ile
        35                  40                  45

Tyr Asp Ala Val Asn Leu Lys Arg Gly Val Pro Ser Arg Phe Arg Gly
    50                  55                  60

Ser Gly Ser Gly Thr Asn Phe Ile Leu Thr Ile Thr Asn Leu Gln Pro
65                  70                  75                  80

Glu Asp Met Ala Thr Tyr Phe Cys Gln His Ser Asp Gly Leu Ser Leu
                85                  90                  95

Ala Phe Gly Gly Gly Thr Lys Leu Glu Ile Lys
            100                 105

<210> SEQ ID NO 26
<211> LENGTH: 321
<212> TYPE: DNA
<213> ORGANISM: Homo sapiens

<400> SEQUENCE: 26
gacatccaga tgacccagtc tccatcctcc ctgtctgcat ctataggaga cagagtcacc      60
atcacttgcc aggcgagtca ggacactgac aaccgtctac attggtatca gcagaagtca     120
ggtagagccc ctaaactcct catctacgat gcagtcaatt tgaaaagggg ggtcccttca     180
aggttccgtg gaagtggatc tgggacaaat tttattttga ccatcaccaa cctgcagcct     240
gaagatatgg caacatattt ctgtcaacat tctgatggtc tgtcactcgc tttcggcgga     300
gggaccaaac tggagatcaa a                                               321

<210> SEQ ID NO 27
<211> LENGTH: 123
<212> TYPE: PRT
<213> ORGANISM: Homo sapiens

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Met Tyr
            20                  25                  30

Ser Met Gln Trp Val Arg Gln Ala Pro Gly Lys Gly Leu Glu Trp Val
        35                  40                  45

Ser Val Ile Gly Ser Ser Gly Gly Gln Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Arg Asp Tyr Tyr Gly Ser Gly Ser Tyr Tyr Leu Asp Pro
            100                 105                 110

Trp Gly Gln Gly Thr Leu Val Thr Val Ser Ser
        115                 120

<210> SEQ ID NO 28
<211> LENGTH: 369
<212> TYPE: DNA
<213> ORGANISM: Homo sapiens

<400> SEQUENCE: 28
gaagttcaat tgttagagtc tggtggcggt cttgttcagc ctggtggttc tttacgtctt      60
tcttgcgctg cttccggatt cactttctct atgtactcta tgcagtgggt tcgccaagct     120
cctggtaaag gtttggagtg gtttctgtt atcggttctt ctggtggcca gactggttat      180
gctgactccg ttaaaggtcg cttcactatc tctagagaca actctaagaa tactctctac     240
ttgcagatga acagcttaag ggctgaggac acggccgtgt attactgtgc gagagtacgc     300
gattactatg gttcggggag ttattatctc gaccctggg gccagggcac cctggtcacc     360
gtctcaagc                                                             369

<210> SEQ ID NO 29
<211> LENGTH: 107
<212> TYPE: PRT
<213> ORGANISM: Homo sapiens

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ser Trp
                85                  90                  95

Thr Phe Gly Gln Gly Thr Lys Val Glu Ile Lys
            100                 105

<210> SEQ ID NO 30

```
<211> LENGTH: 321
<212> TYPE: DNA
<213> ORGANISM: Homo sapiens

<400> SEQUENCE: 30
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cctcgtggac gttcggccaa     300
gggaccaagg tggaaatcaa a                                               321

<210> SEQ ID NO 31
<211> LENGTH: 117
<212> TYPE: PRT
<213> ORGANISM: Homo sapiens

<400> SEQUENCE: 31

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Ser Trp Val Arg Gln Ala Pro Gly Lys Gly Leu Glu Trp Val
        35                  40                  45

Ser Ser Ile Ser Ser Ser Gly Gly Pro Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Tyr Ser Gly Thr Ser Trp Gly Gln Gly Thr Leu
            100                 105                 110

Val Thr Val Ser Ser
        115

<210> SEQ ID NO 32
<211> LENGTH: 351
<212> TYPE: DNA
<213> ORGANISM: Homo sapiens

<400> SEQUENCE: 32
gaagttcaat tgttagagtc tggtggcggt cttgttcagc ctggtggttc tttacgtctt      60
tcttgcgctg cttccggatt cactttctct tggtactcta tgtcttgggt tcgccaagct     120
cctggtaaag gtttggagtg gtttcttcct atctcttctt ctggtggccc tactcattat     180
gctgactccg ttaaaggtcg cttcactatc tctagagaca actctaagaa tactctctac     240
ttgcagatga acagcttaag ggctgaggac acggccgtgt attactgtgc gagagattca     300
tcgtatagtg ggacctcatg ggggcaggga accctggtca ccgtctcaag c              351

<210> SEQ ID NO 33
<211> LENGTH: 110
<212> TYPE: PRT
<213> ORGANISM: Homo sapiens

<400> SEQUENCE: 33

Gln Tyr Glu Leu Thr Gln Pro Pro Ser Val Ser Gly Thr Pro Gly Gln
1               5                   10                  15
```

```
Arg Val Thr Ile Ser Cys Ser Gly Ser Ser Asn Ile Gly Ser Glu
            20                  25                  30

Tyr Val Tyr Trp Phe Gln Gln Leu Pro Gly Thr Ala Pro Arg Leu Leu
        35                  40                  45

Ile Tyr Arg Asn Asp Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Thr Asp Tyr Tyr Cys Thr Thr Trp Asp Ser Leu
                85                  90                  95

Ser Gly Pro Val Phe Gly Gly Gly Thr Lys Leu Thr Val Leu
            100                 105                 110
```

<210> SEQ ID NO 34
<211> LENGTH: 330
<212> TYPE: DNA
<213> ORGANISM: Homo sapiens

<400> SEQUENCE: 34

```
cagtacgaat tgactcagcc accctcagtg tctgggaccc ccgggcagag ggtcaccatc      60
tcttgttctg gaagcagttc caacatcgga agtgagtatg tgtactggtt ccagcagctc     120
ccaggaacgg cccccagact cctcatctat aggaatgatc agcggccctc aggggtccct     180
gaccgattct ctggctccaa gtctggcacc tcagcctccc tggccatcag tgggctccgg     240
tccgaggatg agactgatta ttactgtaca catgggatg acagcctgag tggtccggtg      300
ttcggcggag ggaccaagct gaccgtccta                                      330
```

<210> SEQ ID NO 35
<211> LENGTH: 120
<212> TYPE: PRT
<213> ORGANISM: Homo sapiens

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Pro Met Met Trp Val Arg Gln Ala Pro Gly Lys Gly Leu Glu Trp Val
        35                  40                  45

Ser Ser Ile Trp Pro Ser Gly Phe Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Arg Val Ser Ser Ser Ser Trp Tyr Gly Tyr Leu Tyr Trp Gly Gln
            100                 105                 110

Gly Thr Leu Val Thr Val Ser Ser
        115                 120
```

<210> SEQ ID NO 36
<211> LENGTH: 360
<212> TYPE: DNA
<213> ORGANISM: Homo sapiens

<400> SEQUENCE: 36

```
gaagttcaat tgttagagtc tggtggcggt cttgttcagc ctggtggttc tttacgtctt      60
```

-continued

```
tcttgcgctg cttccggatt cactttctct tattacccta tgatgtgggt tcgccaagct    120
cctggtaaag gtttggagtg ggtttcttct atctggcctt ctggtggctt tactaagtat    180
gctgactccg ttaaaggtcg cttcactatc tctagagaca actctaagaa tactctctac    240
ttgcagatga acagcttaag ggctgaggac acagccacgt attactgtgc gagagttagt    300
agcagcagct ggtacgggta tctctactgg ggccagggaa ccctggtcac cgtctcaagc    360
```

<210> SEQ ID NO 37
<211> LENGTH: 110
<212> TYPE: PRT
<213> ORGANISM: Homo sapiens

<400> SEQUENCE: 37

```
Gln Ser Ala Leu Thr Gln Pro Pro Ser Ala Ser Gly Thr Pro Gly Gln
1               5                   10                  15

Arg Val Thr Ile Ser Cys Ser Gly Ser Ser Asn Ile Gly Arg Asn
            20                  25                  30

Thr Val Asn Trp Tyr Gln Gln Leu Pro Gly Thr Ala Pro Lys Leu Leu
        35                  40                  45

Ile Tyr Ser Asn Asn Gln Arg Pro Ser Gly Val Pro Asp Arg Phe Ala
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Asp Ser Leu
                85                  90                  95

Asn Ala Trp Val Phe Gly Gly Gly Thr Lys Leu Thr Ala Leu
            100                 105                 110
```

<210> SEQ ID NO 38
<211> LENGTH: 330
<212> TYPE: DNA
<213> ORGANISM: Homo sapiens

<400> SEQUENCE: 38

```
cagagcgctt tgactcagcc acccctcagcg tctgggaccc ccgggcagag ggtcaccatc    60
tcttgttctg gaagcagctc caacatcgga cgtaatactg taaactggta ccagcagctc    120
ccaggaacgg cccccaaact cctcatctat agtaataatc agcggccctc aggggtccct    180
gaccgattcg ctggctccaa gtctggcacc tcagcctccc tggccatcag tgggctccag    240
tctgaggatg aggctgatta ttactgtgca gcatgggatg acagcctgaa tgcttgggtg    300
ttcggcggag ggaccaagct gaccgcccta                                      330
```

<210> SEQ ID NO 39
<211> LENGTH: 119
<212> TYPE: PRT
<213> ORGANISM: Homo sapiens

<400> SEQUENCE: 39

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Ser Met Trp Trp Val Arg Gln Ala Pro Gly Lys Gly Leu Glu Trp Val
        35                  40                  45

Ser Ser Ile Val Ser Ser Gly Gly Gln Thr Arg Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Val Lys Gly Tyr Tyr Tyr Tyr Ile Asp Val Trp Gly Lys Gly
        100                 105                 110

Thr Thr Val Thr Val Ser Ser
        115

<210> SEQ ID NO 40
<211> LENGTH: 357
<212> TYPE: DNA
<213> ORGANISM: Homo sapiens

<400> SEQUENCE: 40
gaagttcaat tgttagagtc tggtggcggt ctggttcagc ctggtggttc tttacgtctt     60
tcttgcgctg cttccggatt cactttctct tggtactcta tgtggtgggt tcgccaagct    120
cctggtaaag gtttggagtg ggtttcttct atcgtttctt ctggtggcca gactcgttat    180
gctgactccg ttaaaggtcg cttcactatc tctagagaca actctaagaa tactctctac    240
ttgcagatga acagcttaag ggctgaggac acggctgtgt attactgtgc gagagttaag    300
ggttactact actacataga cgtctggggc aaagggacca cggtcaccgt ctcaagc       357

<210> SEQ ID NO 41
<211> LENGTH: 108
<212> TYPE: PRT
<213> ORGANISM: Homo sapiens

<400> SEQUENCE: 41

Asp Ile Gln Met Thr Gln Ser Pro Gly Thr Leu Ser Leu Ser Pro Gly
1               5                   10                  15

Glu Arg Ala Thr Leu Ser Cys Arg Ala Ser Gln Ser Val Asp Ser Ser
            20                  25                  30

Tyr Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Val Ser Arg Leu Glu
65                  70                  75                  80

Pro Glu Asp Phe Ala Val Tyr Tyr Cys Gln Gln His Gly Tyr Ser Ser
            85                  90                  95

Arg Thr Phe Gly Gln Gly Thr Lys Val Glu Ile Lys
        100                 105

<210> SEQ ID NO 42
<211> LENGTH: 324
<212> TYPE: DNA
<213> ORGANISM: Homo sapiens

<400> SEQUENCE: 42
gacatccaga tgacccagtc tccaggcacc ctgtctttgt ctccagggga gagagccacc     60
ctctcctgca gggccagtca gagtgttgac agcagctact tatcctggta ccagcagaaa    120
cctggccagg ctcccaggct cctcatctat ggtgcatcca ccagggccac tggcatccca    180
gccaggttca gtggcagtgg gtctgggaca gacttcactc tcaccgtcag cagactggag    240
cctgaagatt ttgctgtgta ttattgtcag cagcatggtt actcatccag gacgttcggc    300
caagggacca aggtggaaat caaa                                            324

<210> SEQ ID NO 43
<211> LENGTH: 123
<212> TYPE: PRT
<213> ORGANISM: Homo sapiens

<400> SEQUENCE: 43

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Arg Met Asn Trp Val Arg Gln Ala Pro Gly Lys Gly Leu Glu Trp Val
        35                  40                  45

Ser Ser Ile Tyr Ser Ser Gly Gly Pro Thr Asn Tyr Ala Asp Ser Val
    50                  55                  60

Lys Gly Arg Phe Thr Ile Ser Arg Asp Asn Ser Gln Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Glu Lys Pro Asp Tyr Tyr Asp Ser Ser Gly Tyr Leu Asp Tyr
            100                 105                 110

Trp Gly Gln Gly Thr Leu Val Thr Val Ser Ser
        115                 120

<210> SEQ ID NO 44
<211> LENGTH: 369
<212> TYPE: DNA
<213> ORGANISM: Homo sapiens

<400> SEQUENCE: 44
gaagttcaat tgttagagtc tggtggcggt cttgttcagc ctggtggttc tttacgtctt     60
tcttgcgctg cttccggatt cactttctct tggtaccgta tgaattgggt tcgccaagct    120
cctggtaaag gtttggagtg ggtttcttct atctattctt ctggtggccc tactaattat    180
gctgactccg ttaaaggtcg cttcactatc tctagagaca actctcagaa tactctctac    240
ttgcagatga acagcttaag ggctgaggac acagccgtgt attactgtac gagagagaaa    300
ccagattact atgatagtag tggttatctt gactactggg gccagggcac cctggtcacc    360
gtctcaagc                                                            369

<210> SEQ ID NO 45
<211> LENGTH: 107
<212> TYPE: PRT
<213> ORGANISM: Homo sapiens

<400> SEQUENCE: 45

Asp Ile Gln Met Thr Gln Ser Pro Gly Thr Leu Ser Leu Ser Pro Gly
1               5                   10                  15

Glu Arg Ser Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Gly Val Tyr Tyr Cys His Gln Tyr Gly Arg Pro Pro
                85                  90                  95

```
Val Phe Gly Pro Gly Thr Lys Val Asp Ile Lys
            100                 105

<210> SEQ ID NO 46
<211> LENGTH: 321
<212> TYPE: DNA
<213> ORGANISM: Homo sapiens

<400> SEQUENCE: 46
gacatccaga tgacccagtc tccaggcacc ctgtctttgt ctccagggga aagatccacc      60
ctctcctgca gggccagtca gagtgttagc agcagctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttggagtgta ttactgtcac cagtatggta ggccaccggt tttcggcccc    300
gggaccaaag tggacatcaa a                                              321

<210> SEQ ID NO 47
<211> LENGTH: 5
<212> TYPE: PRT
<213> ORGANISM: Homo sapiens

<400> SEQUENCE: 47

Ser Tyr Gly Met Val
1               5

<210> SEQ ID NO 48
<211> LENGTH: 17
<212> TYPE: PRT
<213> ORGANISM: Homo sapiens

<400> SEQUENCE: 48

Ser Ile Ser Ser Ser Gly Gly Leu Thr Trp Tyr Ala Asp Ser Val Lys
1               5                   10                  15

Gly

<210> SEQ ID NO 49
<211> LENGTH: 10
<212> TYPE: PRT
<213> ORGANISM: Homo sapiens

<400> SEQUENCE: 49

Pro Pro Gly Ile Ala Val Ala Arg Asp Tyr
1               5                   10

<210> SEQ ID NO 50
<211> LENGTH: 5
<212> TYPE: PRT
<213> ORGANISM: Homo sapiens

<400> SEQUENCE: 50

Arg Tyr Asn Met Trp
1               5

<210> SEQ ID NO 51
<211> LENGTH: 17
<212> TYPE: PRT
<213> ORGANISM: Homo sapiens

<400> SEQUENCE: 51

Val Ile Arg Ser Ser Gly Gly Tyr Thr Gly Tyr Ala Asp Ser Val Lys
1               5                   10                  15
```

Gly

<210> SEQ ID NO 52
<211> LENGTH: 16
<212> TYPE: PRT
<213> ORGANISM: Homo sapiens

<400> SEQUENCE: 52

Trp Asn Ser Gly Tyr Ser Tyr Trp Asp Tyr Tyr Gly Met Asp Val
1               5                   10                  15

<210> SEQ ID NO 53
<211> LENGTH: 5
<212> TYPE: PRT
<213> ORGANISM: Homo sapiens

<400> SEQUENCE: 53

Pro Tyr Met Met Val
1               5

<210> SEQ ID NO 54
<211> LENGTH: 17
<212> TYPE: PRT
<213> ORGANISM: Homo sapiens

<400> SEQUENCE: 54

Trp Ile Ser Pro Ser Gly Gly Tyr Thr Phe Tyr Ala Asp Ser Val Lys
1               5                   10                  15

Gly

<210> SEQ ID NO 55
<211> LENGTH: 7
<212> TYPE: PRT
<213> ORGANISM: Homo sapiens

<400> SEQUENCE: 55

Gly Thr Tyr Pro Leu Thr Tyr
1               5

<210> SEQ ID NO 56
<211> LENGTH: 5
<212> TYPE: PRT
<213> ORGANISM: Homo sapiens

<400> SEQUENCE: 56

Asn Tyr Tyr Met Met
1               5

<210> SEQ ID NO 57
<211> LENGTH: 17
<212> TYPE: PRT
<213> ORGANISM: Homo sapiens

<400> SEQUENCE: 57

Val Ile Gly Ser Ser Gly Gly Met Thr Asn Tyr Ala Asp Ser Val Lys
1               5                   10                  15

Gly

<210> SEQ ID NO 58
<211> LENGTH: 21
<212> TYPE: PRT
<213> ORGANISM: Homo sapiens

<400> SEQUENCE: 58

```
Gly Tyr Pro Thr Gly Tyr Tyr Asp Ser Ser Gly Trp Val Tyr Ser Tyr
1               5                   10                  15

Tyr Gly Ile Asp Val
            20

<210> SEQ ID NO 59
<211> LENGTH: 5
<212> TYPE: PRT
<213> ORGANISM: Homo sapiens

<400> SEQUENCE: 59

Met Tyr Ser Met Gln
1               5

<210> SEQ ID NO 60
<211> LENGTH: 17
<212> TYPE: PRT
<213> ORGANISM: Homo sapiens

<400> SEQUENCE: 60

Val Ile Gly Ser Ser Gly Gly Gln Thr Gly Tyr Ala Asp Ser Val Lys
1               5                   10                  15

Gly

<210> SEQ ID NO 61
<211> LENGTH: 14
<212> TYPE: PRT
<213> ORGANISM: Homo sapiens

<400> SEQUENCE: 61

Val Arg Asp Tyr Tyr Gly Ser Gly Ser Tyr Tyr Leu Asp Pro
1               5                   10

<210> SEQ ID NO 62
<211> LENGTH: 5
<212> TYPE: PRT
<213> ORGANISM: Homo sapiens

<400> SEQUENCE: 62

Trp Tyr Ser Met Ser
1               5

<210> SEQ ID NO 63
<211> LENGTH: 17
<212> TYPE: PRT
<213> ORGANISM: Homo sapiens

<400> SEQUENCE: 63

Ser Ile Ser Ser Ser Gly Gly Pro Thr His Tyr Ala Asp Ser Val Lys
1               5                   10                  15

Gly

<210> SEQ ID NO 64
<211> LENGTH: 8
<212> TYPE: PRT
<213> ORGANISM: Homo sapiens

<400> SEQUENCE: 64

Asp Ser Ser Tyr Ser Gly Thr Ser
1               5

<210> SEQ ID NO 65
<211> LENGTH: 5
```

```
<212> TYPE: PRT
<213> ORGANISM: Homo sapiens

<400> SEQUENCE: 65

Tyr Tyr Pro Met Met
1               5

<210> SEQ ID NO 66
<211> LENGTH: 17
<212> TYPE: PRT
<213> ORGANISM: Homo sapiens

<400> SEQUENCE: 66

Ser Ile Trp Pro Ser Gly Gly Phe Thr Lys Tyr Ala Asp Ser Val Lys
1               5                   10                  15
Gly

<210> SEQ ID NO 67
<211> LENGTH: 11
<212> TYPE: PRT
<213> ORGANISM: Homo sapiens

<400> SEQUENCE: 67

Val Ser Ser Ser Ser Trp Tyr Gly Tyr Leu Tyr
1               5                   10

<210> SEQ ID NO 68
<211> LENGTH: 5
<212> TYPE: PRT
<213> ORGANISM: Homo sapiens

<400> SEQUENCE: 68

Trp Tyr Ser Met Trp
1               5

<210> SEQ ID NO 69
<211> LENGTH: 17
<212> TYPE: PRT
<213> ORGANISM: Homo sapiens

<400> SEQUENCE: 69

Ser Ile Val Ser Ser Gly Gly Gln Thr Arg Tyr Ala Asp Ser Val Lys
1               5                   10                  15
Gly

<210> SEQ ID NO 70
<211> LENGTH: 10
<212> TYPE: PRT
<213> ORGANISM: Homo sapiens

<400> SEQUENCE: 70

Val Lys Gly Tyr Tyr Tyr Tyr Ile Asp Val
1               5                   10

<210> SEQ ID NO 71
<211> LENGTH: 5
<212> TYPE: PRT
<213> ORGANISM: Homo sapiens

<400> SEQUENCE: 71

Trp Tyr Arg Met Asn
1               5

<210> SEQ ID NO 72
```

```
<211> LENGTH: 17
<212> TYPE: PRT
<213> ORGANISM: Homo sapiens

<400> SEQUENCE: 72

Ser Ile Tyr Ser Ser Gly Gly Pro Thr Asn Tyr Ala Asp Ser Val Lys
1               5                   10                  15
Gly

<210> SEQ ID NO 73
<211> LENGTH: 14
<212> TYPE: PRT
<213> ORGANISM: Homo sapiens

<400> SEQUENCE: 73

Glu Lys Pro Asp Tyr Tyr Asp Ser Ser Gly Tyr Leu Asp Tyr
1               5                   10

<210> SEQ ID NO 74
<211> LENGTH: 11
<212> TYPE: PRT
<213> ORGANISM: Homo sapiens

<400> SEQUENCE: 74

Arg Ala Ser Gln Gly Ile Ser Asn Tyr Leu Ala
1               5                   10

<210> SEQ ID NO 75
<211> LENGTH: 7
<212> TYPE: PRT
<213> ORGANISM: Homo sapiens

<400> SEQUENCE: 75

Ala Ala Ser Thr Leu Gln Ser
1               5

<210> SEQ ID NO 76
<211> LENGTH: 9
<212> TYPE: PRT
<213> ORGANISM: Homo sapiens

<400> SEQUENCE: 76

Gln Lys Tyr Asn Ser Ala Leu Leu Thr
1               5

<210> SEQ ID NO 77
<211> LENGTH: 11
<212> TYPE: PRT
<213> ORGANISM: Homo sapiens

<400> SEQUENCE: 77

Arg Ala Ser Gln Ser Ile Ser Ser Tyr Leu Asn
1               5                   10

<210> SEQ ID NO 78
<211> LENGTH: 7
<212> TYPE: PRT
<213> ORGANISM: Homo sapiens

<400> SEQUENCE: 78

Ala Ala Ser Ser Leu Gln Ser
1               5

<210> SEQ ID NO 79
<211> LENGTH: 9
```

```
<212> TYPE: PRT
<213> ORGANISM: Homo sapiens

<400> SEQUENCE: 79

Gln Gln Phe Asn Thr Tyr Pro Ile Thr
1               5

<210> SEQ ID NO 80
<211> LENGTH: 11
<212> TYPE: PRT
<213> ORGANISM: Homo sapiens

<400> SEQUENCE: 80

Ser Gly Asp Lys Leu Gly Asp Lys Tyr Val Ser
1               5                   10

<210> SEQ ID NO 81
<211> LENGTH: 7
<212> TYPE: PRT
<213> ORGANISM: Homo sapiens

<400> SEQUENCE: 81

Gln Asp Ser Lys Trp Pro Ser
1               5

<210> SEQ ID NO 82
<211> LENGTH: 9
<212> TYPE: PRT
<213> ORGANISM: Homo sapiens

<400> SEQUENCE: 82

Gln Val Trp Asp Ile Ser His Val Val
1               5

<210> SEQ ID NO 83
<211> LENGTH: 11
<212> TYPE: PRT
<213> ORGANISM: Homo sapiens

<400> SEQUENCE: 83

Gln Ala Ser Gln Asp Thr Asp Asn Arg Leu His
1               5                   10

<210> SEQ ID NO 84
<211> LENGTH: 7
<212> TYPE: PRT
<213> ORGANISM: Homo sapiens

<400> SEQUENCE: 84

Asp Ala Val Asn Leu Lys Arg
1               5

<210> SEQ ID NO 85
<211> LENGTH: 9
<212> TYPE: PRT
<213> ORGANISM: Homo sapiens

<400> SEQUENCE: 85

Gln His Ser Asp Gly Leu Ser Leu Ala
1               5

<210> SEQ ID NO 86
<211> LENGTH: 11
<212> TYPE: PRT
<213> ORGANISM: Homo sapiens
```

```
<400> SEQUENCE: 86

Arg Ala Ser Gln Ser Ile Ser Ser Tyr Leu Asn
1               5                   10

<210> SEQ ID NO 87
<211> LENGTH: 7
<212> TYPE: PRT
<213> ORGANISM: Homo sapiens

<400> SEQUENCE: 87

Ala Ala Ser Ser Leu Gln Ser
1               5

<210> SEQ ID NO 88
<211> LENGTH: 9
<212> TYPE: PRT
<213> ORGANISM: Homo sapiens

<400> SEQUENCE: 88

Gln Gln Ser Tyr Ser Thr Ser Trp Thr
1               5

<210> SEQ ID NO 89
<211> LENGTH: 13
<212> TYPE: PRT
<213> ORGANISM: Homo sapiens

<400> SEQUENCE: 89

Ser Gly Ser Ser Ser Asn Ile Gly Ser Glu Tyr Val Tyr
1               5                   10

<210> SEQ ID NO 90
<211> LENGTH: 7
<212> TYPE: PRT
<213> ORGANISM: Homo sapiens

<400> SEQUENCE: 90

Arg Asn Asp Gln Arg Pro Ser
1               5

<210> SEQ ID NO 91
<211> LENGTH: 11
<212> TYPE: PRT
<213> ORGANISM: Homo sapiens

<400> SEQUENCE: 91

Thr Thr Trp Asp Asp Ser Leu Ser Gly Pro Val
1               5                   10

<210> SEQ ID NO 92
<211> LENGTH: 13
<212> TYPE: PRT
<213> ORGANISM: Homo sapiens

<400> SEQUENCE: 92

Ser Gly Ser Ser Ser Asn Ile Gly Arg Asn Thr Val Asn
1               5                   10

<210> SEQ ID NO 93
<211> LENGTH: 7
<212> TYPE: PRT
<213> ORGANISM: Homo sapiens

<400> SEQUENCE: 93

Ser Asn Asn Gln Arg Pro Ser
```

<210> SEQ ID NO 94
<211> LENGTH: 11
<212> TYPE: PRT
<213> ORGANISM: Homo sapiens

<400> SEQUENCE: 94

Ala Ala Trp Asp Asp Ser Leu Asn Ala Trp Val
1               5                   10

<210> SEQ ID NO 95
<211> LENGTH: 12
<212> TYPE: PRT
<213> ORGANISM: Homo sapiens

<400> SEQUENCE: 95

Arg Ala Ser Gln Ser Val Asp Ser Ser Tyr Leu Ser
1               5                   10

<210> SEQ ID NO 96
<211> LENGTH: 7
<212> TYPE: PRT
<213> ORGANISM: Homo sapiens

<400> SEQUENCE: 96

Gly Ala Ser Thr Arg Ala Thr
1               5

<210> SEQ ID NO 97
<211> LENGTH: 9
<212> TYPE: PRT
<213> ORGANISM: Homo sapiens

<400> SEQUENCE: 97

Gln Gln His Gly Tyr Ser Ser Arg Thr
1               5

<210> SEQ ID NO 98
<211> LENGTH: 12
<212> TYPE: PRT
<213> ORGANISM: Homo sapiens

<400> SEQUENCE: 98

Arg Ala Ser Gln Ser Val Ser Ser Ser Tyr Leu Ala
1               5                   10

<210> SEQ ID NO 99
<211> LENGTH: 7
<212> TYPE: PRT
<213> ORGANISM: Homo sapiens

<400> SEQUENCE: 99

Gly Ala Ser Ser Arg Ala Thr
1               5

<210> SEQ ID NO 100
<211> LENGTH: 8
<212> TYPE: PRT
<213> ORGANISM: Homo sapiens

<400> SEQUENCE: 100

His Gln Tyr Gly Arg Pro Pro Val
1               5

-continued

```
<210> SEQ ID NO 101
<211> LENGTH: 396
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Glu Ser Gly Gly Gly Leu Ala Lys Pro Gly Gly
1               5                   10                  15

Ser Leu Arg Leu Ser Cys Ala Ala Ser Gly Phe Arg Phe Thr Phe Asn
            20                  25                  30

Asn Tyr Tyr Met Asp Trp Val Arg Gln Ala Pro Gly Gln Gly Leu Glu
        35                  40                  45

Trp Val Ser Arg Ile Ser Ser Gly Asp Pro Thr Trp Tyr Ala Asp
    50                  55                  60

Ser Val Lys Gly Arg Phe Thr Ile Ser Arg Glu Asn Ala Lys Asn Thr
65                  70                  75                  80

Leu Phe Leu Gln Met Asn Ser Leu Arg Ala Glu Asp Thr Ala Val Tyr
                85                  90                  95

Tyr Cys Ala Ser Leu Thr Thr Gly Ser Asp Ser Trp Gly Gln Gly Val
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Gly Gly Gly
    210                 215                 220

Gly Ser Gly Gly Gly Gly Ser Gly Gly Gly Gly Ser Asn Pro Ala Ala
225                 230                 235                 240

His Leu Thr Gly Ala Asn Ser Ser Leu Thr Gly Ser Gly Gly Pro Leu
                245                 250                 255

Leu Trp Glu Thr Gln Leu Gly Leu Ala Phe Leu Arg Gly Leu Ser Tyr
            260                 265                 270

His Asp Gly Ala Leu Val Val Thr Lys Ala Gly Tyr Tyr Tyr Ile Tyr
        275                 280                 285

Ser Lys Val Gln Leu Gly Gly Val Gly Cys Pro Leu Gly Leu Ala Ser
    290                 295                 300

Thr Ile Thr His Gly Leu Tyr Lys Arg Thr Pro Arg Tyr Pro Glu Glu
305                 310                 315                 320

Leu Glu Leu Leu Val Ser Gln Gln Ser Pro Cys Gly Arg Ala Thr Ser
                325                 330                 335

Ser Ser Arg Val Trp Trp Asp Ser Ser Phe Leu Gly Gly Val Val His
            340                 345                 350

Leu Glu Ala Gly Glu Glu Val Val Val Arg Val Leu Asp Glu Arg Leu
        355                 360                 365

Val Arg Leu Arg Asp Gly Thr Arg Ser Tyr Phe Gly Ala Phe Met Val
```

```
              370                 375                 380
Gly Gly His His His His His His His His
385                 390                 395

<210> SEQ ID NO 102
<211> LENGTH: 1191
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
gaggtgcagc tggtggagtc tgggggcggc ttggcaaagc tggggggtc cctgagactc      60 tcctgcgcag cctccgggtt caggttcacc ttcaataact actacatgga ctgggtccgc    120
caggctccag ggcaggggct ggagtgggtc tcacgtatta gtagtagtgg tgatcccaca    180
tggtacgcag actccgtgaa gggcagattc accatctcca gagagaacgc caagaacaca    240
ctgtttcttc aaatgaacag cctgagagct gaggacacgg ctgtctatta ctgtgcgagc    300
ttgactacag ggtctgactc ctggggccag ggagtcctgg tcaccgtctc ctcagctagc    360
accaagggcc catcggtctt ccccctggca ccctcctcca gagcacctc tgggggcaca    420 gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcacccca gacctacatc    600
tgcaacgtga atcacaagcc cagcaacacc aaggtggaca agaaagttga gcccaaatct    660
tgtggcggtg gtgggtccgg cggtggtggg tccggcggtg gtgggtccaa cccagcagcg    720
catctcacag gggccaactc cagcttgacc ggcagcgggg ggccgctgtt atgggagact    780
cagctgggcc tggccttcct gaggggcctc agctaccacg atgggccct tgtggtcacc    840 aaagctggct actactacat ctactccaag gtgcagctgg gcggtgtggg ctgcccgctg    900
ggcctggcca gcaccatcac ccacggcctc tacaagcgca caccccgcta ccccgaggag    960
ctggagctgt tggtcagcca gcagtcaccc tgcgacgggc caccagcag ctcccgggtc   1020 tggtgggaca gcagcttcct gggtggtgtg gtacacctgg aggctgggga ggaggtggtc   1080
gtccgtgtgc tggatgaacg cctggttcga ctgcgtgatg gtacccggtc ttacttcggg   1140
gctttcatgg tgggaggaca tcatcatcat caccaccatc accatcactg a           1191

<210> SEQ ID NO 103
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Tyr Tyr
            20                  25                  30

Leu Asn Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Gly Thr Glu Phe Thr Leu Thr Val Ser Ser Leu Gln Pro
```

```
               65                  70                  75                  80
Glu Asp Phe Ala Thr Tyr Tyr Cys Leu Gln Val Tyr Ser Thr Asp Asn
                        85                  90                  95
Ala Phe Gly Gln Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
                130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
                195                 200                 205
Phe Asn Arg Gly Glu Cys
    210

<210> SEQ ID NO 104
<211> LENGTH: 645
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gly Ala Cys Ala Thr Cys Cys Ala Gly Ala Thr Gly Ala Cys Cys Cys
1               5                   10                  15
Ala Gly Thr Cys Thr Cys Cys Ala Thr Cys Thr Thr Cys Cys Cys Thr
                20                  25                  30
Gly Thr Cys Thr Gly Cys Ala Thr Cys Thr Gly Thr Ala Gly Gly Gly
                35                  40                  45
Gly Ala Cys Ala Gly Ala Gly Thr Cys Ala Cys Cys Ala Thr Cys Ala
    50                  55                  60
Cys Thr Thr Gly Cys Ala Gly Gly Gly Cys Ala Ala Gly Thr Cys Ala
65                  70                  75                  80
Gly Gly Ala Cys Ala Thr Thr Ala Gly Gly Thr Ala Thr Thr Ala Thr
                85                  90                  95
Thr Thr Ala Ala Ala Thr Thr Gly Gly Thr Ala Thr Cys Ala Gly Cys
                100                 105                 110
Ala Gly Ala Ala Ala Cys Cys Ala Gly Gly Ala Ala Ala Ala Gly Cys
                115                 120                 125
Thr Cys Cys Thr Ala Ala Gly Cys Thr Cys Cys Thr Gly Ala Thr Cys
                130                 135                 140
Thr Ala Thr Gly Thr Thr Gly Cys Ala Thr Cys Cys Ala Gly Thr Thr
145                 150                 155                 160
Thr Gly Cys Ala Ala Ala Gly Thr Gly Gly Gly Gly Thr Cys Cys Cys
                165                 170                 175
Ala Thr Cys Ala Ala Gly Gly Thr Thr Cys Ala Gly Cys Gly Gly Cys
                180                 185                 190
Ala Gly Thr Gly Gly Ala Thr Cys Thr Gly Gly Gly Ala Cys Ala Gly
                195                 200                 205
Ala Gly Thr Thr Cys Ala Cys Thr Cys Thr Cys Ala Cys Cys Gly Thr
```

-continued

```
                210                 215                 220
Cys Ala Gly Cys Ala Gly Cys Cys Thr Gly Cys Ala Gly Cys Cys Thr
225                 230                 235                 240
Gly Ala Ala Gly Ala Thr Thr Thr Gly Cys Gly Ala Cys Thr Thr
                245                 250                 255
Ala Thr Thr Ala Cys Thr Gly Thr Cys Thr Ala Cys Ala Gly Gly Thr
                260                 265                 270
Thr Thr Ala Thr Ala Gly Thr Ala Cys Cys Cys Thr Cys Gly Gly
            275                 280                 285
Ala Cys Gly Thr Thr Cys Gly Gly Cys Ala Ala Gly Gly Gly Ala
        290                 295                 300
Cys Cys Ala Ala Gly Gly Thr Gly Gly Ala Ala Thr Cys Ala Ala
305                 310                 315                 320
Ala Cys Gly Thr Ala Cys Gly Gly Thr Gly Gly Cys Thr Gly Cys Ala
                325                 330                 335
Cys Cys Ala Thr Cys Thr Gly Thr Cys Thr Thr Cys Ala Thr Cys Thr
                340                 345                 350
Thr Cys Cys Cys Gly Cys Cys Ala Thr Cys Thr Gly Ala Thr Gly Ala
        355                 360                 365
Gly Cys Ala Gly Thr Thr Gly Ala Ala Ala Thr Cys Thr Gly Gly Ala
    370                 375                 380
Ala Cys Thr Gly Cys Cys Thr Cys Thr Gly Thr Thr Gly Thr Gly Thr
385                 390                 395                 400
Gly Cys Cys Thr Gly Cys Thr Gly Ala Ala Thr Ala Ala Cys Thr Thr
                405                 410                 415
Cys Thr Ala Thr Cys Cys Cys Ala Gly Ala Gly Ala Gly Cys Cys
            420                 425                 430
Ala Ala Ala Gly Thr Ala Cys Ala Gly Thr Gly Gly Ala Ala Gly Gly
        435                 440                 445
Thr Gly Gly Ala Thr Ala Ala Cys Gly Cys Cys Thr Cys Cys Ala
450                 455                 460
Ala Thr Cys Gly Gly Gly Thr Ala Ala Cys Thr Cys Cys Cys Ala Gly Gly
465                 470                 475                 480
Gly Ala Gly Ala Gly Thr Gly Thr Cys Ala Cys Ala Gly Ala Gly Cys
                485                 490                 495
Ala Gly Gly Ala Cys Ala Gly Cys Ala Ala Gly Gly Ala Cys Ala Gly
            500                 505                 510
Cys Ala Cys Cys Thr Ala Cys Ala Gly Cys Cys Thr Cys Ala Gly Cys
        515                 520                 525
Ala Gly Cys Ala Cys Cys Cys Thr Gly Ala Cys Gly Cys Thr Gly Ala
530                 535                 540
Gly Cys Ala Ala Ala Gly Cys Ala Gly Ala Cys Thr Ala Cys Gly Ala
545                 550                 555                 560
Gly Ala Ala Ala Cys Ala Cys Ala Ala Gly Thr Cys Thr Ala Cys Ala
                565                 570                 575
Gly Cys Cys Thr Gly Cys Gly Ala Ala Gly Thr Cys Ala Cys Cys Cys
            580                 585                 590
Ala Thr Cys Ala Gly Gly Gly Cys Cys Thr Gly Ala Gly Cys Thr Cys
        595                 600                 605
Gly Cys Cys Cys Gly Thr Cys Ala Cys Ala Ala Ala Gly Ala Gly Cys
    610                 615                 620
Thr Thr Cys Ala Ala Cys Ala Gly Gly Gly Ala Gly Ala Gly Thr
625                 630                 635                 640
```

Gly Thr Thr Gly Ala
            645

<210> SEQ ID NO 105
<211> LENGTH: 653
<212> TYPE: PRT
<213> ORGANISM: Homo sapiens

<400> SEQUENCE: 105

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
            20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
    50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
    130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Arg Leu His Cys Pro Ala Leu Val
            260                 265                 270

Thr Tyr Asn Thr Asp Thr Phe Glu Ser Met Pro Asn Pro Glu Gly Arg
        275                 280                 285

Tyr Thr Phe Gly Ala Ser Cys Val Thr Ala Cys Pro Tyr Asn Tyr Leu
    290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
        355                 360                 365

```
Lys Ile Phe Gly Ser Leu Ala Phe Leu Pro Glu Ser Phe Asp Gly Asp
        370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
        450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
        530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
        610                 615                 620

Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser
                645                 650

<210> SEQ ID NO 106
<211> LENGTH: 653
<212> TYPE: PRT
<213> ORGANISM: Macaca mulatta

<400> SEQUENCE: 106

Met Glu Leu Ala Ala Trp Tyr Arg Trp Gly Leu Leu Ala Leu Leu
1               5                   10                  15

Pro Pro Gly Ala Ala Gly Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95
```

-continued

```
Gln Arg Leu Arg Ile Val Arg Gly Thr Gln Leu Phe Glu Asp Asn Tyr
            100                 105                 110

Ala Leu Ala Val Leu Asp Asn Gly Asp Leu Leu Asn Thr Thr Pro
            115                 120                 125

Val Thr Gly Ala Ser Pro Gly Gly Leu Arg Glu Leu Gln Leu Arg Ser
            130                 135                 140

Leu Thr Glu Ile Leu Lys Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Val Cys Lys Gly Ser Arg Cys Trp Gly Glu Ser
            195                 200                 205

Ser Glu Asp Cys Gln Ser Leu Thr Arg Thr Val Cys Ala Gly Gly Cys
            210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
370                 375                 380

Pro Ala Ser Asn Thr Ala Pro Leu Gln Pro Glu Gln Leu Arg Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Leu Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr Arg Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525
```

Val Asn Cys Ser Gln Phe Leu Arg Gly Gln Glu Cys Val Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Thr Cys Gln
610                 615                 620

Ser Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser
            645                 650

<210> SEQ ID NO 107
<211> LENGTH: 116
<212> TYPE: PRT
<213> ORGANISM: Homo sapiens

<400> SEQUENCE: 107

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Asp Thr Ala Met Gly Val Trp Gly Gln Gly Thr Leu Val
            100                 105                 110

Thr Val Ser Ser
        115

<210> SEQ ID NO 108
<211> LENGTH: 348
<212> TYPE: DNA
<213> ORGANISM: Homo sapiens

<400> SEQUENCE: 108
gaggtgcagc tgttggagtc cggggggaggc ttggtacagc ctgggggggtc cctgagactc      60 tcctgtgcag cctctggatt caccttttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac acggccgtat attactgtgc gaaacgggat     300
acagctatgg gggtctgggg ccagggaacc ctggtcactg tctcctca                   348

<210> SEQ ID NO 109
<211> LENGTH: 214

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Leu Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 110
<211> LENGTH: 645
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110
gacatccaga tgacccagtc tccatcctcc ctgtctgcat ctgtaggaga cagagtcacc      60
atcacttgcc gggcgagtca gggcattagc aattatttag cctggtatca gcagaaacca     120
gggaaagttc ctaagctcct gatctatgct gcatccactt tgcaatcagg ggtcccatct     180
cggttcagtg gcagtggatc tgggacagat tcactctcac catcagcag cctgcagcct     240 gaagatgttg caacttatta ctgtcaaaag tataacagtg ccctcctcac tttcggcgga     300
ggtaccaagg tggagatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttga    645

<210> SEQ ID NO 111
<211> LENGTH: 204
<212> TYPE: PRT
<213> ORGANISM: Homo sapiens

<400> SEQUENCE: 111

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Asp Gly Pro Ala Gly Ser Trp Glu Gln Leu Ile
        35                  40                  45

Gln Glu Arg Arg Ser His Glu Val Asn Pro Ala Ala His Leu Thr Gly
    50                  55                  60

Ala Asn Ser Ser Leu Thr Gly Ser Gly Gly Pro Leu Leu Trp Glu Thr
65                  70                  75                  80

Gln Leu Gly Leu Ala Phe Leu Arg Gly Leu Ser Tyr His Asp Gly Ala
                85                  90                  95

Leu Val Val Thr Lys Ala Gly Tyr Tyr Tyr Ile Tyr Ser Lys Val Gln
            100                 105                 110

Leu Gly Gly Val Gly Cys Pro Leu Gly Leu Ala Ser Thr Ile Thr His
        115                 120                 125

Gly Leu Tyr Lys Arg Thr Pro Arg Tyr Pro Glu Glu Leu Glu Leu Leu
    130                 135                 140

Val Ser Gln Gln Ser Pro Cys Gly Arg Ala Thr Ser Ser Ser Arg Val
145                 150                 155                 160

Trp Trp Asp Ser Ser Phe Leu Gly Gly Val Val His Leu Glu Ala Gly
                165                 170                 175

Glu Glu Val Val Val Arg Val Leu Asp Glu Arg Leu Val Arg Leu Arg
            180                 185                 190

Asp Gly Thr Arg Ser Tyr Phe Gly Ala Phe Met Val
        195                 200

<210> SEQ ID NO 112
<211> LENGTH: 615
<212> TYPE: DNA
<213> ORGANISM: Homo sapiens

<400> SEQUENCE: 112
atggaggaga gtgtcgtacg gccctcagtg tttgtggtgg atggacagac cgacatccca    60
ttcacgaggc tggacgaag ccaccggaga cagtcgtgca gtgtggcccg ggacggacct    120
gcaggctcct gggagcagct gatacaagag cgaaggtctc acgaggtcaa cccagcagcg    180
catctcacag gggccaactc cagcttgacc ggcagcgggg ggccgctgtt atgggagact    240
cagctgggcc tggccttcct gagggggctc agctaccacg atggggccct tgtggtcacc    300
aaagctggct actactacat ctactccaag gtgcagctgg gcggtgtggg ctgcccgctg    360
ggcctggcca gcaccatcac ccacggcctc tacaagcgca cccccgctga ccccgaggag    420
ctggagctgt tggtcagcca gcagtcaccc tgcggacggg ccaccagcag ctcccgggtc    480
tggtgggaca gcagcttcct gggtggtgtg gtacacctgg aggctgggga ggaggtggtc    540
gtccgtgtgc tggatgaacg cctggttcga ctgcgtgatg gtacccggtc ttacttcggg    600
gctttcatgg tgtga    615

-continued

<210> SEQ ID NO 113
<211> LENGTH: 239
<212> TYPE: PRT
<213> ORGANISM: Mus sp.

<400> SEQUENCE: 113

Met Glu Ser Val Val Gln Pro Ser Val Phe Val Val Asp Gly Gln Thr
1               5                   10                  15

Asp Ile Pro Phe Arg Arg Leu Glu Gln Asn His Arg Arg Arg Cys
            20                  25                  30

Gly Thr Val Gln Val Ser Leu Ala Leu Val Leu Leu Leu Gly Ala Gly
        35                  40                  45

Leu Ala Thr Gln Gly Trp Phe Leu Leu Arg Leu His Gln Arg Leu Gly
    50                  55                  60

Asp Ile Val Ala His Leu Pro Asp Gly Gly Lys Gly Ser Trp Glu Lys
65                  70                  75                  80

Leu Ile Gln Asp Gln Arg Ser His Gln Ala Asn Pro Ala Ala His Leu
                85                  90                  95

Thr Gly Ala Asn Ala Ser Leu Ile Gly Ile Gly Gly Pro Leu Leu Trp
            100                 105                 110

Glu Thr Arg Leu Gly Leu Ala Phe Leu Arg Gly Leu Thr Tyr His Asp
        115                 120                 125

Gly Ala Leu Val Thr Met Glu Pro Gly Tyr Tyr Val Tyr Ser Lys
    130                 135                 140

Val Gln Leu Ser Gly Val Gly Cys Pro Gln Gly Leu Ala Asn Gly Leu
145                 150                 155                 160

Pro Ile Thr His Gly Leu Tyr Lys Arg Thr Ser Arg Tyr Pro Lys Glu
                165                 170                 175

Leu Glu Leu Leu Val Ser Arg Arg Ser Pro Cys Gly Arg Ala Asn Ser
            180                 185                 190

Ser Arg Val Trp Trp Asp Ser Ser Phe Leu Gly Gly Val Val His Leu
        195                 200                 205

Glu Ala Gly Glu Glu Val Val Val Arg Val Pro Gly Asn Arg Leu Val
    210                 215                 220

Arg Pro Arg Asp Gly Thr Arg Ser Tyr Phe Gly Ala Phe Met Val
225                 230                 235

<210> SEQ ID NO 114
<211> LENGTH: 720
<212> TYPE: DNA
<213> ORGANISM: Mus sp.

<400> SEQUENCE: 114
atggagagtg tggtacagcc ttcagtgttt gtggtggatg gacagacgga catcccattc        60
aggcggctgg aacagaacca ccggagacgg cgctgtggca ctgtccaggt cagcctggcc       120
ctggtgctgc tgctaggtgc tgggctggcc actcagggct ggtttctcct gagactgcat       180
caacgtcttg gagacatagt agctcatctg ccagatggag caaaggctc ctgggagaag        240 ctgatacaag atcaacgatc tcaccaggcc aacccagcag cacatcttac aggagccaac       300
gccagcttga taggtattgg tggacctctg ttatgggaga cacgacttgg cctggccttc       360
ttgaggggct tgacgtatca tgatgggcc ctggtgacca tggagcccgg ttactactat        420
gtgtactcca aagtgcagct gagcggcgtg ggctgccccc aggggctggc caatggcctc      480
cccatcaccc atggactata caagcgcaca tcccgctacc cgaaggagtt agaactgctg       540
gtcagtcggc ggtcacccctg tggccgggcc aacagctccc gagtctggtg ggacagcagc      600

```
ttcctgggcg gcgtggtaca tctggaggct ggggaagagg tggtggtccg cgtgcctgga        660
aaccgcctgg tcagaccacg tgacggcacc aggtcctatt tcggagcttt catggtctga        720
```

<210> SEQ ID NO 115
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115

```
gatccccggg taccggtcgg cgcgcctcga gatatcttaa ttaag                         45
```

<210> SEQ ID NO 116
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116

```
aattcttaat taagatatct cgaggcgcgc cgaccggtac ccggg                         45
```

<210> SEQ ID NO 117
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117

```
gagccatggg gccggagccg cagtgagcac catg                                     34
```

<210> SEQ ID NO 118
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118

```
ccagatccaa gcaccttcac cttcctcagc tccg                                     34
```

<210> SEQ ID NO 119
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119

```
gcccaaccag gcgcagatgc ggatcctgaa agag                                     34
```

<210> SEQ ID NO 120
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120

```
tcggggcttc tgcggacttg gccttctggt tcac                            34

<210> SEQ ID NO 121
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
ggatccgcgg ccgcaccatg agggtccccg ctcagctcct ggggctcctt ctgctctgg    59

<210> SEQ ID NO 122
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122
cctggggctc cttctgctct ggctccctgg agccagatgt gacatccaga tgacccagtc    60

<210> SEQ ID NO 123
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
agccaccgta cgtttgatct ccaccttggt acc                              33

<210> SEQ ID NO 124
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124
gaggtgcagc tgttggagtc tgggggaggc ttggtccagc ctggggggtc cctgagactc    60
tcctgtgcag cctctggatt caccttcag                                   89

<210> SEQ ID NO 125
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125
tgagacccac tccagcccct tccctggagc ctggcggacc                       40

<210> SEQ ID NO 126
<211> LENGTH: 93
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 126
```

```
tacgcagact ccgtgaaggg ccgattcacc atctccagag acaattccaa gaacacgctg    60
tatctgcaaa tgaacagcct gagagccgag gac                                 93

<210> SEQ ID NO 127
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
tctggattca ccttcagtag ctatggcatg gtctgggtcc gccaggctcc               50

<210> SEQ ID NO 128
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
gggctggagt gggtctcatc cattagttct tctggtggcc tgacatggta cgcagactcc    60
gtgaag                                                               66

<210> SEQ ID NO 129
<211> LENGTH: 102
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 129
tgaggagacg gtgaccaggg ttccctggcc ccagtagtcc cgagcaacgg caataccggg    60
ggggctcgca cagtaataca cggccgtgtc ctcggctctc ag                      102

<210> SEQ ID NO 130
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 130
gttgctacgc gtgtcctgtc cgaggtgcag ctgttggag                           39

<210> SEQ ID NO 131
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
cttggtgcta gctgaggaga cggtgac                                        27

<210> SEQ ID NO 132
<211> LENGTH: 28
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 132

Leu His Trp Arg Leu Gly Glu Met Val Thr Arg Leu Pro Asp Gly Pro
1               5                   10                  15

Ala Gly Ser Trp Gln Glu Arg Arg Ser His Glu Val
            20                  25

<210> SEQ ID NO 133
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Gly Gly Gly Ser Leu His Trp Arg Leu Gly Glu Met Val Thr Arg
1               5                   10                  15

Leu Pro Asp Gly Pro Ala Gly Ser Trp Gln Glu Arg Arg Ser His Glu
            20                  25                  30

Val

<210> SEQ ID NO 134
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Gly Gly Gly Ser Gly Gly Gly Ser Gly Gly Gly Ser Gly
1               5                   10                  15

Gly Gly Gly Ser
            20

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
cttccccgaa ccggtgacgg tg                                            22

<210> SEQ ID NO 136
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 136
gggcagggat cctcacacca tgaaagcccc gaagtaag                           38

<210> SEQ ID NO 137
<211> LENGTH: 71
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 137
gcctgcctga cggacctgca ggctcctggc aagagcgaag gtctcacgag gtcaacccag        60
cagcgcatct c                                                            71

<210> SEQ ID NO 138
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 138
caggtccgtc aggcaggcgg gtgaccatct ctcctagacg ccagtgcagt ttgtcacaag        60
atttgg                                                                  66

<210> SEQ ID NO 139
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
tgcaggtccg tcaggcaggc gggtgaccat ctctcctaga cgccagtgca gggaccctcc        60
accgcctttg tcacaagatt tgg                                               83

<210> SEQ ID NO 140
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 140
ggcggatctg ggggcggcgg gtccggtggt ggtggtagta acccagcagc gcatctc          57

<210> SEQ ID NO 141
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141
ccgccgcccc cagatccgcc cccaccggac cctccaccgc ctttgtcaca agatttgg         58

<210> SEQ ID NO 142
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 142
tggtgggtcc ggcggtggtg ggtccaaccc agcagcgcat ctcac                       45

<210> SEQ ID NO 143
<211> LENGTH: 78

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
agagagggat ccgcggccgc tcagtgatgg tgatggtggt gatgatgatg atgtcctccc    60
accatgaaag ccccgaag                                                  78

<210> SEQ ID NO 144

<400> SEQUENCE: 144

000

<210> SEQ ID NO 145
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: This sequence may encompass one to five
      "Gly Gly Gly Gly Ser" repeating units

<400> SEQUENCE: 145

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Gly Gly Gly Ser
1               5

<210> SEQ ID NO 147
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Gly Gly Gly Ser
1               5

<210> SEQ ID NO 148
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Gly Gly Gly Ser Gly Gly Gly Gly Ser Gly Gly Gly Gly Ser
1               5                   10                  15
```

<210> SEQ ID NO 149
<211> LENGTH: 40
<212> TYPE: PRT
<213> ORGANISM: Artificial Sequence
<220> FEATURE:
<223> OTHER INFORMATION: Description of Artificial Sequence: Synthetic
 polypeptide
<220> FEATURE:
<223> OTHER INFORMATION: This sequence may encompass one to eight
 "Gly Gly Gly Gly Ser" repeating units

<400> SEQUENCE: 149

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
 6x His tag

<400> SEQUENCE: 150

His His His His His His
1               5

<210> SEQ ID NO 151
<211> LENGTH: 10
<212> TYPE: PRT
<213> ORGANISM: Artificial Sequence
<220> FEATURE:
<223> OTHER INFORMATION: Description of Artificial Sequence: Synthetic
 peptide

<400> SEQUENCE: 151

Gly Gly Gly Gly Ser Gly Gly Gly Gly Ser
1               5                   10

<210> SEQ ID NO 152

<400> SEQUENCE: 152

000

<210> SEQ ID NO 153
<211> LENGTH: 1350
<212> TYPE: DNA
<213> ORGANISM: Homo sapiens

<400> SEQUENCE: 153
gaggtgcagc tgttggagtc tgggggaggc ttggtccagc ctggggggtc cctgagactc      60
tcctgtgcag cctctggatt caccttcagt agctatggca tgtctgggt ccgccaggct     120 ccagggaagg gctggagtg gtctcatcc attagttctt ctggtggcct gacatggtac      180
gcagactccg tgaagggccg attcaccatc tccagagaca attccaagaa cacgctgtat    240
ctgcaaatga acagcctgag agccgaggac acggccgtgt attactgtgc gagccccccc   300
ggtattgccg ttgctcggga ctactgggc cagggaaccc tggtcaccgt ctcctcagct    360
agcaccaagg gcccatcggt cttccccctg gcaccctcct ccaagagcac ctctggggc    420

```
acagcggccc tgggctgcct ggtcaaggac tacttcccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
gcctaccgtg tggtcagcgt cctcaccgtc ctgcaccagg actggctgaa tggcaaggag    960
tacaagtgca aggtctccaa caaagccctc ccagccccca tcgagaaaac catctccaaa    1020
gccaaagggc agccccgaga accacaggtg tacaccctgc ccccatcccg ggatgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                     1350

<210> SEQ ID NO 154
<211> LENGTH: 449
<212> TYPE: PRT
<213> ORGANISM: Homo sapiens

<400> SEQUENCE: 154

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Val Trp Val Arg Gln Ala Pro Gly Lys Gly Leu Glu Trp Val
        35                  40                  45

Ser Ser Ile Ser Ser Ser Gly Gly Leu Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Pro Gly Ile Ala Val Ala Arg Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Ala Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445
Lys

<210> SEQ ID NO 155
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 155
gaggagcagt acaacagcgc ctaccgtgtg gtcagcgtc                          39

<210> SEQ ID NO 156
<211> LENGTH: 357
<212> TYPE: DNA
<213> ORGANISM: Homo sapiens

<400> SEQUENCE: 156
gaggtgcagc tgttggagtc tgggggaggc ttggtccagc ctgggggtc cctgagactc    60 tcctgtgcag cctctggatt caccttcagt agctatggca tggtctgggt ccgccaggct   120
ccagggaagg ggctggagtg gtctcatcc attagttctt ctggtggcct gacatggtac    180
gcagactccg tgaagggccg attcaccatc tccagagaca attccaagaa cacgctgtat   240
ctgcaaatga acagcctgag agccgaggac acggccgtgt attactgtgc gagcccccc    300 ggtattgccg ttgctcggga ctactggggc cagggaaccc tggtcaccgt ctcctca     357

<210> SEQ ID NO 157
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 157
gttgctacgc gtgtcctgtc cgaggtgcag ctgttggag                           39

<210> SEQ ID NO 158
<211> LENGTH: 74
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 158
gctcttggag gagggtgcca gggggaagac cgatgggccc ttggtgctag cgcttgagac    60
ggtgaccatg gttc                                                     74

<210> SEQ ID NO 159
<211> LENGTH: 87
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 159
accgtcaccg gttcggggaa gtagtccttc accaggcagc ccagggcggc ggtgccgccg    60
ctggtgctct tgctgctggg ggccagg                                       87

<210> SEQ ID NO 160
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160 acgcgt                                                               6

<210> SEQ ID NO 161
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161 accggt                                                               6

<210> SEQ ID NO 162
<211> LENGTH: 1182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 162

```
gaggtgcagc tgttggagtc cggcggtggc ctggtgcagc tgggggggtc cctgagactc    60
tcctgcgcag ctagcggctt caccttcagc atttaccgta tgcagtgggt gcgccaggct   120
cctggaaagg ggctggagtg ggtttccggt atctctccct ctggtggcac gacgtggtat   180
gctgactccg tgaagggccg gttcacaatc tccagagaca attccaagaa cactctgtac   240
ctgcaaatga acagcctgag agctgaggat actgcagtgt actactgcgc cagatggtcc   300
gggggctccg gatacgcctt cgacatctgg ggacagggaa ccatggtcac cgtctcaagc   360
gcctcaacga aggggcccag cgtgttcccc ctggccccca gcagcaagag caccagcggc   420
ggcaccgccg ccctgggctg cctggtgaag gactacttcc ccgaaccggt gacggtgtcg   480
tggaactcag gcgccctgac cagcggcgtg cacaccttcc cggctgtcct acagtcctca   540
ggactctact ccctcagcag cgtggtgacc gtgccctcca gcagcttggg cacccagacc   600
tacatctgca acgtgaatca caagcccagc aacaccaagg tggacaagaa agttgagccc   660
aaatcttgtg acaaaggcgg tggagggtcc ggtgggggcg gatctggggg cggcgggtcc   720
ggtggtggtg gtagtaaccc agcagcgcat ctcacagggg ccaactccag cttgaccggc   780
agcggggggc cgctgttatg ggagactcag ctgggcctgg ccttcctgag gggcctcagc   840
taccacgatg gggcccttgt ggtcaccaaa gctggctact actacatcta ctccaaggtg   900
cagctgggcg tgtgggctg cccgctgggc ctggccagca ccatcaccca cggcctctac   960
aagcgcacac cccgctaccc cgaggagctg agctgttgg tcagccagca gtcaccctgc  1020
ggacgggcca ccagcagctc ccgggtctgg tgggacagca gcttcctggg tggtgtggta  1080
cacctggagg ctggggagga ggtggtcgtc cgtgtgctgg atgaacgcct ggttcgactg  1140
cgtgatggta cccggtctta cttcggggct ttcatggtgt ga                     1182
```

<210> SEQ ID NO 163
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Arg Met Gln Trp Val Arg Gln Ala Pro Gly Lys Gly Leu Glu Trp Val
        35                  40                  45

Ser Gly Ile Ser Pro Ser Gly Gly Thr Thr Trp Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Ser Gly Gly Ser Gly Tyr Ala Phe Asp Ile Trp Gly Gln
            100                 105                 110

Gly Thr Met Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Gly Gly Gly Gly Ser Gly Gly Gly Ser Gly Gly Gly Gly Ser
225                 230                 235                 240

Gly Gly Gly Gly Ser Asn Pro Ala Ala His Leu Thr Gly Ala Asn Ser
                245                 250                 255

Ser Leu Thr Gly Ser Gly Gly Pro Leu Leu Trp Glu Thr Gln Leu Gly
            260                 265                 270

Leu Ala Phe Leu Arg Gly Leu Ser Tyr His Asp Gly Ala Leu Val Val
        275                 280                 285

Thr Lys Ala Gly Tyr Tyr Tyr Ile Tyr Ser Lys Val Gln Leu Gly Gly
    290                 295                 300

Val Gly Cys Pro Leu Gly Leu Ala Ser Thr Ile Thr His Gly Leu Tyr
305                 310                 315                 320

Lys Arg Thr Pro Arg Tyr Pro Glu Glu Leu Glu Leu Leu Val Ser Gln
                325                 330                 335

Gln Ser Pro Cys Gly Arg Ala Thr Ser Ser Ser Arg Val Trp Trp Asp
            340                 345                 350

Ser Ser Phe Leu Gly Gly Val Val His Leu Glu Ala Gly Glu Glu Val
        355                 360                 365

Val Val Arg Val Leu Asp Glu Arg Leu Val Arg Leu Arg Asp Gly Thr
    370                 375                 380

Arg Ser Tyr Phe Gly Ala Phe Met Val
385                 390

<210> SEQ ID NO 164
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ile Tyr Arg Met Gln
1               5

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Ile Ser Pro Ser Gly Gly Thr Thr Trp Tyr Ala Asp Ser Val Lys
1               5                   10                  15

Gly

<210> SEQ ID NO 166
<211> LENGTH: 11
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 166

Trp Ser Gly Gly Ser Gly Tyr Ala Phe Asp Ile
1               5                   10

<210> SEQ ID NO 167
<211> LENGTH: 645
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 167

```
gacatccaga tgacccagtc tccactctcc ctgtctgcat ctgtaggaga cagagtcacc    60
atcacttgcc aggcgagtcg ggacattaga aactatttaa attggtatca acaaaaacca   120
gggaaagccc cgaagctcct gatctacgat gcatccagtt tgcaaacagg ggtcccatca   180
aggttcggtg cagtggatc tgggacagac tttagtttca ccatcggcag cctgcagcct   240
gaagatattg caacatatta ctgtcaacag tttgatagtc tccctcacac ttttggccag   300
gggaccaaac tggagatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gttga              645
```

<210> SEQ ID NO 168
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 168

Asp Ile Gln Met Thr Gln Ser Pro Leu Ser Leu Ser Ala Ser Val Gly
1               5                   10                  15

Asp Arg Val Thr Ile Thr Cys Gln Ala Ser Arg Asp Ile Arg Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Ser Leu Gln Thr Gly Val Pro Ser Arg Phe Gly Gly
    50                  55                  60

Ser Gly Ser Gly Thr Asp Phe Ser Phe Thr Ile Gly Ser Leu Gln Pro
65                  70                  75                  80

Glu Asp Ile Ala Thr Tyr Tyr Cys Gln Gln Phe Asp Ser Leu Pro His
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 169
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gln Ala Ser Arg Asp Ile Arg Asn Tyr Leu Asn
1               5                   10

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Asp Ala Ser Ser Leu Gln Thr
1               5

<210> SEQ ID NO 171
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Gln Gln Phe Asp Ser Leu Pro His Thr
1               5

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Thr His Thr Cys Pro Pro Cys Pro
1               5

<210> SEQ ID NO 173
<211> LENGTH: 1176
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 173

```
gaggtgcagc tggtggagtc tgggggcggc ttggcaaagc ctggggggtc cctgagactc      60
tcctgcgcag cctccgggtt caggttcacc ttcaataact actacatgga ctgggtccgc     120
caggctccag ggcaggggct ggagtgggtc tcacgtatta gtagtagtgg tgatcccaca     180
tggtacgcag actccgtgaa gggcagattc accatctcca gagagaacgc caagaacaca     240
ctgtttcttc aaatgaacag cctgagagct gaggacacgg ctgtctatta ctgtgcgagc     300
ttgactacag ggtctgactc ctggggccag ggagtcctgg tcaccgtctc ctcagctagc     360
accaagggcc catcggtctt ccccctggca ccctcctcca gagcacctc tgggggcaca      420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct tgggcaccca gacctacatc     600
tgcaacgtga atcacaagcc cagcaacacc aaggtggaca agaaagttga gcccaaatct     660
tgtgacaaag cggtggagg gtccggtggg ggcggatctg ggggcggcgg gtccggtggt     720
ggtggtagta acccagcagc gcatctcaca ggggccaact ccagcttgac cggcagcggg     780
gggccgctgt tatgggagac tcagctgggc ctggccttcc tgaggggcct cagctaccac     840
gatgggccc ttgtggtcac caaagctggc tactactaca tctactccaa ggtgcagctg      900
ggcggtgtgg gctgcccgct gggcctggcc agcaccatca cccacggcct ctacaagcgc     960
acacccgct accccgagga gctggagctg ttggtcagcc agcagtcacc ctgcggacgg     1020
gccaccagca gctcccgggt ctggtgggac agcagcttcc tgggtggtgt ggtacacctg    1080
gaggctgggg aggaggtggt cgtccgtgtg ctggatgaac gcctggttcg actgcgtgat    1140
ggtacccggt cttacttcgg ggctttcatg gtgtga                              1176
```

<210> SEQ ID NO 174
<211> LENGTH: 391
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

```
Glu Val Gln Leu Val Glu Ser Gly Gly Gly Leu Ala Lys Pro Gly Gly
1               5                   10                  15

Ser Leu Arg Leu Ser Cys Ala Ala Ser Gly Phe Arg Phe Thr Phe Asn
            20                  25                  30

Asn Tyr Tyr Met Asp Trp Val Arg Gln Ala Pro Gly Gln Gly Leu Glu
        35                  40                  45

Trp Val Ser Arg Ile Ser Ser Ser Gly Asp Pro Thr Trp Tyr Ala Asp
    50                  55                  60

Ser Val Lys Gly Arg Phe Thr Ile Ser Arg Glu Asn Ala Lys Asn Thr
65                  70                  75                  80

Leu Phe Leu Gln Met Asn Ser Leu Arg Ala Glu Asp Thr Ala Val Tyr
                85                  90                  95

Tyr Cys Ala Ser Leu Thr Thr Gly Ser Asp Ser Trp Gly Gln Gly Val
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
    195                 200                 205

Asn Thr Lys Val Asp Lys Lys Val Glu Pro Lys Ser Cys Asp Lys Gly
210                 215                 220

Gly Gly Gly Ser Gly Gly Gly Ser Gly Gly Gly Ser Gly Gly
225                 230                 235                 240

Gly Gly Ser Asn Pro Ala Ala His Leu Thr Gly Ala Asn Ser Ser Leu
            245                 250                 255

Thr Gly Ser Gly Gly Pro Leu Leu Trp Glu Thr Gln Leu Gly Leu Ala
        260                 265                 270

Phe Leu Arg Gly Leu Ser Tyr His Asp Gly Ala Leu Val Val Thr Lys
    275                 280                 285

Ala Gly Tyr Tyr Tyr Ile Tyr Ser Lys Val Gln Leu Gly Gly Val Gly
290                 295                 300

Cys Pro Leu Gly Leu Ala Ser Thr Ile Thr His Gly Leu Tyr Lys Arg
305                 310                 315                 320

Thr Pro Arg Tyr Pro Glu Glu Leu Glu Leu Leu Val Ser Gln Gln Ser
            325                 330                 335

Pro Cys Gly Arg Ala Thr Ser Ser Arg Val Trp Trp Asp Ser Ser
        340                 345                 350

Phe Leu Gly Gly Val Val His Leu Glu Ala Gly Glu Glu Val Val Val
    355                 360                 365

Arg Val Leu Asp Glu Arg Leu Val Arg Leu Arg Asp Gly Thr Arg Ser
370                 375                 380

Tyr Phe Gly Ala Phe Met Val
385                 390

<210> SEQ ID NO 175
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 175
gagcccaaat cttgtgacaa aactcacaca tgcccaccgt gcccaggcgg tggagggtcc      60
ggtgg                                                                  65

<210> SEQ ID NO 176
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 176
ccaccggacc ctccaccgcc tgggcacggt gggcatgtgt gagttttgtc acaagatttg      60
ggctc                                                                  65

<210> SEQ ID NO 177
<211> LENGTH: 6
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 177 ggatcc                                                                    6

<210> SEQ ID NO 178
<211> LENGTH: 1203
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 178
gaggtgcagc tgttggagtc tgggggaggc ttggtccagc ctggggggtc cctgagactc      60
tcctgtgcag cctctggatt caccttcagt agctatggca tggtctgggt ccgccaggct     120
ccagggaagg ggctggagtg gtctcatcc attagttctt ctggtggcct gacatggtac     180
gcagactccg tgaagggccg attcaccatc tccagagaca attccaagaa cacgctgtat     240
ctgcaaatga acagcctgag agccgaggac acggccgtgt attactgtgc gagccccccc     300
ggtattgccg ttgctcggga ctactggggc cagggaaccc tggtcaccgt ctcctcagct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccaggcg gtggagggtc cggtggggc     720 ggatctgggg gcggcgggtc cggtggtggt ggtagtaacc cagcagcgca tctcacaggg     780
gccaactcca gcttgaccgg cagcgggggg ccgctgttat gggagactca gctgggcctg     840
gccttcctga ggggcctcag ctaccacgat ggggcccttg tggtcaccaa agctggctac     900
tactacatct actccaaggt gcagctgggc ggtgtgggct gcccgctggg cctggccagc     960
accatcaccc acggcctcta caagcgcaca ccccgctacc ccgaggagct ggagctgttg    1020
gtcagccagc agtcaccctg cggacgggcc accagcagct cccgggtctg gtgggacagc    1080
agcttcctgg gtggtgtggt acacctggag gctggggagg aggtggtcgt ccgtgtgctg    1140
gatgaacgcc tggttcgact gcgtgatggt acccggtctt acttcggggc tttcatggtg    1200
tga                                                                 1203

<210> SEQ ID NO 179
<211> LENGTH: 400
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 179

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
                   20                  25                  30
Gly Met Val Trp Val Arg Gln Ala Pro Gly Lys Gly Leu Glu Trp Val
             35                  40                  45

Ser Ser Ile Ser Ser Ser Gly Gly Leu Thr Trp Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ser Pro Pro Gly Ile Ala Val Ala Arg Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Gly Gly Gly Ser Gly Gly Gly Gly
225                 230                 235                 240

Gly Ser Gly Gly Gly Gly Ser Gly Gly Gly Gly Ser Asn Pro Ala Ala
                245                 250                 255

His Leu Thr Gly Ala Asn Ser Ser Leu Thr Gly Ser Gly Gly Pro Leu
            260                 265                 270

Leu Trp Glu Thr Gln Leu Gly Leu Ala Phe Leu Arg Gly Leu Ser Tyr
        275                 280                 285

His Asp Gly Ala Leu Val Val Thr Lys Ala Gly Tyr Tyr Tyr Ile Tyr
290                 295                 300

Ser Lys Val Gln Leu Gly Gly Val Gly Cys Pro Leu Gly Leu Ala Ser
305                 310                 315                 320

Thr Ile Thr His Gly Leu Tyr Lys Arg Thr Pro Arg Tyr Pro Glu Glu
                325                 330                 335

Leu Glu Leu Leu Val Ser Gln Gln Ser Pro Cys Gly Arg Ala Thr Ser
            340                 345                 350

Ser Ser Arg Val Trp Trp Asp Ser Ser Phe Leu Gly Gly Val Val His
        355                 360                 365

Leu Glu Ala Gly Glu Glu Val Val Arg Val Leu Asp Glu Arg Leu
370                 375                 380

Val Arg Leu Arg Asp Gly Thr Arg Ser Tyr Phe Gly Ala Phe Met Val
385                 390                 395                 400

<210> SEQ ID NO 180
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 180 gcggccgc                                                                    8

<210> SEQ ID NO 181
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181 cgtacg                                                                      6

<210> SEQ ID NO 182
<211> LENGTH: 6
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182 gctagc                                                                      6
```